US007855320B2

(12) United States Patent
Davies et al.

(10) Patent No.: US 7,855,320 B2
(45) Date of Patent: Dec. 21, 2010

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics Inc., Indianapolis, IN (US)

( * ) Notice: Subject to any disclaimer, the term of this patent is extended or adjusted under 35 U.S.C. 154(b) by 274 days.

(21) Appl. No.: 11/940,279

(22) Filed: Nov. 14, 2007

(65) Prior Publication Data

US 2008/0127367 A1 May 29, 2008

Related U.S. Application Data

(60) Provisional application No. 60/866,059, filed on Nov. 15, 2006.

(51) Int. Cl.
*C12N 15/82* (2006.01)
*C12N 5/04* (2006.01)
*A01H 5/00* (2006.01)

(52) U.S. Cl. ....................... 800/278; 800/298; 800/306; 800/312; 800/320.1; 800/320.3; 800/322; 435/410; 435/412; 435/415; 435/416; 435/419

(58) Field of Classification Search ....................... None
See application file for complete search history.

(56) References Cited

U.S. PATENT DOCUMENTS

| | | | | |
|---|---|---|---|---|
| 5,322,783 | A | 6/1994 | Tomes et al. | |
| 5,538,880 | A | 7/1996 | Lundquist et al. | |
| 5,550,318 | A | 8/1996 | Adams et al. | |
| 5,563,055 | A | 10/1996 | Townsend et al. | |
| 5,610,042 | A | 3/1997 | Chang et al. | |
| 5,639,790 | A | 6/1997 | Voelker et al. | |
| 5,704,160 | A | 1/1998 | Bergquist et al. | |
| 5,952,544 | A | 9/1999 | Browse et al. | |
| 6,229,033 | B1 | 5/2001 | Knowlton | |
| 6,248,939 | B1 | 6/2001 | Leto et al. | |
| 2003/0046723 | A1 | 3/2003 | Heard et al. | |
| 2004/0019927 | A1 | 1/2004 | Sherman et al. | |
| 2004/0025202 | A1 | 2/2004 | Laurie et al. | |
| 2006/0048240 | A1 | 3/2006 | Alexandrov et al. | |
| 2006/0150283 | A1 * | 7/2006 | Alexandrov et al. | 800/288 |
| 2006/0277630 | A1 | 12/2006 | Lightner et al. | |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | WO 2004/035798 | 4/2004 |
| WO | 2004/093528 | 11/2004 |
| WO | WO 2004/093532 | 11/2004 |
| WO | 2005/047516 | 5/2005 |
| WO | 2005/107437 | 11/2005 |
| WO | 2007/053482 | 5/2007 |

OTHER PUBLICATIONS

Blast Results.*

Anoop et al., "Modulation of citrate metabolism alters aluminum tolerance in yeast and transgenic canola overexpressing a mitochondrial citrate synthase," *Plant Physiol.*, 132:2205-2217, 2003.

Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.

Dehesh et al., "Overexpression of 3-ketoacyl-acyl-carrier protein synthase IIIs in plants reduces the rate of lipid synthesis," *Plant Physiol.*, 125:1103-1114, 2001.

Eastmond and Graham, "Re-examining the role of glyoxylate cycle in oilseeds," *Trends Plant Sci.*, 6(2):72-77, 2001.

Eccleston and Ohlrogge, "Expression of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.

Fatland et al., "Molecular biology of cytosolic acetyl-CoA generation," *Biochem. Soc. Trans.*, 28(6):593-595, 2000.

Fatland et al., "Reverse genetic characterization of cytosolic acetyl-CoA generation by ATP-citrate lyase in *Arabidopsis," Plant Cell*, 17:182-203, 2005.

Focks and Benning, "*wrinkledl*: A novel, low-seed-oil mutant of *Arabidopsis* with a deficiency in the seed-specific regulation of carbohydrate metabolism," *Plant Physiol.*, 118:91-101, 1998.

Girke et al., "Microarray analysis of developing *Arabidopsis* seeds," *Plant Physiol.*, 124:1570-1581, 2000.

Katavic et al., "Utility of the *Arabidopsis FAE1* and yeast *SLC1-1* genes for improvements in erucic acid and oil content in rapeseed," *Biochem Soc. Trans.*, 28(6):935-937, 2000.

Larson et al., "Acyl CoA profiles of transgenic plants that accumulate medium-chain fatty acids indicate inefficient storage lipid synthesis in developing oilseeds," *Plant J.*, 32:519-527, 2002.

Lin et al., "The Pex16p Homolog SSE1 and Storage Organelle Formation in *Arabidopsis* Seeds," *Science*, 284:328-330, 1999.

Liu and Butow, "A transcriptional switch in the expression of yeast tricarboxylic acid cycle genes in response to a reduction or loss of respiratory function," *Mol. Cell. Biol.*, 19:6720-6728, 1999.

Mekhedov et al., "Toward a Functional Catalog of the Plant Genome. A Survey of Genes for Lipid Biosynthesis," *Plant Physiology*, 122:389-401, 2000.

Moire et al., "Impact of Unusual Fatty Acid Synthesis on Futile Cycling through β-Oxidation and on Gene Expression in Transgenic Plants," *Plant Physiology*, 134:432-442, 2004.

(Continued)

*Primary Examiner*—Eileen B O Hara
(74) *Attorney, Agent, or Firm*—Donald R. Stuart; Klarquist Sparkman LLP

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

22 Claims, No Drawings

OTHER PUBLICATIONS

Neuhaus et al., "Nonphotosynthetic Metabolism in Plastids," *Annu. Rev. Plant Physiol. Plant Mol.*, 51:111-140, 2000.
O'Hara et al., "Fatty Acid and Lipid Biosynthetic Genes Are Expressed at Constant Molar Ratios But Different Absolute Levels during Embryogenesis," *Plant Physiology*, 129:310-320, 2002.
Pritchard et al., "Germination and storage reserve mobilization are regulated independently in *Arabidopsis," The Plant Journal*, 31(5):639-647, 2002.
Rangasamy and Ratledge, "Genetic enhancement of fatty acid synthesis by targeting rat liver ATP:citrate lyase into plastids of tobacco," *Plant Physiol*., 122:1231-1238, 2000.
Rangasamy et al., "Compartmentation of ATP:Citrate Lyase in Plants," *Plant Physiology*, 122:1225-1230, 2000.
Ratledge et al., "Correlation of ATP/Citrate Lyase Activity with Lipid Accumulation in Developing Seeds of *Brassica napus* L.," Lipids, 32(1):7-12, 1997.
Rawsthorne, Stephen, "Carbon flux and fatty acid synthesis in plants," *Progress in Lipid Research*, 41:182-196 (2002).
Ruuska et al., "Contrapuntal Networks of Gene Expression during *Arabidopsis* Seed Filling," *The Plant Cell*, 14:1191-1206, 2002.
Rylott et al., "Co-ordinate regulation of genes involved in storage lipid mobilization in *Arabidopsis thaliana," Biochem Soc. Trans*., 29:283-287, 2001.
Schnarrenberger and Martin, "Evolution of the enzymes of the citric acid cycle and the glyoxylate cycle of higher plants, A case study of endosymbiotic gene transfer," *Eur. J. Biochem*., 269:868-883, 2002.
Schnurr et al., "Characterization of an acyl-CoA synthetase from *Arabidopsis thaliana," Biochem Soc. Trans*., 28(6):957-958, 2000.
Shockey et al., "Characterization of the AMP-binding protein gene family in *Arabidopsis thaliana*: will the real acyl-CoA synthetases please stand up?" *Biochem Soc. Trans*., 28(6):955-957, 2000.
Thelen et al., "Biotin carboxyl carrier protein isoforms in Brassicaceae oilseeds," *Biochem. Soc. Trans*., 28(6):595-598, 2000.
White et al., "A new set of *Arabidopsis* expressed sequence tags from developing seeds. The metabolic pathway from carbohydrates to seed oil," *Plant Physiol*., 124:1582-1594, 2000.
Comai et al., "Efficient discovery of DNA polymorphisms in natural populations by Ecotilling," *The Plant Journal*, 37:778-786 (2004).
Zou et al., "Modification of Seed Oil Content and Acyl Composition in the Brassicaceae by Expression of a Yeast *sn*-2 Acyltransferase Gene," *The Plant Cell*, 9:909-923 (1997).
Bateman et al., "Pfam 3.1: 1313 multiple alignments and profile HMMs match the majority of proteins," *Nucleic Acids Res*., 27:260-262 (1999).
Bert et al., "Comparative genetic analysis of quantitative traits in sunflower (*Helianthus annuus* L.). 2. Characterisation of QTL involved in developmental and agronomic traits," *Theor. Appl. Genet*., 107:181-9 (2003).
Browse et al., "Fluxes through the prokaryotic and eukaryotic pathways of lipid synthesis in the '16:3' plant *Arabidopsis thaliana," Biochem J.* 235:25-31 (1986).
Chapple and Carpita, "Plant cell walls as targets for biotechnology," *Current Opinion in Plant Biology*, 1:179-185 (1998).
Christensen et al., *9th International Conference on Arabidopsis Research*, Univ. of Wisconsin-Madison, Jun. 24-28, Abstract 165 (1998).
Christou et al., "Inheritance and expression of foreign genes in transgenic soybean plants," *Proc. Natl. Acad. Sci. USA*, 86:7500-7504 (1989).
Colbert et al., "High-throughput screening for induced point mutations," *Plant Physiol.* 126:480-484 (2001).
De Block et al., "Transformation of *Brassica napus* and *Brassica oleracea* Using *Agrobacterium tumefaciens* and the Expression of the bar and neo Genes in the Transgenic Plants," *Plant Physiol*., 91:694-701 (1989).
Douglas et al., "Nutritional evaluation of low phytate and high protein corns," *Poultry Sci*. 79:1586-1591 (2000).
Edwards et al., "Protein and energy evaluation of soybean meals processed from genetically modified high-protein soybeans," *Poultry Sci*. 79:525-527 (1999).
Everett et al., "Genetic engineering of sunflower (*Helianthus annuus* L.)," *Bio/Technology*, 5:1201 (1987).
Falco et al., "Transgenic canola and soybean seeds with increased lysine," *Bio/Technology*, 13:577-582 (1995).
Feldmann et al., "A Dwarf Mutant of *Arabidopsis* Generated by T-DNA Insertion Mutagenesis," *Science*, 243:1351-1354 (1989).
Focks and Benning, "wrinkled1: A novel, low-seed-oil mutant of *Arabidopsis* with a deficiency in the seed-specific regulation of carbohydrate metabolism," *Plant Physiol*., 118:91-101 (1998).
Fridborg et al., "The *Arabidopsis* dwarf mutant *shi* exhibits reduced gibberellin responses conferred by overexpression of a new putative zinc finger protein," *Plant Cell*, 11:1019-1032 (1999).
Hayashi et al., "Activation of a plant gene by T-DNA tagging: auxin-independent growth in vitro," *Science*, 258:1350-1353 (1992).
Honig and Rackis, "Determination of the total pepsin-pancreatin indigestible content (dietary fiber) of soybean products, wheat bran, and corn bran," *J. Agri. Food Chem*., 27:1262-1266 (1979).
Jako et al., "Seed-specific over-expression of an *Arabidopsis* cDNA encoding a diacylglycerol acyltransferase enhances seed oil content and seed weight," *Plant Physiol*., 126(2):861-74 (2001).
James and Dooner, "Isolation of EMS-induced mutants in *Arabidopsis* altered in seed fatty acid composition," *Theor. Appl. Genet*., 80:241-245 (1990).
Kardailsky et al., "Activation tagging of the floral inducer FT," *Science*, 286:1962-1965 (1999).
Katavic et al., "Alteration of seed fatty acid composition by an ethyl methanesulfonate-induced mutation in *Arabidopsis thaliana* affecting diacylglycerol acyltransferase activity," *Plant Physiol*., 108:399-409 (1995).
Kline et al., "High velocity microprojectiles for delivering nucleic acids into living cells," *Nature*, 327:70-73 (1987).
Lemieux et al., "Mutants of *Arabidopsis* with alterations in seed lipid fatty acid composition," *Theor. Appl. Genet*., 80:234-240 (1990).
Lionneton et al., "Development of an AFLP-based linkage map and localization of QTLs for seed fatty acid content in condiment mustard (*Brassica juncea*)," *Genome*, 45:1203-15 (2002).
McCallum et al., "Targeted screening for induced mutations," *Nature Biotechnology*, 18:455-457 (2000).
Moore et al., "Chromatography of Amino Acids on Sulfonated Polystyrene Resins," *Anal. Chem*., 30:1185-1190 (1958).
Mulder et al., "The InterPro Database, 2003 brings increased coverage and new features," *Nucleic Acids Res*., 31:315-318, 2003.
Okuley et al., "*Arabidopsis FAD2* gene encodes the enzyme that is essential for polyunsaturated lipid synthesis," *Plant Cell*, 6:147-158 (1994).
Parsons et al., "Nutritional evaluation of soybean meals varying in oligosaccharide content," *Poultry Sci*., 79:1127-1131 (2000).
Schaffer et al., "The late elongated hypocotyl mutation of *Arabidopsis* disrupts circadian rhythms and the photoperiodic control of flowering," *Cell*, 93:1219-1229 (1998).
Shewry, "Seed storage proteins: structures and biosynthesis," *Plant Cell*, 7:945-956 (1995).
Weigel et al., "Activation tagging in *Arabidopsis," Plant Physiology*, 122:1003-1013 (2000).
Wilson et al., "A Dissociation insertion causes a semidominant mutation that increases expression of TINY, an *Arabidopsis* gene related to APETALA2," *Plant Cell*, 8:659-671 (1996).
Yadav et al., "Cloning of higher plant omega-3 fatty acid desaturases," *Plant Physiol*., 103:467-476 (1993).

* cited by examiner

SEQUENCE LISTING

<160> NUMBER OF SEQ ID NOS: 100

<210> SEQ ID NO 1
<211> LENGTH: 1854
<212> TYPE: DNA
<213> ORGANISM: Arabidopsis thaliana

<400> SEQUENCE: 1

```
atggttcgtt cacatcttct ccgtgccacg ccagaagctt ctccgcttaa accggcatcg     60

tctccgtcaa actgcaggtt gtcactttct cccgttgaac ttagattata ttttattagg    120

gacgacgact tcaaagtcaa agtcgacatt ttcaaaacgt catatcaaaa ctccctgttt    180

gaattgccgt gttgtgacaa gtcagagttc cttaccagtc tcagattttc ggatcttttc    240

aacctccctg gtgaatatgt gccgatgaat cctgagatct ttagcgcaat gagagcgggg    300

aacatagagc ttctggaaaa gttgaaaagc tacgaaacgc caatggcatg tcttaagagc    360

gatggcggag attctgttct tcaccttgct gctgcttcgg gtcatcttga actagtgaag    420

aacataatca ctgaatgtcc ttgtctttta ttggagccaa actcgaagta tcagattccg    480

cttcatgtgg ccgctcgtgc tggccgttca gcagttgtga aggctcttgt tgcttctgta    540

ttatattttt cacctagagt gcctgaagaa gatagggata gactgaatat atatgttctg    600

aaggacatag atggagatac tcctctgcat gcggccttga aagacctcca tgaaaaagca    660

gaggagcgca tcagaaaact atccttgtct caccttatta tgcattggcg acgtagcaga    720

tgcatttcat ttcctgatgc atcaacacgc caaatggaga cagctgcctg tctagtgaat    780

gcagaccaac atgcctcatt tcttgcgaat aaagatggaa catctccctt gtatttggca    840

gttgaagctg gtaatgtatc acttgtgaga gcgatgttga accgtcctgg taataaaatc    900

caaggaaaaa cctctacctt agcttcacaa ttggaaggga gaaaatcgct tttacacgca    960

gccctcaagg ccaaaaatac agatgttctt aatgttattc ttaatgatga cccgagcctt   1020

gtcaacgagc gagatgaaga agggcgaact tgtctttctg ttggagcatc catggggtat   1080

tacaaaggaa tatgtaagct attagatcga tcaacaaaga gtgtttatga atgcgacaaa   1140

gatggttcct ttccaattca tatggctgta gagaaaggtc atttgaaagt tgtgaaagag   1200

attctaaaac gttgtccaga ttcgaaagag ctggttaaca aacaaggtca aaacatgctt   1260

cacattgcag caaagagtgc gaaagtggga tcttttcttt tgggttatat aaggagactt   1320

gatacggaga atcatctgat cgaggagcaa gatgtggatg ggaatgcacc tttgcaccta   1380

gccaccataa attggcgctg tcgaactgtt gataaacttg ctgcctttgc ttctaccgaa   1440

acaaaaaatcc tgaatataca gaacaaagat ggattgagac ctctggatat tgcagagtta   1500

aatctacagc ctgactacgt tttacgggag agattgacgt tgatggtact gctgtgcgtt   1560

tacgcaccga aaagtgttgg ttggctaccg acgagtggaa tgacactaag aagcagatca   1620

gagcctctag acgctaaaaa atacaaagac catatcaacg ctcttctgct ggtggcaact   1680

cttgtagcca ctgttacatt tgctgcaggt tttacaatac ctggtggctt taacagctct   1740

gctccaaaca tgggtatggc cactttggcc gatgactcca ccctcttctt ttttctggta   1800

ttagacacct tggcgatgca aagctctatt gtagcaatag ttgctctgat ttag         1854
```

<210> SEQ ID NO 2
<211> LENGTH: 617
<212> TYPE: PRT
<213> ORGANISM: Arabidopsis thaliana

<400> SEQUENCE: 2

```
Met Val Arg Ser His Leu Leu Arg Ala Thr Pro Glu Ala Ser Pro Leu
1               5                   10                  15

Lys Pro Ala Ser Ser Pro Ser Asn Cys Arg Leu Ser Leu Ser Pro Val
            20                  25                  30

Glu Leu Arg Leu Tyr Phe Ile Arg Asp Asp Asp Phe Lys Val Lys Val
        35                  40                  45

Asp Ile Phe Lys Thr Ser Tyr Gln Asn Ser Leu Phe Glu Leu Pro Cys
    50                  55                  60

Cys Asp Lys Ser Glu Phe Leu Thr Ser Leu Arg Phe Ser Asp Leu Phe
65                  70                  75                  80

Asn Leu Pro Gly Glu Tyr Val Pro Met Asn Pro Glu Ile Phe Ser Ala
                85                  90                  95

Met Arg Ala Gly Asn Ile Glu Leu Leu Glu Lys Leu Lys Ser Tyr Glu
            100                 105                 110

Thr Pro Met Ala Cys Leu Lys Ser Asp Gly Gly Asp Ser Val Leu His
        115                 120                 125

Leu Ala Ala Ala Ser Gly His Leu Glu Leu Val Lys Asn Ile Ile Thr
    130                 135                 140

Glu Cys Pro Cys Leu Leu Leu Glu Pro Asn Ser Lys Tyr Gln Ile Pro
145                 150                 155                 160

Leu His Val Ala Ala Arg Ala Gly Arg Ser Ala Val Val Lys Ala Leu
                165                 170                 175

Val Ala Ser Val Leu Tyr Phe Ser Pro Arg Val Pro Glu Glu Asp Arg
            180                 185                 190

Asp Arg Leu Asn Ile Tyr Val Leu Lys Asp Ile Asp Gly Asp Thr Pro
        195                 200                 205

Leu His Ala Ala Leu Lys Asp Leu His Glu Lys Ala Glu Glu Arg Ile
    210                 215                 220

Arg Lys Leu Ser Leu Ser His Leu Ile Met His Trp Arg Arg Ser Arg
225                 230                 235                 240

Cys Ile Ser Phe Ser Asp Ala Ser Thr Arg Gln Met Glu Thr Ala Ala
                245                 250                 255

Cys Leu Val Asn Ala Asp Gln His Ala Ser Phe Leu Ala Asn Lys Asp
            260                 265                 270

Gly Thr Ser Pro Leu Tyr Leu Ala Val Glu Ala Gly Asn Val Ser Leu
        275                 280                 285

Val Arg Ala Met Leu Asn Arg Pro Gly Asn Lys Ile Gln Gly Lys Thr
    290                 295                 300

Ser Thr Leu Ala Ser Gln Leu Glu Gly Arg Lys Ser Leu Leu His Ala
305                 310                 315                 320

Ala Leu Lys Ala Lys Asn Thr Asp Val Leu Asn Val Ile Leu Asn Asp
                325                 330                 335

Asp Pro Ser Leu Val Asn Glu Arg Asp Glu Glu Gly Arg Thr Cys Leu
            340                 345                 350

Ser Val Gly Ala Ser Met Gly Tyr Tyr Lys Gly Ile Cys Lys Leu Leu
        355                 360                 365

Asp Arg Ser Thr Lys Ser Val Tyr Glu Cys Asp Lys Asp Gly Ser Phe
```

-continued

```
    370                 375                 380

Pro Ile His Met Ala Val Glu Lys Gly His Leu Lys Val Val Lys Glu
385                 390                 395                 400

Ile Leu Lys Arg Cys Pro Asp Ser Lys Glu Leu Val Asn Lys Gln Gly
                405                 410                 415

Gln Asn Met Leu His Ile Ala Ala Lys Ser Ala Lys Val Gly Ser Phe
            420                 425                 430

Leu Leu Gly Tyr Ile Arg Arg Leu Asp Thr Glu Asn His Leu Ile Glu
        435                 440                 445

Glu Gln Asp Val Asp Gly Asn Ala Pro Leu His Leu Ala Thr Ile Asn
    450                 455                 460

Trp Arg Cys Arg Thr Val Asp Lys Leu Ala Ala Phe Ala Ser Thr Glu
465                 470                 475                 480

Thr Lys Ile Leu Asn Ile Gln Asn Lys Asp Gly Leu Arg Pro Leu Asp
                485                 490                 495

Ile Ala Glu Leu Asn Leu Gln Pro Asp Tyr Val Leu Arg Glu Arg Leu
            500                 505                 510

Thr Leu Met Val Leu Leu Cys Val Tyr Ala Pro Lys Ser Val Gly Trp
        515                 520                 525

Leu Pro Thr Ser Gly Met Thr Leu Arg Ser Arg Ser Glu Pro Leu Asp
    530                 535                 540

Ala Lys Lys Tyr Lys Asp His Ile Asn Ala Leu Leu Leu Val Ala Thr
545                 550                 555                 560

Leu Val Ala Thr Val Thr Phe Ala Ala Gly Phe Thr Ile Pro Gly Gly
                565                 570                 575

Phe Asn Ser Ser Ala Pro Asn Met Gly Met Ala Thr Leu Ala Asp Asp
            580                 585                 590

Ser Thr Leu Phe Phe Phe Leu Val Leu Asp Thr Leu Ala Met Gln Ser
        595                 600                 605

Ser Ile Val Ala Ile Val Ala Leu Ile
    610                 615


<210> SEQ ID NO 3
<211> LENGTH: 1890
<212> TYPE: DNA
<213> ORGANISM: Arabidopsis thaliana

<400> SEQUENCE: 3

atgggtaagg ttcaagagtt tgaaaaggtt atggaggaga atgaaattcc tgttcttgat     60

caggtcactt ttcaggggaa tacgattctg catcttgcag ctatttatgg tcatgaccac    120

ctagtgcggc gtatccttgc ctatgagcta aacattctta gaaattggaa acgtggctta    180

aattgcaact tcgtcccaag tttctctcat tatcagactc ttttggtgag acgaaactac    240

aagggagacc ttgctctcca tgtagcagct gctgcaggac acaagttgat agttggcctt    300

cttattgatt gcctaaggca gcttccgcaa gatataacta tggtgattgg atcagagcaa    360

atggtaattg gaaacatttt cagagtttcc aacaatgatg ggaatactgc attgcacctc    420

tccctgaaag gaaaccatgt atctgtttct ttgcaacttg ttcgtgaaga tcgtagcact    480

tgctttcttc tggacaagga ggatgtatct ccactgtata tggcagctga agctggatat    540

gtttcacttg tggagcatat gttacggggt ttggatgcaa gctttgttgg gaaatccgtt    600

ttgtgtgctg cagtgaaaag ccagaatctt gatatattga cagctgtatt agagagtgac    660

tcagatctgg tagaatcgag ggatgaagat ggaagaactc cacttgccac tgcagcatcc    720
```

-continued

```
attggttatg acattggagt gcagcatatg ctaaccagat ttgcaagttc tacacaggtt    780

gcttacatta agaatgaaga tggttctttc cccatccact cagcctgcag tgctaggtgc    840

acctcagctc tcaaggtgat cttaaaacac cacccagaca caatagaaat gcttaactca    900

cagggtcaaa acgttcttca tgtcgctgct aaaagcggga atgcacgagc tgttggctat    960

ctgctcagaa aatctgacgt caaaaggtta atcaatgaac aagacataga aggaaacaca   1020

ccgttacatt tagccagcag taattctcat cccaaggttt ggttgatatg gatggcattg   1080

gtggctgctg gtaccactag agctccacga gttcatctga gagcagacat ccctggtctg   1140

acaacagatg aggacttaat cctaaaaatt cacaaggata gagtaaacac tctccttgtg   1200

gtggcaacac tagtggctac aatggctttt gctgcaggct tgagtgtgcc actaggttac   1260

aacagcacag agttcaagtc aaatgtcaaa cattcttacg aagaatctgc atttcatgct   1320

tttgtcatct gcaatagcat tgccgtatat actgctgtta tatcgacagt tgctcttata   1380

gggacacaat tggctgacct aaaatgcatg ctgaccacct tcaagtttat tgtgccactc   1440

ctggggtttt ctattatcgc catgtctttg gcttttgttg caggcttata cctggtcttg   1500

ggacatcatt attggcttgc catatttgtc ttggcctcag gcggtttcta tctcatggct   1560

ctacttctgc tcatcatccc ttacgcttcg ccttatactt ttacactatc aagaagcctg   1620

aattctttag tacagaatat gtcgaaggaa gatgttgatt ccgtaaatca actagttcct   1680

gcaccaacag aagagttggc attgatcaaa gccatccaag tcaatcgctg tatacaaggt   1740

aatattgggg taacatcttt gtcatattac ctgttgaaac acgtagctcc aatcaatgtt   1800

ctactacatc taaagctgtg gaaccattat agtttggttt tttcaggtca cctctatgat   1860

ggtcccaaga aaacatactc acaactttag                                    1890
```

```
<210> SEQ ID NO 4
<211> LENGTH: 629
<212> TYPE: PRT
<213> ORGANISM: Arabidopsis thaliana

<400> SEQUENCE: 4

Met Gly Lys Val Gln Glu Phe Glu Lys Val Met Glu Glu Asn Glu Ile
1               5                   10                  15

Pro Val Leu Asp Gln Val Thr Phe Gln Gly Asn Thr Ile Leu His Leu
            20                  25                  30

Ala Ala Ile Tyr Gly His Asp His Leu Val Arg Arg Ile Leu Ala Tyr
        35                  40                  45

Glu Leu Asn Ile Leu Arg Asn Trp Lys Arg Gly Leu Asn Cys Asn Phe
    50                  55                  60

Val Pro Ser Phe Ser His Tyr Gln Thr Leu Leu Val Arg Arg Asn Tyr
65                  70                  75                  80

Lys Gly Asp Leu Ala Leu His Val Ala Ala Ala Ala Gly His Lys Leu
                85                  90                  95

Ile Val Gly Leu Leu Ile Asp Cys Leu Arg Gln Leu Pro Gln Asp Ile
            100                 105                 110

Thr Met Val Ile Gly Ser Glu Gln Met Val Ile Gly Asn Ile Phe Arg
        115                 120                 125

Val Ser Asn Asn Asp Gly Asn Thr Ala Leu His Leu Ser Leu Lys Gly
    130                 135                 140

Asn His Val Ser Val Ser Leu Gln Leu Val Arg Glu Asp Arg Ser Thr
145                 150                 155                 160

Cys Phe Leu Leu Asp Lys Glu Asp Val Ser Pro Leu Tyr Met Ala Ala
```

-continued

```
                165                 170                 175

Glu Ala Gly Tyr Val Ser Leu Val Glu His Met Leu Arg Gly Leu Asp
            180                 185                 190

Ala Ser Phe Val Gly Lys Ser Val Leu Cys Ala Ala Val Lys Ser Gln
        195                 200                 205

Asn Leu Asp Ile Leu Thr Ala Val Leu Glu Ser Asp Ser Asp Leu Val
    210                 215                 220

Glu Ser Arg Asp Glu Asp Gly Arg Thr Pro Leu Ala Thr Ala Ala Ser
225                 230                 235                 240

Ile Gly Tyr Asp Ile Gly Val Gln His Met Leu Thr Arg Phe Ala Ser
                245                 250                 255

Ser Thr Gln Val Ala Tyr Ile Lys Asn Glu Asp Gly Ser Phe Pro Ile
            260                 265                 270

His Ser Ala Cys Ser Ala Arg Cys Thr Ser Ala Leu Lys Val Ile Leu
        275                 280                 285

Lys His His Pro Asp Thr Ile Glu Met Leu Asn Ser Gln Gly Gln Asn
    290                 295                 300

Val Leu His Val Ala Ala Lys Ser Gly Asn Ala Arg Ala Val Gly Tyr
305                 310                 315                 320

Leu Leu Arg Lys Ser Asp Val Lys Arg Leu Ile Asn Glu Gln Asp Ile
                325                 330                 335

Glu Gly Asn Thr Pro Leu His Leu Ala Ser Ser Asn Ser His Pro Lys
            340                 345                 350

Val Trp Leu Ile Trp Met Ala Leu Val Ala Ala Gly Thr Thr Arg Ala
        355                 360                 365

Pro Arg Val His Leu Arg Ala Asp Ile Pro Gly Leu Thr Thr Asp Glu
    370                 375                 380

Asp Leu Ile Leu Lys Ile His Lys Asp Arg Val Asn Thr Leu Leu Val
385                 390                 395                 400

Val Ala Thr Leu Val Ala Thr Met Ala Phe Ala Ala Gly Leu Ser Val
                405                 410                 415

Pro Leu Gly Tyr Asn Ser Thr Glu Phe Lys Ser Asn Val Lys His Ser
            420                 425                 430

Tyr Glu Glu Ser Ala Phe His Ala Phe Val Ile Cys Asn Ser Ile Ala
        435                 440                 445

Val Tyr Thr Ala Val Ile Ser Thr Val Ala Leu Ile Gly Thr Gln Leu
    450                 455                 460

Ala Asp Leu Lys Cys Met Leu Thr Thr Phe Lys Phe Ile Val Pro Leu
465                 470                 475                 480

Leu Gly Phe Ser Ile Ile Ala Met Ser Leu Ala Phe Val Ala Gly Leu
                485                 490                 495

Tyr Leu Val Leu Gly His His Tyr Trp Leu Ala Ile Phe Val Leu Ala
            500                 505                 510

Ser Gly Gly Phe Tyr Leu Met Ala Leu Leu Leu Leu Ile Ile Pro Tyr
        515                 520                 525

Ala Ser Pro Tyr Thr Phe Thr Leu Ser Arg Ser Leu Asn Ser Leu Val
    530                 535                 540

Gln Asn Met Ser Lys Glu Asp Val Asp Ser Val Asn Gln Leu Val Pro
545                 550                 555                 560

Ala Pro Thr Glu Glu Leu Ala Leu Ile Lys Ala Ile Gln Val Asn Arg
                565                 570                 575

Cys Ile Gln Gly Asn Ile Gly Val Thr Ser Leu Ser Tyr Tyr Leu Leu
            580                 585                 590
```

-continued

```
Lys His Val Ala Pro Ile Asn Val Leu Leu His Leu Lys Leu Trp Asn
        595                 600                 605

His Tyr Ser Leu Val Phe Ser Gly His Leu Tyr Asp Gly Pro Lys Lys
    610                 615                 620

Thr Tyr Ser Gln Leu
625


<210> SEQ ID NO 5
<211> LENGTH: 2320
<212> TYPE: DNA
<213> ORGANISM: Arabidopsis thaliana

<400> SEQUENCE: 5

gtgggaacga agtagactta aactattcag gaaaaaaaaa attctctatt attgaacaaa     60

gtagacttaa aaaaaacatt tcaatcagat ggagaaagct tgtggtgatg ataggtcccg    120

cttactcagg aagatttcaa cggaaagcaa ggtaatagtc tagactctag aatggatctt    180

cttcagctgc tcctagattg acgatctcat actcgcatat ccagaaacca tcctactctc    240

cctttgattt tgatcctcgg tgctttagcc gttcgagaaa gagagcaatt ttcacttccg    300

gtctcgtatt cttcgggatc tcggactcaa tcatcgggaa caaggcgact tccgccgact    360

gatgaagaac gagtctcgga catctgaaga aatcagcaag ctaggaatat tttcaggagt    420

gggattttca atgggaaggc cggatgtgca cttggatcga cgagtagcag aaaaccatca    480

ggcaatacca agaaacaatg tcagatccac accatctctc gatttgtcca ctctcttcga    540

cgaaaccagt gaaactaagc cgatggatcc aaagacgatg gctgcagtaa gagcaggtaa    600

ggaaaattac ctgagaagta ataacagtta cattagtgtt gctccaacct tagtgaacga    660

ccgtggaaat acaatacttc atcttgctgc ttcatcgggt cacgtaagcc ttgtgcgtta    720

tataatccag aaatgcccag gtttgctact gaagtcaaat atgatgggag aagttgctct    780

ccatttggca gcagaagcag gccatctaga tgttgtatgg aatctaattg atttcataaa    840

tgatatatct tgtactaacc ttcctgttgc aaaaaggata tattttgcta agaacaaaaa    900

ccaagacact gctttgcatg ttgctttgaa agggaaacat gaggtggtcg cttcctattt    960

ggtctctgca gcgaaatctt tgtcttttgt tgcaaacaga gatgggtttt ctcccttgta   1020

tcttgctatt gaagctggac atacaagtct tgtgacaaca atgtgtcacg gaacaaatga   1080

attaagttca aaggttggag gaagatccat tgtacatgca gcattgaagg ctaataggaa   1140

agatatcctt gatgctttac ttagcaaaga tgcaagtctt atcaacttga gagatgaagg   1200

aaggacttct ctttcttttg gagcatccat aggatattat caagggtttt cctatctttt   1260

cgacaaaaat cgagacaagg tttatgtcag cgatgatgat ggcttatttc caactcatat   1320

ggcggccaag tatggtcatg ttcaaattct tgaggaaatt cttaagcatt gtccagaggc   1380

aattgagttg cttgatagag acggtcaaaa tattcttcac cttgcggcaa agtatgggaa   1440

actcaaagtc atcaagttta tcctaagctg ttgtaaggat aagaacaaga aaaagttgat   1500

taatgaacaa gatgtgaatg gaaacacacc gttgcatcta gccaccataa actggcaccc   1560

taaagttgtg agtatgttta cttgggacca tagagttgac ctgaaaaaaa gaaactacat   1620

tggtttcaca gctttagatg ttgctgagga gaacattgat tcgagctaca tagttcacca   1680

gagattgact tggatggctt tgatcaatgc tggtgcacca aaaagttcta ctccaattac   1740

agaaaatctt agatcattca agaagccaga tggtggaaag tacaaagatc gagtcaatac   1800

tcttatgttg gttgcaactc tagtagccac tatgactttc actgcaggat tcacattacc   1860
```

```
tggtgggtac aacgactctt ttccccactt gggaatggcc gttttggcca agagaacggc   1920

ttttcaagtc tttcttgtat gcgacacatt ggcaatgtac tcttctatca taacaatagt   1980

tgctctcatt tgggcacaac tcggtgatct ttctatcata ctcaaagcct tcaacatagc   2040

acttccattt ctcggacttg ctcttacatc aatgtcaata gcatttatgg ctggcacgta   2100

tgttgcggta agccatctcc ccttgcttgg ttatttcgtt ttgggtattg gaatcatctt   2160

cctattggtt ttgttgctgc tccttgttcc ttatgtgtct ccatatgctc atgcccaacc   2220

ccttcttcga cacattttct actatcccta tttccttaag cttttggctg ctggtgacaa   2280

caaaaatatt gttgatgtgt acactgcatc agatgaatga                         2320


<210> SEQ ID NO 6
<211> LENGTH: 652
<212> TYPE: PRT
<213> ORGANISM: Arabidopsis thaliana

<400> SEQUENCE: 6

Met Lys Asn Glu Ser Arg Thr Ser Glu Glu Ile Ser Lys Leu Gly Ile
1               5                   10                  15

Phe Ser Gly Val Gly Phe Ser Met Gly Arg Pro Asp Val His Leu Asp
            20                  25                  30

Arg Arg Val Ala Glu Asn His Gln Ala Ile Pro Arg Asn Asn Val Arg
        35                  40                  45

Ser Thr Pro Ser Leu Asp Leu Ser Thr Leu Phe Asp Glu Thr Ser Glu
    50                  55                  60

Thr Lys Pro Met Asp Pro Lys Thr Met Ala Ala Val Arg Ala Gly Lys
65                  70                  75                  80

Glu Asn Tyr Leu Arg Ser Asn Asn Ser Tyr Ile Ser Val Ala Pro Thr
                85                  90                  95

Leu Val Asn Asp Arg Gly Asn Thr Ile Leu His Leu Ala Ala Ser Ser
            100                 105                 110

Gly His Val Ser Leu Val Arg Tyr Ile Ile Gln Lys Cys Pro Gly Leu
        115                 120                 125

Leu Leu Lys Ser Asn Met Met Gly Glu Val Ala Leu His Leu Ala Ala
    130                 135                 140

Glu Ala Gly His Leu Asp Val Val Trp Asn Leu Ile Asp Phe Ile Asn
145                 150                 155                 160

Asp Ile Ser Cys Thr Asn Leu Pro Val Ala Lys Arg Ile Tyr Phe Ala
                165                 170                 175

Lys Asn Lys Asn Gln Asp Thr Ala Leu His Val Ala Leu Lys Gly Lys
            180                 185                 190

His Glu Val Val Ala Ser Tyr Leu Val Ser Ala Ala Lys Ser Leu Ser
        195                 200                 205

Phe Val Ala Asn Arg Asp Gly Phe Ser Pro Leu Tyr Leu Ala Ile Glu
    210                 215                 220

Ala Gly His Thr Ser Leu Val Thr Thr Met Cys His Gly Thr Asn Glu
225                 230                 235                 240

Leu Ser Ser Lys Val Gly Gly Arg Ser Ile Val His Ala Ala Leu Lys
                245                 250                 255

Ala Asn Arg Lys Asp Ile Leu Asp Ala Leu Leu Ser Lys Asp Ala Ser
            260                 265                 270

Leu Ile Asn Leu Arg Asp Glu Gly Arg Thr Ser Leu Ser Phe Gly Ala
        275                 280                 285
```

-continued

```
Ser Ile Gly Tyr Tyr Gln Gly Phe Ser Tyr Leu Phe Asp Lys Asn Arg
    290                 295                 300

Asp Lys Val Tyr Val Ser Asp Asp Asp Gly Leu Phe Pro Thr His Met
305                 310                 315                 320

Ala Ala Lys Tyr Gly His Val Gln Ile Leu Glu Glu Ile Leu Lys His
                325                 330                 335

Cys Pro Glu Ala Ile Glu Leu Leu Asp Arg Asp Gly Gln Asn Ile Leu
            340                 345                 350

His Leu Ala Ala Lys Tyr Gly Lys Leu Lys Val Ile Lys Phe Ile Leu
        355                 360                 365

Ser Cys Cys Lys Asp Lys Asn Lys Lys Lys Leu Ile Asn Glu Gln Asp
    370                 375                 380

Val Asn Gly Asn Thr Pro Leu His Leu Ala Thr Ile Asn Trp His Pro
385                 390                 395                 400

Lys Val Val Ser Met Phe Thr Trp Asp His Arg Val Asp Leu Lys Lys
                405                 410                 415

Arg Asn Tyr Ile Gly Phe Thr Ala Leu Asp Val Ala Glu Glu Asn Ile
            420                 425                 430

Asp Ser Ser Tyr Ile Val His Gln Arg Leu Thr Trp Met Ala Leu Ile
        435                 440                 445

Asn Ala Gly Ala Pro Lys Ser Ser Thr Pro Ile Thr Glu Asn Leu Arg
    450                 455                 460

Ser Phe Lys Lys Pro Asp Gly Gly Lys Tyr Lys Asp Arg Val Asn Thr
465                 470                 475                 480

Leu Met Leu Val Ala Thr Leu Val Ala Thr Met Thr Phe Thr Ala Gly
                485                 490                 495

Phe Thr Leu Pro Gly Gly Tyr Asn Asp Ser Phe Pro His Leu Gly Met
            500                 505                 510

Ala Val Leu Ala Lys Arg Thr Ala Phe Gln Val Phe Leu Val Cys Asp
        515                 520                 525

Thr Leu Ala Met Tyr Ser Ser Ile Ile Thr Ile Val Ala Leu Ile Trp
    530                 535                 540

Ala Gln Leu Gly Asp Leu Ser Ile Ile Leu Lys Ala Phe Asn Ile Ala
545                 550                 555                 560

Leu Pro Phe Leu Gly Leu Ala Leu Thr Ser Met Ser Ile Ala Phe Met
                565                 570                 575

Ala Gly Thr Tyr Val Ala Val Ser His Leu Pro Leu Leu Gly Tyr Phe
            580                 585                 590

Val Leu Gly Ile Gly Ile Ile Phe Leu Leu Val Leu Leu Leu Leu Leu
        595                 600                 605

Val Pro Tyr Val Ser Pro Tyr Ala His Ala Gln Pro Leu Leu Arg His
    610                 615                 620

Ile Phe Tyr Tyr Pro Tyr Phe Leu Lys Leu Leu Ala Ala Gly Asp Asn
625                 630                 635                 640

Lys Asn Ile Val Asp Val Tyr Thr Ala Ser Asp Glu
                645                 650
```

<210> SEQ ID NO 7
<211> LENGTH: 1890
<212> TYPE: DNA
<213> ORGANISM: Arabidopsis thaliana

<400> SEQUENCE: 7

```
atgggtaagg ttcaagagtt tgaaaaggtt atggaggaga atgaaattcc tgttcttgat      60
```

-continued

```
caggtcactt ttcaggggaa tacgattctg catcttgcag ctatttatgg tcatgaccac    120

ctagtgcggc gtatccttgc ctatgagcta aacattctta gaaattggaa acgtggctta    180

aattgcaact tcgtcccaag tttctctcat tatcagactc ttttggtgag acgaaactac    240

aagggagacc ttgctctcca tgtagcagct gctgcaggac acaagttgat agttggcctt    300

cttattgatt gcctaaggca gcttccgcaa gatataacta tggtgattgg atcagagcaa    360

atggtaattg gaaacatttt cagagtttcc aacaatgatg ggaatactgc attgcacctc    420

tccctgaaag gaaaccatgt atctgtttct ttgcaacttg ttcgtgaaga tcgtagcact    480

tgctttcttc tggacaagga ggatgtatct ccactgtata tggcagctga agctggatat    540

gtttcacttg tggagcatat gttacggggt ttggatgcaa gctttgttgg gaaatccgtt    600

ttgtgtgctg cagtgaaaag ccagaatctt gatatattga cagctgtatt agagagtgac    660

tcagatctgg tagaatcgag ggatgaagat ggaagaactc cacttgccac tgcagcatcc    720

attggttatg acattggagt gcagcatatg ctaaccagat ttgcaagttc tacacaggtt    780

gcttacatta agaatgaaga tggttctttc cccatccact cagcctgcag tgctaggtgc    840

acctcagctc tcaaggtgat cttaaaacac cacccagaca caatagaaat gcttaactca    900

cagggtcaaa acgttcttca tgtcgctgct aaaagcggga atgcacgagc tgttggctat    960

ctgctcagaa aatctgacgt caaaaggtta atcaatgaac aagacataga aggaaacaca   1020

ccgttacatt tagccagcag taattctcat cccaaggttt ggttgatatg gatggcattg   1080

gtggctgctg gtaccactag agctccacga gttcatctga gagcagacat ccctggtctg   1140

acaacagatg aggacttaat cctaaaaatt cacaaggata gagtaaacac tctccttgtg   1200

gtggcaacac tagtggctac aatggctttt gctgcaggct tgagtgtgcc actaggttac   1260

aacagcacag agttcaagtc aaatgtcaaa cattcttacg aagaatctgc atttcatgct   1320

tttgtcatct gcaatagcat tgccgtatat actgctgtta tatcgacagt tgctcttata   1380

gggacacaat tggctgacct aaaatgcatg ctgaccacct tcaagtttat tgtgccactc   1440

ctggggtttt ctattatcgc catgtctttg gcttttgttg caggcttata cctggtcttg   1500

ggacatcatt attggcttgc catatttgtc ttggcctcag gcggtttcta tctcatggct   1560

ctacttctgc tcatcatccc ttacgcttcg ccttatactt ttacactatc aagaagcctg   1620

aattctttag tacagaatat gtcgaaggaa gatgttgatt ccgtaaatca actagttcct   1680

gcaccaacag aagagttggc attgatcaaa gccatccaag tcaatcgctg tatacaaggt   1740

aatattgggg taacatcttt gtcatattac ctgttgaaac acgtagctcc aatcaatgtt   1800

ctactacatc taaagctgtg gaaccattat agtttggttt tttcaggtca cctctatgat   1860

ggtcccaaga aaacatactc acaactttag                                    1890
```

```
<210> SEQ ID NO 8
<211> LENGTH: 629
<212> TYPE: PRT
<213> ORGANISM: Arabidopsis thaliana

<400> SEQUENCE: 8

Met Gly Lys Val Gln Glu Phe Glu Lys Val Met Glu Glu Asn Glu Ile
1               5                   10                  15

Pro Val Leu Asp Gln Val Thr Phe Gln Gly Asn Thr Ile Leu His Leu
            20                  25                  30

Ala Ala Ile Tyr Gly His Asp His Leu Val Arg Arg Ile Leu Ala Tyr
        35                  40                  45
```

```
Glu Leu Asn Ile Leu Arg Asn Trp Lys Arg Gly Leu Asn Cys Asn Phe
    50                  55                  60

Val Pro Ser Phe Ser His Tyr Gln Thr Leu Leu Val Arg Arg Asn Tyr
65                  70                  75                  80

Lys Gly Asp Leu Ala Leu His Val Ala Ala Ala Gly His Lys Leu
                85                  90                  95

Ile Val Gly Leu Leu Ile Asp Cys Leu Arg Gln Leu Pro Gln Asp Ile
            100                 105                 110

Thr Met Val Ile Gly Ser Glu Gln Met Val Ile Gly Asn Ile Phe Arg
        115                 120                 125

Val Ser Asn Asn Asp Gly Asn Thr Ala Leu His Leu Ser Leu Lys Gly
    130                 135                 140

Asn His Val Ser Val Ser Leu Gln Leu Val Arg Glu Asp Arg Ser Thr
145                 150                 155                 160

Cys Phe Leu Leu Asp Lys Glu Asp Val Ser Pro Leu Tyr Met Ala Ala
                165                 170                 175

Glu Ala Gly Tyr Val Ser Leu Val Glu His Met Leu Arg Gly Leu Asp
            180                 185                 190

Ala Ser Phe Val Gly Lys Ser Val Leu Cys Ala Ala Val Lys Ser Gln
        195                 200                 205

Asn Leu Asp Ile Leu Thr Ala Val Leu Glu Ser Asp Ser Asp Leu Val
    210                 215                 220

Glu Ser Arg Asp Glu Asp Gly Arg Thr Pro Leu Ala Thr Ala Ala Ser
225                 230                 235                 240

Ile Gly Tyr Asp Ile Gly Val Gln His Met Leu Thr Arg Phe Ala Ser
                245                 250                 255

Ser Thr Gln Val Ala Tyr Ile Lys Asn Glu Asp Gly Ser Phe Pro Ile
            260                 265                 270

His Ser Ala Cys Ser Ala Arg Cys Thr Ser Ala Leu Lys Val Ile Leu
        275                 280                 285

Lys His His Pro Asp Thr Ile Glu Met Leu Asn Ser Gln Gly Gln Asn
    290                 295                 300

Val Leu His Val Ala Ala Lys Ser Gly Asn Ala Arg Ala Val Gly Tyr
305                 310                 315                 320

Leu Leu Arg Lys Ser Asp Val Lys Arg Leu Ile Asn Glu Gln Asp Ile
                325                 330                 335

Glu Gly Asn Thr Pro Leu His Leu Ala Ser Ser Asn Ser His Pro Lys
            340                 345                 350

Val Trp Leu Ile Trp Met Ala Leu Val Ala Ala Gly Thr Thr Arg Ala
        355                 360                 365

Pro Arg Val His Leu Arg Ala Asp Ile Pro Gly Leu Thr Thr Asp Glu
    370                 375                 380

Asp Leu Ile Leu Lys Ile His Lys Asp Arg Val Asn Thr Leu Leu Val
385                 390                 395                 400

Val Ala Thr Leu Val Ala Thr Met Ala Phe Ala Ala Gly Leu Ser Val
                405                 410                 415

Pro Leu Gly Tyr Asn Ser Thr Glu Phe Lys Ser Asn Val Lys His Ser
            420                 425                 430

Tyr Glu Glu Ser Ala Phe His Ala Phe Val Ile Cys Asn Ser Ile Ala
        435                 440                 445

Val Tyr Thr Ala Val Ile Ser Thr Val Ala Leu Ile Gly Thr Gln Leu
    450                 455                 460

Ala Asp Leu Lys Cys Met Leu Thr Thr Phe Lys Phe Ile Val Pro Leu
```

-continued

```
465                 470                 475                 480

Leu Gly Phe Ser Ile Ile Ala Met Ser Leu Ala Phe Val Ala Gly Leu
                485                 490                 495

Tyr Leu Val Leu Gly His His Tyr Trp Leu Ala Ile Phe Val Leu Ala
            500                 505                 510

Ser Gly Gly Phe Tyr Leu Met Ala Leu Leu Leu Leu Ile Ile Pro Tyr
        515                 520                 525

Ala Ser Pro Tyr Thr Phe Thr Leu Ser Arg Ser Leu Asn Ser Leu Val
    530                 535                 540

Gln Asn Met Ser Lys Glu Asp Val Asp Ser Val Asn Gln Leu Val Pro
545                 550                 555                 560

Ala Pro Thr Glu Glu Leu Ala Leu Ile Lys Ala Ile Gln Val Asn Arg
                565                 570                 575

Cys Ile Gln Gly Asn Ile Gly Val Thr Ser Leu Ser Tyr Tyr Leu Leu
            580                 585                 590

Lys His Val Ala Pro Ile Asn Val Leu Leu His Leu Lys Leu Trp Asn
        595                 600                 605

His Tyr Ser Leu Val Phe Ser Gly His Leu Tyr Asp Gly Pro Lys Lys
    610                 615                 620

Thr Tyr Ser Gln Leu
625


<210> SEQ ID NO 9
<211> LENGTH: 342
<212> TYPE: DNA
<213> ORGANISM: Arabidopsis thaliana

<400> SEQUENCE: 9

atggagcact cttatgggag cacagttgag gctgatataa atgttctcga cactcgtctt      60

cctcctaggc tatttgcaac taaccgttac cctgatgcac ggttagcgaa tcctcttaga     120

ttctctttag ttgagtttgg ttctgtaact agtttgccgt gtggtgaatt tccgaaggag     180

tatgaacctg actactttcc tagacgtgtc aatgggacga atgattactg ggatgttttg     240

attgggaaag ataagaatgt aacactagct gatgtttcct ctaagttcca agcgttaaaa     300

gggattgagg accctttaaa actcccctgg ctcttctttt ga                        342


<210> SEQ ID NO 10
<211> LENGTH: 113
<212> TYPE: PRT
<213> ORGANISM: Arabidopsis thaliana

<400> SEQUENCE: 10

Met Glu His Ser Tyr Gly Ser Thr Val Glu Ala Asp Ile Asn Val Leu
1               5                   10                  15

Asp Thr Arg Leu Pro Pro Arg Leu Phe Ala Thr Asn Arg Tyr Pro Asp
            20                  25                  30

Ala Arg Leu Ala Asn Pro Leu Arg Phe Ser Leu Val Glu Phe Gly Ser
        35                  40                  45

Val Thr Ser Leu Pro Cys Gly Glu Phe Pro Lys Glu Tyr Glu Pro Asp
    50                  55                  60

Tyr Phe Pro Arg Arg Val Asn Gly Thr Asn Asp Tyr Trp Asp Val Leu
65                  70                  75                  80

Ile Gly Lys Asp Lys Asn Val Thr Leu Ala Asp Val Ser Ser Lys Phe
                85                  90                  95

Gln Ala Leu Lys Gly Ile Glu Asp Pro Leu Lys Leu Pro Trp Leu Phe
```

-continued

```
            100                 105                 110

Phe


<210> SEQ ID NO 11
<211> LENGTH: 777
<212> TYPE: DNA
<213> ORGANISM: Arabidopsis thaliana

<400> SEQUENCE: 11

atgagatcaa aatcgaagca ggtgttgcta ctatggcttg agggttttcg agaagcttgt      60

tctcttcacc gtgttgtcat tctctgtctc aggtcgagaa agcttctctt aagaactggg     120

cagtgttttc ttttgaatgg tttgattttc ttaggaaggt ataacgatat tgcaaagcat     180

ggattcgagg caattgagat atctgactta aactcagctg aagcattaag acaaggtgaa     240

gctctggcgt ccctgaatat ggcaaatgct gaaaggcctt ctggtcttgg aggggtgatg     300

atcggtatag gagagcaggt gtactcgata cttctcctga catttttttt tcttgaggtt     360

tgtgttgttg gtgttatacc atacattggg aagatattga atttcttact tctttcatgg     420

atgtatgcct actattgtta cgagaagccc ctgcgtgttg gccattttct ttctctcgcc     480

tcttgtgagc ggagcgctta tggccatctt atttccattg gatcaggacc tgaaaaattg     540

attggggccc cgagaagaac gtggaaatgt gcagtcttcg tggctagtca gaagattata     600

tgcatttgtg ttgatagtca tactgtcttc ttggtgatat tgtcaagtac agactcatgc     660

ttcagcaatt tccgtgcggc tttgaggtca tctgacacgc acgctcatgg ccgacgacat     720

gctgctgcaa actccaaagc aacagacatg aagaatacaa gatttatgtt aaagtag        777


<210> SEQ ID NO 12
<211> LENGTH: 258
<212> TYPE: PRT
<213> ORGANISM: Arabidopsis thaliana

<400> SEQUENCE: 12

Met Arg Ser Lys Ser Lys Gln Val Leu Leu Leu Trp Leu Glu Gly Phe
1               5                   10                  15

Arg Glu Ala Cys Ser Leu His Arg Val Val Ile Leu Cys Leu Arg Ser
            20                  25                  30

Arg Lys Leu Leu Leu Arg Thr Gly Gln Cys Phe Leu Leu Asn Gly Leu
        35                  40                  45

Ile Phe Leu Gly Arg Tyr Asn Asp Ile Ala Lys His Gly Phe Glu Ala
    50                  55                  60

Ile Glu Ile Ser Asp Leu Asn Ser Ala Glu Ala Leu Arg Gln Gly Glu
65                  70                  75                  80

Ala Leu Ala Ser Leu Asn Met Ala Asn Ala Glu Arg Pro Ser Gly Leu
                85                  90                  95

Gly Gly Val Met Ile Gly Ile Gly Glu Gln Val Tyr Ser Ile Leu Leu
            100                 105                 110

Leu Thr Phe Phe Phe Leu Glu Val Cys Val Val Gly Val Ile Pro Tyr
        115                 120                 125

Ile Gly Lys Ile Leu Asn Phe Leu Leu Leu Ser Trp Met Tyr Ala Tyr
    130                 135                 140

Tyr Cys Tyr Glu Lys Pro Leu Arg Val Gly His Phe Leu Ser Leu Ala
145                 150                 155                 160

Ser Cys Glu Arg Ser Ala Tyr Gly His Leu Ile Ser Ile Gly Ser Gly
                165                 170                 175
```

-continued

```
Pro Glu Lys Leu Ile Gly Ala Pro Arg Arg Thr Trp Lys Cys Ala Val
            180                 185                 190

Phe Val Ala Ser Gln Lys Ile Ile Cys Ile Cys Val Asp Ser His Thr
        195                 200                 205

Val Phe Leu Val Ile Leu Ser Ser Thr Asp Ser Cys Phe Ser Asn Phe
    210                 215                 220

Arg Ala Ala Leu Arg Ser Ser Asp Thr His Ala His Gly Arg Arg His
225                 230                 235                 240

Ala Ala Ala Asn Ser Lys Ala Thr Asp Met Lys Asn Thr Arg Phe Met
                245                 250                 255

Leu Lys


<210> SEQ ID NO 13
<211> LENGTH: 1206
<212> TYPE: DNA
<213> ORGANISM: Arabidopsis thaliana

<400> SEQUENCE: 13

gtctcaatta ttctccccgc ccctctatgt agacgtgtga atattagaga gattgataac      60

gaactcctca caacatcata tctcaagttc accacccaaa agaaaaaaca cacacacatc     120

ttagagagat gaaagagact aattttggcg agaaaacgcg cgttctggta gttggtggga     180

cgggatcatt ggggaggagg attgtaagtg cgtgtttggc tgagggacac gagacttatg     240

ttctccagcg gccggagatt ggagtggaca tcgagaaggt gcagctactt ctttctttca     300

aaagactcgg cgcacatctt gtggaaggct cattctccga tcaccaaagc cttgtctctg     360

ccgtaaagca agtcgacgtg gttgtctccg ccatgtccgg tgtccacttc cgcacccaca     420

acatccccgt tcagctcaag ctcgtcgcag ccatcaaaga ggccggtaac gtcaagcgtt     480

tcttaccatc agaatttgga atggatccgt cacgtatggg acatgccatg ccaccaggaa     540

gtgaaacatt tgatcaaaaa atggaaatac gaaatgcaat taaggccgcc gggatctccc     600

acacatacct cgtcggtgct tgttttgccg catacttcgg cggaaattta tctcaaatgg     660

gaactttgtt ccctccgaaa aacaaagttg atatttatgg ggacggaaat gttaaagtgg     720

tgttcgtaga tgaagatgac atggcaaaat atacagcgaa gacgcttaat gatccccgaa     780

cgttgaataa aactgtgtat gttagaccta ccgacaacat tctcacacaa atggaactag     840

ttcagatatg ggagaaacta accgaaaaag agttggagaa gacctatgtt tcaggaaacg     900

actttcttgc tgacattgaa gataaggaga tatcacacca agcgggacta ggacactttt     960

atcacatata ctacgaaggt tgtctcacag atcatgaagt tggagacgac gaagaagcta    1020

ctaaactcta tccggatgtg aagtacaaac gcatggatga atatttgaaa attttcgtat    1080

aatgttacat atatgtgaaa cacatcgcca tttccttatt tttatgtttt accatggcct    1140

tttgttttgt ttgcttgaag atgttttccg aatttatttt aaaatttaaa tgtttcagtt    1200

atggat                                                               1206


<210> SEQ ID NO 14
<211> LENGTH: 317
<212> TYPE: PRT
<213> ORGANISM: Arabidopsis thaliana

<400> SEQUENCE: 14

Met Lys Glu Thr Asn Phe Gly Glu Lys Thr Arg Val Leu Val Val Gly
1               5                   10                  15

Gly Thr Gly Ser Leu Gly Arg Arg Ile Val Ser Ala Cys Leu Ala Glu
```

-continued

```
            20                  25                  30

Gly His Glu Thr Tyr Val Leu Gln Arg Pro Glu Ile Gly Val Asp Ile
        35                  40                  45

Glu Lys Val Gln Leu Leu Leu Ser Phe Lys Arg Leu Gly Ala His Leu
    50                  55                  60

Val Glu Gly Ser Phe Ser Asp His Gln Ser Leu Val Ser Ala Val Lys
65                  70                  75                  80

Gln Val Asp Val Val Val Ser Ala Met Ser Gly Val His Phe Arg Thr
                85                  90                  95

His Asn Ile Pro Val Gln Leu Lys Leu Val Ala Ala Ile Lys Glu Ala
            100                 105                 110

Gly Asn Val Lys Arg Phe Leu Pro Ser Glu Phe Gly Met Asp Pro Ser
        115                 120                 125

Arg Met Gly His Ala Met Pro Pro Gly Ser Glu Thr Phe Asp Gln Lys
    130                 135                 140

Met Glu Ile Arg Asn Ala Ile Lys Ala Ala Gly Ile Ser His Thr Tyr
145                 150                 155                 160

Leu Val Gly Ala Cys Phe Ala Ala Tyr Phe Gly Gly Asn Leu Ser Gln
                165                 170                 175

Met Gly Thr Leu Phe Pro Pro Lys Asn Lys Val Asp Ile Tyr Gly Asp
            180                 185                 190

Gly Asn Val Lys Val Val Phe Val Asp Glu Asp Asp Met Ala Lys Tyr
        195                 200                 205

Thr Ala Lys Thr Leu Asn Asp Pro Arg Thr Leu Asn Lys Thr Val Tyr
    210                 215                 220

Val Arg Pro Thr Asp Asn Ile Leu Thr Gln Met Glu Leu Val Gln Ile
225                 230                 235                 240

Trp Glu Lys Leu Thr Glu Lys Glu Leu Glu Lys Thr Tyr Val Ser Gly
                245                 250                 255

Asn Asp Phe Leu Ala Asp Ile Glu Asp Lys Glu Ile Ser His Gln Ala
            260                 265                 270

Gly Leu Gly His Phe Tyr His Ile Tyr Tyr Glu Gly Cys Leu Thr Asp
        275                 280                 285

His Glu Val Gly Asp Asp Glu Glu Ala Thr Lys Leu Tyr Pro Asp Val
    290                 295                 300

Lys Tyr Lys Arg Met Asp Glu Tyr Leu Lys Ile Phe Val
305                 310                 315
```

<210> SEQ ID NO 15
<211> LENGTH: 1335
<212> TYPE: DNA
<213> ORGANISM: Arabidopsis thaliana

<400> SEQUENCE: 15

```
atcttcccgc catgtgtatg tggtaactaa caaaagcttc gattacttta tcctctcact      60

ctctaatggc ttcttcttct ctacctcttt ctcttccgtt tccactccga tctcttacta     120

gtaccactcg atctctacca tttcaatgtt ctcctctctt tttctctatt ccttcttcaa     180

tcgtttgctt ctccactcaa aatcccgacc gcgaagaggt ccggtggctc cgggaagagc     240

agagatggat tcgcgaggag caacgatgga ttcgtgaaga acagagatgg atacgcgaac     300

gtgaatcgct tctacaagag atttcggatc tacagctcag aattcaatcc ctagagtcac     360

gaaattcgca attggggaat tctattcccg atacgatttc gaatatcgct gctttgcttc     420

aggttttgaa ggagaagaat cggatttctg agagtggatt gagcgcaacg ccgatggtat     480
```

-continued

```
tggagagtac gagagaacaa attgttgagg aggtggaaga agaagagaag cgagtgatta    540

ttgctgaaga gaaagttagg gtttcggagc cggtgaagaa gatcaagagg aggatattga    600

aagttggaag cgaaggcgac gatgttcaag ctttgcagga agctctgttg aaattaggat    660

tctattcggg cgaagaggat atggagttct cgagcttttc aagtgggact gcaagtgctg    720

ttaagacttg gcaagcatcg cttggggtcc gtgaggatgg ggtaatgaca gcagagcttc    780

ttcagaggtt gttcatggat gaagacgtag agacagataa ggatgaagca agtacaatga    840

agaaagagga agctggtaat ggggcggtat ttacttcagt gacacaagtc cctgagaaga    900

agcaatcaat cgtgaaagat caaagtgaca gagaagttga cgttactcaa aatcgggttt    960

ttcttcttgg agaaaacaga tggaaagatc cctccaggct cattggcagg aacaaaccgg   1020

tagacagaag tgaatcaaca aacaccaaaa cgaggtgcat cacttgtcga ggggagggtc   1080

gattgatgtg cctagagtgc gatggaaccg gtgagccaaa cattgagccg cagttcatgg   1140

agtgggttgg tgaagatacg aagtgtccgt actgtgaagg tcttggctat acagtttgcg   1200

atgtctgcga cggcaaaaaa aacttataat aatgattcat atttaattta atgaaaaaac   1260

aaattagttt gttttccaaa tcgcataata tggttgttta agagagatat atatataaat   1320

ttagtgaaca agtac                                                    1335


<210> SEQ ID NO 16
<211> LENGTH: 387
<212> TYPE: PRT
<213> ORGANISM: Arabidopsis thaliana

<400> SEQUENCE: 16

Met Ala Ser Ser Ser Leu Pro Leu Ser Leu Pro Phe Pro Leu Arg Ser
1               5                   10                  15

Leu Thr Ser Thr Thr Arg Ser Leu Pro Phe Gln Cys Ser Pro Leu Phe
            20                  25                  30

Phe Ser Ile Pro Ser Ser Ile Val Cys Phe Ser Thr Gln Asn Pro Asp
        35                  40                  45

Arg Glu Glu Val Arg Trp Leu Arg Glu Glu Gln Arg Trp Ile Arg Glu
    50                  55                  60

Glu Gln Arg Trp Ile Arg Glu Glu Gln Arg Trp Ile Arg Glu Arg Glu
65                  70                  75                  80

Ser Leu Leu Gln Glu Ile Ser Asp Leu Gln Leu Arg Ile Gln Ser Leu
                85                  90                  95

Glu Ser Arg Asn Ser Gln Leu Gly Asn Ser Ile Pro Asp Thr Ile Ser
            100                 105                 110

Asn Ile Ala Ala Leu Leu Gln Val Leu Lys Glu Lys Asn Arg Ile Ser
        115                 120                 125

Glu Ser Gly Leu Ser Ala Thr Pro Met Val Leu Glu Ser Thr Arg Glu
    130                 135                 140

Gln Ile Val Glu Glu Val Glu Glu Glu Glu Lys Arg Val Ile Ile Ala
145                 150                 155                 160

Glu Glu Lys Val Arg Val Ser Glu Pro Val Lys Lys Ile Lys Arg Arg
                165                 170                 175

Ile Leu Lys Val Gly Ser Glu Gly Asp Asp Val Gln Ala Leu Gln Glu
            180                 185                 190

Ala Leu Leu Lys Leu Gly Phe Tyr Ser Gly Glu Glu Asp Met Glu Phe
        195                 200                 205

Ser Ser Phe Ser Ser Gly Thr Ala Ser Ala Val Lys Thr Trp Gln Ala
```

-continued

```
    210                 215                 220

Ser Leu Gly Val Arg Glu Asp Gly Val Met Thr Ala Glu Leu Leu Gln
225                 230                 235                 240

Arg Leu Phe Met Asp Glu Asp Val Glu Thr Asp Lys Asp Glu Ala Ser
                245                 250                 255

Thr Met Lys Lys Glu Glu Ala Gly Asn Gly Ala Val Phe Thr Ser Val
            260                 265                 270

Thr Gln Val Pro Glu Lys Lys Gln Ser Ile Val Lys Asp Gln Ser Asp
        275                 280                 285

Arg Glu Val Asp Val Thr Gln Asn Arg Val Phe Leu Leu Gly Glu Asn
    290                 295                 300

Arg Trp Glu Asp Pro Ser Arg Leu Ile Gly Arg Asn Lys Pro Val Asp
305                 310                 315                 320

Arg Ser Glu Ser Thr Asn Thr Lys Thr Arg Cys Ile Thr Cys Arg Gly
                325                 330                 335

Glu Gly Arg Leu Met Cys Leu Glu Cys Asp Gly Thr Gly Glu Pro Asn
            340                 345                 350

Ile Glu Pro Gln Phe Met Glu Trp Val Gly Glu Asp Thr Lys Cys Pro
        355                 360                 365

Tyr Cys Glu Gly Leu Gly Tyr Thr Val Cys Asp Val Cys Asp Gly Lys
    370                 375                 380

Lys Asn Leu
385


<210> SEQ ID NO 17
<211> LENGTH: 1065
<212> TYPE: DNA
<213> ORGANISM: Arabidopsis thaliana

<400> SEQUENCE: 17

atgtctttgc ttctcaatca gcactcgaag ctctgctttc ggaaacctgt gctggtgaga      60

tcctctcctc atctttctaa tggcctctca tctttgtcgt tgcaaactga ttctcagact     120

cgtgtcttgc tctgcgctga tccatgtgga ggtaatcggg gaatagccat gactatgagg     180

tctagtcgtt ttcttcgaac cctttctttc gaagggtggg aagagatgag tgagaacgaa     240

gataagattt gtgcagagct gctcaaggaa atgggagcga taggatcatg cggtggatgg     300

ctacctactt tgaaggacgg cgtgttgcgt ctccgagaag tgaatctaaa ccatgaaacg     360

gatcggaaac gcatttcgct gcctcctctt gtgactctgc ctcattgcca aacacaatat     420

gtcaccaacg tggccatgtc tacgtcttcc cctgaagaag aggactgtgt tgtggctgtc     480

aagttcctgg gacctcaact cagcttttgc agacccgctc aaagcaattc cgagtggatc     540

aacatcagaa tgacagaccc ctgcttcttc tcctcccctg tcatgttgtc caagaaaaat     600

gagatgttgc gcatagctgg ctctggaggc caactcatcg gatcatggga tctccaaaac     660

catagcaaca accccaagtt gcagatcttg cggtttcaaa accttcccaa gctgtccgag     720

acaaaacgag aacttctgga gtcgtgctac acaagtgaac acttggtgga gtcaataacc     780

accagtgaaa ctttcattgt taagttgtac atgaagacgg cagagatcga caaaggtatt     840

ccgagaaaga aaacagaagc aataatggtg ttcaggctag acgaagaagg aaacgctgtt     900

tacactcaag acatcggaga tcaaagcatt tttctcacaa attctgaagc tttctgtttc     960

ccttcgagct cctctctcag cctgggtcga cctaacttcg tcaaaatcgt tgatgtcaac    1020

gaagacagat atttcaagct ggctaaacaa aagtgggatt gttag                    1065
```

<210> SEQ ID NO 18
<211> LENGTH: 354
<212> TYPE: PRT
<213> ORGANISM: Arabidopsis thaliana

<400> SEQUENCE: 18

```
Met Ser Leu Leu Leu Asn Gln His Ser Lys Leu Cys Phe Arg Lys Pro
1               5                   10                  15

Val Leu Val Arg Ser Ser Pro His Leu Ser Asn Gly Leu Ser Ser Leu
            20                  25                  30

Ser Leu Gln Thr Asp Ser Gln Thr Arg Val Leu Leu Cys Ala Asp Pro
        35                  40                  45

Cys Gly Gly Asn Arg Gly Ile Ala Met Thr Met Arg Ser Ser Arg Phe
    50                  55                  60

Leu Arg Thr Leu Ser Phe Glu Gly Trp Glu Glu Met Ser Glu Asn Glu
65                  70                  75                  80

Asp Lys Ile Cys Ala Glu Leu Leu Lys Glu Met Gly Ala Ile Gly Ser
                85                  90                  95

Cys Gly Gly Trp Leu Pro Thr Leu Lys Asp Gly Val Leu Arg Leu Arg
            100                 105                 110

Glu Val Asn Leu Asn His Glu Thr Asp Arg Lys Arg Ile Ser Leu Pro
        115                 120                 125

Pro Leu Val Thr Leu Pro His Cys Gln Thr Gln Tyr Val Thr Asn Val
    130                 135                 140

Ala Met Ser Thr Ser Ser Pro Glu Glu Glu Asp Cys Val Val Ala Val
145                 150                 155                 160

Lys Phe Leu Gly Pro Gln Leu Ser Phe Cys Arg Pro Ala Gln Ser Asn
                165                 170                 175

Ser Glu Trp Ile Asn Ile Arg Met Thr Asp Pro Cys Phe Phe Ser Ser
            180                 185                 190

Pro Val Met Leu Ser Lys Lys Asn Glu Met Leu Arg Ile Ala Gly Ser
        195                 200                 205

Gly Gly Gln Leu Ile Gly Ser Trp Asp Leu Gln Asn His Ser Asn Asn
    210                 215                 220

Pro Lys Leu Gln Ile Leu Arg Phe Gln Asn Leu Pro Lys Leu Ser Glu
225                 230                 235                 240

Thr Lys Arg Glu Leu Leu Glu Ser Cys Tyr Thr Ser Glu His Leu Val
                245                 250                 255

Glu Ser Ile Thr Thr Ser Glu Thr Phe Ile Val Lys Leu Tyr Met Lys
            260                 265                 270

Thr Ala Glu Ile Asp Lys Gly Ile Pro Arg Lys Lys Thr Glu Ala Ile
        275                 280                 285

Met Val Phe Arg Leu Asp Glu Glu Gly Asn Ala Val Tyr Thr Gln Asp
    290                 295                 300

Ile Gly Asp Gln Ser Ile Phe Leu Thr Asn Ser Glu Ala Phe Cys Phe
305                 310                 315                 320

Pro Ser Ser Ser Ser Leu Ser Leu Gly Arg Pro Asn Phe Val Lys Ile
                325                 330                 335

Val Asp Val Asn Glu Asp Arg Tyr Phe Lys Leu Ala Lys Gln Lys Trp
            340                 345                 350

Asp Cys
```

<210> SEQ ID NO 19
<211> LENGTH: 585

<212> TYPE: DNA
<213> ORGANISM: Arabidopsis thaliana

<400> SEQUENCE: 19

```
atggtgacaa gtgaagctaa aggaactgtg acattaagct ctaaagatcg actcatatct     60
ctcatagaga gaaaagcgag ggaagaaaag aaaaacggag atggtggtct agaaaagatg    120
atgcttcagc agttcaagcc aagagagatt cagattagtg aagaagtgag tagagatgta    180
acaggtgatg tgaatcttga gcccgtggat caaacagctg ctgaagaaac ggatcacatg    240
gctccgtact ccacagaaat caatgaagat atcattgtga gggacgataa aacatcaaag    300
aaaagaaaag atccttttga aggtatggag agcatgagta gaacgggaaa gtccgttatg    360
gtctttggag acaattcaaa ggtatcaaag ccaatgcaaa gggaaagaga aagaagaagc    420
aacaacaata gtaagaagca gagacccata tacaaccatt atgcaaatgg ttcaggatgg    480
tgggactgtg atatggaagg tgttgactcg gaagaagtgg gacatagaga agtgtgggaa    540
ggagttggct cgacaacatt cggagatata gttgattggc actaa                    585
```

<210> SEQ ID NO 20
<211> LENGTH: 194
<212> TYPE: PRT
<213> ORGANISM: Arabidopsis thaliana

<400> SEQUENCE: 20

```
Met Val Thr Ser Glu Ala Lys Gly Thr Val Thr Leu Ser Ser Lys Asp
1               5                   10                  15

Arg Leu Ile Ser Leu Ile Glu Arg Lys Ala Arg Glu Glu Lys Lys Asn
            20                  25                  30

Gly Asp Gly Gly Leu Glu Lys Met Met Leu Gln Gln Phe Lys Pro Arg
        35                  40                  45

Glu Ile Gln Ile Ser Glu Glu Val Ser Arg Asp Val Thr Gly Asp Val
    50                  55                  60

Asn Leu Glu Pro Val Asp Gln Thr Ala Ala Glu Glu Thr Asp His Met
65                  70                  75                  80

Ala Pro Tyr Ser Thr Glu Ile Asn Glu Asp Ile Ile Val Arg Asp Asp
                85                  90                  95

Lys Thr Ser Lys Lys Arg Lys Asp Pro Phe Glu Gly Met Glu Ser Met
            100                 105                 110

Ser Arg Thr Gly Lys Ser Val Met Val Phe Gly Asp Asn Ser Lys Val
        115                 120                 125

Ser Lys Pro Met Gln Arg Glu Arg Glu Arg Arg Ser Asn Asn Asn Ser
    130                 135                 140

Lys Lys Gln Arg Pro Ile Tyr Asn His Tyr Ala Asn Gly Ser Gly Trp
145                 150                 155                 160

Trp Asp Cys Asp Met Glu Gly Val Asp Ser Glu Glu Val Gly His Arg
                165                 170                 175

Glu Val Trp Glu Gly Val Gly Ser Thr Thr Phe Gly Asp Ile Val Asp
            180                 185                 190

Trp His
```

<210> SEQ ID NO 21
<211> LENGTH: 1895
<212> TYPE: DNA
<213> ORGANISM: Arabidopsis thaliana

<400> SEQUENCE: 21

-continued

```
gtgtgaccag agaatcacaa acacagagag attcatcatc gaatcataaa gctctgtttt     60
caagaagaaa atatgcatct gattaatgcg gtggcggcgg cgaggatttt atccggaatc    120
ggacaatcta acggtaataa cggaggagaa gcgattccgt ttggatcgtt tgagtggatc    180
acttacgccg gaatatcttg tttcctcgta ctcttcgccg ggattatgtc tggtcttact    240
ttgggactta tgtctcttgg tcttgtcgag cttgagattc ttcaacgtag tgctgcgatt    300
tttccggttg ttcagaaaca gcatcagctt ttagtgacac tgcttctgtg taatgctatg    360
gctatggagg ggcttcctat atatttggat aagttattca atgaatacgt tgcgattatt    420
ctttctgtca cattcgttct tgcttacggt gaggttattc ctcaagcgat atgcactagg    480
tatggactcg cggttggagc gaattttgtc tggcttgtcc gcattttaat gactctctgc    540
tatccgattg cctttcccat tggcaagatt ttagatttgg tgctgggaca caatgatgct    600
ttatttaggc gggctcagtt gaaagctctt gtatccattc acagccaaga ggctggtaag    660
ggaggtgagc ttacacatga tgagacgaca atcattagtg gagctcttga tttgactgag    720
aagactgcac aagaagccat gacaccaatt gagtctacct tctccttgga tgtaaattca    780
aaattggatt gggaagctat ggggaagatt ctggcacgag gccatagccg cgttcctgtc    840
tactctggga atccgaaaaa cgttatcgga cttctcttgg tgaagagtct tcttacagtt    900
cgccctgaaa cagagaccct tgtcagcgca gtttgtatac gccggattcc aagggttcca    960
gctgatatgc ctctctatga tatactgaat gagtttcaaa agggaagcag tcacatggct   1020
gcagttgtga aggttaaggg gaaaagcaaa gtcccacctt caactttgct tgaagaacac   1080
actgatgaaa gcaatgactc cgacttgact gcacctttgt tactaaaacg agagggaaac   1140
catgacaatg tcattgtcac aatcgacaag gctaatggac aatctttctt tcaaaacaac   1200
gagagtggac ctcacgggtt ttcacatact tcagaggcta tcgaggatgg tgaggtaatt   1260
ggtatcatca ctttagaaga tgtctttgaa gaacttttgc aagaagagat tgtggatgaa   1320
actgatgaat atgttgacgt acataaaagg attcgagtag cagcagcagc ggctgcttca   1380
tcaatagcga gagctccttc aagccggaag ttgcttgcgc aaaagggaac tggaggacaa   1440
aataagcaag ggcagacgaa taaagttcct ggtcaggaac aagataaaat gcttggaact   1500
attaccgagc cgattcgaag aaacaactga tgttgtgttc ttgcttaagg aggcaaaaac   1560
tctgttgcgg tataaagaaa gaaaacaaag aataaattat aagatccagg ttcttctgta   1620
tactttgatc catcacataa attatatata tataaaaata taaaaagtca gcagaagcaa   1680
tggttcaacc cgatttttga agatgctttg tttccttgta ttatacaaaa tacctacaat   1740
ttgtaattta ctccgtaact tgattctttt ttcctttttg ttcactcaat ttttcgtaga   1800
atgcagtagt aatagttagc tatatggtca catactgttg tggccgctat tttgtaattg   1860
cacttttgaa acaatggatc aaaagtttct ccatc                              1895
```

```
<210> SEQ ID NO 22
<211> LENGTH: 485
<212> TYPE: PRT
<213> ORGANISM: Arabidopsis thaliana

<400> SEQUENCE: 22

Met His Leu Ile Asn Ala Val Ala Ala Ala Arg Ile Leu Ser Gly Ile
1               5                   10                  15

Gly Gln Ser Asn Gly Asn Asn Gly Gly Glu Ala Ile Pro Phe Gly Ser
            20                  25                  30

Phe Glu Trp Ile Thr Tyr Ala Gly Ile Ser Cys Phe Leu Val Leu Phe
```

-continued

```
        35                  40                  45

Ala Gly Ile Met Ser Gly Leu Thr Leu Gly Leu Met Ser Leu Gly Leu
    50                  55                  60

Val Glu Leu Glu Ile Leu Gln Arg Ser Ala Ala Ile Phe Pro Val Val
65                  70                  75                  80

Gln Lys Gln His Gln Leu Leu Val Thr Leu Leu Leu Cys Asn Ala Met
                85                  90                  95

Ala Met Glu Gly Leu Pro Ile Tyr Leu Asp Lys Leu Phe Asn Glu Tyr
            100                 105                 110

Val Ala Ile Ile Leu Ser Val Thr Phe Val Leu Ala Tyr Gly Glu Val
        115                 120                 125

Ile Pro Gln Ala Ile Cys Thr Arg Tyr Gly Leu Ala Val Gly Ala Asn
    130                 135                 140

Phe Val Trp Leu Val Arg Ile Leu Met Thr Leu Cys Tyr Pro Ile Ala
145                 150                 155                 160

Phe Pro Ile Gly Lys Ile Leu Asp Leu Val Leu Gly His Asn Asp Ala
                165                 170                 175

Leu Phe Arg Arg Ala Gln Leu Lys Ala Leu Val Ser Ile His Ser Gln
            180                 185                 190

Glu Ala Gly Lys Gly Gly Glu Leu Thr His Asp Glu Thr Thr Ile Ile
        195                 200                 205

Ser Gly Ala Leu Asp Leu Thr Glu Lys Thr Ala Gln Glu Ala Met Thr
    210                 215                 220

Pro Ile Glu Ser Thr Phe Ser Leu Asp Val Asn Ser Lys Leu Asp Trp
225                 230                 235                 240

Glu Ala Met Gly Lys Ile Leu Ala Arg Gly His Ser Arg Val Pro Val
                245                 250                 255

Tyr Ser Gly Asn Pro Lys Asn Val Ile Gly Leu Leu Leu Val Lys Ser
            260                 265                 270

Leu Leu Thr Val Arg Pro Glu Thr Glu Thr Leu Val Ser Ala Val Cys
        275                 280                 285

Ile Arg Arg Ile Pro Arg Val Pro Ala Asp Met Pro Leu Tyr Asp Ile
    290                 295                 300

Leu Asn Glu Phe Gln Lys Gly Ser Ser His Met Ala Ala Val Val Lys
305                 310                 315                 320

Val Lys Gly Lys Ser Lys Val Pro Pro Ser Thr Leu Leu Glu Glu His
                325                 330                 335

Thr Asp Glu Ser Asn Asp Ser Asp Leu Thr Ala Pro Leu Leu Leu Lys
            340                 345                 350

Arg Glu Gly Asn His Asp Asn Val Ile Val Thr Ile Asp Lys Ala Asn
        355                 360                 365

Gly Gln Ser Phe Phe Gln Asn Asn Glu Ser Gly Pro His Gly Phe Ser
    370                 375                 380

His Thr Ser Glu Ala Ile Glu Asp Gly Glu Val Ile Gly Ile Ile Thr
385                 390                 395                 400

Leu Glu Asp Val Phe Glu Glu Leu Leu Gln Glu Glu Ile Val Asp Glu
                405                 410                 415

Thr Asp Glu Tyr Val Asp Val His Lys Arg Ile Arg Val Ala Ala Ala
            420                 425                 430

Ala Ala Ala Ser Ser Ile Ala Arg Ala Pro Ser Ser Arg Lys Leu Leu
        435                 440                 445

Ala Gln Lys Gly Thr Gly Gly Gln Asn Lys Gln Gly Gln Thr Asn Lys
    450                 455                 460
```

```
Val Pro Gly Gln Glu Gln Asp Lys Met Leu Gly Thr Ile Thr Glu Pro
465                 470                 475                 480

Ile Arg Arg Asn Asn
                485


<210> SEQ ID NO 23
<211> LENGTH: 1914
<212> TYPE: DNA
<213> ORGANISM: Arabidopsis thaliana

<400> SEQUENCE: 23

agagaatcac aaacacagag agattcatca tcgaatcata aagctctgtt ttcaagaaga     60

aaatatgcat ctgattaatg cggtggcggc ggcgaggatt ttatccggaa tcggacaatc    120

taacggtaat aacggaggag aagcgattcc gtttggatcg tttgagtgga tcacttacgc    180

cggaatatct tgtttcctcg tactcttcgc cgggattatg tctggtctta ctttgggact    240

tatgtctctt ggtcttgtcg agcttgagat tcttcaacgt agtggtactc ctaatgagaa    300

gaaacaagcc gctgcgattt ttccggttgt tcagaaacag catcagcttt tagtgacact    360

gcttctgtgt aatgctatgg ctatggaggg gcttcctata tatttggata agttattcaa    420

tgaatacgtt gcgattattc tttctgtcac attcgttctt gcttacggtg aggttattcc    480

tcaagcgata tgcactaggt atggactcgc ggttggagcg aattttgtct ggcttgtccg    540

cattttaatg actctctgct atccgattgc ctttcccatt ggcaagattt tagatttggt    600

gctgggacac aatgatgctt tatttaggcg ggctcagttg aaagctcttg tatccattca    660

cagccaagag gctggtaagg gaggtgagct tacacatgat gagacgacaa tcattagtgg    720

agctcttgat ttgactgaga agactgcaca agaagccatg acaccaattg agtctacctt    780

ctccttggat gtaaattcaa aattggattg ggaagctatg gggaagattc tggcacgagg    840

ccatagccgc gttcctgtct actctgggaa tccgaaaaac gttatcggac ttctcttggt    900

gaagagtctt cttacagttc gccctgaaac agagaccctt gtcagcgcag tttgtatacg    960

ccggattcca agggttccag ctgatatgcc tctctatgat atactgaatg agtttcaaaa   1020

gggaagcagt cacatggctg cagttgtgaa ggttaagggg aaaagcaaag tcccaccttc   1080

aactttgctt gaagaacaca ctgatgaaag caatgactcc gacttgactg cacctttgtt   1140

actaaaacga gagggaaacc atgacaatgt cattgtcaca atcgacaagg ctaatggaca   1200

atctttcttt caaaacaacg agagtggacc tcacgggttt tcacatactt cagaggctat   1260

cgaggatggt gaggtaattg gtatcatcac tttagaagat gtctttgaag aacttttgca   1320

agaagagatt gtggatgaaa ctgatgaata tgttgacgta cataaaagga ttcgagtagc   1380

agcagcagcg gctgcttcat caatagcgag agctccttca agccggaagt tgcttgcgca   1440

aaagggaact ggaggacaaa ataagcaagg gcagacgaat aaagttcctg gtcaggaaca   1500

agataaaatg cttggaacta ttaccgagcc gattcgaaga aacaactgat gttgtgttct   1560

tgcttaagga ggcaaaaact ctgttgcggt ataaagaaag aaaacaaaga ataaattata   1620

agatccaggt tcttctgtat actttgatcc atcacataaa ttatatatat ataaaaatat   1680

aaaaagtcag cagaagcaat ggttcaaccc gatttttgaa gatgctttgt ttccttgtat   1740

tatacaaaat acctacaatt tgtaatttac tccgtaactt gattcttttt tcctttttgt   1800

tcactcaatt tttcgtagaa tgcagtagta atagttagct atatggtcac atactgttgt   1860

ggccgctatt ttgtaattgc acttttgaaa caatggatca aaagtttctc catc         1914
```

-continued

<210> SEQ ID NO 24
<211> LENGTH: 494
<212> TYPE: PRT
<213> ORGANISM: Arabidopsis thaliana

<400> SEQUENCE: 24

```
Met His Leu Ile Asn Ala Val Ala Ala Ala Arg Ile Leu Ser Gly Ile
1               5                   10                  15

Gly Gln Ser Asn Gly Asn Asn Gly Gly Glu Ala Ile Pro Phe Gly Ser
            20                  25                  30

Phe Glu Trp Ile Thr Tyr Ala Gly Ile Ser Cys Phe Leu Val Leu Phe
        35                  40                  45

Ala Gly Ile Met Ser Gly Leu Thr Leu Gly Leu Met Ser Leu Gly Leu
    50                  55                  60

Val Glu Leu Glu Ile Leu Gln Arg Ser Gly Thr Pro Asn Glu Lys Lys
65                  70                  75                  80

Gln Ala Ala Ala Ile Phe Pro Val Val Gln Lys Gln His Gln Leu Leu
                85                  90                  95

Val Thr Leu Leu Leu Cys Asn Ala Met Ala Met Glu Gly Leu Pro Ile
            100                 105                 110

Tyr Leu Asp Lys Leu Phe Asn Glu Tyr Val Ala Ile Ile Leu Ser Val
        115                 120                 125

Thr Phe Val Leu Ala Tyr Gly Glu Val Ile Pro Gln Ala Ile Cys Thr
    130                 135                 140

Arg Tyr Gly Leu Ala Val Gly Ala Asn Phe Val Trp Leu Val Arg Ile
145                 150                 155                 160

Leu Met Thr Leu Cys Tyr Pro Ile Ala Phe Pro Ile Gly Lys Ile Leu
                165                 170                 175

Asp Leu Val Leu Gly His Asn Asp Ala Leu Phe Arg Arg Ala Gln Leu
            180                 185                 190

Lys Ala Leu Val Ser Ile His Ser Gln Glu Ala Gly Lys Gly Gly Glu
        195                 200                 205

Leu Thr His Asp Glu Thr Thr Ile Ile Ser Gly Ala Leu Asp Leu Thr
    210                 215                 220

Glu Lys Thr Ala Gln Glu Ala Met Thr Pro Ile Glu Ser Thr Phe Ser
225                 230                 235                 240

Leu Asp Val Asn Ser Lys Leu Asp Trp Glu Ala Met Gly Lys Ile Leu
                245                 250                 255

Ala Arg Gly His Ser Arg Val Pro Val Tyr Ser Gly Asn Pro Lys Asn
            260                 265                 270

Val Ile Gly Leu Leu Leu Val Lys Ser Leu Leu Thr Val Arg Pro Glu
        275                 280                 285

Thr Glu Thr Leu Val Ser Ala Val Cys Ile Arg Arg Ile Pro Arg Val
    290                 295                 300

Pro Ala Asp Met Pro Leu Tyr Asp Ile Leu Asn Glu Phe Gln Lys Gly
305                 310                 315                 320

Ser Ser His Met Ala Ala Val Val Lys Val Lys Gly Lys Ser Lys Val
                325                 330                 335

Pro Pro Ser Thr Leu Leu Glu Glu His Thr Asp Glu Ser Asn Asp Ser
            340                 345                 350

Asp Leu Thr Ala Pro Leu Leu Leu Lys Arg Glu Gly Asn His Asp Asn
        355                 360                 365

Val Ile Val Thr Ile Asp Lys Ala Asn Gly Gln Ser Phe Phe Gln Asn
    370                 375                 380
```

-continued

```
Asn Glu Ser Gly Pro His Gly Phe Ser His Thr Ser Glu Ala Ile Glu
385                 390                 395                 400

Asp Gly Glu Val Ile Gly Ile Ile Thr Leu Glu Asp Val Phe Glu Glu
                405                 410                 415

Leu Leu Gln Glu Glu Ile Val Asp Glu Thr Asp Glu Tyr Val Asp Val
            420                 425                 430

His Lys Arg Ile Arg Val Ala Ala Ala Ala Ala Ala Ser Ser Ile Ala
        435                 440                 445

Arg Ala Pro Ser Ser Arg Lys Leu Leu Ala Gln Lys Gly Thr Gly Gly
    450                 455                 460

Gln Asn Lys Gln Gly Gln Thr Asn Lys Val Pro Gly Gln Glu Gln Asp
465                 470                 475                 480

Lys Met Leu Gly Thr Ile Thr Glu Pro Ile Arg Arg Asn Asn
                485                 490


<210> SEQ ID NO 25
<211> LENGTH: 2175
<212> TYPE: DNA
<213> ORGANISM: Arabidopsis thaliana

<400> SEQUENCE: 25

atggagactg caacgaggac tcaccaacag agaaaactga tctcatcttt cctcgatatc      60

accgttaacc aaactgtgga aatcgcaaca cagttccttg aggcaacaac ctggaacctt     120

gaagatgcga tcaacctctt tctcatcgct cggagaaacc ctcatcatca ccatggagaa     180

gaactagtcc ctcttccttt accttcgaag aagaatactc tctacgacta cgatcctttc     240

atgtctcaca acacttcggt cgcagtatgt cctgaagaga tctgggacga cgagtcgaca     300

tctgaggaat ccgattctag gttgtcttct ttgtaccgtc ctcctccaag tctgtttttc     360

cacggttcgt ttgaagatgc gaaagcaacg tcctctagag aggatctatg gttgcttgtc     420

tatgatgata ccagcgaagg tcagaaaata tctactttct acaagatcga ctctgttcct     480

cctgtggtgc ttctcatcga tcccatcact ggccagaaga tgcgtatgtg gagcggtgtg     540

attgaacctc agggctttct cgaggatttg atgaagtaca tggattctgg tcctcacgaa     600

cacgttgcat ctctgacaag caacaaacgt atgaaaacag agaagatctc ctgttcaagt     660

aacaacgctg atgatcaaga catggctact ttctggggaa acgctattga agaagaaaag     720

actgtaatca aatctggaaa ggaggagact tttacgtctg atcgcgttgt ggctccttct     780

tgggggccag aatttgaaga cataatgact ttatccgaac atgaggagga aacttgtttg     840

tcatgcgacc tgcttgagtt tccggttttg acagaagagc ctaaagcaga ctgtgataga     900

agcgttgtgt gcagtatttg tgttcgattt ccagatggga gaagaaagca gaggaagttt     960

ctcaagagcg aaccgattca gcttctctgg tctttctgtt attctcacat ggaggaatcc    1020

gagaaaaagg agttcaagct tgtgcaggcg attcctggtg cttccaagac tctggattat    1080

ggagctaagg ccacgtttgt tcaatctggg atcgctaatt cgatgatttc agttacttgg    1140

gacattaact tgccactgga ttcaaagaag actgtcctaa gtggatgcag ggttatgatt    1200

ggtcaaattg ctagtagtgg cctaactaag aagctgatga taaagagaaa catgtgggct    1260

aaggttcgtg gtgtggctat gatgaaccca gtggagcatc ctcatggagg aaggacagag    1320

ttaggttctc atatacttaa tcgagatgta tgggcgaacg acgcggtttc gagaaccatt    1380

gagtcccact tcatcgtatg gcaggtctat gatgatacaa acgaaggtca gaaaatctct    1440

agtttctaca agatcgaagc tcctcctcct gtggtgtttg taatcaatcc catcactggc    1500
```

-continued

```
cagaagatgc atatgtggag cggcgtgatt gaagctgaga gtattgtcga ggatttgatg   1560

atgttttggg acgctggtcc tcacgaaaac attgcttctc tgacaaggaa caggcgcacg   1620

gaaactgcgg agacttgttt gtcaagctac aacttctatg aaacccctgc tccttcctgg   1680

ggtgaagagt ttgaagagga ggataattgg tcgtcaagaa gcaacaataa tcaagtcgtg   1740

gctcctactt gggagaaaga acttgaagaa caagacgagt gggagatttg gtcgtcacgc   1800

agtgacactg atgacttcgt gcctcctttt atgggggacg aatatgaaga tccggatgaa   1860

gtaaaggagg aggagatatg tttagtgttc ccggttttga cagaagagcc aaaaggagac   1920

tgtgatcgaa gcgttgtgtg tagtctctgc gttcgatttc cagatgggag aagaaagcag   1980

aggaagtttc tcaagagcga accgattcag cttctttggt cattctgtta ttctcacatt   2040

gatgaatctg agaaaaaggc attcaagctg gtgcaggcga ttcccggtgc ttcaaagact   2100

ctagattgtg aagctgacgc cacgttcgac caatctgggc ttgctaattc gctgatctcg   2160

gttacttggg aatga                                                    2175
```

```
<210> SEQ ID NO 26
<211> LENGTH: 724
<212> TYPE: PRT
<213> ORGANISM: Arabidopsis thaliana

<400> SEQUENCE: 26

Met Glu Thr Ala Thr Arg Thr His Gln Gln Arg Lys Leu Ile Ser Ser
1               5                   10                  15

Phe Leu Asp Ile Thr Val Asn Gln Thr Val Glu Ile Ala Thr Gln Phe
            20                  25                  30

Leu Glu Ala Thr Thr Trp Asn Leu Glu Asp Ala Ile Asn Leu Phe Leu
        35                  40                  45

Ile Ala Arg Arg Asn Pro His His His His Gly Glu Glu Leu Val Pro
    50                  55                  60

Leu Pro Leu Pro Ser Lys Lys Asn Thr Leu Tyr Asp Tyr Asp Pro Phe
65                  70                  75                  80

Met Ser His Asn Thr Ser Val Ala Val Cys Pro Glu Glu Ile Trp Asp
                85                  90                  95

Asp Glu Ser Thr Ser Glu Glu Ser Asp Ser Arg Leu Ser Ser Leu Tyr
            100                 105                 110

Arg Pro Pro Pro Ser Leu Phe Phe His Gly Ser Phe Glu Asp Ala Lys
        115                 120                 125

Ala Thr Ser Ser Arg Glu Asp Leu Trp Leu Leu Val Tyr Asp Asp Thr
    130                 135                 140

Ser Glu Gly Gln Lys Ile Ser Thr Phe Tyr Lys Ile Asp Ser Val Pro
145                 150                 155                 160

Pro Val Val Leu Leu Ile Asp Pro Ile Thr Gly Gln Lys Met Arg Met
                165                 170                 175

Trp Ser Gly Val Ile Glu Pro Gln Gly Phe Leu Glu Asp Leu Met Lys
            180                 185                 190

Tyr Met Asp Ser Gly Pro His Glu His Val Ala Ser Leu Thr Ser Asn
        195                 200                 205

Lys Arg Met Lys Thr Glu Lys Ile Ser Cys Ser Ser Asn Asn Ala Asp
    210                 215                 220

Asp Gln Asp Met Ala Thr Phe Trp Gly Asn Ala Ile Glu Glu Glu Lys
225                 230                 235                 240

Thr Val Ile Lys Ser Gly Lys Glu Glu Thr Phe Thr Ser Asp Arg Val
```

-continued

```
                245                 250                 255

Val Ala Pro Ser Trp Gly Pro Glu Phe Glu Asp Ile Met Thr Leu Ser
            260                 265                 270

Glu His Glu Glu Glu Thr Cys Leu Ser Cys Asp Leu Leu Glu Phe Pro
        275                 280                 285

Val Leu Thr Glu Glu Pro Lys Ala Asp Cys Asp Arg Ser Val Val Cys
    290                 295                 300

Ser Ile Cys Val Arg Phe Pro Asp Gly Arg Arg Lys Gln Arg Lys Phe
305                 310                 315                 320

Leu Lys Ser Glu Pro Ile Gln Leu Leu Trp Ser Phe Cys Tyr Ser His
                325                 330                 335

Met Glu Glu Ser Glu Lys Lys Glu Phe Lys Leu Val Gln Ala Ile Pro
            340                 345                 350

Gly Ala Ser Lys Thr Leu Asp Tyr Gly Ala Lys Ala Thr Phe Val Gln
        355                 360                 365

Ser Gly Ile Ala Asn Ser Met Ile Ser Val Thr Trp Asp Ile Asn Leu
    370                 375                 380

Pro Leu Asp Ser Lys Lys Thr Val Leu Ser Gly Cys Arg Val Met Ile
385                 390                 395                 400

Gly Gln Ile Ala Ser Ser Gly Leu Thr Lys Lys Leu Met Ile Lys Arg
                405                 410                 415

Asn Met Trp Ala Lys Val Arg Gly Val Ala Met Met Asn Pro Val Glu
            420                 425                 430

His Pro His Gly Gly Arg Thr Glu Leu Gly Ser His Ile Leu Asn Arg
        435                 440                 445

Asp Val Trp Ala Asn Asp Ala Val Ser Arg Thr Ile Glu Ser His Phe
    450                 455                 460

Ile Val Trp Gln Val Tyr Asp Asp Thr Asn Glu Gly Gln Lys Ile Ser
465                 470                 475                 480

Ser Phe Tyr Lys Ile Glu Ala Pro Pro Pro Val Val Phe Val Ile Asn
                485                 490                 495

Pro Ile Thr Gly Gln Lys Met His Met Trp Ser Gly Val Ile Glu Ala
            500                 505                 510

Glu Ser Ile Val Glu Asp Leu Met Met Phe Trp Asp Ala Gly Pro His
        515                 520                 525

Glu Asn Ile Ala Ser Leu Thr Arg Asn Arg Arg Thr Glu Thr Ala Glu
    530                 535                 540

Thr Cys Leu Ser Ser Tyr Asn Phe Tyr Glu Thr Pro Ala Pro Ser Trp
545                 550                 555                 560

Gly Glu Glu Phe Glu Glu Glu Asp Asn Trp Ser Ser Arg Ser Asn Asn
                565                 570                 575

Asn Gln Val Val Ala Pro Thr Trp Glu Lys Glu Leu Glu Glu Gln Asp
            580                 585                 590

Glu Trp Glu Ile Trp Ser Ser Arg Ser Asp Thr Asp Asp Phe Val Pro
        595                 600                 605

Pro Phe Met Gly Asp Glu Tyr Glu Asp Pro Asp Glu Val Lys Glu Glu
    610                 615                 620

Glu Ile Cys Leu Val Phe Pro Val Leu Thr Glu Glu Pro Lys Gly Asp
625                 630                 635                 640

Cys Asp Arg Ser Val Val Cys Ser Leu Cys Val Arg Phe Pro Asp Gly
                645                 650                 655

Arg Arg Lys Gln Arg Lys Phe Leu Lys Ser Glu Pro Ile Gln Leu Leu
            660                 665                 670
```

```
Trp Ser Phe Cys Tyr Ser His Ile Asp Glu Ser Glu Lys Lys Ala Phe
        675                 680                 685

Lys Leu Val Gln Ala Ile Pro Gly Ala Ser Lys Thr Leu Asp Cys Glu
    690                 695                 700

Ala Asp Ala Thr Phe Asp Gln Ser Gly Leu Ala Asn Ser Leu Ile Ser
705                 710                 715                 720

Val Thr Trp Glu


<210> SEQ ID NO 27
<211> LENGTH: 1140
<212> TYPE: DNA
<213> ORGANISM: Arabidopsis thaliana

<400> SEQUENCE: 27

atgttctcat ctacaacttc tcacacaagc gggtgggatt cggatgacga gactaaagtg     60

actcaactct tgtcgtctga accagcctac ccgtttttat tgattgaata catcactaac    120

atccaaaatt cttcttcgga tggtcgcgta atagtatacg acgacgattc ttcaaaggga    180

aaggcaacaa aagtcactat taaggacaag aaactcgaga aggaggtcat tgaggcgatg    240

actgtcggat ttttacgtga tggattaaaa ttctatcttt cgtacagaag cagcgaccat    300

caacctgtga tcacttatga gacctccaat cccaaactag aaaacttgac cattcattta    360

ccttctgtac ccaccggtac caaaatccat aacctagcca tgtcctctat acctgttcaa    420

gataaagatt gggtagtggg tgtcaaatta tcgggatctc gggttagtct ttgcaggcct    480

tttggcagct ctaaatggat caacatgaaa ttcatgtctc agtgtataaa ccctttatct    540

agcctcatgt tctccaagag agatcaaagg ttctacattc caagttacgg aggcaactac    600

ttgtgctact tggatctcaa ctctaaggag ggtgatgatc atttcaactc taggcaggag    660

aatgggcaac ccagcttcat cgacttggat tatgaaaatc ttccagagtc ggtgtttaag    720

cagttggcgg gagtgagttc atgttccaag acagatcacc ttgtggagtc acccaccggc    780

caacttttcc tcgtcaagtg gttcgtggag gacgtggagg acctttgcga caatacaccc    840

atgcacgtaa caaaaaagtt catggtgttt agagcaaatg aggcttctga cgaaaagaag    900

aagactatga tctacacaga acacattgga gatctttgca tttttcttgg acatagtgag    960

gctttctgca tcccggctag tacgtcgtgt ggactcgagc ctaactgcat ctattttgtt   1020

ggcaataact ttggtgttta tgatctcacc accgaaactt gctctacctt ttacactagt   1080

gtaaggccac taaagaacgt tagtttccct tactggcctc cgccaacccc tatctactag   1140


<210> SEQ ID NO 28
<211> LENGTH: 379
<212> TYPE: PRT
<213> ORGANISM: Arabidopsis thaliana

<400> SEQUENCE: 28

Met Phe Ser Ser Thr Thr Ser His Thr Ser Gly Trp Asp Ser Asp Asp
1               5                   10                  15

Glu Thr Lys Val Thr Gln Leu Leu Ser Ser Glu Pro Ala Tyr Pro Phe
            20                  25                  30

Leu Leu Ile Glu Tyr Ile Thr Asn Ile Gln Asn Ser Ser Ser Asp Gly
        35                  40                  45

Arg Val Ile Val Tyr Asp Asp Asp Ser Ser Lys Gly Lys Ala Thr Lys
    50                  55                  60

Val Thr Ile Lys Asp Lys Lys Leu Glu Lys Glu Val Ile Glu Ala Met
```

-continued

```
65                  70                  75                  80

Thr Val Gly Phe Leu Arg Asp Gly Leu Lys Phe Tyr Leu Ser Tyr Arg
                85                  90                  95

Ser Ser Asp His Gln Pro Val Ile Thr Tyr Glu Thr Ser Asn Pro Lys
            100                 105                 110

Leu Glu Asn Leu Thr Ile His Leu Pro Ser Val Pro Thr Gly Thr Lys
        115                 120                 125

Ile His Asn Leu Ala Met Ser Ser Ile Pro Val Gln Asp Lys Asp Trp
    130                 135                 140

Val Val Gly Val Lys Leu Ser Gly Ser Arg Val Ser Leu Cys Arg Pro
145                 150                 155                 160

Phe Gly Ser Ser Lys Trp Ile Asn Met Lys Phe Met Ser Gln Cys Ile
                165                 170                 175

Asn Pro Leu Ser Ser Leu Met Phe Ser Lys Arg Asp Gln Arg Phe Tyr
            180                 185                 190

Ile Pro Ser Tyr Gly Gly Asn Tyr Leu Cys Tyr Leu Asp Leu Asn Ser
        195                 200                 205

Lys Glu Gly Asp Asp His Phe Asn Ser Arg Gln Glu Asn Gly Gln Pro
    210                 215                 220

Ser Phe Ile Asp Leu Asp Tyr Glu Asn Leu Pro Glu Ser Val Phe Lys
225                 230                 235                 240

Gln Leu Ala Gly Val Ser Ser Cys Ser Lys Thr Asp His Leu Val Glu
                245                 250                 255

Ser Pro Thr Gly Gln Leu Phe Leu Val Lys Trp Phe Val Glu Asp Val
            260                 265                 270

Glu Asp Leu Cys Asp Asn Thr Pro Met His Val Thr Lys Lys Phe Met
        275                 280                 285

Val Phe Arg Ala Asn Glu Ala Ser Asp Glu Lys Lys Lys Thr Met Ile
    290                 295                 300

Tyr Thr Glu His Ile Gly Asp Leu Cys Ile Phe Leu Gly His Ser Glu
305                 310                 315                 320

Ala Phe Cys Ile Pro Ala Ser Thr Ser Cys Gly Leu Glu Pro Asn Cys
                325                 330                 335

Ile Tyr Phe Val Gly Asn Asn Phe Gly Val Tyr Asp Leu Thr Thr Glu
            340                 345                 350

Thr Cys Ser Thr Phe Tyr Thr Ser Val Arg Pro Leu Lys Asn Val Ser
        355                 360                 365

Phe Pro Tyr Trp Pro Pro Pro Thr Pro Ile Tyr
    370                 375
```

<210> SEQ ID NO 29
<211> LENGTH: 687
<212> TYPE: DNA
<213> ORGANISM: Arabidopsis thaliana

<400> SEQUENCE: 29

```
gagactcgct ctaagaccca gtttgactcg ttgatcaacg aaagtgtgag tttgaggtga     60

aagatgacgg cgacgataga tcggaggtta tcaacgctga atccaaacgc gccggtgttt    120

gatccggtgg aatttcgtga ggtggaggat ttttcaccga aatggtggga tctagtaacg    180

acttcgaaat ggttccgtga cttttggctc agtgctaact ctgagaatga gttcctcggc    240

ggcgacgatt tctcagttat ggaagaagag ttcgaggaga tgatcgcatc gtctgatggt    300

ggatccatgg ctgatacagt tacagaagca gatgtggcta gttatttgaa gatgcttttg    360
```

-continued

```
aacatagcgg agtctacgaa agagaagatt tatagatcga aggtttcgtc ttgttcacca    420

aagtataatc agaagaagta catgaatccg aactttaatt gtcgccggaa tcatcatatc    480

tatcagccac ggtgaagctt ctagaaggaa caaagctctt cttcttcttc tttcgagatg    540

ataatcagag tcgtgtctgt gtttatggct gaatctgatc ttttctgctt tcttgttttt    600

tgtaattctg tgaatattcc tactttctat aataacatca ctttatgtta tgagcataac    660

caaattgaaa tcgaaccagg tcgaatc                                        687


<210> SEQ ID NO 30
<211> LENGTH: 143
<212> TYPE: PRT
<213> ORGANISM: Arabidopsis thaliana

<400> SEQUENCE: 30

Met Thr Ala Thr Ile Asp Arg Arg Leu Ser Thr Leu Asn Pro Asn Ala
1               5                   10                  15

Pro Val Phe Asp Pro Val Glu Phe Arg Glu Val Glu Asp Phe Ser Pro
            20                  25                  30

Lys Trp Trp Asp Leu Val Thr Thr Ser Lys Trp Phe Arg Asp Phe Trp
        35                  40                  45

Leu Ser Ala Asn Ser Glu Asn Glu Phe Leu Gly Gly Asp Asp Phe Ser
    50                  55                  60

Val Met Glu Glu Glu Phe Glu Glu Met Ile Ala Ser Ser Asp Gly Gly
65                  70                  75                  80

Ser Met Ala Asp Thr Val Thr Glu Ala Asp Val Ala Ser Tyr Leu Lys
                85                  90                  95

Met Leu Leu Asn Ile Ala Glu Ser Thr Lys Glu Lys Ile Tyr Arg Ser
            100                 105                 110

Lys Val Ser Ser Cys Ser Pro Lys Tyr Asn Gln Lys Lys Tyr Met Asn
        115                 120                 125

Pro Asn Phe Asn Cys Arg Arg Asn His His Ile Tyr Gln Pro Arg
    130                 135                 140


<210> SEQ ID NO 31
<211> LENGTH: 1363
<212> TYPE: DNA
<213> ORGANISM: Arabidopsis thaliana

<400> SEQUENCE: 31

aactattcac tagtaataat ctgaaaaaat tagtactaga tttcatgatg atgatgaaaa     60

gattgatgat ttgagtcaca aaatcttgtt ttttgaaagt tgtgtgatct tcttgtttgc    120

atagtgaatt agttttgatt tgaaaagatt ttaagtaatg gagaagaaat cagaagaaga    180

tgggaacaac acgacgaaag aaaagatctt tagagcggat aagattgatt tgaagagttt    240

agatagacag cttgagaaac atctgagtag ggtttggtcg aggaaccttg aggtgaatcc    300

taaagctaag gaagaatggg agattgattt ggctaagctt gaaacaagta atgttattgc    360

tcgtggtact tatggtactg tctacaaagg catttatgat ggacaagatg ttgcagtgaa    420

ggtgcttgat tgggaagatg atgggaatga aacaacggcc aagaccgcta caaatcgagc    480

tttgttccgt caagaggtca ctgtttggca caaactcaac catccaaatg tcacaaagtt    540

tgttggagcg tcgatgggaa caacgaatct taatatacga tcagctgatt cgaaaggctc    600

gttgcctcaa caagcatgtt gtgtggttgt ggaatatctt cctggtggaa cattgaaaca    660

acacttgatt cgtcataaga gcaagaaact cgcttttaaa gccgttatca aactcgctct    720
```

-continued

```
tgatctcgcc agagggctaa gctatttgca ctcagagaag attgtccacc gcgatgtgaa    780

aacagagaac atgcttttgg atgctcagaa gaatttgaaa atagcggatt ttggagtagc    840

acgagtggaa gctcttaatc caaaagacat gacaggagaa accggtactc ttggatacat    900

ggctcctgag gtcattgatg gtaagccata caacagaagg tgcgatgttt acagctttgg    960

gatatgttta tgggaaatct actgctgcga tatgccttat cctgatctta gctttgtcga   1020

tgtttcttcc gcggttgtct tacataatct gagaccggag ataccgagat gctgtccgac   1080

tgcattggcg ggcataatga agacatgttg ggatgggaat ccgcagaaac ggccggagat   1140

gaaggaggtg gtgaaaatgc ttgaaggtgt tgataccagt aaaggtggcg gaatgatacc   1200

ggaagatcaa agtcggggct gtttctgctt tgctcctgct cgtggacctt aaatttccct   1260

ttctacctct gtttggtttt attgtcttgt ttttgtcgac atttaactga atgccccttt   1320

tgcttcttct ccaagaaact tcttttaaca agatttgtta aat                      1363


<210> SEQ ID NO 32
<211> LENGTH: 364
<212> TYPE: PRT
<213> ORGANISM: Arabidopsis thaliana

<400> SEQUENCE: 32

Met Glu Lys Lys Ser Glu Glu Asp Gly Asn Asn Thr Thr Lys Glu Lys
1               5                   10                  15

Ile Phe Arg Ala Asp Lys Ile Asp Leu Lys Ser Leu Asp Arg Gln Leu
            20                  25                  30

Glu Lys His Leu Ser Arg Val Trp Ser Arg Asn Leu Glu Val Asn Pro
        35                  40                  45

Lys Ala Lys Glu Glu Trp Glu Ile Asp Leu Ala Lys Leu Glu Thr Ser
    50                  55                  60

Asn Val Ile Ala Arg Gly Thr Tyr Gly Thr Val Tyr Lys Gly Ile Tyr
65                  70                  75                  80

Asp Gly Gln Asp Val Ala Val Lys Val Leu Asp Trp Glu Asp Asp Gly
                85                  90                  95

Asn Glu Thr Thr Ala Lys Thr Ala Thr Asn Arg Ala Leu Phe Arg Gln
            100                 105                 110

Glu Val Thr Val Trp His Lys Leu Asn His Pro Asn Val Thr Lys Phe
        115                 120                 125

Val Gly Ala Ser Met Gly Thr Thr Asn Leu Asn Ile Arg Ser Ala Asp
    130                 135                 140

Ser Lys Gly Ser Leu Pro Gln Gln Ala Cys Cys Val Val Val Glu Tyr
145                 150                 155                 160

Leu Pro Gly Gly Thr Leu Lys Gln His Leu Ile Arg His Lys Ser Lys
                165                 170                 175

Lys Leu Ala Phe Lys Ala Val Ile Lys Leu Ala Leu Asp Leu Ala Arg
            180                 185                 190

Gly Leu Ser Tyr Leu His Ser Glu Lys Ile Val His Arg Asp Val Lys
        195                 200                 205

Thr Glu Asn Met Leu Leu Asp Ala Gln Lys Asn Leu Lys Ile Ala Asp
    210                 215                 220

Phe Gly Val Ala Arg Val Glu Ala Leu Asn Pro Lys Asp Met Thr Gly
225                 230                 235                 240

Glu Thr Gly Thr Leu Gly Tyr Met Ala Pro Glu Val Ile Asp Gly Lys
                245                 250                 255

Pro Tyr Asn Arg Arg Cys Asp Val Tyr Ser Phe Gly Ile Cys Leu Trp
```

-continued

```
        260                 265                 270

Glu Ile Tyr Cys Cys Asp Met Pro Tyr Pro Asp Leu Ser Phe Val Asp
        275                 280                 285

Val Ser Ser Ala Val Val Leu His Asn Leu Arg Pro Glu Ile Pro Arg
    290                 295                 300

Cys Cys Pro Thr Ala Leu Ala Gly Ile Met Lys Thr Cys Trp Asp Gly
305                 310                 315                 320

Asn Pro Gln Lys Arg Pro Glu Met Lys Glu Val Val Lys Met Leu Glu
                325                 330                 335

Gly Val Asp Thr Ser Lys Gly Gly Gly Met Ile Pro Glu Asp Gln Ser
            340                 345                 350

Arg Gly Cys Phe Cys Phe Ala Pro Ala Arg Gly Pro
        355                 360


<210> SEQ ID NO 33
<211> LENGTH: 2359
<212> TYPE: DNA
<213> ORGANISM: Arabidopsis thaliana

<400> SEQUENCE: 33

aatttgtaaa ttaaaaagga acctctcgtt ttcttctctc tcccgcttct tgctgagtcg      60

ccgaccctct gagaagaata aggtctaaca atggaagtct gagatggttt cttcagtttc     120

taattataaa agagaatttg gttttaattt ctctttattg tttatctcgt cctcgatttc     180

aagagtttga tttctgtaac tttgagcttc cttcaaagca aatgaaaggt gtcgtcgtga     240

gtatactcga attgtatttc ccatggtgaa taaaggataa ggaagtgttg tgtcttcatt     300

tcaatagata aaacaatcta aacatggcgt attctgttgt tcggcttcga aaggtttcag     360

ctttggggat ttctcgtgtt cttcaagctg ataaaggaag tttgtggcgg tttcactttg     420

aacctgagtt tggtgacctt ttgagattag gtgtcttgac taggaattat agaaagaact     480

ctggatctcc aaagtttgat ttcactggca ctggaaccac ctcaaagttc gatttcactg     540

atctcacctg tcctcataca tggtatccta tagctcggaa gaagaagcgt aaggtcattc     600

tacatgttgg cccgacaaac agcgggaaga catatagtgc ccttaagcac cttgaacaga     660

gttcttcagg tgtatattgt ggtccgttaa gattgttggc atgggaggta gctaaacggt     720

taaacaaagc aaatgttcca tgtgatttga tcacgggaca agagaaagac ttagtggaag     780

gggcaacaca caaagctgtg acagttgaaa tggctgatgt tacatctgtc tacgattgtg     840

ccatcattga cgaaattcag atggtgggat gtaaacaaag ggatttgca tttactcgtg     900

ctttacttgg aatcgcggct gatgagctac atttatgtgg cgatccagct gtcgtacctc     960

ttgttgaaga tatactgaaa gtaactggag atgatgtcga ggttcatacc tatgagaggc    1020

tttcaccatt agtccctttg aaggttcctg tttcatcagt ttccagtatt aaaactgggg    1080

attgtcttgt cactttttcc cgaaaagata tatatgcgta taagaaaaca attgaacgtg    1140

cggggaagca tctttgctct gtggtttatg gttcgttgcc tccagagact cgcacggcac    1200

aggcaacaag gtttaacgat gagaccaatg actttgatgt gcttgttgcc agcgatgcga    1260

ttggcatggg tcttaatttg aatatttcaa ggattatctt ctcgaccctt caaaaatatg    1320

atggttccga gaccagagac ctaacagtat ctgagattaa acaaattgca gggagagctg    1380

gcaggtttca atcaaagttc cctattggcg aagtaacttg tttgcacaaa gaggatcttc    1440

cgttgcttca ctcttctctc aagtctccat cacctattct tgagcgtgct ggactatttc    1500

caacatttga cctcctatct gggtattccc aagcacaccc tacacacggg ttgtaccaga    1560
```

```
tattggaaca ttttgttgaa aatgctaagc tgtcttcaaa ctacttcatc tctaatgttg   1620

aagacatgat gaaagttgct gccattgttg atgaattacc cctcggattg caagagaagt   1680

atcttttcgt ggtcagtcca gttgatgtaa atgacgaaat ttcaggtcag ggacttgcac   1740

agtttgctca aaacttctcg aaggcaggca ttgtgaggct ccgggagata cttgcacctg   1800

acagagtgaa ggttcccaaa acacctacag aactcaagga acttgaatcc attcacaagg   1860

ttttggatct gtacgtatgg ttaagcttaa ggctagagga ttcttttcct gaccgcgaag   1920

tagcagcttc gcaaaagtca atctgcaatt tattgattga gcaattctta gagggaaata   1980

gactaaactc tcctgcccgc ttctcacgat atctaaggcg gcaaaaactc tcagaataaa   2040

cttcaagttt ggttggacaa ttgtcttgtt cttctcgttg gtttgttcac caaggaaaaa   2100

agtaaagaca agatcttaac agtatttgat aatggtgcac tcaaaaattg tcattaacag   2160

tagataaacc atttgattta tttgttcatt ttatcatttc gttaaacatg acatgcttta   2220

agatgtaaga aatgcattaa taatatttgt cacatgcatt ccataatatt gtttttactt   2280

cagatatgaa gtcactttgt agcaatagcg tgaatcagtt tattttgttg aatttgatga   2340

tgaaataagt tttgtctcg                                                2359


<210> SEQ ID NO 34
<211> LENGTH: 571
<212> TYPE: PRT
<213> ORGANISM: Arabidopsis thaliana

<400> SEQUENCE: 34

Met Ala Tyr Ser Val Val Arg Leu Arg Lys Val Ser Ala Leu Gly Ile
1               5                   10                  15

Ser Arg Val Leu Gln Ala Asp Lys Gly Ser Leu Trp Arg Phe His Phe
            20                  25                  30

Glu Pro Glu Phe Gly Asp Leu Leu Arg Leu Gly Val Leu Thr Arg Asn
        35                  40                  45

Tyr Arg Lys Asn Ser Gly Ser Pro Lys Phe Asp Phe Thr Gly Thr Gly
    50                  55                  60

Thr Thr Ser Lys Phe Asp Phe Thr Asp Leu Thr Cys Pro His Thr Trp
65                  70                  75                  80

Tyr Pro Ile Ala Arg Lys Lys Lys Arg Lys Val Ile Leu His Val Gly
                85                  90                  95

Pro Thr Asn Ser Gly Lys Thr Tyr Ser Ala Leu Lys His Leu Glu Gln
            100                 105                 110

Ser Ser Ser Gly Val Tyr Cys Gly Pro Leu Arg Leu Leu Ala Trp Glu
        115                 120                 125

Val Ala Lys Arg Leu Asn Lys Ala Asn Val Pro Cys Asp Leu Ile Thr
    130                 135                 140

Gly Gln Glu Lys Asp Leu Val Glu Gly Ala Thr His Lys Ala Val Thr
145                 150                 155                 160

Val Glu Met Ala Asp Val Thr Ser Val Tyr Asp Cys Ala Ile Ile Asp
                165                 170                 175

Glu Ile Gln Met Val Gly Cys Lys Gln Arg Gly Phe Ala Phe Thr Arg
            180                 185                 190

Ala Leu Leu Gly Ile Ala Ala Asp Glu Leu His Leu Cys Gly Asp Pro
        195                 200                 205

Ala Val Val Pro Leu Val Glu Asp Ile Leu Lys Val Thr Gly Asp Asp
    210                 215                 220
```

-continued

```
Val Glu Val His Thr Tyr Glu Arg Leu Ser Pro Leu Val Pro Leu Lys
225                 230                 235                 240

Val Pro Val Ser Ser Val Ser Ser Ile Lys Thr Gly Asp Cys Leu Val
                245                 250                 255

Thr Phe Ser Arg Lys Asp Ile Tyr Ala Tyr Lys Lys Thr Ile Glu Arg
            260                 265                 270

Ala Gly Lys His Leu Cys Ser Val Val Tyr Gly Ser Leu Pro Pro Glu
        275                 280                 285

Thr Arg Thr Ala Gln Ala Thr Arg Phe Asn Asp Glu Thr Asn Asp Phe
    290                 295                 300

Asp Val Leu Val Ala Ser Asp Ala Ile Gly Met Gly Leu Asn Leu Asn
305                 310                 315                 320

Ile Ser Arg Ile Ile Phe Ser Thr Leu Gln Lys Tyr Asp Gly Ser Glu
                325                 330                 335

Thr Arg Asp Leu Thr Val Ser Glu Ile Lys Gln Ile Ala Gly Arg Ala
            340                 345                 350

Gly Arg Phe Gln Ser Lys Phe Pro Ile Gly Glu Val Thr Cys Leu His
        355                 360                 365

Lys Glu Asp Leu Pro Leu Leu His Ser Ser Leu Lys Ser Pro Ser Pro
    370                 375                 380

Ile Leu Glu Arg Ala Gly Leu Phe Pro Thr Phe Asp Leu Leu Ser Gly
385                 390                 395                 400

Tyr Ser Gln Ala His Pro Thr His Gly Leu Tyr Gln Ile Leu Glu His
                405                 410                 415

Phe Val Glu Asn Ala Lys Leu Ser Ser Asn Tyr Phe Ile Ser Asn Val
            420                 425                 430

Glu Asp Met Met Lys Val Ala Ala Ile Val Asp Glu Leu Pro Leu Gly
        435                 440                 445

Leu Gln Glu Lys Tyr Leu Phe Val Val Ser Pro Val Asp Val Asn Asp
    450                 455                 460

Glu Ile Ser Gly Gln Gly Leu Ala Gln Phe Ala Gln Asn Phe Ser Lys
465                 470                 475                 480

Ala Gly Ile Val Arg Leu Arg Glu Ile Leu Ala Pro Asp Arg Val Lys
                485                 490                 495

Val Pro Lys Thr Pro Thr Glu Leu Lys Glu Leu Glu Ser Ile His Lys
            500                 505                 510

Val Leu Asp Leu Tyr Val Trp Leu Ser Leu Arg Leu Glu Asp Ser Phe
        515                 520                 525

Pro Asp Arg Glu Val Ala Ala Ser Gln Lys Ser Ile Cys Asn Leu Leu
    530                 535                 540

Ile Glu Gln Phe Leu Glu Gly Asn Arg Leu Asn Ser Pro Ala Arg Phe
545                 550                 555                 560

Ser Arg Tyr Leu Arg Arg Gln Lys Leu Ser Glu
                565                 570
```

<210> SEQ ID NO 35
<211> LENGTH: 3906
<212> TYPE: DNA
<213> ORGANISM: Arabidopsis thaliana

<400> SEQUENCE: 35

```
atggagatag cttcttcttc tggcagccgg agatacgacg ttttcccaag ctttcgtgga      60

gaagatgtcc gtgactcatt cctcagccat cttctcaagg agctcagggg caaagcaatc     120

acattcatag atgatgagat cgagaggagc cgctcaatcg gcccggagct tttatcggca     180
```

-continued

```
ataaaagaat cgagaatagc aatcgttatc ttctctaaga actatgcttc atccacctgg    240
tgcctgaatg aattggtgga gattcacaag tgttatacga atttgaatca aatggtgatt    300
ccgattttct tccacgttga tgcttcggaa gttaaaaaac agaccggcga atttggaaag    360
gtctttgaag agacatgcaa ggctaaatca gaggatgaga aacaaagttg gaagcaagct    420
ctagcagctg ttgcagttat ggccggatat gatcttcgga aatggcctag tgaagcagcc    480
atgattgaag agcttgccga ggatgttttg agaaaaacta tgacaccatc ggatgatttt    540
ggcgacttag tcggaattga aaatcatata gaggcaataa aatcagtatt gtgcttggaa    600
tccaaggaag ctagaataat ggtcgggatt tggggacaat cagggattgg taagagtacc    660
ataggaagag ctctttacag taaactctct atccagttcc accatcgcgc tttcataaca    720
tataaaagca ccagcggtag tgacgtctct ggcatgaagt tgaggtggga aaaagaactt    780
ctctcggaaa tcttaggtca aaaggacata aagatagagc attttggtgt ggtggagcaa    840
aggttaaagc aacagaaagt tcttatcctt cttgatgatg tggatagtct agagtttctt    900
aagaccttgg tgggaaaagc tgaatggttt ggatctggaa gcagaataat tgtgatcact    960
caagataggc aacttctcaa ggctcatgag attgacctta tatatgaggt ggagttccca   1020
tctgaacatc ttgctcttac gatgttatgc cgatctgctt ttgggaaaga ctctccacct   1080
gatgatttta aggaactagc atttgaagtt gcgaagcttg ccggtaatct tccgttgggt   1140
cttagtgtcc ttggttcgtc tttaaaggga aggaccaaag aatggtggat ggagatgatg   1200
cctaggctcc gaaatggttt gaacggagat attatgaaaa cattaagagt cagctacgat   1260
agattacatc aaaaagatca agatatgttc ctttacatcg cgtgtttatt caatggtttt   1320
gaagtcagtt acgtcaaaga tttacttaaa gataatgttg ggtttacaat gttgactgag   1380
aagtccctca tacgtattac accggatgga tatatagaga tgcacaattt gctagagaaa   1440
ttgggtagag aaattgatcg tgcaaagtcc aagggtaatc ctggaaaacg tcgatttctg   1500
acgaattttg aagatattca tgaagtagtg accgagaaaa ctgggacaga aactcttctt   1560
ggaatacgtt tgccattcga ggaatatttt tcgacaaggc cgttattaat agataaagaa   1620
tcgttcaaag gcatgcgtaa tctgcaatat ctagaaattg gttattacgg ggatctacct   1680
cagagcctcg tttatttgcc ccttaaactc agattgctag actgggatga ttgtccattg   1740
aagtctttgc catctacttt taaggcggaa tatctagtta acctcataat gaagtatagt   1800
aagcttgaga aactgtggga aggaactctg ccccttggaa gtctcaagga gatgaatttg   1860
aggtattcca acaatttgaa agaaattcca gatctttctt tagccataaa cctcgaggaa   1920
ttagatcttg ttggatgcaa atctttggtg acacttcctt cctcgattca gaatgccact   1980
aaactgatct atttagatat gagtgattgc aaaaagctag agagttttcc aaccgatctc   2040
aacttggaat ctctcgagta cctcaatctc actggatgcc cgaatttgag aaactttcca   2100
gcaatcaaaa tgggatgttc agacgttgac tttccggaag ggagaaatga gatcgtggta   2160
gaagattgtt tctggaacaa gaatctccct gctggactag attatctcga ctgccttacg   2220
agatgtatgc cttgtgaatt tcgcccagaa caactcgctt ttctcaatgt gaggggctac   2280
aagcatgaga agctatggga aggcatccag tcgcttggaa gtctcgaagg gatggatctg   2340
tcagaatctg aaaacctgac agaaattcca gatctttcaa aggccaccaa gctcgagtct   2400
ttgatactca acaactgcaa aagtttggtg acacttcctt ctacaattgg gaatcttcat   2460
agattggtga ggttggaaat gaaagaatgc acagggctgg aggttcttcc gaccgatgtc   2520
```

-continued

```
aacttgtcat ctctcgaaac cctcgatctc agtggttgct caagtttgag aagttttcct   2580

ctgatttcaa ctaatattgt atggctctat ctggaaaaca ccgccattga agaaattcct   2640

tctacaattg ggaatcttca tagattggtg aggttagaaa tgaaaaaatg cacagggctg   2700

gaggttcttc cgaccgatgt caacttgtca tctctcgaaa ccctcgatct cagtggttgc   2760

tcaagtttga gaagttttcc tctgatttca gagagtatca aatggctcta tctggaaaac   2820

accgccattg aagaaattcc agatctttca aaggccacta atctgaagaa tttgaaactc   2880

aacaattgca aaagtttggt gacacttcct actactatag gaaatctcca aaaattggtg   2940

agctttgaaa tgaaagaatg cacagggctg gaggttcttc cgatcgatgt caacttgtca   3000

tctcttatga tcctcgatct cagtggttgc tcaagtctga gaacttttcc tctgatttca   3060

actaatattg tatggctcta tctggaaaac accgccattg aagaaatccc ttctacaatt   3120

gggaatcttc atagattggt gaagttagaa atgaaagaat gcacagggct ggaggttctt   3180

ccgaccgatg tcaacttgtc atctcttatg atcctcgatc tcagtggttg ctcaagtctg   3240

agaacttttc ctctgatttc aactagaatc gaatgtctct atctgcaaaa caccgccatt   3300

gaagaagttc cctgctgcat tgaggatttc acgaggctca ctgtacttat gatgtattgt   3360

tgccagaggt tgaaaaccat ctccccaaac attttcagac ttacaagact tgagctcgcc   3420

gactttacag actgtagagg tgtcatcaag gcgttgagtg atgcaactgt ggtagcgaca   3480

atggaagacc acgtttcttg tgtaccatta tctgaaaaca ttgaatatat ctgggataag   3540

ttgtatcatc ttccatctaa attgaatttc aacgatgtgg agtttaagtt ttgttgctcc   3600

aataggatca aagaatgcgg tgtacgactc atgtatgtct ctcaagaaga gaacaaccaa   3660

cagactacga gaagcgagaa gcggatgcgg atgacatcgg ggacatctga agaagatatc   3720

aacttaccct atggcctaat tgtagcggac acaggattgg ccgctctaaa tatggagctt   3780

tcgttagggc agggagaacc atcatcatca acatctctag agggggaagc tttgtgtgtt   3840

gattacatga taactgaaga acaagataaa ggaattccta tcttgtttcc tgtttctggt   3900

aactga                                                              3906
```

<210> SEQ ID NO 36
<211> LENGTH: 1301
<212> TYPE: PRT
<213> ORGANISM: Arabidopsis thaliana

<400> SEQUENCE: 36

```
Met Glu Ile Ala Ser Ser Ser Gly Ser Arg Arg Tyr Asp Val Phe Pro
1               5                   10                  15

Ser Phe Arg Gly Glu Asp Val Arg Asp Ser Phe Leu Ser His Leu Leu
            20                  25                  30

Lys Glu Leu Arg Gly Lys Ala Ile Thr Phe Ile Asp Asp Glu Ile Glu
        35                  40                  45

Arg Ser Arg Ser Ile Gly Pro Glu Leu Leu Ser Ala Ile Lys Glu Ser
    50                  55                  60

Arg Ile Ala Ile Val Ile Phe Ser Lys Asn Tyr Ala Ser Ser Thr Trp
65                  70                  75                  80

Cys Leu Asn Glu Leu Val Glu Ile His Lys Cys Tyr Thr Asn Leu Asn
                85                  90                  95

Gln Met Val Ile Pro Ile Phe Phe His Val Asp Ala Ser Glu Val Lys
            100                 105                 110

Lys Gln Thr Gly Glu Phe Gly Lys Val Phe Glu Glu Thr Cys Lys Ala
        115                 120                 125
```

-continued

```
Lys Ser Glu Asp Glu Lys Gln Ser Trp Lys Gln Ala Leu Ala Ala Val
    130                 135                 140

Ala Val Met Ala Gly Tyr Asp Leu Arg Lys Trp Pro Ser Glu Ala Ala
145                 150                 155                 160

Met Ile Glu Glu Leu Ala Glu Asp Val Leu Arg Lys Thr Met Thr Pro
                165                 170                 175

Ser Asp Asp Phe Gly Asp Leu Val Gly Ile Glu Asn His Ile Glu Ala
            180                 185                 190

Ile Lys Ser Val Leu Cys Leu Glu Ser Lys Glu Ala Arg Ile Met Val
        195                 200                 205

Gly Ile Trp Gly Gln Ser Gly Ile Gly Lys Ser Thr Ile Gly Arg Ala
    210                 215                 220

Leu Tyr Ser Lys Leu Ser Ile Gln Phe His His Arg Ala Phe Ile Thr
225                 230                 235                 240

Tyr Lys Ser Thr Ser Gly Ser Asp Val Ser Gly Met Lys Leu Arg Trp
                245                 250                 255

Glu Lys Glu Leu Leu Ser Glu Ile Leu Gly Gln Lys Asp Ile Lys Ile
            260                 265                 270

Glu His Phe Gly Val Val Glu Gln Arg Leu Lys Gln Gln Lys Val Leu
        275                 280                 285

Ile Leu Leu Asp Asp Val Asp Ser Leu Glu Phe Leu Lys Thr Leu Val
    290                 295                 300

Gly Lys Ala Glu Trp Phe Gly Ser Gly Ser Arg Ile Ile Val Ile Thr
305                 310                 315                 320

Gln Asp Arg Gln Leu Leu Lys Ala His Glu Ile Asp Leu Ile Tyr Glu
                325                 330                 335

Val Glu Phe Pro Ser Glu His Leu Ala Leu Thr Met Leu Cys Arg Ser
            340                 345                 350

Ala Phe Gly Lys Asp Ser Pro Pro Asp Asp Phe Lys Glu Leu Ala Phe
        355                 360                 365

Glu Val Ala Lys Leu Ala Gly Asn Leu Pro Leu Gly Leu Ser Val Leu
    370                 375                 380

Gly Ser Ser Leu Lys Gly Arg Thr Lys Glu Trp Trp Met Glu Met Met
385                 390                 395                 400

Pro Arg Leu Arg Asn Gly Leu Asn Gly Asp Ile Met Lys Thr Leu Arg
                405                 410                 415

Val Ser Tyr Asp Arg Leu His Gln Lys Asp Gln Asp Met Phe Leu Tyr
            420                 425                 430

Ile Ala Cys Leu Phe Asn Gly Phe Glu Val Ser Tyr Val Lys Asp Leu
        435                 440                 445

Leu Lys Asp Asn Val Gly Phe Thr Met Leu Thr Glu Lys Ser Leu Ile
    450                 455                 460

Arg Ile Thr Pro Asp Gly Tyr Ile Glu Met His Asn Leu Leu Glu Lys
465                 470                 475                 480

Leu Gly Arg Glu Ile Asp Arg Ala Lys Ser Lys Gly Asn Pro Gly Lys
                485                 490                 495

Arg Arg Phe Leu Thr Asn Phe Glu Asp Ile His Glu Val Val Thr Glu
            500                 505                 510

Lys Thr Gly Thr Glu Thr Leu Leu Gly Ile Arg Leu Pro Phe Glu Glu
        515                 520                 525

Tyr Phe Ser Thr Arg Pro Leu Leu Ile Asp Lys Glu Ser Phe Lys Gly
    530                 535                 540
```

-continued

```
Met Arg Asn Leu Gln Tyr Leu Glu Ile Gly Tyr Tyr Gly Asp Leu Pro
545                 550                 555                 560

Gln Ser Leu Val Tyr Leu Pro Leu Lys Leu Arg Leu Leu Asp Trp Asp
                565                 570                 575

Asp Cys Pro Leu Lys Ser Leu Pro Ser Thr Phe Lys Ala Glu Tyr Leu
            580                 585                 590

Val Asn Leu Ile Met Lys Tyr Ser Lys Leu Glu Lys Leu Trp Glu Gly
        595                 600                 605

Thr Leu Pro Leu Gly Ser Leu Lys Glu Met Asn Leu Arg Tyr Ser Asn
    610                 615                 620

Asn Leu Lys Glu Ile Pro Asp Leu Ser Leu Ala Ile Asn Leu Glu Glu
625                 630                 635                 640

Leu Asp Leu Val Gly Cys Lys Ser Leu Val Thr Leu Pro Ser Ser Ile
                645                 650                 655

Gln Asn Ala Thr Lys Leu Ile Tyr Leu Asp Met Ser Asp Cys Lys Lys
            660                 665                 670

Leu Glu Ser Phe Pro Thr Asp Leu Asn Leu Glu Ser Leu Glu Tyr Leu
        675                 680                 685

Asn Leu Thr Gly Cys Pro Asn Leu Arg Asn Phe Pro Ala Ile Lys Met
    690                 695                 700

Gly Cys Ser Asp Val Asp Phe Pro Glu Gly Arg Asn Glu Ile Val Val
705                 710                 715                 720

Glu Asp Cys Phe Trp Asn Lys Asn Leu Pro Ala Gly Leu Asp Tyr Leu
                725                 730                 735

Asp Cys Leu Thr Arg Cys Met Pro Cys Glu Phe Arg Pro Glu Gln Leu
            740                 745                 750

Ala Phe Leu Asn Val Arg Gly Tyr Lys His Glu Lys Leu Trp Glu Gly
        755                 760                 765

Ile Gln Ser Leu Gly Ser Leu Glu Gly Met Asp Leu Ser Glu Ser Glu
    770                 775                 780

Asn Leu Thr Glu Ile Pro Asp Leu Ser Lys Ala Thr Lys Leu Glu Ser
785                 790                 795                 800

Leu Ile Leu Asn Asn Cys Lys Ser Leu Val Thr Leu Pro Ser Thr Ile
                805                 810                 815

Gly Asn Leu His Arg Leu Val Arg Leu Glu Met Lys Glu Cys Thr Gly
            820                 825                 830

Leu Glu Val Leu Pro Thr Asp Val Asn Leu Ser Ser Leu Glu Thr Leu
        835                 840                 845

Asp Leu Ser Gly Cys Ser Ser Leu Arg Ser Phe Pro Leu Ile Ser Thr
    850                 855                 860

Asn Ile Val Trp Leu Tyr Leu Glu Asn Thr Ala Ile Glu Glu Ile Pro
865                 870                 875                 880

Ser Thr Ile Gly Asn Leu His Arg Leu Val Arg Leu Glu Met Lys Lys
                885                 890                 895

Cys Thr Gly Leu Glu Val Leu Pro Thr Asp Val Asn Leu Ser Ser Leu
            900                 905                 910

Glu Thr Leu Asp Leu Ser Gly Cys Ser Ser Leu Arg Ser Phe Pro Leu
        915                 920                 925

Ile Ser Glu Ser Ile Lys Trp Leu Tyr Leu Glu Asn Thr Ala Ile Glu
    930                 935                 940

Glu Ile Pro Asp Leu Ser Lys Ala Thr Asn Leu Lys Asn Leu Lys Leu
945                 950                 955                 960

Asn Asn Cys Lys Ser Leu Val Thr Leu Pro Thr Thr Ile Gly Asn Leu
```

-continued

```
                965                 970                 975

Gln Lys Leu Val Ser Phe Glu Met Lys Glu Cys Thr Gly Leu Glu Val
            980                 985                 990

Leu Pro Ile Asp Val Asn Leu Ser  Ser Leu Met Ile Leu  Asp Leu Ser
        995                 1000                1005

Gly Cys  Ser Ser Leu Arg Thr  Phe Pro Leu Ile Ser  Thr Asn Ile
    1010                 1015                 1020

Val Trp  Leu Tyr Leu Glu Asn  Thr Ala Ile Glu Glu  Ile Pro Ser
    1025                 1030                 1035

Thr Ile  Gly Asn Leu His Arg  Leu Val Lys Leu Glu  Met Lys Glu
    1040                 1045                 1050

Cys Thr  Gly Leu Glu Val Leu  Pro Thr Asp Val Asn  Leu Ser Ser
    1055                 1060                 1065

Leu Met  Ile Leu Asp Leu Ser  Gly Cys Ser Ser Leu  Arg Thr Phe
    1070                 1075                 1080

Pro Leu  Ile Ser Thr Arg Ile  Glu Cys Leu Tyr Leu  Gln Asn Thr
    1085                 1090                 1095

Ala Ile  Glu Glu Val Pro Cys  Cys Ile Glu Asp Phe  Thr Arg Leu
    1100                 1105                 1110

Thr Val  Leu Met Met Tyr Cys  Cys Gln Arg Leu Lys  Thr Ile Ser
    1115                 1120                 1125

Pro Asn  Ile Phe Arg Leu Thr  Arg Leu Glu Leu Ala  Asp Phe Thr
    1130                 1135                 1140

Asp Cys  Arg Gly Val Ile Lys  Ala Leu Ser Asp Ala  Thr Val Val
    1145                 1150                 1155

Ala Thr  Met Glu Asp His Val  Ser Cys Val Pro Leu  Ser Glu Asn
    1160                 1165                 1170

Ile Glu  Tyr Ile Trp Asp Lys  Leu Tyr His Leu Pro  Ser Lys Leu
    1175                 1180                 1185

Asn Phe  Asn Asp Val Glu Phe  Lys Phe Cys Cys Ser  Asn Arg Ile
    1190                 1195                 1200

Lys Glu  Cys Gly Val Arg Leu  Met Tyr Val Ser Gln  Glu Glu Asn
    1205                 1210                 1215

Asn Gln  Gln Thr Thr Arg Ser  Glu Lys Arg Met Arg  Met Thr Ser
    1220                 1225                 1230

Gly Thr  Ser Glu Glu Asp Ile  Asn Leu Pro Tyr Gly  Leu Ile Val
    1235                 1240                 1245

Ala Asp  Thr Gly Leu Ala Ala  Leu Asn Met Glu Leu  Ser Leu Gly
    1250                 1255                 1260

Gln Gly  Glu Pro Ser Ser Ser  Thr Ser Leu Glu Gly  Glu Ala Leu
    1265                 1270                 1275

Cys Val  Asp Tyr Met Ile Thr  Glu Glu Gln Asp Lys  Gly Ile Pro
    1280                 1285                 1290

Ile Leu  Phe Pro Val Ser Gly  Asn
    1295                 1300
```

<210> SEQ ID NO 37
<211> LENGTH: 3219
<212> TYPE: DNA
<213> ORGANISM: Arabidopsis thaliana

<400> SEQUENCE: 37

```
atggcggcgg cttcttcttc ttgcagccgg agatacgatg ttttcccaag cttcagtggg      60

gtagatgttc gcaagacgtt cctcagcaat ctactcgagg cgttcgaccg cagatcaatc     120
```

-continued

```
aatacattca tggatcatgg catcgaacga agccgtacaa tagcccctga gctaatatca    180
gcgattagag aagcaaggat ctcaatcgtg atcttctcta agaactatgc ttcttccact    240
tggtgcttgg atgaattggt tgagatccac aatcgcttaa atgattgggg tcaattggtg    300
atttcagttt tttacgacgt tgatccttcg gaagttagaa aacagaccgg cgaatttggc    360
gatgttttta aaaagacatg cgaggacaaa gaagaggatc agaaacaaag atggatgcaa    420
gctctagtag acataacaaa tatagccgga gaagatcttc gaaacgggcc tagtgaagca    480
gccatggttg taaagatagc taatgatgtt tcgaataagc ttatttcacc atcgaattct    540
tttggcgatt tcgtcggaat tgaagctcat ttagaggcaa tgaattcaat attgtgcttg    600
gaatccaagg aagctagaat ggttgggatt tgggggcctt cagggattgg taagagtacc    660
ataggaaaag ctctatacag tcaactcttt tgccaattcc actttcacgc tttcgtacct    720
cacgtctata gcatgaagtc tgaatgggaa gaaatatttc tgtcaaaaat tcttggtaag    780
gatataaaga taggagggaa gttaggtgta gtggagcaaa tgttaaatca gaagaaagtt    840
cttatcgttc ttgatgatgt ggatgatcca gagtttctta agaccttggt gggggaaact    900
aaatggtttg gacctggaag cagaattatt gtgatcactc aagatatgca acttcttaag    960
gctcatgata ttgacctttt atatgaggtg aagttcccat ctctagatct tgctcttaag   1020
atgttatgcc gatctgcttt tggggaaaac tctccacctg atgattttaa ggcactagca   1080
tttgaagttg cagtgcttgc cggtaatctt cctttgggtc tcagtgtcct tggttcgtct   1140
ttaaaacgaa ggaccaaaga agagtggatg gagatgatgc ctaggttccg aaatggtttg   1200
aacggagata ttatgaaaac attaagagtc agctacgata gattacatca aaaagatcaa   1260
gatatgttcc tttacatcgc gtgtttattc aatggttttg aagtcagtta cgtcaacgat   1320
ttacttgaag ataatgttgg ggttacaatg ttggttgaga agtccctcat acgtattaca   1380
ccggatggag atatagagat gcacaatttg ctagagaaat tgggtataga aattgatcgt   1440
gcaaagtcca aggaaacagt tcttggaata cgtttctgca cagctttccg atcaaaagag   1500
ctattaccaa tagatgaaaa atcgttccaa ggcatgcgta atctccaatg tctatcagtt   1560
actggggatt atatggatct acctcagagc ctcgtttatt tgccccctaa actcagattg   1620
ctagactggg ataggtgtcc attgaaatgt ttgccttata gttttaaggc ggattacctc   1680
attcaactca caatgatggg aagtaagctt gagaagctgt gggaaggaac tgtgccactt   1740
ggaagcctca agaggatgaa tatgcatggt tccagatatt tgagagaaat ttcagatctt   1800
tctaatgcca gaaacctcga ggaattaaat ctttcggaat gcagatcttt ggtgacactt   1860
tcttcctcga ttcagaatgc cattaaactg atctatttag atatgagggg ttgcacaaag   1920
ctagagagtt ttccaactca tctcaacttg gaatctcttg agtacctcga aaattgtata   1980
tggaacaaga atctccctgg tcttgattat ctcgcctgcc ttgtgagatg tatgccatgt   2040
gaatttcgcc caaatgatct ggttcgtctc atagtgagag gcaaccaaat gcttgagaag   2100
ctatgggaag gcgtccagtc gcttgcaagt ctcgtggaga tggatatgtc agaatgtgga   2160
aacctgacag aaattccaga tctttcaaag gccactaatc tggtgaattt atatctctct   2220
aattgcaaaa gtttggtgac agttccttct acaattggga atctccaaaa attggtgagg   2280
ttggaaatga aagaatgcac agggctggag gttcttccaa ccgatgtcaa cttgtcatct   2340
cttaaaatgc ttgatctgag tggttgctca agtttgagaa cttttcctct gatttcaaag   2400
agtatcaaat ggctctatct ggaaaacacc gctattgaag aagttccctg ctgcattgaa   2460
```

-continued

```
aatttctcgt ggctcactgt acttatgatg tattgttgca agaggttgaa aaacatctcg   2520

ccaaacattt tcagactgac aattcttaag ctcgtcgact ttacagaatg tagaggtgtc   2580

aacgtggcga tgagtgatgc cagtgtggaa gatcactctt cttatatacc attatatgaa   2640

aacattgagt atactcgtca tcgtttctgg gaaaacctta accacaaaca tttggcctgt   2700

agggcaggtg gagtctcgga caagtgggaa ggagttggcc ataagctcgg acaaagggaa   2760

atcatgcggg ctaagctagg atctccacct cgagcagctg ggcgagtgac ggttgagctc   2820

gaggcagctg gtcgactgtc tgaccagctg ggcggttacc cggacggtta cttgggcggt   2880

tacggtcgaa cgggtgctcg cccaaagggg agggtgccca agacctttag aggcaccaga   2940

acacacagaa aataccggaa actcactatt aaactctcgt cctttcggga gaataaatcg   3000

tcggaggaaa tcggtagtcg gactgtgacc ggcaaggaag aagaagggtc ggatcgaccg   3060

aacatcgtga aggaaggaac gactaatggg ctgggtagaa tcgggtcatg tgcaacctac   3120

acaagactca gtccgggcaa gggatcggct agggcgggga cgcggctcgg tggaggaccg   3180

gagggaacca atggtgatcg tgggaaggac ttggcttag                           3219
```

<210> SEQ ID NO 38
<211> LENGTH: 1072
<212> TYPE: PRT
<213> ORGANISM: Arabidopsis thaliana

<400> SEQUENCE: 38

```
Met Ala Ala Ala Ser Ser Ser Cys Ser Arg Arg Tyr Asp Val Phe Pro
1               5                   10                  15

Ser Phe Ser Gly Val Asp Val Arg Lys Thr Phe Leu Ser Asn Leu Leu
            20                  25                  30

Glu Ala Phe Asp Arg Arg Ser Ile Asn Thr Phe Met Asp His Gly Ile
        35                  40                  45

Glu Arg Ser Arg Thr Ile Ala Pro Glu Leu Ile Ser Ala Ile Arg Glu
    50                  55                  60

Ala Arg Ile Ser Ile Val Ile Phe Ser Lys Asn Tyr Ala Ser Ser Thr
65                  70                  75                  80

Trp Cys Leu Asp Glu Leu Val Glu Ile His Asn Arg Leu Asn Asp Trp
                85                  90                  95

Gly Gln Leu Val Ile Ser Val Phe Tyr Asp Val Asp Pro Ser Glu Val
            100                 105                 110

Arg Lys Gln Thr Gly Glu Phe Gly Asp Val Phe Lys Lys Thr Cys Glu
        115                 120                 125

Asp Lys Glu Glu Asp Gln Lys Gln Arg Trp Met Gln Ala Leu Val Asp
    130                 135                 140

Ile Thr Asn Ile Ala Gly Glu Asp Leu Arg Asn Gly Pro Ser Glu Ala
145                 150                 155                 160

Ala Met Val Val Lys Ile Ala Asn Asp Val Ser Asn Lys Leu Ile Ser
                165                 170                 175

Pro Ser Asn Ser Phe Gly Asp Phe Val Gly Ile Glu Ala His Leu Glu
            180                 185                 190

Ala Met Asn Ser Ile Leu Cys Leu Glu Ser Lys Glu Ala Arg Met Val
        195                 200                 205

Gly Ile Trp Gly Pro Ser Gly Ile Gly Lys Ser Thr Ile Gly Lys Ala
    210                 215                 220

Leu Tyr Ser Gln Leu Phe Cys Gln Phe His Phe His Ala Phe Val Pro
225                 230                 235                 240
```

-continued

```
His Val Tyr Ser Met Lys Ser Glu Trp Glu Glu Ile Phe Leu Ser Lys
                245                 250                 255

Ile Leu Gly Lys Asp Ile Lys Ile Gly Gly Lys Leu Gly Val Val Glu
            260                 265                 270

Gln Met Leu Asn Gln Lys Lys Val Leu Ile Val Leu Asp Asp Val Asp
        275                 280                 285

Asp Pro Glu Phe Leu Lys Thr Leu Val Gly Glu Thr Lys Trp Phe Gly
    290                 295                 300

Pro Gly Ser Arg Ile Ile Val Ile Thr Gln Asp Met Gln Leu Leu Lys
305                 310                 315                 320

Ala His Asp Ile Asp Leu Leu Tyr Glu Val Lys Phe Pro Ser Leu Asp
                325                 330                 335

Leu Ala Leu Lys Met Leu Cys Arg Ser Ala Phe Gly Glu Asn Ser Pro
            340                 345                 350

Pro Asp Asp Phe Lys Ala Leu Ala Phe Glu Val Ala Val Leu Ala Gly
        355                 360                 365

Asn Leu Pro Leu Gly Leu Ser Val Leu Gly Ser Ser Leu Lys Arg Arg
    370                 375                 380

Thr Lys Glu Glu Trp Met Glu Met Met Pro Arg Phe Arg Asn Gly Leu
385                 390                 395                 400

Asn Gly Asp Ile Met Lys Thr Leu Arg Val Ser Tyr Asp Arg Leu His
                405                 410                 415

Gln Lys Asp Gln Asp Met Phe Leu Tyr Ile Ala Cys Leu Phe Asn Gly
            420                 425                 430

Phe Glu Val Ser Tyr Val Asn Asp Leu Leu Glu Asp Asn Val Gly Val
        435                 440                 445

Thr Met Leu Val Glu Lys Ser Leu Ile Arg Ile Thr Pro Asp Gly Asp
    450                 455                 460

Ile Glu Met His Asn Leu Leu Glu Lys Leu Gly Ile Glu Ile Asp Arg
465                 470                 475                 480

Ala Lys Ser Lys Glu Thr Val Leu Gly Ile Arg Phe Cys Thr Ala Phe
                485                 490                 495

Arg Ser Lys Glu Leu Leu Pro Ile Asp Glu Lys Ser Phe Gln Gly Met
            500                 505                 510

Arg Asn Leu Gln Cys Leu Ser Val Thr Gly Asp Tyr Met Asp Leu Pro
        515                 520                 525

Gln Ser Leu Val Tyr Leu Pro Pro Lys Leu Arg Leu Leu Asp Trp Asp
    530                 535                 540

Arg Cys Pro Leu Lys Cys Leu Pro Tyr Ser Phe Lys Ala Asp Tyr Leu
545                 550                 555                 560

Ile Gln Leu Thr Met Met Gly Ser Lys Leu Glu Lys Leu Trp Glu Gly
                565                 570                 575

Thr Val Pro Leu Gly Ser Leu Lys Arg Met Asn Met His Gly Ser Arg
            580                 585                 590

Tyr Leu Arg Glu Ile Ser Asp Leu Ser Asn Ala Arg Asn Leu Glu Glu
        595                 600                 605

Leu Asn Leu Ser Glu Cys Arg Ser Leu Val Thr Leu Ser Ser Ser Ile
    610                 615                 620

Gln Asn Ala Ile Lys Leu Ile Tyr Leu Asp Met Arg Gly Cys Thr Lys
625                 630                 635                 640

Leu Glu Ser Phe Pro Thr His Leu Asn Leu Glu Ser Leu Glu Tyr Leu
                645                 650                 655

Glu Asn Cys Ile Trp Asn Lys Asn Leu Pro Gly Leu Asp Tyr Leu Ala
```

```
            660                 665                 670

Cys Leu Val Arg Cys Met Pro Cys Glu Phe Arg Pro Asn Asp Leu Val
        675                 680                 685

Arg Leu Ile Val Arg Gly Asn Gln Met Leu Glu Lys Leu Trp Glu Gly
    690                 695                 700

Val Gln Ser Leu Ala Ser Leu Val Glu Met Asp Met Ser Glu Cys Gly
705                 710                 715                 720

Asn Leu Thr Glu Ile Pro Asp Leu Ser Lys Ala Thr Asn Leu Val Asn
                725                 730                 735

Leu Tyr Leu Ser Asn Cys Lys Ser Leu Val Thr Val Pro Ser Thr Ile
            740                 745                 750

Gly Asn Leu Gln Lys Leu Val Arg Leu Glu Met Lys Glu Cys Thr Gly
        755                 760                 765

Leu Glu Val Leu Pro Thr Asp Val Asn Leu Ser Ser Leu Lys Met Leu
    770                 775                 780

Asp Leu Ser Gly Cys Ser Ser Leu Arg Thr Phe Pro Leu Ile Ser Lys
785                 790                 795                 800

Ser Ile Lys Trp Leu Tyr Leu Glu Asn Thr Ala Ile Glu Glu Val Pro
                805                 810                 815

Cys Cys Ile Glu Asn Phe Ser Trp Leu Thr Val Leu Met Met Tyr Cys
            820                 825                 830

Cys Lys Arg Leu Lys Asn Ile Ser Pro Asn Ile Phe Arg Leu Thr Ile
        835                 840                 845

Leu Lys Leu Val Asp Phe Thr Glu Cys Arg Gly Val Asn Val Ala Met
    850                 855                 860

Ser Asp Ala Ser Val Glu Asp His Ser Ser Tyr Ile Pro Leu Tyr Glu
865                 870                 875                 880

Asn Ile Glu Tyr Thr Arg His Arg Phe Trp Glu Asn Leu Asn His Lys
                885                 890                 895

His Leu Ala Cys Arg Ala Gly Gly Val Ser Asp Lys Trp Glu Gly Val
            900                 905                 910

Gly His Lys Leu Gly Gln Arg Glu Ile Met Arg Ala Lys Leu Gly Ser
        915                 920                 925

Pro Pro Arg Ala Ala Gly Arg Val Thr Val Glu Leu Glu Ala Ala Gly
    930                 935                 940

Arg Leu Ser Asp Gln Leu Gly Gly Tyr Pro Asp Gly Tyr Leu Gly Gly
945                 950                 955                 960

Tyr Gly Arg Thr Gly Ala Arg Pro Lys Gly Arg Val Pro Lys Thr Phe
                965                 970                 975

Arg Gly Thr Arg Thr His Arg Lys Tyr Arg Lys Leu Thr Ile Lys Leu
            980                 985                 990

Ser Ser Phe Arg Glu Asn Lys Ser  Ser Glu Glu Ile Gly  Ser Arg Thr
        995                 1000                1005

Val Thr  Gly Lys Glu Glu Glu  Gly Ser Asp Arg Pro  Asn Ile Val
    1010                1015                1020

Lys Glu  Gly Thr Thr Asn Gly  Leu Gly Arg Ile Gly  Ser Cys Ala
    1025                1030                1035

Thr Tyr  Thr Arg Leu Ser Pro  Gly Lys Gly Ser Ala  Arg Ala Gly
    1040                1045                1050

Thr Arg  Leu Gly Gly Gly Pro  Glu Gly Thr Asn Gly  Asp Arg Gly
    1055                1060                1065

Lys Asp  Leu Ala
    1070
```

<210> SEQ ID NO 39
<211> LENGTH: 3969
<212> TYPE: DNA
<213> ORGANISM: Arabidopsis thaliana

<400> SEQUENCE: 39
atgggatcag tgatcaacac tatcgttgga aacttgaagc tgtcaatttc aaatattcac 60
ataagatatg aggatctaga gagcctatgt tataagtgca gcaatcccgg ccacccgttc 120
tcagctggtg ttactctaga gaaactctca gctgtaacca ttgatgagag tggaaaggaa 180
acttttatta ctggcgggac tctggactcc atccaaaagg tgcctatagt aagaagcacg 240
gaaattgaat tgggctgctc tctagaaggg ttagtgttct gtaacagatc tttgtatgaa 300
actaatatct ggatgactgc attgggaaag gaatacccat gccaagaaac aaaagcaggg 360
tctgttgaac ttgatcggct tgcattctat cttgattctg acatgtctcc gtggcatatt 420
gacaaaccat gggaggtttt aactcctttt gagtgggatc agatttttag atatggaaca 480
aaggatggta agccagctga ctgcctcacg agaaagcatt tctatattct gcaacctgtc 540
tcagggaatg cgaagtactc taagtcccaa gcaaatgaat cttcaaatgc tgttcaacct 600
ttgcagaagg catatgtaaa cttagacgat gtgacacttt gtttatcaaa gggaggatac 660
agggatgtca tgaaacttgc tgataatttt gctgcattta atcagcgttt gaaatatgca 720
cattaccgtc catctgttcc agttaaaatc gacgcaaaat cttggtggaa atatgcttac 780
agagttgttt cagaacaaat taagatagca aggtatctaa atgtaaacct ttatcttttt 840
tttttaactg atgccggctt tttgcgtaat ttgcatcggt tgtggaaaca tcttcctttg 900
cagttcctta ccgggagaat gtcatgggag cacgttttaa agtacactag tctacgcaag 960
agatacatca cacagtatgc ttcgttgctg aaatctgata tcagtaggat agttgttgat 1020
gatgatgaag aaattgaggc ccttgatcgg gaacttgata ccgatgtcat tttgcaatgg 1080
aggatgttgg cgcacaagtt tgttgagagg tcggtacagg cagaaaatta ctcgaagaag 1140
caacaggcta aaagttcatg gtggccgttt ggagggaaga gtgaagtgtc tggaggtgaa 1200
ggagaatcta ttcaattcac agatgaagat tgggaacggt taaataaagt catagggtac 1260
aaagaaggtg atgagcaatc aattatcaac aatgcaaaac ctgatgctct ccatactttc 1320
ttggaggtac agatgaagcg tagtgcttca aaactttatg atggggagaa ggaatgcctt 1380
gctgagttat catgtgaagg tcttaattgc tccgttaagc ttttcccaga aacgaagata 1440
gctgacatta aattagggag atatcgcttg tcatcaccaa gtggtctgct tgctgagtat 1500
ctaaaggatt ccattgatgg aattgtcaac ttcttcgaaa gcagtactgc tgtgagccag 1560
acaatagctt tggagactgc agctgctgta caggacgact ataagcatga actgacagag 1620
gaaatggata tgtatctgca gtttgattta gttttgagtg atgtgtccgc tttacttgtt 1680
gatggtgatt attcctggaa acaattatcc tcaaaaagag cttctagttc tggtagggaa 1740
agcagtgtaa ctttcttgcc agttattgat aagtgtgggg tactcttaaa acttcaacag 1800
attcgtcgac caaacccagc gtacccatca accagacttg ctgtgcggct accctcatta 1860
ggctttcact tctcaccggc tcggtaccat aggttgatgc aagttgcaca gatatttcaa 1920
actaaggatg atgagagctc tcagattcta cgtccatggg aagaagctga ttttgagggg 1980
tggttgtcta ttcttagctg gaagggaaga gaagcttcgt ggcagcggcg gtatttatgc 2040
ttagttggtc catttatcta cgtgctcgaa agtcctggct caaaatctta taagaagtat 2100

-continued

```
accagcttac gcgggaagca tatatacaaa gttcccgtag agcttgctgg aggagtagaa   2160
catgtcttgt ccattcgtaa tgcttcacgg atcagtgaga aggttatgga ggatgtaaat   2220
gcactcatat tgatgtttga ttctgaagac tccagaaaaa catggcatag ccgtttgcag   2280
ggcgctgtct atcgggcctc gggttctgct cccatagccg gtctttctga tacttcatct   2340
gacagtgagg agtcagaaac agaacagaaa gatggtttcg atttgtctaa cttggagagt   2400
gtatatgtaa ccggtgtgct tgatgaactc aaaatatgtt tcagttatgg tcatcaggat   2460
gatgcttctt tcatggcggt gcttctcgcc agagagagta aattgttcga gtttagggcc   2520
ttaggtggga aggtaagatg gtggtatgct tctaaattat ctttttgtca tttcttattc   2580
tttttactga aagtatgttt gcctttgacg aaccaggttg aagtttcgat gagagggagt   2640
gatatgttta ttgggactgt actgaaatct ctggaaatag aagatttgtc ttcagaaatg   2700
cttccatcct ttgaagatgc tgagagcagg agccctgaac ggcttgatcc tacttctagt   2760
gaaggggagg aaaagttcta tgaagcacca gaaatcttgg ttgattccat tgactataca   2820
tctctcagga cccctagttt tagtcgcatt gatggattgc tccctgttga caacaagaat   2880
atcactaagc caagcaatga gacaactgag tcactggata gtttcgtgaa ggctcaaata   2940
gtcatatacc atcagacgtc acctcaatat aaaaacattg ataaccaggt gatggtaact   3000
ttagctactt tatcattttt ctgtcgaagg ccaacaattc ttgctatttt ggagtttgta   3060
aatgctatca atgttgagga tccaagctgt gaatcttttg aggacaactc tcctgtagct   3120
ggagagcata cttctccaag aagagatgga tttgaagatt ctagggatgc agctgtcaag   3180
ggtttgttag ggaaggggaa atctagaatc attttcaact tggaattgaa catggctcgg   3240
gcgcagatat tcctaatgaa tgagaatgga actaagtttg ctacattgtc acaagacaat   3300
ctgctgacag atattaaggt gtctttccga actcgttcag tattaaggca agtcttggaa   3360
atttacgaat cagtgatgac agcctcccag acaaccatat gtacttttgg atctgtgata   3420
tgcgagaccc tggaggaact tcttttgttg aggtattggt tgtttgtttc ttttcacttt   3480
tctctttgtg gaatgagaat ggattgcgta gatgagatac atttggtttt cacatcattc   3540
agtatcattg atgaagatta tgaaggtttc gactactgcc tatctgggca gttttctgaa   3600
gtgcgcattg tttatctgaa tcgctttatt caagaggttg ctgaatactt tatgggactg   3660
gtgccaagtg attcaaaagg ggttgtcaag atgaaggatc aaattacgga ctcagagaag   3720
tggtttacga ctagcgaaat tgaaggatct ccggcactta agttggatct atctcttaag   3780
aagcccataa ttgttatgcc tcgtcacact gatagccctg attacctgaa gctagatatt   3840
gtgcatataa ctgtggacaa tacctttcag tggtttgctg gagacaaaaa tgagctgaat   3900
gcagttcacg tggaaactat gaaaataatg gtgaggactc tcgttatttg gctgttagga   3960
ggagcatga                                                           3969
```

<210> SEQ ID NO 40
<211> LENGTH: 1322
<212> TYPE: PRT
<213> ORGANISM: Arabidopsis thaliana

<400> SEQUENCE: 40

```
Met Gly Ser Val Ile Asn Thr Ile Val Gly Asn Leu Lys Leu Ser Ile
1               5                   10                  15

Ser Asn Ile His Ile Arg Tyr Glu Asp Leu Glu Ser Leu Cys Tyr Lys
            20                  25                  30

Cys Ser Asn Pro Gly His Pro Phe Ser Ala Gly Val Thr Leu Glu Lys
```

-continued

```
        35                  40                  45

Leu Ser Ala Val Thr Ile Asp Glu Ser Gly Lys Glu Thr Phe Ile Thr
    50                  55                  60

Gly Gly Thr Leu Asp Ser Ile Gln Lys Val Pro Ile Val Arg Ser Thr
65                  70                  75                  80

Glu Ile Glu Leu Gly Cys Ser Leu Glu Gly Leu Val Phe Cys Asn Arg
                85                  90                  95

Ser Leu Tyr Glu Thr Asn Ile Trp Met Thr Ala Leu Gly Lys Glu Tyr
            100                 105                 110

Pro Cys Gln Glu Thr Lys Ala Gly Ser Val Glu Leu Asp Arg Leu Ala
        115                 120                 125

Phe Tyr Leu Asp Ser Asp Met Ser Pro Trp His Ile Asp Lys Pro Trp
    130                 135                 140

Glu Val Leu Thr Pro Phe Glu Trp Asp Gln Ile Phe Arg Tyr Gly Thr
145                 150                 155                 160

Lys Asp Gly Lys Pro Ala Asp Cys Leu Thr Arg Lys His Phe Tyr Ile
                165                 170                 175

Leu Gln Pro Val Ser Gly Asn Ala Lys Tyr Ser Lys Ser Gln Ala Asn
            180                 185                 190

Glu Ser Ser Asn Ala Val Gln Pro Leu Gln Lys Ala Tyr Val Asn Leu
        195                 200                 205

Asp Asp Val Thr Leu Cys Leu Ser Lys Gly Gly Tyr Arg Asp Val Met
    210                 215                 220

Lys Leu Ala Asp Asn Phe Ala Ala Phe Asn Gln Arg Leu Lys Tyr Ala
225                 230                 235                 240

His Tyr Arg Pro Ser Val Pro Val Lys Ile Asp Ala Lys Ser Trp Trp
                245                 250                 255

Lys Tyr Ala Tyr Arg Val Val Ser Glu Gln Ile Lys Ile Ala Arg Tyr
            260                 265                 270

Leu Asn Val Asn Leu Tyr Leu Phe Phe Leu Thr Asp Ala Gly Phe Leu
        275                 280                 285

Arg Asn Leu His Arg Leu Trp Lys His Leu Pro Leu Gln Phe Leu Thr
    290                 295                 300

Gly Arg Met Ser Trp Glu His Val Leu Lys Tyr Thr Ser Leu Arg Lys
305                 310                 315                 320

Arg Tyr Ile Thr Gln Tyr Ala Ser Leu Leu Lys Ser Asp Ile Ser Arg
                325                 330                 335

Ile Val Val Asp Asp Asp Glu Glu Ile Glu Ala Leu Asp Arg Glu Leu
            340                 345                 350

Asp Thr Asp Val Ile Leu Gln Trp Arg Met Leu Ala His Lys Phe Val
        355                 360                 365

Glu Arg Ser Val Gln Ala Glu Asn Tyr Ser Lys Lys Gln Gln Ala Lys
    370                 375                 380

Ser Ser Trp Trp Pro Phe Gly Gly Lys Ser Glu Val Ser Gly Gly Glu
385                 390                 395                 400

Gly Glu Ser Ile Gln Phe Thr Asp Glu Asp Trp Glu Arg Leu Asn Lys
                405                 410                 415

Val Ile Gly Tyr Lys Glu Gly Asp Glu Gln Ser Ile Ile Asn Asn Ala
            420                 425                 430

Lys Pro Asp Ala Leu His Thr Phe Leu Glu Val Gln Met Lys Arg Ser
        435                 440                 445

Ala Ser Lys Leu Tyr Asp Gly Glu Lys Glu Cys Leu Ala Glu Leu Ser
    450                 455                 460
```

```
Cys Glu Gly Leu Asn Cys Ser Val Lys Leu Phe Pro Glu Thr Lys Ile
465                 470                 475                 480

Ala Asp Ile Lys Leu Gly Arg Tyr Arg Leu Ser Ser Pro Ser Gly Leu
                485                 490                 495

Leu Ala Glu Tyr Leu Lys Asp Ser Ile Asp Gly Ile Val Asn Phe Phe
            500                 505                 510

Glu Ser Ser Thr Ala Val Ser Gln Thr Ile Ala Leu Glu Thr Ala Ala
        515                 520                 525

Ala Val Gln Asp Asp Tyr Lys His Glu Leu Thr Glu Glu Met Asp Met
    530                 535                 540

Tyr Leu Gln Phe Asp Leu Val Leu Ser Asp Val Ser Ala Leu Leu Val
545                 550                 555                 560

Asp Gly Asp Tyr Ser Trp Lys Gln Leu Ser Ser Lys Arg Ala Ser Ser
                565                 570                 575

Ser Gly Arg Glu Ser Ser Val Thr Phe Leu Pro Val Ile Asp Lys Cys
            580                 585                 590

Gly Val Leu Leu Lys Leu Gln Gln Ile Arg Arg Pro Asn Pro Ala Tyr
        595                 600                 605

Pro Ser Thr Arg Leu Ala Val Arg Leu Pro Ser Leu Gly Phe His Phe
    610                 615                 620

Ser Pro Ala Arg Tyr His Arg Leu Met Gln Val Ala Gln Ile Phe Gln
625                 630                 635                 640

Thr Lys Asp Asp Glu Ser Ser Gln Ile Leu Arg Pro Trp Glu Glu Ala
                645                 650                 655

Asp Phe Glu Gly Trp Leu Ser Ile Leu Ser Trp Lys Gly Arg Glu Ala
            660                 665                 670

Ser Trp Gln Arg Arg Tyr Leu Cys Leu Val Gly Pro Phe Ile Tyr Val
        675                 680                 685

Leu Glu Ser Pro Gly Ser Lys Ser Tyr Lys Lys Tyr Thr Ser Leu Arg
    690                 695                 700

Gly Lys His Ile Tyr Lys Val Pro Val Glu Leu Ala Gly Gly Val Glu
705                 710                 715                 720

His Val Leu Ser Ile Arg Asn Ala Ser Arg Ile Ser Glu Lys Val Met
                725                 730                 735

Glu Asp Val Asn Ala Leu Ile Leu Met Phe Asp Ser Glu Asp Ser Arg
            740                 745                 750

Lys Thr Trp His Ser Arg Leu Gln Gly Ala Val Tyr Arg Ala Ser Gly
        755                 760                 765

Ser Ala Pro Ile Ala Gly Leu Ser Asp Thr Ser Ser Asp Ser Glu Glu
    770                 775                 780

Ser Glu Thr Glu Gln Lys Asp Gly Phe Asp Leu Ser Asn Leu Glu Ser
785                 790                 795                 800

Val Tyr Val Thr Gly Val Leu Asp Glu Leu Lys Ile Cys Phe Ser Tyr
                805                 810                 815

Gly His Gln Asp Asp Ala Ser Phe Met Ala Val Leu Leu Ala Arg Glu
            820                 825                 830

Ser Lys Leu Phe Glu Phe Arg Ala Leu Gly Gly Lys Val Arg Trp Trp
        835                 840                 845

Tyr Ala Ser Lys Leu Ser Phe Cys His Phe Leu Phe Phe Leu Leu Lys
    850                 855                 860

Val Cys Leu Pro Leu Thr Asn Gln Val Glu Val Ser Met Arg Gly Ser
865                 870                 875                 880
```

-continued

```
Asp Met Phe Ile Gly Thr Val Leu Lys Ser Leu Glu Ile Glu Asp Leu
                885                 890                 895

Ser Ser Glu Met Leu Pro Ser Phe Glu Asp Ala Glu Ser Arg Ser Pro
            900                 905                 910

Glu Arg Leu Asp Pro Thr Ser Ser Glu Gly Glu Glu Lys Phe Tyr Glu
        915                 920                 925

Ala Pro Glu Ile Leu Val Asp Ser Ile Asp Tyr Thr Ser Leu Arg Thr
    930                 935                 940

Pro Ser Phe Ser Arg Ile Asp Gly Leu Leu Pro Val Asp Asn Lys Asn
945                 950                 955                 960

Ile Thr Lys Pro Ser Asn Glu Thr Thr Glu Ser Leu Asp Ser Phe Val
                965                 970                 975

Lys Ala Gln Ile Val Ile Tyr His Gln Thr Ser Pro Gln Tyr Lys Asn
            980                 985                 990

Ile Asp Asn Gln Val Met Val Thr  Leu Ala Thr Leu Ser  Phe Phe Cys
        995                 1000                1005

Arg Arg  Pro Thr Ile Leu Ala  Ile Leu Glu Phe Val  Asn Ala Ile
    1010                 1015                 1020

Asn Val  Glu Asp Pro Ser Cys  Glu Ser Phe Glu Asp  Asn Ser Pro
    1025                 1030                 1035

Val Ala  Gly Glu His Thr Ser  Pro Arg Arg Asp Gly  Phe Glu Asp
    1040                 1045                 1050

Ser Arg  Asp Ala Ala Val Lys  Gly Leu Leu Gly Lys  Gly Lys Ser
    1055                 1060                 1065

Arg Ile  Ile Phe Asn Leu Glu  Leu Asn Met Ala Arg  Ala Gln Ile
    1070                 1075                 1080

Phe Leu  Met Asn Glu Asn Gly  Thr Lys Phe Ala Thr  Leu Ser Gln
    1085                 1090                 1095

Asp Asn  Leu Leu Thr Asp Ile  Lys Val Ser Phe Arg  Thr Arg Ser
    1100                 1105                 1110

Val Leu  Arg Gln Val Leu Glu  Ile Tyr Glu Ser Val  Met Thr Ala
    1115                 1120                 1125

Ser Gln  Thr Thr Ile Cys Thr  Phe Gly Ser Val Ile  Cys Glu Thr
    1130                 1135                 1140

Leu Glu  Glu Leu Leu Leu Leu  Arg Tyr Trp Leu Phe  Val Ser Phe
    1145                 1150                 1155

His Phe  Ser Leu Cys Gly Met  Arg Met Asp Cys Val  Asp Glu Ile
    1160                 1165                 1170

His Leu  Val Phe Thr Ser Phe  Ser Ile Ile Asp Glu  Asp Tyr Glu
    1175                 1180                 1185

Gly Phe  Asp Tyr Cys Leu Ser  Gly Gln Phe Ser Glu  Val Arg Ile
    1190                 1195                 1200

Val Tyr  Leu Asn Arg Phe Ile  Gln Glu Val Ala Glu  Tyr Phe Met
    1205                 1210                 1215

Gly Leu  Val Pro Ser Asp Ser  Lys Gly Val Val Lys  Met Lys Asp
    1220                 1225                 1230

Gln Ile  Thr Asp Ser Glu Lys  Trp Phe Thr Thr Ser  Glu Ile Glu
    1235                 1240                 1245

Gly Ser  Pro Ala Leu Lys Leu  Asp Leu Ser Leu Lys  Lys Pro Ile
    1250                 1255                 1260

Ile Val  Met Pro Arg His Thr  Asp Ser Pro Asp Tyr  Leu Lys Leu
    1265                 1270                 1275

Asp Ile  Val His Ile Thr Val  Asp Asn Thr Phe Gln  Trp Phe Ala
```

-continued

```
    1280                1285                1290

Gly Asp  Lys Asn Glu Leu Asn  Ala Val His Val Glu  Thr Met Lys
    1295                1300                1305

Ile Met  Val Arg Thr Leu Val  Ile Trp Leu Leu Gly  Gly Ala
    1310                1315                1320


<210> SEQ ID NO 41
<211> LENGTH: 1788
<212> TYPE: DNA
<213> ORGANISM: Arabidopsis thaliana

<400> SEQUENCE: 41

gcgcatttct cagaaattat atgggactct cgaaagcatg atgctttttg ttgtctcact     60

tgtaatttgt tcgggacttt gttgctgaag aaaactaagc aatgtctgta gaaacatggt    120

tcatgattca gaagactact actagctcat gagttcactg gtacttggaa ttaagatgat    180

tgatcagttc atcaactttg taattcgacc tcctagggct gagtatgatc ctgatcagta    240

tttgtgggag aaggagttta gcctcggtgg cacaaagtgt aaaagacaag acttggagct    300

tacaaattcg aggggtcaca ctttgcgttg cagtcattat gttccctcat cttctcggga    360

ggatactcct ctcccctgtg ttatatactg tcatggcaat agtggatgta gggcagatgc    420

aaatgaggca gttatggttc tcctcccatc taacataact gttttcaccc ttgacttctc    480

ggggtcaggc ttatctgagg gtgattatgt aagccttggc tggcatgaga aggatgatct    540

caagactgtg gtatcttacc tgagaaacag caatcaagta tcccgtattg gactttgggg    600

acgatctatg ggtgcagtta ccagccttct ctatggagca gaagatcctt caattgctgg    660

aatggtccta gacagtgcat tttcaaactt atttgatctg atgatggaac tagtggatgt    720

ctacaaaatc cgacttccga aattcacagt taaagtggct gtgcagtaca tgcggcgtat    780

aattcagaaa aaggcgaagt ttaatattat ggatctcaat tgtgttaagg tttcgcccaa    840

gacttttatt ccagctttat ttgggcatgc aagcggagac aaattcatcc aacctcatca    900

ctctgacctc attctcaagt gctatgcggg agacaaaaat atcatcaagt ttgatggtga    960

tcacaactct tcgcgcccgc agtcttatta tgattcagta ttagtattct tctacaatgt   1020

tcttcgcccg cctccaattt cttcatctta ctcatctaaa cttgaaagtt attacagttt   1080

gggagatgtc aatagcgcta ctggtttgga tgagagtttt ctgtatgaga tcatatctgg   1140

tcttcgttcg gcatgtatcg atgttgcaag ttcttcttct gcacctcctg cccctctaac   1200

cacaaagcca acgaatgagc tcctttcaga agctatgccc atgatagata cagataccgt   1260

gcttgtggaa gataatgatc acaacgtgga cgaccctgaa aacttcgagg gaaagcgtat   1320

tgatcagttt gaagaaggct gttcatttac aagctccaac agggaaagct ggggcagatg   1380

ctcttcacta ggaggcactg aagaagatga gagtttgaca gctggcgagg gtgatcaggt   1440

cgagaaaact gctgatgtaa acacggaacg aaagccaaga gattctagta gagaagaaga   1500

agaagaagac agtaaggaga agaagattaa gaacggaggt gaaacagatg caaagaagcc   1560

tagacacgaa aaattggaaa gattggaggc ctttagcaaa agactgcggc attacatcct   1620

aaagcgagta aaccatagaa gacatcgttc accttgacaa acaaagttga agaaaatgct   1680

ctaattgttg tatatctctg aatcttgtaa tgtacacttc tccttcgact tggcaaatgg   1740

aatcacacgt ggccagttta acctcaatca tatccttacc attgtttc                1788


<210> SEQ ID NO 42
<211> LENGTH: 502
```

<212> TYPE: PRT
<213> ORGANISM: Arabidopsis thaliana

<400> SEQUENCE: 42

```
Met Ser Ser Leu Val Leu Gly Ile Lys Met Ile Asp Gln Phe Ile Asn
1               5                   10                  15

Phe Val Ile Arg Pro Pro Arg Ala Glu Tyr Asp Pro Asp Gln Tyr Leu
            20                  25                  30

Trp Glu Lys Glu Phe Ser Leu Gly Gly Thr Lys Cys Lys Arg Gln Asp
        35                  40                  45

Leu Glu Leu Thr Asn Ser Arg Gly His Thr Leu Arg Cys Ser His Tyr
    50                  55                  60

Val Pro Ser Ser Ser Arg Glu Asp Thr Pro Leu Pro Cys Val Ile Tyr
65                  70                  75                  80

Cys His Gly Asn Ser Gly Cys Arg Ala Asp Ala Asn Glu Ala Val Met
                85                  90                  95

Val Leu Leu Pro Ser Asn Ile Thr Val Phe Thr Leu Asp Phe Ser Gly
            100                 105                 110

Ser Gly Leu Ser Glu Gly Asp Tyr Val Ser Leu Gly Trp His Glu Lys
        115                 120                 125

Asp Asp Leu Lys Thr Val Val Ser Tyr Leu Arg Asn Ser Asn Gln Val
    130                 135                 140

Ser Arg Ile Gly Leu Trp Gly Arg Ser Met Gly Ala Val Thr Ser Leu
145                 150                 155                 160

Leu Tyr Gly Ala Glu Asp Pro Ser Ile Ala Gly Met Val Leu Asp Ser
                165                 170                 175

Ala Phe Ser Asn Leu Phe Asp Leu Met Met Glu Leu Val Asp Val Tyr
            180                 185                 190

Lys Ile Arg Leu Pro Lys Phe Thr Val Lys Val Ala Val Gln Tyr Met
        195                 200                 205

Arg Arg Ile Ile Gln Lys Lys Ala Lys Phe Asn Ile Met Asp Leu Asn
    210                 215                 220

Cys Val Lys Val Ser Pro Lys Thr Phe Ile Pro Ala Leu Phe Gly His
225                 230                 235                 240

Ala Ser Gly Asp Lys Phe Ile Gln Pro His His Ser Asp Leu Ile Leu
                245                 250                 255

Lys Cys Tyr Ala Gly Asp Lys Asn Ile Ile Lys Phe Asp Gly Asp His
            260                 265                 270

Asn Ser Ser Arg Pro Gln Ser Tyr Tyr Asp Ser Val Leu Val Phe Phe
        275                 280                 285

Tyr Asn Val Leu Arg Pro Pro Pro Ile Ser Ser Ser Tyr Ser Ser Lys
    290                 295                 300

Leu Glu Ser Tyr Tyr Ser Leu Gly Asp Val Asn Ser Ala Thr Gly Leu
305                 310                 315                 320

Asp Glu Ser Phe Leu Tyr Glu Ile Ile Ser Gly Leu Arg Ser Ala Cys
                325                 330                 335

Ile Asp Val Ala Ser Ser Ser Ser Ala Pro Pro Ala Pro Leu Thr Thr
            340                 345                 350

Lys Pro Thr Asn Glu Leu Leu Ser Glu Ala Met Pro Met Ile Asp Thr
        355                 360                 365

Asp Thr Val Leu Val Glu Asp Asn Asp His Asn Val Asp Asp Pro Glu
    370                 375                 380

Asn Phe Glu Gly Lys Arg Ile Asp Gln Phe Glu Glu Gly Cys Ser Phe
385                 390                 395                 400
```

-continued

```
Thr Ser Ser Asn Arg Glu Ser Trp Gly Arg Cys Ser Ser Leu Gly Gly
                405                 410                 415

Thr Glu Glu Asp Glu Ser Leu Thr Ala Gly Glu Gly Asp Gln Val Glu
            420                 425                 430

Lys Thr Ala Asp Val Asn Thr Glu Arg Lys Pro Arg Asp Ser Ser Arg
        435                 440                 445

Glu Glu Glu Glu Glu Asp Ser Lys Glu Lys Lys Ile Lys Asn Gly Gly
    450                 455                 460

Glu Thr Asp Ala Lys Lys Pro Arg His Glu Lys Leu Glu Arg Leu Glu
465                 470                 475                 480

Ala Phe Ser Lys Arg Leu Arg His Tyr Ile Leu Lys Arg Val Asn His
                485                 490                 495

Arg Arg His Arg Ser Pro
            500


<210> SEQ ID NO 43
<211> LENGTH: 618
<212> TYPE: DNA
<213> ORGANISM: Arabidopsis thaliana

<400> SEQUENCE: 43

atgtcttatg cttatagatt taagtatatc atcatcggtg atactggagt agggaaatca      60

tgccttctgc ttaagttcac cgacaagagg tttcaagcag tgcatgatct caccattggt     120

gttgaatttg ggccaagac gatcactatc gacaacaaac ccatcaaact tcagatctgg     180

gatacggctg gtcaagaatc atttaggtct gttacaaggt catactatag agggcgtgcc     240

ggtacattgc ttgtatatga tatcacaagg agggagacat ttaaccatct agccagctgg     300

ctagaagagg caagacagca tgcaagtgaa aatatgacga caatgctcat tgggaataag     360

tgtgatcttg aagataaaag gacagtgagt acagaggaag gagaacagtt tgctagggag     420

catggtctta tattcatgga ggcctctgct aagactgctc acaatgtcga ggaggcattc     480

gtcgagacag ccgcaacaat atacaaaagg attcaagatg gtgtggttga tgaggcaaat     540

gagcctggaa taactccagg gccgtttggt ggaaaagatg catcctcctc acagcaaaga     600

agagggtgct gcggctga                                                   618


<210> SEQ ID NO 44
<211> LENGTH: 205
<212> TYPE: PRT
<213> ORGANISM: Arabidopsis thaliana

<400> SEQUENCE: 44

Met Ser Tyr Ala Tyr Arg Phe Lys Tyr Ile Ile Ile Gly Asp Thr Gly
1               5                   10                  15

Val Gly Lys Ser Cys Leu Leu Leu Lys Phe Thr Asp Lys Arg Phe Gln
            20                  25                  30

Ala Val His Asp Leu Thr Ile Gly Val Glu Phe Gly Ala Lys Thr Ile
        35                  40                  45

Thr Ile Asp Asn Lys Pro Ile Lys Leu Gln Ile Trp Asp Thr Ala Gly
    50                  55                  60

Gln Glu Ser Phe Arg Ser Val Thr Arg Ser Tyr Tyr Arg Gly Arg Ala
65                  70                  75                  80

Gly Thr Leu Leu Val Tyr Asp Ile Thr Arg Arg Glu Thr Phe Asn His
                85                  90                  95

Leu Ala Ser Trp Leu Glu Glu Ala Arg Gln His Ala Ser Glu Asn Met
```

-continued

```
            100                 105                 110

Thr Thr Met Leu Ile Gly Asn Lys Cys Asp Leu Glu Asp Lys Arg Thr
        115                 120                 125

Val Ser Thr Glu Glu Gly Glu Gln Phe Ala Arg Glu His Gly Leu Ile
    130                 135                 140

Phe Met Glu Ala Ser Ala Lys Thr Ala His Asn Val Glu Glu Ala Phe
145                 150                 155                 160

Val Glu Thr Ala Ala Thr Ile Tyr Lys Arg Ile Gln Asp Gly Val Val
                165                 170                 175

Asp Glu Ala Asn Glu Pro Gly Ile Thr Pro Gly Pro Phe Gly Gly Lys
            180                 185                 190

Asp Ala Ser Ser Ser Gln Gln Arg Arg Gly Cys Cys Gly
        195                 200                 205


<210> SEQ ID NO 45
<211> LENGTH: 962
<212> TYPE: DNA
<213> ORGANISM: Arabidopsis thaliana

<400> SEQUENCE: 45

ggaaaacaaa ccgtcaatct ccgtctttat agagaaaaaa agattctctt ctcttctcgt      60

tctcatcatc gtcttaaaga aggaattcga tttttcgcct gaacctgcgg atttttcgat     120

tcttcaaatt caatgtctta tgcttatctc ttcaagtata tcatcatcgg cgatactgga     180

gtggggaaat catgtcttct gcttcagttc accgacaaga ggtttcagcc ggtgcatgac     240

cttaccattg gtgttgaatt tggggctagg atgatcacca tcgataacaa acctatcaag     300

cttcagatct gggatacggc tggtcaagaa tcctttaggt ctattacaag gtcatactat     360

agaggagctg caggggcatt gcttgtctat gatatcacaa ggagggagac atttaaccat     420

ctagctagct ggctagaaga tgcaaggcag catgcaaatg caaatatgac gataatgctc     480

attgggaata agtgtgatct tgctcacaga agggcagtga gtacagagga aggagagcag     540

tttgcaaagg agcacggtct tatattcatg gaggcctctg ccaagactgc tcagaatgtt     600

gaggaggcat tcattaagac agctgcaaca atatacaaga agattcaaga tggtgtgttt     660

gatgtgtcaa atgagtcata tggaatcaaa gttggatatg gaggaattcc aggaccatca     720

ggtggaagag atggatcaac ctcgcaagga ggagggtgct gcggctgaga tgggaaaaat     780

atgtctatgt cattatgtaa aaatgatcac atatgatata gcaaaaatgt ctctgcttct     840

ttctatagtt gtaaatcgtt ttggaattcg atttggtgac tgtgttgtgg ttggttttgg     900

aacggtttga caatacacgt gtatgcctat tcatatatct aaaaattaag atgtgtttgc     960

gt                                                                    962


<210> SEQ ID NO 46
<211> LENGTH: 211
<212> TYPE: PRT
<213> ORGANISM: Arabidopsis thaliana

<400> SEQUENCE: 46

Met Ser Tyr Ala Tyr Leu Phe Lys Tyr Ile Ile Ile Gly Asp Thr Gly
1               5                   10                  15

Val Gly Lys Ser Cys Leu Leu Leu Gln Phe Thr Asp Lys Arg Phe Gln
            20                  25                  30

Pro Val His Asp Leu Thr Ile Gly Val Glu Phe Gly Ala Arg Met Ile
        35                  40                  45
```

-continued

```
Thr Ile Asp Asn Lys Pro Ile Lys Leu Gln Ile Trp Asp Thr Ala Gly
    50                  55                  60

Gln Glu Ser Phe Arg Ser Ile Thr Arg Ser Tyr Tyr Arg Gly Ala Ala
65                  70                  75                  80

Gly Ala Leu Leu Val Tyr Asp Ile Thr Arg Arg Glu Thr Phe Asn His
                85                  90                  95

Leu Ala Ser Trp Leu Glu Asp Ala Arg Gln His Ala Asn Ala Asn Met
            100                 105                 110

Thr Ile Met Leu Ile Gly Asn Lys Cys Asp Leu Ala His Arg Arg Ala
        115                 120                 125

Val Ser Thr Glu Glu Gly Glu Gln Phe Ala Lys Glu His Gly Leu Ile
    130                 135                 140

Phe Met Glu Ala Ser Ala Lys Thr Ala Gln Asn Val Glu Glu Ala Phe
145                 150                 155                 160

Ile Lys Thr Ala Ala Thr Ile Tyr Lys Lys Ile Gln Asp Gly Val Phe
                165                 170                 175

Asp Val Ser Asn Glu Ser Tyr Gly Ile Lys Val Gly Tyr Gly Gly Ile
            180                 185                 190

Pro Gly Pro Ser Gly Gly Arg Asp Gly Ser Thr Ser Gln Gly Gly Gly
        195                 200                 205

Cys Cys Gly
    210
```

<210> SEQ ID NO 47
<211> LENGTH: 2161
<212> TYPE: DNA
<213> ORGANISM: Arabidopsis thaliana

<400> SEQUENCE: 47

```
atggaaacga aagacaagaa agaaaaagga catatggttt taaattccga caacgttttc     60

ggttcggtgt cttcgtctcc gacaacaaca atccaaaacc ctaattactt tacctccttc    120

gagaacccta atttccctta catttttccg aaagaagagt atgaggtgat gagcaagatc    180

gaaagcgggt cgggtaagtc aaccgggtcg ggtcatgacc cagtggagaa tactgcaatc    240

gaacaagagc ctcctgcggc gaagaagaaa cgttaccata gacatactgc tagtcagatt    300

caacaaatgg aagcattgtt taaggaaaat gctcatccgg ataccaaaac aagattgaga    360

ttaagtaaaa aacttggtct ctcgccgata caagtcaagt tttggtttca aaacaaacgt    420

acccaaatca aggcacaaca aagtagaagc gataatgcaa agctaaaagc agagaatgag    480

actctaaaga cagagagtca aaatattcag tccaattttc aatgcctttt ttgctctact    540

tgtggccaca atctccgcct cgaaaacgct cgcctccgcc aagagcttga tcgtttacgc    600

agcattgttt ccatgaggaa tccttctcct tcacaagaga ttaccccgga gactaataag    660

aacaacaacg ataatatgtt gattgcggaa gaagaaaagg cgattgatat ggaacttgca    720

gtttcttgtg ctcgagaatt agcaaagatg tgtgacataa atgagccctt gtggaataag    780

aagagactag acaatgagag tgtgtgtctg aatgaggaag agtataagaa gatgttctta    840

tggcctctaa tgaatgatga tgatcgtttt cgcagagaag cttcaagagc taatgcagtc    900

atcatgttga actgcataac cctcgtcaaa gcattccttg atgctgataa atggtcggaa    960

atgttcttcc ccatagtctc aagcgccaaa acggctcaga tcatttcttc tggagcttct   1020

ggaccaagtg gtactcttct tctgatgttt gcagagttac aagtagtgtc tccattggta   1080

ccaacaagag aagcttattt tcttcggtat gtggagcaaa atgctgaaga aggaaaatgg   1140
```

-continued

```
atggttgtag atttcccgat cgataggatc aaaccagcat cagctactac tactgatcaa   1200

taccggagaa aaccttctgg ttgcatcatt caagcaatgc gtaacggata ctctcaggtc   1260

acatgggtag agcacgtaga agtagaagag aagcacgtgc aggacgaggt tgttagagag   1320

tttgtggaga gcggtgtggc ctttggcgct gaacggtggc tatctgtgtt gaagagacaa   1380

tgtgaaagga tggctagtct catggctaca aacatcactg accttggagt gataccttct   1440

gtagaagcga ggaagaactt gatgaagctg tcacagagaa tggtgaaaac tttctgtctg   1500

aacataatca attcacacgg acaagcacca acaaaggaca cagttaaaat cgtaagcagg   1560

aaagtttgcg gtggtcttgt tccttgtgcc gtgtcagtca cgcttctccc ttattctcat   1620

caacaagtct ttgatcttct ccgcgacaat caacgtctct ctcagctgga gatcttgttc   1680

atgggtagtt catttcaaga agttgctcat atcgctaatg gctcacatct tggaaatagc   1740

atctctcttc ttcggatcaa tgtggagagc aattcatcgc ataatgtaga gttgatgctt   1800

caagaaacat gcaccgataa ctccgggagt ctcctggtgt actctaccgt cgaccccgtc   1860

gctgttcagc tcgccatgaa cggcgaagat ccttctgaaa taccactttt gcccgttgga   1920

ttctctgttg ttccagtgaa tccatccgat ggtgtcgagg gcagttccgt cagttcgcct   1980

tcgtgcttgc tcactgttgc aatacaggtc ttggggagca acgtcaccac cgaaagactc   2040

gatctttcca ccgtctccgt catcaatcac cgtatttgcg ccactgtcaa ccgtatcact   2100

tccgcgctcg tcaacgacgt cggtaattaa gagaagattt ggagggtatt ttggtaaata   2160

a                                                                   2161
```

```
<210> SEQ ID NO 48
<211> LENGTH: 709
<212> TYPE: PRT
<213> ORGANISM: Arabidopsis thaliana

<400> SEQUENCE: 48

Met Glu Thr Lys Asp Lys Lys Glu Lys Gly His Met Val Leu Asn Ser
1               5                   10                  15

Asp Asn Val Phe Gly Ser Val Ser Ser Ser Pro Thr Thr Thr Ile Gln
            20                  25                  30

Asn Pro Asn Tyr Phe Thr Ser Phe Glu Asn Pro Asn Phe Pro Tyr Ile
        35                  40                  45

Phe Pro Lys Glu Glu Tyr Glu Val Met Ser Lys Ile Glu Ser Gly Ser
    50                  55                  60

Gly Lys Ser Thr Gly Ser Gly His Asp Pro Val Glu Asn Thr Ala Ile
65                  70                  75                  80

Glu Gln Glu Pro Pro Ala Ala Lys Lys Lys Arg Tyr His Arg His Thr
                85                  90                  95

Ala Ser Gln Ile Gln Gln Met Glu Ala Leu Phe Lys Glu Asn Ala His
            100                 105                 110

Pro Asp Thr Lys Thr Arg Leu Arg Leu Ser Lys Lys Leu Gly Leu Ser
        115                 120                 125

Pro Ile Gln Val Lys Phe Trp Phe Gln Asn Lys Arg Thr Gln Ile Lys
    130                 135                 140

Ala Gln Gln Ser Arg Ser Asp Asn Ala Lys Leu Lys Ala Glu Asn Glu
145                 150                 155                 160

Thr Leu Lys Thr Glu Ser Gln Asn Ile Gln Ser Asn Phe Gln Cys Leu
                165                 170                 175

Phe Cys Ser Thr Cys Gly His Asn Leu Arg Leu Glu Asn Ala Arg Leu
            180                 185                 190
```

-continued

```
Arg Gln Glu Leu Asp Arg Leu Arg Ser Ile Val Ser Met Arg Asn Pro
        195                 200                 205

Ser Pro Ser Gln Glu Ile Thr Pro Glu Thr Asn Lys Asn Asn Asn Asp
    210                 215                 220

Asn Met Leu Ile Ala Glu Glu Glu Lys Ala Ile Asp Met Glu Leu Ala
225                 230                 235                 240

Val Ser Cys Ala Arg Glu Leu Ala Lys Met Cys Asp Ile Asn Glu Pro
                245                 250                 255

Leu Trp Asn Lys Lys Arg Leu Asp Asn Glu Ser Val Cys Leu Asn Glu
            260                 265                 270

Glu Glu Tyr Lys Lys Met Phe Leu Trp Pro Leu Met Asn Asp Asp Asp
        275                 280                 285

Arg Phe Arg Arg Glu Ala Ser Arg Ala Asn Ala Val Ile Met Leu Asn
    290                 295                 300

Cys Ile Thr Leu Val Lys Ala Phe Leu Asp Ala Asp Lys Trp Ser Glu
305                 310                 315                 320

Met Phe Phe Pro Ile Val Ser Ser Ala Lys Thr Ala Gln Ile Ile Ser
                325                 330                 335

Ser Gly Ala Ser Gly Pro Ser Gly Thr Leu Leu Leu Met Phe Ala Glu
            340                 345                 350

Leu Gln Val Val Ser Pro Leu Val Pro Thr Arg Glu Ala Tyr Phe Leu
        355                 360                 365

Arg Tyr Val Glu Gln Asn Ala Glu Glu Gly Lys Trp Met Val Val Asp
    370                 375                 380

Phe Pro Ile Asp Arg Ile Lys Pro Ala Ser Ala Thr Thr Thr Asp Gln
385                 390                 395                 400

Tyr Arg Arg Lys Pro Ser Gly Cys Ile Ile Gln Ala Met Arg Asn Gly
                405                 410                 415

Tyr Ser Gln Val Thr Trp Val Glu His Val Glu Val Glu Glu Lys His
            420                 425                 430

Val Gln Asp Glu Val Val Arg Glu Phe Val Glu Ser Gly Val Ala Phe
        435                 440                 445

Gly Ala Glu Arg Trp Leu Ser Val Leu Lys Arg Gln Cys Glu Arg Met
    450                 455                 460

Ala Ser Leu Met Ala Thr Asn Ile Thr Asp Leu Gly Val Ile Pro Ser
465                 470                 475                 480

Val Glu Ala Arg Lys Asn Leu Met Lys Leu Ser Gln Arg Met Val Lys
                485                 490                 495

Thr Phe Cys Leu Asn Ile Ile Asn Ser His Gly Gln Ala Pro Thr Lys
            500                 505                 510

Asp Thr Val Lys Ile Val Ser Arg Lys Val Cys Gly Gly Leu Val Pro
        515                 520                 525

Cys Ala Val Ser Val Thr Leu Leu Pro Tyr Ser His Gln Gln Val Phe
    530                 535                 540

Asp Leu Leu Arg Asp Asn Gln Arg Leu Ser Gln Leu Glu Ile Leu Phe
545                 550                 555                 560

Met Gly Ser Ser Phe Gln Glu Val Ala His Ile Ala Asn Gly Ser His
                565                 570                 575

Leu Gly Asn Ser Ile Ser Leu Leu Arg Ile Asn Val Glu Ser Asn Ser
            580                 585                 590

Ser His Asn Val Glu Leu Met Leu Gln Glu Thr Cys Thr Asp Asn Ser
        595                 600                 605
```

-continued

```
Gly Ser Leu Leu Val Tyr Ser Thr Val Asp Pro Val Ala Val Gln Leu
    610                 615                 620

Ala Met Asn Gly Glu Asp Pro Ser Glu Ile Pro Leu Leu Pro Val Gly
625                 630                 635                 640

Phe Ser Val Val Pro Val Asn Pro Ser Asp Gly Val Glu Gly Ser Ser
                645                 650                 655

Val Ser Ser Pro Ser Cys Leu Leu Thr Val Ala Ile Gln Val Leu Gly
            660                 665                 670

Ser Asn Val Thr Thr Glu Arg Leu Asp Leu Ser Thr Val Ser Val Ile
        675                 680                 685

Asn His Arg Ile Cys Ala Thr Val Asn Arg Ile Thr Ser Ala Leu Val
    690                 695                 700

Asn Asp Val Gly Asn
705
```

<210> SEQ ID NO 49
<211> LENGTH: 1321
<212> TYPE: DNA
<213> ORGANISM: Arabidopsis thaliana

<400> SEQUENCE: 49

```
aggtcccact tttttctttt atttttcact cttcttcaca tcaaatccgc gaccagagat      60

ttttctttcc tttgattttt cgtttcgttt cgtttcaaat attgttcctc ctgtgtgaag     120

gaaaaacaat cttccatttc aatccgcgtc aacgcgattt tcttcatgac gatgacaaca     180

gttaaagtga gcaatgtttc tctaggagca accgatagag atctcaagga gttcttttcc     240

ttttctggcg atattctgta ccttgagacg cagagcgaga ctgagcggac taaactggca     300

tatgtcactt ttaaggatct acaaggagct gaaactgcgg ttcttctctc gggagcaacg     360

attgttgatt cttcagtcat tgtctctatg gctcctgatt accaactgtc ccctgaggct     420

ttagcttcct tggaacccaa ggacagcaat aaatctccca aggcaggtga ctccgtgttg     480

agaaaagccg aagatgttgt gagcagcatg cttgcaaagg gctttatcct gggaaaagat     540

gccatagcta aagccaaaag tgttgacgag aagcaccagc taacatctac agcatcagcc     600

aaagtcgcat cttttgacaa gaaaattggt ttcactgata agatcaacac aggcacggtg     660

gtagtgggag aaaaggtcag ggaagttgat cagaagtacc aagtctcaga gaaaaccaaa     720

tcagcaatcg ctgcagcgga gcagacagtg agcaatgcag gttcagctat aatgaagaac     780

cggtatgttc tcacaggtgc cacgtgggtt actggagcat tcaacaaagt tgctaaagct     840

gcagaagaag ttggacaaaa ggctaaagag aaagttggta tggctgagga agaggataag     900

aggaaagtgg ttgatgagtt tgctagagtt cacttgtctg aatcaccaaa ggcagcttca     960

tcaacgcaag aagccgaacg tgaatcaaaa ctctctgaat ctcctgaagc aaagaaagat    1020

tctgaacatc ttgagccaca atcgaaacca ttgcagcaac aatctcctcc acctatggct    1080

tcagctcctg ctccggctca accttgagat atgcaatcaa agacctttct gattcttgtt    1140

gtaaacggta aaacttggaa ctaatctctc tcagattgtt gaagatgaag attgaacttg    1200

ttatttagga cgaagacttg tgttcttgta acattggatt catggtcgat ttggtaatta    1260

gaccttaaaa agaaaacaat tttgttcttt tcgtttttct taaacttatt taaaccgggc    1320

t                                                                    1321
```

<210> SEQ ID NO 50
<211> LENGTH: 313
<212> TYPE: PRT

<213> ORGANISM: Arabidopsis thaliana

<400> SEQUENCE: 50

```
Met Thr Met Thr Thr Val Lys Val Ser Asn Val Ser Leu Gly Ala Thr
1               5                   10                  15

Asp Arg Asp Leu Lys Glu Phe Phe Ser Phe Ser Gly Asp Ile Leu Tyr
            20                  25                  30

Leu Glu Thr Gln Ser Glu Thr Glu Arg Thr Lys Leu Ala Tyr Val Thr
        35                  40                  45

Phe Lys Asp Leu Gln Gly Ala Glu Thr Ala Val Leu Leu Ser Gly Ala
    50                  55                  60

Thr Ile Val Asp Ser Ser Val Ile Val Ser Met Ala Pro Asp Tyr Gln
65                  70                  75                  80

Leu Ser Pro Glu Ala Leu Ala Ser Leu Glu Pro Lys Asp Ser Asn Lys
                85                  90                  95

Ser Pro Lys Ala Gly Asp Ser Val Leu Arg Lys Ala Glu Asp Val Val
            100                 105                 110

Ser Ser Met Leu Ala Lys Gly Phe Ile Leu Gly Lys Asp Ala Ile Ala
        115                 120                 125

Lys Ala Lys Ser Val Asp Glu Lys His Gln Leu Thr Ser Thr Ala Ser
    130                 135                 140

Ala Lys Val Ala Ser Phe Asp Lys Lys Ile Gly Phe Thr Asp Lys Ile
145                 150                 155                 160

Asn Thr Gly Thr Val Val Val Gly Glu Lys Val Arg Glu Val Asp Gln
                165                 170                 175

Lys Tyr Gln Val Ser Glu Lys Thr Lys Ser Ala Ile Ala Ala Ala Glu
            180                 185                 190

Gln Thr Val Ser Asn Ala Gly Ser Ala Ile Met Lys Asn Arg Tyr Val
        195                 200                 205

Leu Thr Gly Ala Thr Trp Val Thr Gly Ala Phe Asn Lys Val Ala Lys
    210                 215                 220

Ala Ala Glu Glu Val Gly Gln Lys Ala Lys Glu Lys Val Gly Met Ala
225                 230                 235                 240

Glu Glu Glu Asp Lys Arg Lys Val Val Asp Glu Phe Ala Arg Val His
                245                 250                 255

Leu Ser Glu Ser Pro Lys Ala Ala Ser Ser Thr Gln Glu Ala Glu Arg
            260                 265                 270

Glu Ser Lys Leu Ser Glu Ser Pro Glu Ala Lys Lys Asp Ser Glu His
        275                 280                 285

Leu Glu Pro Gln Ser Lys Pro Leu Gln Gln Gln Ser Pro Pro Pro Met
    290                 295                 300

Ala Ser Ala Pro Ala Pro Ala Gln Pro
305                 310
```

<210> SEQ ID NO 51
<211> LENGTH: 1309
<212> TYPE: DNA
<213> ORGANISM: Arabidopsis thaliana

<400> SEQUENCE: 51

```
caatctctct ctccgcggtt cacgtttttt ctcaatctgt ccggagagag agaaactcac      60

cggggaatct tgaaatcacc atcacatcct ctcttccctc gatctccgtt atcgactgta     120

aatcgaattt tgttgttgct ttgttttctt gggcgaataa aagaggataa tttagtggcg     180

gggttttcga gaaagagaga gaaagaatga gttttcaaga tttagaggcg ggaagaggaa     240
```

-continued

```
gatcattagc ttcttcaagg aacatcaatg gtggtggtag tagacaagac acgactcaag    300

atgttgcttc tggtatattt cagatcaata caagtgtttc cactttccat cgtcttgtca    360

atactcttgg tactcctaaa gatacgcctg agctcagaga gaagctgcat aagacaagat    420

tatatattgg acagttagtg aaagatacat cagctaaact taaagaagct agtgaaactg    480

atcatcaaag aggtgtaaat caaaagaaga agattgtgga tgctaagctt gcaaaggact    540

ttcaagctgt gttgaaagag tttcaaaagg ctcagcgtct tgctgctgaa agagaaaccg    600

tatatgctcc tcttgtccac aagccatctc ttccctcaag ctacacatcc agtgagatag    660

atgtgaatgg agataagcat ccagagcagc gtgcccttct tgtggaatca aaaagacaag    720

aacttgtact gttggacaat gagattgcgt tcaatgaggc tgttattgag gaaagagagc    780

aagggataca agaaattcag cagcaaattg gcgaggtgca cgagatcttc aaagacttgg    840

cagtgttggt gcacgatcaa ggaaacatga tagatgatat tggtactcac atcgataact    900

cttacgctgc aactgcccaa ggaaaatccc atctcgtaag gcatcaaaga cacaaagatc    960

aaattcttct ctgacgtgct tgctcttggt gatttttggt atcgtgctca tgattgttat   1020

tatagtgctc gcagtttgat ttccccaagc tcataaaagc atggacaagt gcttcatcat   1080

caatcaagaa gcatcaatga gtatatgttt gtcacgactc tctttgttcc tacaatttag   1140

tctgttggac tattggtctc ttgtttcttg ttatcgagta tatagagtag ttcactttgg   1200

tttgatttgg cttgtgtttg ctgagtcttg gttctgaagg agagagtgtt actgctttgt   1260

ctctgtaata taacttggtt ctgaaggaaa atcctctgtt tgtgttctt              1309
```

<210> SEQ ID NO 52
<211> LENGTH: 255
<212> TYPE: PRT
<213> ORGANISM: Arabidopsis thaliana

<400> SEQUENCE: 52

```
Met Ser Phe Gln Asp Leu Glu Ala Gly Arg Gly Arg Ser Leu Ala Ser
1               5                   10                  15

Ser Arg Asn Ile Asn Gly Gly Gly Ser Arg Gln Asp Thr Thr Gln Asp
            20                  25                  30

Val Ala Ser Gly Ile Phe Gln Ile Asn Thr Ser Val Ser Thr Phe His
        35                  40                  45

Arg Leu Val Asn Thr Leu Gly Thr Pro Lys Asp Thr Pro Glu Leu Arg
    50                  55                  60

Glu Lys Leu His Lys Thr Arg Leu Tyr Ile Gly Gln Leu Val Lys Asp
65                  70                  75                  80

Thr Ser Ala Lys Leu Lys Glu Ala Ser Glu Thr Asp His Gln Arg Gly
                85                  90                  95

Val Asn Gln Lys Lys Lys Ile Val Asp Ala Lys Leu Ala Lys Asp Phe
            100                 105                 110

Gln Ala Val Leu Lys Glu Phe Gln Lys Ala Gln Arg Leu Ala Ala Glu
        115                 120                 125

Arg Glu Thr Val Tyr Ala Pro Leu Val His Lys Pro Ser Leu Pro Ser
    130                 135                 140

Ser Tyr Thr Ser Ser Glu Ile Asp Val Asn Gly Asp Lys His Pro Glu
145                 150                 155                 160

Gln Arg Ala Leu Leu Val Glu Ser Lys Arg Gln Glu Leu Val Leu Leu
                165                 170                 175

Asp Asn Glu Ile Ala Phe Asn Glu Ala Val Ile Glu Glu Arg Glu Gln
```

-continued

```
            180                 185                 190

Gly Ile Gln Glu Ile Gln Gln Gln Ile Gly Glu Val His Glu Ile Phe
        195                 200                 205

Lys Asp Leu Ala Val Leu Val His Asp Gln Gly Asn Met Ile Asp Asp
    210                 215                 220

Ile Gly Thr His Ile Asp Asn Ser Tyr Ala Ala Thr Ala Gln Gly Lys
225                 230                 235                 240

Ser His Leu Val Arg His Gln Arg His Lys Asp Gln Ile Leu Leu
                245                 250                 255


<210> SEQ ID NO 53
<211> LENGTH: 1662
<212> TYPE: DNA
<213> ORGANISM: Arabidopsis thaliana

<400> SEQUENCE: 53

agagttggaa ttttcccggg gaagctcttt tcaatggagg tccttgcgag ctcttcatta     60

tccccaattt cttttactaa gcctaacaaa ataaacccta atttctcaat ccagatttca    120

aaagctagca aatttagtta tgctcgtagt cgtagtaaca tttcaaggag caatgcagca    180

aacccaggag tcgtgttcgt ctgtaataga tttctgtgtg ttatcgaaag aaatgatcag    240

aggaaattat ctgggaaggt tatgatgaaa tcttctgtta atttcagaca gaatctctct    300

gttgcattag ttcggatcgt ttctgttctg cttgtctctt ccatttctgt tgttaccact    360

gattcaccac catcatgggg tcttactgaa gagaatcttc tcttcctcga ggcttggaga    420

acaattgatc gtgcttatat tgataaaacc tttaatggac aaagctggtt tcgttacaga    480

gagactgctt tacgaaatga gcctatgaac actcgagaag agacatacat ggctatcaag    540

aaaatggtgg caacactaga tgatcctttt actcgattct tggagcccgg aaagttcaag    600

agtttgcggt cggggactca aggggcggtt acgggtgttg ggctgtcgat aggttacccc    660

actgcatcag atggaccacc agctgggctt gttgttatat cagctgctcc aggaggtcct    720

gcaaataggg cggggatatt acctggcgat gttattcaag gaattgataa tacaaccaca    780

gaaactctta ccatatacga tgctgcacag atgttgcagg gacctgaagg aagtgcagtg    840

gagctagcga ttcgcagtgg acctgaaacg agactcttaa ctttgacgcg agagcgggtt    900

tctgtgaatc cagtgaagtc aagattatgt gaacttcctg gttctgggag taactcccct    960

aagattggct atatcaagct aacaacattc aatcaaaatg cttctagtgc ggtaagggaa   1020

gctattgaaa ccttgagagg caacaatgta aacgcattcg tcttggacct tcgagacaat   1080

agtggaggtt ctttcccaga aggaattgag attgctaaat tttggttaga taaaggagtg   1140

attgtgtata tttgcgatag tcgaggtgtt agagatatat atgatactga tggaagcaat   1200

gctatagcaa cctctgagcc tcttgccgtt cttgttaaca aaggcaccgc gagtgccagc   1260

gagatattag caggtgcctt gaaagataat aaacgtgctc tggtttatgg agaaccaact   1320

tacggaaaag gcaagataca gtcggttttt gagctttctg atggttcggg cttggcagta   1380

acagttgctc gatatgaaac accagctcac acagatatag acaaagtcgg tgtaactcct   1440

gatcatccat tgccaaagtc gtttccgaaa gatgaagagg cgttctgtgg atgccttaag   1500

gatcctacag ctgcttgtta tctcaatcaa ggcctacttt tttctagatg attttgtttt   1560

gttcaaactt tgttctgaca acatatgact aaaatttatt gactcaagct ttgtactttt   1620

gaagattcgc catagcttta gctaatcgaa accagaaatt tc                       1662
```

<210> SEQ ID NO 54
<211> LENGTH: 505
<212> TYPE: PRT
<213> ORGANISM: Arabidopsis thaliana

<400> SEQUENCE: 54

```
Met Glu Val Leu Ala Ser Ser Ser Leu Ser Pro Ile Ser Phe Thr Lys
1               5                   10                  15

Pro Asn Lys Ile Asn Pro Asn Phe Ser Ile Gln Ile Ser Lys Ala Ser
            20                  25                  30

Lys Phe Ser Tyr Ala Arg Ser Arg Ser Asn Ile Ser Arg Ser Asn Ala
        35                  40                  45

Ala Asn Pro Gly Val Val Phe Val Cys Asn Arg Phe Leu Cys Val Ile
    50                  55                  60

Glu Arg Asn Asp Gln Arg Lys Leu Ser Gly Lys Val Met Met Lys Ser
65                  70                  75                  80

Ser Val Asn Phe Arg Gln Asn Leu Ser Val Ala Leu Val Arg Ile Val
                85                  90                  95

Ser Val Leu Leu Val Ser Ser Ile Ser Val Val Thr Thr Asp Ser Pro
            100                 105                 110

Pro Ser Trp Gly Leu Thr Glu Glu Asn Leu Leu Phe Leu Glu Ala Trp
        115                 120                 125

Arg Thr Ile Asp Arg Ala Tyr Ile Asp Lys Thr Phe Asn Gly Gln Ser
    130                 135                 140

Trp Phe Arg Tyr Arg Glu Thr Ala Leu Arg Asn Glu Pro Met Asn Thr
145                 150                 155                 160

Arg Glu Glu Thr Tyr Met Ala Ile Lys Lys Met Val Ala Thr Leu Asp
                165                 170                 175

Asp Pro Phe Thr Arg Phe Leu Glu Pro Gly Lys Phe Lys Ser Leu Arg
            180                 185                 190

Ser Gly Thr Gln Gly Ala Val Thr Gly Val Gly Leu Ser Ile Gly Tyr
        195                 200                 205

Pro Thr Ala Ser Asp Gly Pro Pro Ala Gly Leu Val Val Ile Ser Ala
    210                 215                 220

Ala Pro Gly Gly Pro Ala Asn Arg Ala Gly Ile Leu Pro Gly Asp Val
225                 230                 235                 240

Ile Gln Gly Ile Asp Asn Thr Thr Thr Glu Thr Leu Thr Ile Tyr Asp
                245                 250                 255

Ala Ala Gln Met Leu Gln Gly Pro Glu Gly Ser Ala Val Glu Leu Ala
            260                 265                 270

Ile Arg Ser Gly Pro Glu Thr Arg Leu Leu Thr Leu Thr Arg Glu Arg
        275                 280                 285

Val Ser Val Asn Pro Val Lys Ser Arg Leu Cys Glu Leu Pro Gly Ser
    290                 295                 300

Gly Ser Asn Ser Pro Lys Ile Gly Tyr Ile Lys Leu Thr Thr Phe Asn
305                 310                 315                 320

Gln Asn Ala Ser Ser Ala Val Arg Glu Ala Ile Glu Thr Leu Arg Gly
                325                 330                 335

Asn Asn Val Asn Ala Phe Val Leu Asp Leu Arg Asp Asn Ser Gly Gly
            340                 345                 350

Ser Phe Pro Glu Gly Ile Glu Ile Ala Lys Phe Trp Leu Asp Lys Gly
        355                 360                 365

Val Ile Val Tyr Ile Cys Asp Ser Arg Gly Val Arg Asp Ile Tyr Asp
    370                 375                 380
```

-continued

```
Thr Asp Gly Ser Asn Ala Ile Ala Thr Ser Glu Pro Leu Ala Val Leu
385                 390                 395                 400

Val Asn Lys Gly Thr Ala Ser Ala Ser Glu Ile Leu Ala Gly Ala Leu
                405                 410                 415

Lys Asp Asn Lys Arg Ala Leu Val Tyr Gly Glu Pro Thr Tyr Gly Lys
            420                 425                 430

Gly Lys Ile Gln Ser Val Phe Glu Leu Ser Asp Gly Ser Gly Leu Ala
        435                 440                 445

Val Thr Val Ala Arg Tyr Glu Thr Pro Ala His Thr Asp Ile Asp Lys
    450                 455                 460

Val Gly Val Thr Pro Asp His Pro Leu Pro Lys Ser Phe Pro Lys Asp
465                 470                 475                 480

Glu Glu Ala Phe Cys Gly Cys Leu Lys Asp Pro Thr Ala Ala Cys Tyr
                485                 490                 495

Leu Asn Gln Gly Leu Leu Phe Ser Arg
            500                 505
```

<210> SEQ ID NO 55
<211> LENGTH: 1692
<212> TYPE: DNA
<213> ORGANISM: Arabidopsis thaliana

<400> SEQUENCE: 55

```
agagttggaa ttttcccggg gaagctcttt tcaatggagg tccttgcgag ctcttcatta     60

tccccaattt cttttactaa gcctaacaaa ataaacccta atttctcaat ccaggtgaaa    120

ttgtgggtaa aacaacctcc aaagatttca aaagctagca aatttagtta tgctcgtagt    180

cgtagtaaca tttcaaggag caatgcagca aacccaggag tcgtgttcgt ctgtaataga    240

tttctgtgtg ttatcgaaag aaatgatcag aggaaattat ctgggaaggt tatgatgaaa    300

tcttctgtta atttcagaca gaatctctct gttgcattag ttcggatcgt ttctgttctg    360

cttgtctctt ccatttctgt tgttaccact gattcaccac catcatgggg tcttactgaa    420

gagaatcttc tcttcctcga ggcttggaga acaattgatc gtgcttatat tgataaaacc    480

tttaatggac aaagctggtt tcgttacaga gagactgctt tacgaaatga gcctatgaac    540

actcgagaag agacatacat ggctatcaag aaaatggtgg caacactaga tgatcctttt    600

actcgattct tggagcccgg aaagttcaag agtttgcggt cggggactca aggggcggtt    660

acgggtgttg ggctgtcgat aggttacccc actgcatcag atggaccacc agctgggctt    720

gttgttatat cagctgctcc aggaggtcct gcaaataggg cggggatatt acctggcgat    780

gttattcaag gaattgataa tacaaccaca gaaactctta ccatatacga tgctgcacag    840

atgttgcagg gacctgaagg aagtgcagtg gagctagcga ttcgcagtgg acctgaaacg    900

agactcttaa ctttgacgcg agagcgggtt tctgtgaatc cagtgaagtc aagattatgt    960

gaacttcctg gttctgggag taactcccct aagattggct atatcaagct aacaacattc   1020

aatcaaaatg cttctagtgc ggtaagggaa gctattgaaa ccttgagagg caacaatgta   1080

aacgcattcg tcttggacct tcgagacaat agtggaggtt ctttcccaga aggaattgag   1140

attgctaaat tttggttaga taaaggagtg attgtgtata tttgcgatag tcgaggtgtt   1200

agagatatat atgatactga tggaagcaat gctatagcaa cctctgagcc tcttgccgtt   1260

cttgttaaca aaggcaccgc gagtgccagc gagatattag caggtgcctt gaaagataat   1320

aaacgtgctc tggtttatgg agaaccaact tacggaaaag gcaagataca gtcggttttt   1380

gagctttctg atggttcggg cttggcagta acagttgctc gatatgaaac accagctcac   1440
```

-continued

```
acagatatag acaaagtcgg tgtaactcct gatcatccat tgccaaagtc gtttccgaaa   1500

gatgaagagg cgttctgtgg atgccttaag gatcctacag ctgcttgtta tctcaatcaa   1560

ggcctacttt tttctagatg attttgtttt gttcaaactt tgttctgaca acatatgact   1620

aaaatttatt gactcaagct ttgtactttt gaagattcgc catagcttta gctaatcgaa   1680

accagaaatt tc                                                       1692
```

<210> SEQ ID NO 56
<211> LENGTH: 515
<212> TYPE: PRT
<213> ORGANISM: Arabidopsis thaliana

<400> SEQUENCE: 56

```
Met Glu Val Leu Ala Ser Ser Ser Leu Ser Pro Ile Ser Phe Thr Lys
1               5                   10                  15

Pro Asn Lys Ile Asn Pro Asn Phe Ser Ile Gln Val Lys Leu Trp Val
            20                  25                  30

Lys Gln Pro Pro Lys Ile Ser Lys Ala Ser Lys Phe Ser Tyr Ala Arg
        35                  40                  45

Ser Arg Ser Asn Ile Ser Arg Ser Asn Ala Ala Asn Pro Gly Val Val
    50                  55                  60

Phe Val Cys Asn Arg Phe Leu Cys Val Ile Glu Arg Asn Asp Gln Arg
65                  70                  75                  80

Lys Leu Ser Gly Lys Val Met Met Lys Ser Ser Val Asn Phe Arg Gln
                85                  90                  95

Asn Leu Ser Val Ala Leu Val Arg Ile Val Ser Val Leu Leu Val Ser
            100                 105                 110

Ser Ile Ser Val Val Thr Thr Asp Ser Pro Pro Ser Trp Gly Leu Thr
        115                 120                 125

Glu Glu Asn Leu Leu Phe Leu Glu Ala Trp Arg Thr Ile Asp Arg Ala
    130                 135                 140

Tyr Ile Asp Lys Thr Phe Asn Gly Gln Ser Trp Phe Arg Tyr Arg Glu
145                 150                 155                 160

Thr Ala Leu Arg Asn Glu Pro Met Asn Thr Arg Glu Glu Thr Tyr Met
                165                 170                 175

Ala Ile Lys Lys Met Val Ala Thr Leu Asp Asp Pro Phe Thr Arg Phe
            180                 185                 190

Leu Glu Pro Gly Lys Phe Lys Ser Leu Arg Ser Gly Thr Gln Gly Ala
        195                 200                 205

Val Thr Gly Val Gly Leu Ser Ile Gly Tyr Pro Thr Ala Ser Asp Gly
    210                 215                 220

Pro Pro Ala Gly Leu Val Val Ile Ser Ala Ala Pro Gly Gly Pro Ala
225                 230                 235                 240

Asn Arg Ala Gly Ile Leu Pro Gly Asp Val Ile Gln Gly Ile Asp Asn
                245                 250                 255

Thr Thr Thr Glu Thr Leu Thr Ile Tyr Asp Ala Ala Gln Met Leu Gln
            260                 265                 270

Gly Pro Glu Gly Ser Ala Val Glu Leu Ala Ile Arg Ser Gly Pro Glu
        275                 280                 285

Thr Arg Leu Leu Thr Leu Thr Arg Glu Arg Val Ser Val Asn Pro Val
    290                 295                 300

Lys Ser Arg Leu Cys Glu Leu Pro Gly Ser Gly Ser Asn Ser Pro Lys
305                 310                 315                 320
```

-continued

```
Ile Gly Tyr Ile Lys Leu Thr Thr Phe Asn Gln Asn Ala Ser Ser Ala
                325                 330                 335

Val Arg Glu Ala Ile Glu Thr Leu Arg Gly Asn Asn Val Asn Ala Phe
            340                 345                 350

Val Leu Asp Leu Arg Asp Asn Ser Gly Gly Ser Phe Pro Glu Gly Ile
        355                 360                 365

Glu Ile Ala Lys Phe Trp Leu Asp Lys Gly Val Ile Val Tyr Ile Cys
    370                 375                 380

Asp Ser Arg Gly Val Arg Asp Ile Tyr Asp Thr Asp Gly Ser Asn Ala
385                 390                 395                 400

Ile Ala Thr Ser Glu Pro Leu Ala Val Leu Val Asn Lys Gly Thr Ala
                405                 410                 415

Ser Ala Ser Glu Ile Leu Ala Gly Ala Leu Lys Asp Asn Lys Arg Ala
            420                 425                 430

Leu Val Tyr Gly Glu Pro Thr Tyr Gly Lys Gly Lys Ile Gln Ser Val
        435                 440                 445

Phe Glu Leu Ser Asp Gly Ser Gly Leu Ala Val Thr Val Ala Arg Tyr
    450                 455                 460

Glu Thr Pro Ala His Thr Asp Ile Asp Lys Val Gly Val Thr Pro Asp
465                 470                 475                 480

His Pro Leu Pro Lys Ser Phe Pro Lys Asp Glu Glu Ala Phe Cys Gly
                485                 490                 495

Cys Leu Lys Asp Pro Thr Ala Ala Cys Tyr Leu Asn Gln Gly Leu Leu
            500                 505                 510

Phe Ser Arg
        515


<210> SEQ ID NO 57
<211> LENGTH: 1639
<212> TYPE: DNA
<213> ORGANISM: Arabidopsis thaliana

<400> SEQUENCE: 57

atgtttgtaa atttcaaata cttctctttc tttatccgta cgaaaatgga cggtgttacc      60

ggcggaggaa cgaatatcgg cgaggctgtg acggcgccac caccgcggaa tccgcatcca     120

gcgactttac ttaatgcgaa ctctttaccg ccccctttcc ttagcaagac gtatgacatg     180

gtggaagatc cggcgacgga cgcgattgtc tcatggagtc cgacgaacaa tagcttcatt     240

gtttgggatc caccggagtt ttctcgtgat cttctaccta aatacttcaa acacaacaat     300

ttctccagct ttgttcgcca gttaaacacc tatggtttta ggaaagtgga tccagatcga     360

tgggaatttg ctaatgaagg tttcttaaga ggtcaaaaac atctattgaa gaagataagc     420

cggagaaaat ctgttcaggg acatggtagt agtagtagta atccacaatc tcagcaatta     480

tctcagggtc aaggttcaat ggctgcatta tcttcatgtg ttgaggttgg gaaatttggg     540

ttagaggaag aagttgaaca gcttaaaaga gacaaaaacg tgttgatgca ggaactcgtt     600

aagttacgcc agcagcaaca aacaacagat aataaacttc aggttttggt taaacatctt     660

caggttatgg agcagaggca acaacagatt atgtctttcc ttgctaaagc tgtacagaat     720

cctactttcc tctctcagtt tatacagaag cagactgata gtaatatgca tgtaaccgag     780

gccaataaga agcggagact cagagaggat agtactgctg ctactgagag taatagtcat     840

agccatagct tggaagcatc agatggacag atagttaagt atcagccact tagaaacgat     900

tcaatgatgt ggaacatgat gaaaacagat gataagtatc cgtttcttga cgggttctca     960
```

```
tctccaaacc aggtatcagg agtcactctt caagaggtac tacccataac ttcaggacag   1020

tcacaggcat atgcatctgt accatcagga cagcctttat catacttacc ctctacttca   1080

acttctctcc cggataccat aatgccagag acttcccaga taccacaatt gacacgagag   1140

agtatcaacg acttccctac agaaaacttc atggatacag agaagaatgt tccagaggca   1200

ttcatctctc caagcccatt ccttgatggt ggttcagtcc cgattcagct tgagggaata   1260

cccgaagacc ccgagattga tgaactaatg agtaactttg aattccttga agaatatatg   1320

ccagaaagcc cagtttttgg agatgcaact acactagaga acaacaacaa caacaacaac   1380

aacaacaaca acaacaacaa caacaacaac aacaacaaca caaatggtag acatatggat   1440

aagcttatag aagaattggg tcttctcaca tcagaaacag aacactagta aaggattatg   1500

tttagtatcc attgtaaagt ctttctctac taacattatc gttaggactc agtagtacgg   1560

ttgcaacttt gtgcagaaat ctttccttgg ataatagaag agttgtattt attattaaaa   1620

agaaaatgcc attttttct                                                1639


<210> SEQ ID NO 58
<211> LENGTH: 495
<212> TYPE: PRT
<213> ORGANISM: Arabidopsis thaliana

<400> SEQUENCE: 58

Met Phe Val Asn Phe Lys Tyr Phe Ser Phe Phe Ile Arg Thr Lys Met
1               5                   10                  15

Asp Gly Val Thr Gly Gly Gly Thr Asn Ile Gly Glu Ala Val Thr Ala
            20                  25                  30

Pro Pro Pro Arg Asn Pro His Pro Ala Thr Leu Leu Asn Ala Asn Ser
        35                  40                  45

Leu Pro Pro Pro Phe Leu Ser Lys Thr Tyr Asp Met Val Glu Asp Pro
    50                  55                  60

Ala Thr Asp Ala Ile Val Ser Trp Ser Pro Thr Asn Asn Ser Phe Ile
65                  70                  75                  80

Val Trp Asp Pro Pro Glu Phe Ser Arg Asp Leu Leu Pro Lys Tyr Phe
                85                  90                  95

Lys His Asn Asn Phe Ser Ser Phe Val Arg Gln Leu Asn Thr Tyr Gly
            100                 105                 110

Phe Arg Lys Val Asp Pro Asp Arg Trp Glu Phe Ala Asn Glu Gly Phe
        115                 120                 125

Leu Arg Gly Gln Lys His Leu Leu Lys Lys Ile Ser Arg Arg Lys Ser
    130                 135                 140

Val Gln Gly His Gly Ser Ser Ser Ser Asn Pro Gln Ser Gln Gln Leu
145                 150                 155                 160

Ser Gln Gly Gln Gly Ser Met Ala Ala Leu Ser Ser Cys Val Glu Val
                165                 170                 175

Gly Lys Phe Gly Leu Glu Glu Glu Val Glu Gln Leu Lys Arg Asp Lys
            180                 185                 190

Asn Val Leu Met Gln Glu Leu Val Lys Leu Arg Gln Gln Gln Gln Thr
        195                 200                 205

Thr Asp Asn Lys Leu Gln Val Leu Val Lys His Leu Gln Val Met Glu
    210                 215                 220

Gln Arg Gln Gln Gln Ile Met Ser Phe Leu Ala Lys Ala Val Gln Asn
225                 230                 235                 240

Pro Thr Phe Leu Ser Gln Phe Ile Gln Lys Gln Thr Asp Ser Asn Met
                245                 250                 255
```

```
His Val Thr Glu Ala Asn Lys Lys Arg Arg Leu Arg Glu Asp Ser Thr
            260                 265                 270

Ala Ala Thr Glu Ser Asn Ser His Ser His Ser Leu Glu Ala Ser Asp
        275                 280                 285

Gly Gln Ile Val Lys Tyr Gln Pro Leu Arg Asn Asp Ser Met Met Trp
    290                 295                 300

Asn Met Met Lys Thr Asp Asp Lys Tyr Pro Phe Leu Asp Gly Phe Ser
305                 310                 315                 320

Ser Pro Asn Gln Val Ser Gly Val Thr Leu Gln Glu Val Leu Pro Ile
                325                 330                 335

Thr Ser Gly Gln Ser Gln Ala Tyr Ala Ser Val Pro Ser Gly Gln Pro
            340                 345                 350

Leu Ser Tyr Leu Pro Ser Thr Ser Thr Ser Leu Pro Asp Thr Ile Met
        355                 360                 365

Pro Glu Thr Ser Gln Ile Pro Gln Leu Thr Arg Glu Ser Ile Asn Asp
    370                 375                 380

Phe Pro Thr Glu Asn Phe Met Asp Thr Glu Lys Asn Val Pro Glu Ala
385                 390                 395                 400

Phe Ile Ser Pro Ser Pro Phe Leu Asp Gly Gly Ser Val Pro Ile Gln
                405                 410                 415

Leu Glu Gly Ile Pro Glu Asp Pro Glu Ile Asp Glu Leu Met Ser Asn
            420                 425                 430

Phe Glu Phe Leu Glu Glu Tyr Met Pro Glu Ser Pro Val Phe Gly Asp
        435                 440                 445

Ala Thr Thr Leu Glu Asn Asn Asn Asn Asn Asn Asn Asn Asn Asn Asn
    450                 455                 460

Asn Asn Asn Asn Asn Asn Asn Asn Asn Thr Asn Gly Arg His Met Asp
465                 470                 475                 480

Lys Leu Ile Glu Glu Leu Gly Leu Leu Thr Ser Glu Thr Glu His
                485                 490                 495
```

<210> SEQ ID NO 59
<211> LENGTH: 1025
<212> TYPE: DNA
<213> ORGANISM: Arabidopsis thaliana

<400> SEQUENCE: 59

```
gaggaaggag agtgagagag agagagagaa atgagttcgt cctcgtcgcc ggcgattgaa      60

ccagacacac cggacctgat ttgccagctc gataatgttc aaggaatggt cgatgcactc     120

acttgcgtcc gatggaaacg ccaccagaat caggttgtct tcaagccaaa gtttatcttc     180

aacgcgagct attcacgaaa tacgagtatg gagctcaagg taggccgaga ttcggaatca     240

gcttagggct tcttgttgat tgcttgaaca cattttcatc acctggacat tctaatacta     300

tagaaatcaa gtatccagga cctgatatgg agcttcttct caaatctgtt gataccttaa     360

actcttgcat ctactctgag ataagaacta gaattcccga aactgttact tgggactaca     420

actttgagca ggcgggaatc gcgccactta cttttacagt aaagtcagcg gcgttgaagg     480

aagcaataga tgatcttgaa tggcctggtt caagtgtaca gatcagtctt caaaaggaac     540

ccccttgtgt aatctttaga ggagaaggac atggagactt gcagatagac ttcatgtatt     600

atgccaacac agatcttctc cttgcctttc attgtgatac cgaagtctct tacgggtaca     660

aatacaagtt tttgaaagca acaacggcaa acataccggg aaacgtagtg agagaaaaca     720

ggggaagcaa actaacaata ggaagaggag gaatgttgaa agttcagcac ttggtttcag     780
```

-continued

```
tttctaaagc tttagctcca caagtggaat ccgcagggta tcagccaccg agtcggattg    840

cttatataga gttctttgtg aagcctgaag agcctgctga ttaatagatt ttctccttca    900

gttactttat ctttgtaatt ctagttcttc tttttagtca gtctctcaat actatcagta    960

tcagtatcag aaagaaagaa agaaaaagtt taaggcttgc aaagaaaaac tgcgtgtggt   1020

ttcac                                                               1025
```

<210> SEQ ID NO 60
<211> LENGTH: 250
<212> TYPE: PRT
<213> ORGANISM: Arabidopsis thaliana

<400> SEQUENCE: 60

```
Met Glu Thr Pro Pro Glu Ser Gly Cys Leu Gln Ala Lys Val Tyr Leu
1               5                   10                  15

Gln Arg Glu Leu Phe Thr Lys Tyr Glu Tyr Gly Ala Gln Gly Arg Pro
            20                  25                  30

Arg Phe Gly Ile Ser Leu Gly Leu Leu Val Asp Cys Leu Asn Thr Phe
        35                  40                  45

Ser Ser Pro Gly His Ser Asn Thr Ile Glu Ile Lys Tyr Pro Gly Pro
    50                  55                  60

Asp Met Glu Leu Leu Leu Lys Ser Val Asp Thr Leu Asn Ser Cys Ile
65                  70                  75                  80

Tyr Ser Glu Ile Arg Thr Arg Ile Pro Glu Thr Val Thr Trp Asp Tyr
                85                  90                  95

Asn Phe Glu Gln Ala Gly Ile Ala Pro Leu Thr Phe Thr Val Lys Ser
            100                 105                 110

Ala Ala Leu Lys Glu Ala Ile Asp Asp Leu Glu Trp Pro Gly Ser Ser
        115                 120                 125

Val Gln Ile Ser Leu Gln Lys Glu Pro Pro Cys Val Ile Phe Arg Gly
    130                 135                 140

Glu Gly His Gly Asp Leu Gln Ile Asp Phe Met Tyr Tyr Ala Asn Thr
145                 150                 155                 160

Asp Leu Leu Leu Ala Phe His Cys Asp Thr Glu Val Ser Tyr Gly Tyr
                165                 170                 175

Lys Tyr Lys Phe Leu Lys Ala Thr Thr Ala Asn Ile Pro Gly Asn Val
            180                 185                 190

Val Arg Glu Asn Arg Gly Ser Lys Leu Thr Ile Gly Arg Gly Gly Met
        195                 200                 205

Leu Lys Val Gln His Leu Val Ser Val Ser Lys Ala Leu Ala Pro Gln
    210                 215                 220

Val Glu Ser Ala Gly Tyr Gln Pro Pro Ser Arg Ile Ala Tyr Ile Glu
225                 230                 235                 240

Phe Phe Val Lys Pro Glu Glu Pro Ala Asp
                245                 250
```

<210> SEQ ID NO 61
<211> LENGTH: 1017
<212> TYPE: DNA
<213> ORGANISM: Arabidopsis thaliana

<400> SEQUENCE: 61

```
ggaaggagag tgagagagag agagagaaat gagttcgtcc tcgtcgccgg cgattgaacc     60

agacacaccg gacctgattt gccagctcga taatgttcaa ggaatggtcg atgcactcac    120
```

-continued

```
ttgcgtccga tggaaacgcc accaggatgc tttagtagaa ttatctgaac acggaatagt    180

tttgattgtt gaagaatcag gttgtcttca agccaaagtt tatcttcaac gcgagctatt    240

cacgaaatac gagtatggag ctcaaggtag gccgagattc ggaatcagct tagggcttct    300

tgttgattgc ttgaacacat tttcatcacc tggacattct aatactatag aaatcaagta    360

tccaggacct gatatggagc ttcttctcaa atctgttgat accttaaact cttgcatcta    420

ctctgagata agaactagaa ttcccgaaac tgttacttgg gactacaact ttgagcaggc    480

gggaatcgcg ccacttactt ttacagtaaa gtcagcggcg ttgaaggaag caatagatga    540

tcttgaatgg cctggttcaa gtgtacagat cagtcttcaa aaggaacccc cttgtgtaat    600

ctttagagga gaaggacatg gagacttgca gatagacttc atgtattatg ccaacacaga    660

tcttctcctt gcctttcatt gtgataccga agtctcttac gggtacaaat acaagttttt    720

gaaagcaaca acggcaaaca taccgggaaa cgtagtgaga gaaaacaggg gaagcaaact    780

aacaatagga agaggaggaa tgttgaaagt tcagcacttg gtttcagttt ctaaagcttt    840

agctccacaa gtggaatccg cagggtatca gccaccgagt cggattgctt atatagagtt    900

ctttgtgaag cctgaagagc ctgctgatta atagattttc tccttcagtt actttatctt    960

tgtaattcta gttcttcttt ttagtcagtc tctcaatact atcagtatca gtatcag      1017
```

```
<210> SEQ ID NO 62
<211> LENGTH: 300
<212> TYPE: PRT
<213> ORGANISM: Arabidopsis thaliana

<400> SEQUENCE: 62

Met Ser Ser Ser Ser Ser Pro Ala Ile Glu Pro Asp Thr Pro Asp Leu
1               5                   10                  15

Ile Cys Gln Leu Asp Asn Val Gln Gly Met Val Asp Ala Leu Thr Cys
            20                  25                  30

Val Arg Trp Lys Arg His Gln Asp Ala Leu Val Glu Leu Ser Glu His
        35                  40                  45

Gly Ile Val Leu Ile Val Glu Glu Ser Gly Cys Leu Gln Ala Lys Val
    50                  55                  60

Tyr Leu Gln Arg Glu Leu Phe Thr Lys Tyr Glu Tyr Gly Ala Gln Gly
65                  70                  75                  80

Arg Pro Arg Phe Gly Ile Ser Leu Gly Leu Leu Val Asp Cys Leu Asn
                85                  90                  95

Thr Phe Ser Ser Pro Gly His Ser Asn Thr Ile Glu Ile Lys Tyr Pro
            100                 105                 110

Gly Pro Asp Met Glu Leu Leu Leu Lys Ser Val Asp Thr Leu Asn Ser
        115                 120                 125

Cys Ile Tyr Ser Glu Ile Arg Thr Arg Ile Pro Glu Thr Val Thr Trp
    130                 135                 140

Asp Tyr Asn Phe Glu Gln Ala Gly Ile Ala Pro Leu Thr Phe Thr Val
145                 150                 155                 160

Lys Ser Ala Ala Leu Lys Glu Ala Ile Asp Asp Leu Glu Trp Pro Gly
                165                 170                 175

Ser Ser Val Gln Ile Ser Leu Gln Lys Glu Pro Pro Cys Val Ile Phe
            180                 185                 190

Arg Gly Glu Gly His Gly Asp Leu Gln Ile Asp Phe Met Tyr Tyr Ala
        195                 200                 205

Asn Thr Asp Leu Leu Leu Ala Phe His Cys Asp Thr Glu Val Ser Tyr
    210                 215                 220
```

-continued

```
Gly Tyr Lys Tyr Lys Phe Leu Lys Ala Thr Thr Ala Asn Ile Pro Gly
225                 230                 235                 240

Asn Val Val Arg Glu Asn Arg Gly Ser Lys Leu Thr Ile Gly Arg Gly
                245                 250                 255

Gly Met Leu Lys Val Gln His Leu Val Ser Val Ser Lys Ala Leu Ala
            260                 265                 270

Pro Gln Val Glu Ser Ala Gly Tyr Gln Pro Pro Ser Arg Ile Ala Tyr
        275                 280                 285

Ile Glu Phe Phe Val Lys Pro Glu Glu Pro Ala Asp
    290                 295                 300
```

<210> SEQ ID NO 63
<211> LENGTH: 3909
<212> TYPE: DNA
<213> ORGANISM: Arabidopsis thaliana

<400> SEQUENCE: 63

```
atgttgaggt cacggcgttc acgttcccgt cacggtgcac aagcttgcgc cgttatgtct      60

gccgttcttc ttctcgcttc cgtctcactt ctctacactc gtctctcact cttctcatct     120

cactcgccga atcacctccg ctctggctcc agcgaagaca cagttttgtt ccctgattct     180

gtcctcgtct cagattccga cgttgaaacc accggcggag gaggaagagg atccactacc     240

tcaaccgaag acagaatcga cgagcacgac gatgcgatcg aagacgacgg cgtttcgaat     300

gaggaagatg agaatcaaga cgcagagcaa gagcaagaag tggatcttaa tcggaacaag     360

gctgcttcat cttctgggtt ttacttcgat catgttaatg gagttataag aagagctttc     420

aataaacgat ctatagatga atgggattac gattacacag gttttagtat agattctgat     480

agttcaggag ataagagtag tagagctgcg tttggatctg atgatgttcc tttagatgaa     540

tctattcgta ggaagattgt tgaggttacg agtgtggaag atgccttgtt gttaaaatct     600

ggtaaaaagg tctcgccttt gagacaaggt tggggagatt ggtttgataa gaaaggtgat     660

ttcttgagga gagatagaat gtttaagtcg aatattgaga ctttgaatcc gttgaataat     720

ccaatgttgc aggatcctga tagtgttggg aatactggat tgactagagg tgataaggtt     780

gtgcagaaat ggaggttgaa tcagattaag agaaaccctt ttatggcaaa gaagccattg     840

agtgttgttt cagagaagaa ggaaccaaat gagtttaggt tgctgagtag tgttggtgag     900

atcaagagag gtgaacgtaa gacattagac aatgatgaga aaattgagag agaggaacag     960

aagaatgtgg aatctgagag gaagcatgat gaggttacag aacatatgta tgcagatgga    1020

acaaaatggg gatattatcc tggtatagaa ccgagtttgt cgttttcgga ttttatggat    1080

tcgtttttta gaaaggagaa atgttctatg agagtgttta tggtgtggaa ttcacctggt    1140

tggatgttta gtgttagaca tcaaagaggg cttgagagct tactgtctca gcatcgagat    1200

gcttgtgttg tggttttctc agagactgtt gagcttgatt tcttcaggaa cagctttgtg    1260

aaagatagtt ataaagttgc tgtggcaatg cccaaccttg atgagttgct gcaggatact    1320

cctactcatg tatttgcttc tgtatggttt gattggagaa aaactaagtt ctatcctact    1380

cactacagtg aactcgttcg gcttgccgcc ctttataaat atggcggggt ttacctcgat    1440

tctgatgtga tagttttggg ttcattatcg tctttgagaa atactattgg catggaggat    1500

caggtagccg gtgaatcact gaacggtgct gttatgtcat tcgaaaagaa aagcccattc    1560

ttacttgaat gcttgaacga gtactacttg acttacgatg ataagtgttt gcgatgcaac    1620

ggagcagatc tcttgacccg agtagctaaa cggtttttaa acgggaagaa tcggcgtatg    1680
```

-continued

```
aatcaacagg agctgaacat tcgaccgtcc tctgttttct tcccaatcaa ctcacaacag   1740
atcacaaact attttgcata ccctgcaata gaagatgaga gatcgcagca agacgaatcg   1800
ttcaagaaga tactcaatga gtccttaacg ttccatttct ggaacagcgt aacttcctca   1860
ctgatccctg aacctgagag ccttgtggct aaattgatct cttccgatca tgaatccagt   1920
gatttgtctc ttccttcttc tccatcatcg tcaccttctc aatgtctcgt taaatcggtc   1980
tgttcattgg tttgtacttc ctatcttcgt caaaaccatg tcgtatcatc cccacaccga   2040
gtcaatctcg acttcgatgc taattctctt acccacgagc aagcgatcac tgtggtggct   2100
tcactcgcga gcgaatctgg ttcgatggtt gctctgtgct tcttctattg ggcagtgggt   2160
ttcgaaaagt tccgacattt catgagattg tatctcgtaa ccgctgattc tttgcttgct   2220
aatgggaatt tgcagaaagc tcacgaggtt atgcgatgca tgcttagaaa tttctcggag   2280
attgggagat tgaatgaggc tgttggtatg gttatggata tgcagaatca ggggttaaca   2340
cctagctcga taactatgaa ttgtgttctc gaaattgccg ttgagttggg tttgattgaa   2400
tatgcagaga atgtgttcga cgaaatgtct gtgagaggag tagttccgga ttctagttct   2460
tataagctta tggttattgg ttgttttaga gatggtaaga ttcaggaagc tgatagatgg   2520
ttaactggaa tgattcaaag aggatttatt cctgataacg ctacatgtac cttgattctc   2580
actgcattgt gtgagaatgg tttagtgaat agagcgattt ggtatttccg taagatgatt   2640
gatctagggt ttaagccaaa cttgataaat tttacgtctt tgattgatgg gttatgcaag   2700
aagggtagta tcaagcaggc ttttgaaatg ttagaggaaa tggttagaaa tgggtggaag   2760
ccaaatgtgt atacacacac ggctttaatt gatgggctat gtaaaagagg atggactgag   2820
aaagcgttta ggctgttcct gaaactcgtt cgtagtgata cttacaaacc caatgtgcat   2880
acttatactt cgatgattgg tgggtattgc aaggaagata agttgaaccg tgcagagatg   2940
ttgtttagta gaatgaaaga acagggtttg tttccgaacg tgaacacgta tacaacactc   3000
atcaatggtc actgtaaagc aggaagcttc ggtagagcgt acgagttgat gaatttgatg   3060
ggtgatgaag gttttatgcc gaatatttat acgtataatg cagctattga cagtctctgt   3120
aagaaatcaa gggcacctga ggcatatgag ttgctgaata aagcattttc ttgtggatta   3180
gaagctgatg gagttactta cactattctt attcaagaac agtgtaagca aaatgacatt   3240
aaccaagctc ttgctttttt ctgtcggatg aataagactg gttttgaagc cgatatgcgc   3300
ctgaacaaca tactgatagc tgcattttgt aggcaaaaga aaatgaagga aagtgagagg   3360
ctttttcagt tggtggtgag tcttggattg attccaacga aggagactta tacgtctatg   3420
ataagctgtt attgtaaaga aggcgacatt gatctggctt tgaaatattt tcacaacatg   3480
aagaggcatg gttgtgttcc tgatagcttc acttatggtt cactaataag cggtctctgc   3540
aagaagtcca tggtagatga agcttgtaag ctttacgaag cgatgattga cagaggttta   3600
tctcctcctg aggtaactcg agtcacatta gcatatgagt attgtaagag gaatgattca   3660
gccaatgcaa tgattctgct tgaaccttta gataagaagc tgtggattag aacggttagg   3720
acacttgtta gaaagttatg tagcgagaag aaagttggag tggcagctct gttctttcag   3780
aaattgttgg agaaggacag tagtgctgat cgtgttacct tagctgcttt cactacagct   3840
tgttctgagt ctggcaaaaa caaccttgtt actgatttga ctgagagaat ctccagagga   3900
gtaggctag                                                           3909
```

<210> SEQ ID NO 64

<211> LENGTH: 1302
<212> TYPE: PRT
<213> ORGANISM: Arabidopsis thaliana

<400> SEQUENCE: 64

```
Met Leu Arg Ser Arg Arg Ser Arg Ser Arg His Gly Ala Gln Ala Cys
1               5                   10                  15

Ala Val Met Ser Ala Val Leu Leu Leu Ala Ser Val Ser Leu Leu Tyr
            20                  25                  30

Thr Arg Leu Ser Leu Phe Ser Ser His Ser Pro Asn His Leu Arg Ser
        35                  40                  45

Gly Ser Ser Glu Asp Thr Val Leu Phe Pro Asp Ser Val Leu Val Ser
    50                  55                  60

Asp Ser Asp Val Glu Thr Thr Gly Gly Gly Gly Arg Gly Ser Thr Thr
65                  70                  75                  80

Ser Thr Glu Asp Arg Ile Asp Glu His Asp Asp Ala Ile Glu Asp Asp
                85                  90                  95

Gly Val Ser Asn Glu Glu Asp Glu Asn Gln Asp Ala Glu Gln Glu Gln
            100                 105                 110

Glu Val Asp Leu Asn Arg Asn Lys Ala Ala Ser Ser Ser Gly Phe Tyr
        115                 120                 125

Phe Asp His Val Asn Gly Val Ile Arg Arg Ala Phe Asn Lys Arg Ser
    130                 135                 140

Ile Asp Glu Trp Asp Tyr Asp Tyr Thr Gly Phe Ser Ile Asp Ser Asp
145                 150                 155                 160

Ser Ser Gly Asp Lys Ser Ser Arg Ala Ala Phe Gly Ser Asp Asp Val
                165                 170                 175

Pro Leu Asp Glu Ser Ile Arg Arg Lys Ile Val Glu Val Thr Ser Val
            180                 185                 190

Glu Asp Ala Leu Leu Leu Lys Ser Gly Lys Lys Val Ser Pro Leu Arg
        195                 200                 205

Gln Gly Trp Gly Asp Trp Phe Asp Lys Lys Gly Asp Phe Leu Arg Arg
    210                 215                 220

Asp Arg Met Phe Lys Ser Asn Ile Glu Thr Leu Asn Pro Leu Asn Asn
225                 230                 235                 240

Pro Met Leu Gln Asp Pro Asp Ser Val Gly Asn Thr Gly Leu Thr Arg
                245                 250                 255

Gly Asp Lys Val Val Gln Lys Trp Arg Leu Asn Gln Ile Lys Arg Asn
            260                 265                 270

Pro Phe Met Ala Lys Lys Pro Leu Ser Val Val Ser Glu Lys Lys Glu
        275                 280                 285

Pro Asn Glu Phe Arg Leu Leu Ser Ser Val Gly Glu Ile Lys Arg Gly
    290                 295                 300

Glu Arg Lys Thr Leu Asp Asn Asp Glu Lys Ile Glu Arg Glu Glu Gln
305                 310                 315                 320

Lys Asn Val Glu Ser Glu Arg Lys His Asp Glu Val Thr Glu His Met
                325                 330                 335

Tyr Ala Asp Gly Thr Lys Trp Gly Tyr Tyr Pro Gly Ile Glu Pro Ser
            340                 345                 350

Leu Ser Phe Ser Asp Phe Met Asp Ser Phe Phe Arg Lys Glu Lys Cys
        355                 360                 365

Ser Met Arg Val Phe Met Val Trp Asn Ser Pro Gly Trp Met Phe Ser
    370                 375                 380

Val Arg His Gln Arg Gly Leu Glu Ser Leu Leu Ser Gln His Arg Asp
```

-continued

```
385                 390                 395                 400

Ala Cys Val Val Val Phe Ser Glu Thr Val Glu Leu Asp Phe Phe Arg
                405                 410                 415

Asn Ser Phe Val Lys Asp Ser Tyr Lys Val Ala Val Ala Met Pro Asn
            420                 425                 430

Leu Asp Glu Leu Leu Gln Asp Thr Pro Thr His Val Phe Ala Ser Val
        435                 440                 445

Trp Phe Asp Trp Arg Lys Thr Lys Phe Tyr Pro Thr His Tyr Ser Glu
    450                 455                 460

Leu Val Arg Leu Ala Ala Leu Tyr Lys Tyr Gly Gly Val Tyr Leu Asp
465                 470                 475                 480

Ser Asp Val Ile Val Leu Gly Ser Leu Ser Ser Leu Arg Asn Thr Ile
                485                 490                 495

Gly Met Glu Asp Gln Val Ala Gly Glu Ser Leu Asn Gly Ala Val Met
            500                 505                 510

Ser Phe Glu Lys Lys Ser Pro Phe Leu Leu Glu Cys Leu Asn Glu Tyr
        515                 520                 525

Tyr Leu Thr Tyr Asp Asp Lys Cys Leu Arg Cys Asn Gly Ala Asp Leu
    530                 535                 540

Leu Thr Arg Val Ala Lys Arg Phe Leu Asn Gly Lys Asn Arg Arg Met
545                 550                 555                 560

Asn Gln Gln Glu Leu Asn Ile Arg Pro Ser Ser Val Phe Phe Pro Ile
                565                 570                 575

Asn Ser Gln Gln Ile Thr Asn Tyr Phe Ala Tyr Pro Ala Ile Glu Asp
            580                 585                 590

Glu Arg Ser Gln Gln Asp Glu Ser Phe Lys Lys Ile Leu Asn Glu Ser
        595                 600                 605

Leu Thr Phe His Phe Trp Asn Ser Val Thr Ser Ser Leu Ile Pro Glu
    610                 615                 620

Pro Glu Ser Leu Val Ala Lys Leu Ile Ser Ser Asp His Glu Ser Ser
625                 630                 635                 640

Asp Leu Ser Leu Pro Ser Ser Pro Ser Ser Ser Pro Ser Gln Cys Leu
                645                 650                 655

Val Lys Ser Val Cys Ser Leu Val Cys Thr Ser Tyr Leu Arg Gln Asn
            660                 665                 670

His Val Val Ser Ser Pro His Arg Val Asn Leu Asp Phe Asp Ala Asn
        675                 680                 685

Ser Leu Thr His Glu Gln Ala Ile Thr Val Val Ala Ser Leu Ala Ser
    690                 695                 700

Glu Ser Gly Ser Met Val Ala Leu Cys Phe Phe Tyr Trp Ala Val Gly
705                 710                 715                 720

Phe Glu Lys Phe Arg His Phe Met Arg Leu Tyr Leu Val Thr Ala Asp
                725                 730                 735

Ser Leu Leu Ala Asn Gly Asn Leu Gln Lys Ala His Glu Val Met Arg
            740                 745                 750

Cys Met Leu Arg Asn Phe Ser Glu Ile Gly Arg Leu Asn Glu Ala Val
        755                 760                 765

Gly Met Val Met Asp Met Gln Asn Gln Gly Leu Thr Pro Ser Ser Ile
    770                 775                 780

Thr Met Asn Cys Val Leu Glu Ile Ala Val Glu Leu Gly Leu Ile Glu
785                 790                 795                 800

Tyr Ala Glu Asn Val Phe Asp Glu Met Ser Val Arg Gly Val Val Pro
                805                 810                 815
```

-continued

```
Asp Ser Ser Ser Tyr Lys Leu Met Val Ile Gly Cys Phe Arg Asp Gly
            820                 825                 830

Lys Ile Gln Glu Ala Asp Arg Trp Leu Thr Gly Met Ile Gln Arg Gly
        835                 840                 845

Phe Ile Pro Asp Asn Ala Thr Cys Thr Leu Ile Leu Thr Ala Leu Cys
    850                 855                 860

Glu Asn Gly Leu Val Asn Arg Ala Ile Trp Tyr Phe Arg Lys Met Ile
865                 870                 875                 880

Asp Leu Gly Phe Lys Pro Asn Leu Ile Asn Phe Thr Ser Leu Ile Asp
                885                 890                 895

Gly Leu Cys Lys Lys Gly Ser Ile Lys Gln Ala Phe Glu Met Leu Glu
            900                 905                 910

Glu Met Val Arg Asn Gly Trp Lys Pro Asn Val Tyr Thr His Thr Ala
        915                 920                 925

Leu Ile Asp Gly Leu Cys Lys Arg Gly Trp Thr Glu Lys Ala Phe Arg
    930                 935                 940

Leu Phe Leu Lys Leu Val Arg Ser Asp Thr Tyr Lys Pro Asn Val His
945                 950                 955                 960

Thr Tyr Thr Ser Met Ile Gly Gly Tyr Cys Lys Glu Asp Lys Leu Asn
                965                 970                 975

Arg Ala Glu Met Leu Phe Ser Arg Met Lys Glu Gln Gly Leu Phe Pro
            980                 985                 990

Asn Val Asn Thr Tyr Thr Thr Leu  Ile Asn Gly His Cys  Lys Ala Gly
        995                 1000                1005

Ser Phe  Gly Arg Ala Tyr Glu  Leu Met Asn Leu Met  Gly Asp Glu
    1010                1015                1020

Gly Phe  Met Pro Asn Ile Tyr  Thr Tyr Asn Ala Ala  Ile Asp Ser
    1025                1030                1035

Leu Cys  Lys Lys Ser Arg Ala  Pro Glu Ala Tyr Glu  Leu Leu Asn
    1040                1045                1050

Lys Ala  Phe Ser Cys Gly Leu  Glu Ala Asp Gly Val  Thr Tyr Thr
    1055                1060                1065

Ile Leu  Ile Gln Glu Gln Cys  Lys Gln Asn Asp Ile  Asn Gln Ala
    1070                1075                1080

Leu Ala  Phe Phe Cys Arg Met  Asn Lys Thr Gly Phe  Glu Ala Asp
    1085                1090                1095

Met Arg  Leu Asn Asn Ile Leu  Ile Ala Ala Phe Cys  Arg Gln Lys
    1100                1105                1110

Lys Met  Lys Glu Ser Glu Arg  Leu Phe Gln Leu Val  Val Ser Leu
    1115                1120                1125

Gly Leu  Ile Pro Thr Lys Glu  Thr Tyr Thr Ser Met  Ile Ser Cys
    1130                1135                1140

Tyr Cys  Lys Glu Gly Asp Ile  Asp Leu Ala Leu Lys  Tyr Phe His
    1145                1150                1155

Asn Met  Lys Arg His Gly Cys  Val Pro Asp Ser Phe  Thr Tyr Gly
    1160                1165                1170

Ser Leu  Ile Ser Gly Leu Cys  Lys Lys Ser Met Val  Asp Glu Ala
    1175                1180                1185

Cys Lys  Leu Tyr Glu Ala Met  Ile Asp Arg Gly Leu  Ser Pro Pro
    1190                1195                1200

Glu Val  Thr Arg Val Thr Leu  Ala Tyr Glu Tyr Cys  Lys Arg Asn
    1205                1210                1215
```

-continued

```
Asp Ser  Ala Asn Ala Met Ile  Leu Leu Glu Pro Leu  Asp Lys Lys
    1220                 1225                 1230

Leu Trp  Ile Arg Thr Val Arg  Thr Leu Val Arg Lys  Leu Cys Ser
    1235                 1240                 1245

Glu Lys  Lys Val Gly Val Ala  Ala Leu Phe Phe Gln  Lys Leu Leu
    1250                 1255                 1260

Glu Lys  Asp Ser Ser Ala Asp  Arg Val Thr Leu Ala  Ala Phe Thr
    1265                 1270                 1275

Thr Ala  Cys Ser Glu Ser Gly  Lys Asn Asn Leu Val  Thr Asp Leu
    1280                 1285                 1290

Thr Glu  Arg Ile Ser Arg Gly  Val Gly
    1295                 1300
```

<210> SEQ ID NO 65
<211> LENGTH: 1028
<212> TYPE: DNA
<213> ORGANISM: Arabidopsis thaliana

<400> SEQUENCE: 65

```
ggctgataaa ccaaccaggc aacgaccaat ggaccctcct agtcctcctc ctcctcccat     60

tcctgaatcc cgaccacgac ctcttactcc tcccgtgctc ctaacccgac cacgacctcc    120

tcttccttat gctcgccctc ttcagccacc gcaaagtctt ccaccccgac cacgacccca    180

ggtgtttgtt agtttccgag gaaaggagct gcgccacggc ttcgtgagtc atgtagtgaa    240

agccttgaga attgcagggg tcaacgtttt cattgatagc aacgagatga aagggagaga    300

ccttcaaaac ctcttcaaga gaatcgaaaa ctcaaagatg gcactcgtga tcttctctga    360

ccggttctcg gagtcagact ggtgcttaaa cgagctcgtg aagattgatg attgcgtgaa    420

ggaagggaaa ctaacagtga tccctgtctt ctacagggtc aatacagacg acgtgaaaaa    480

tttcaaaggt aaatttggaa gttgttttat agaaacggtg cagagacagt ctcctaagga    540

ggaacctatg gccgaacgtt gggtgaactc tgtgaaatct atttcgtcca agaccggctt    600

cacctcagaa gtccacagaa tagatagcta tcttgtggat gcgattgttc gggacgttaa    660

gagacagcta ccatacgttc ccactaaaga gaaggaattg cccattgaaa cagagatttt    720

cttcgctctt gttttggctg gtctctgtaa tttcatagca cctttaatat tcaatgacac    780

gagtttctac aagactcctc aatggtttgt aggtgttttg tttttggttc taatccgcag    840

gaagttcgcc tgaccgtgtg agtgatcgcg tgctttgaca tgatcaggct cgtgtttgta    900

cttgtacatg tgtgtgtttt gtgtgtttgt taatatttat atataaagaa aatgtgcata    960

atttacccat atatatgcat tacccgcttt tcatgcctgt gtgagttgga atatgtgtaa   1020

ctgttaag                                                            1028
```

<210> SEQ ID NO 66
<211> LENGTH: 274
<212> TYPE: PRT
<213> ORGANISM: Arabidopsis thaliana

<400> SEQUENCE: 66

```
Met Asp Pro Pro Ser Pro Pro Pro Pro Pro Ile Pro Glu Ser Arg Pro
1               5                   10                  15

Arg Pro Leu Thr Pro Pro Val Leu Leu Thr Arg Pro Arg Pro Pro Leu
            20                  25                  30

Pro Tyr Ala Arg Pro Leu Gln Pro Pro Gln Ser Leu Pro Pro Arg Pro
        35                  40                  45
```

-continued

```
Arg Pro Gln Val Phe Val Ser Phe Arg Gly Lys Glu Leu Arg His Gly
    50                  55                  60

Phe Val Ser His Val Val Lys Ala Leu Arg Ile Ala Gly Val Asn Val
65                  70                  75                  80

Phe Ile Asp Ser Asn Glu Met Lys Gly Arg Asp Leu Gln Asn Leu Phe
                85                  90                  95

Lys Arg Ile Glu Asn Ser Lys Met Ala Leu Val Ile Phe Ser Asp Arg
            100                 105                 110

Phe Ser Glu Ser Asp Trp Cys Leu Asn Glu Leu Val Lys Ile Asp Asp
        115                 120                 125

Cys Val Lys Glu Gly Lys Leu Thr Val Ile Pro Val Phe Tyr Arg Val
    130                 135                 140

Asn Thr Asp Asp Val Lys Asn Phe Lys Gly Lys Phe Gly Ser Cys Phe
145                 150                 155                 160

Ile Glu Thr Val Gln Arg Gln Ser Pro Lys Glu Glu Pro Met Ala Glu
                165                 170                 175

Arg Trp Val Asn Ser Val Lys Ser Ile Ser Ser Lys Thr Gly Phe Thr
            180                 185                 190

Ser Glu Val His Arg Ile Asp Ser Tyr Leu Val Asp Ala Ile Val Arg
        195                 200                 205

Asp Val Lys Arg Gln Leu Pro Tyr Val Pro Thr Lys Glu Lys Glu Leu
    210                 215                 220

Pro Ile Glu Thr Glu Ile Phe Phe Ala Leu Val Leu Ala Gly Leu Cys
225                 230                 235                 240

Asn Phe Ile Ala Pro Leu Ile Phe Asn Asp Thr Ser Phe Tyr Lys Thr
                245                 250                 255

Pro Gln Trp Phe Val Gly Val Leu Phe Leu Val Leu Ile Arg Arg Lys
            260                 265                 270

Phe Ala


<210> SEQ ID NO 67
<211> LENGTH: 1296
<212> TYPE: DNA
<213> ORGANISM: Arabidopsis thaliana

<400> SEQUENCE: 67

atggcctttt cttttgacct agccgtcatc ttccaacggg agagaagaat gaagaggaaa      60

tcaagagtaa caataagaag aagaagacga agagacatgt gcaagagcca cgaaccgatg     120

ccatatattc ctttcgatct cgtgatcgag attctaacaa gacttcctgc caagtccctt     180

atgagattca aatccgtctc aaagctctgg tcatctttga tttgttcccg aacgttcacc     240

aaccgtttgc taagggttcc atcattcata cagcgtctat acgtgacttt gaccttcttg     300

gacaacagcc tgcagcgcaa aagcaaatta ctatcatcgt cgtcttctcc tggctcggac     360

attagtacaa tgtcatcatt tgtagttgac cgagatttga ccaccccatc gatgaaaggc     420

tactacctct ctcacgtttt acgcggcttg atgtgcttcg taaaggagcc aagtgtgaaa     480

atatacaaca ctaccactcg acaacttgtt gtcttacccg acatagaaga atccaacatc     540

atagctgaag accacaagaa taagaagatc atgtatcgta ttggacacga tcccgttggt     600

gatcaatata aagtggtttg catagttgca agacctaatg acgaattcgg agagctcaga     660

aggtacttgt ccgagcattg ggtcttcata ctaggaggag ataaatcaag tggatggaga     720

aaaattcctt gcccatctcc ccatcttcct ataacacaaa tattaagtat caacgggcgt     780

atgcattacc tcgcttgggt acagaagttt gatcctatgc ttgtgacttt cgactttagt     840
```

-continued

```
tctgaggaaa tcagtattct ccaagcacct gaagatatcc gttggtttaa atctaaccct    900

atagaatact atggaaaagt agctctttta aatctttccg atcttaaaag agaatgtacg    960

atgaacctat gggttatgga agatgtagag aagaatatgt ggtcggagaa gactttggta   1020

gtgcatcctt ctcaaatgga tatagtcaag agcactagtt tgagggtagc aggtacaact   1080

agaaacaatg aggttatctt ggtacctcat aatatacgtt atactctaac cggagaggtt   1140

atcgtggaac ctcaaaatac aactctttta tacatttttc tctatgattt acaaaagaat   1200

ctgatgagaa aagttgaaat taaagaacca ccatatcata ctaaattttg ggatgttgtt   1260

gggttagatg atgttgagaa cttcatgtat ctttaa                             1296
```

<210> SEQ ID NO 68
<211> LENGTH: 431
<212> TYPE: PRT
<213> ORGANISM: Arabidopsis thaliana

<400> SEQUENCE: 68

```
Met Ala Phe Ser Phe Asp Leu Ala Val Ile Phe Gln Arg Glu Arg Arg
1               5                   10                  15

Met Lys Arg Lys Ser Arg Val Thr Ile Arg Arg Arg Arg Arg Arg Asp
            20                  25                  30

Met Cys Lys Ser His Glu Pro Met Pro Tyr Ile Pro Phe Asp Leu Val
        35                  40                  45

Ile Glu Ile Leu Thr Arg Leu Pro Ala Lys Ser Leu Met Arg Phe Lys
    50                  55                  60

Ser Val Ser Lys Leu Trp Ser Ser Leu Ile Cys Ser Arg Thr Phe Thr
65                  70                  75                  80

Asn Arg Leu Leu Arg Val Pro Ser Phe Ile Gln Arg Leu Tyr Val Thr
                85                  90                  95

Leu Thr Phe Leu Asp Asn Ser Leu Gln Arg Lys Ser Lys Leu Leu Ser
            100                 105                 110

Ser Ser Ser Ser Pro Gly Ser Asp Ile Ser Thr Met Ser Ser Phe Val
        115                 120                 125

Val Asp Arg Asp Leu Thr Thr Pro Ser Met Lys Gly Tyr Tyr Leu Ser
    130                 135                 140

His Val Leu Arg Gly Leu Met Cys Phe Val Lys Glu Pro Ser Val Lys
145                 150                 155                 160

Ile Tyr Asn Thr Thr Thr Arg Gln Leu Val Val Leu Pro Asp Ile Glu
                165                 170                 175

Glu Ser Asn Ile Ile Ala Glu Asp His Lys Asn Lys Lys Ile Met Tyr
            180                 185                 190

Arg Ile Gly His Asp Pro Val Gly Asp Gln Tyr Lys Val Val Cys Ile
        195                 200                 205

Val Ala Arg Pro Asn Asp Glu Phe Gly Glu Leu Arg Arg Tyr Leu Ser
    210                 215                 220

Glu His Trp Val Phe Ile Leu Gly Gly Asp Lys Ser Ser Gly Trp Arg
225                 230                 235                 240

Lys Ile Pro Cys Pro Ser Pro His Leu Pro Ile Thr Gln Ile Leu Ser
                245                 250                 255

Ile Asn Gly Arg Met His Tyr Leu Ala Trp Val Gln Lys Phe Asp Pro
            260                 265                 270

Met Leu Val Thr Phe Asp Phe Ser Ser Glu Glu Ile Ser Ile Leu Gln
        275                 280                 285
```

-continued

```
Ala Pro Glu Asp Ile Arg Trp Phe Lys Ser Asn Pro Ile Glu Tyr Tyr
    290                 295                 300

Gly Lys Val Ala Leu Leu Asn Leu Ser Asp Leu Lys Arg Glu Cys Thr
305                 310                 315                 320

Met Asn Leu Trp Val Met Glu Asp Val Glu Lys Asn Met Trp Ser Glu
                325                 330                 335

Lys Thr Leu Val Val His Pro Ser Gln Met Asp Ile Val Lys Ser Thr
            340                 345                 350

Ser Leu Arg Val Ala Gly Thr Thr Arg Asn Asn Glu Val Ile Leu Val
        355                 360                 365

Pro His Asn Ile Arg Tyr Thr Leu Thr Gly Glu Val Ile Val Glu Pro
    370                 375                 380

Gln Asn Thr Thr Leu Leu Tyr Ile Phe Leu Tyr Asp Leu Gln Lys Asn
385                 390                 395                 400

Leu Met Arg Lys Val Glu Ile Lys Glu Pro Pro Tyr His Thr Lys Phe
                405                 410                 415

Trp Asp Val Val Gly Leu Asp Asp Val Glu Asn Phe Met Tyr Leu
            420                 425                 430


<210> SEQ ID NO 69
<211> LENGTH: 1338
<212> TYPE: DNA
<213> ORGANISM: Arabidopsis thaliana

<400> SEQUENCE: 69

atggctttta gtttcgacct agccgtcatc ctccagcggg agagaagaag aacgaagagg      60

agacgaagag acttgtgcaa gagccgccaa ccgataccgg agataccttt cgatctcgtg     120

atagagattc tcacgagact gcctgctaaa tcccttatga ggttcaaatc cgtctcaaag     180

ctctggtcat ccttgatttg ttcgcgaaac tttaccaacc gcctgctaaa gctgtcctcc     240

ccaccgcgtt tatttatgtg tttgagctcc tccgacaaca gccacctcaa aactgtacta     300

ctatcattgt cttctcctcc tgactcggac attacaatgt cttccagtgt aattgatcaa     360

gatttgacca tgccgggtat gaaaggctac cagatctctc acgtttttcg cggcttgatg     420

tgcttggtaa aaaaatcaag tgcccaaata tacaatacca cgactagaca acttgttgtc     480

ttacctgaca tagaagaatc caccatctta gctgaagaac acaagagtaa gaagatcatg     540

taccatatcg gacacgatcc cgtttatgat caatataaag tggtttgcat agtttctaga     600

gctagtgacg aagttgaaga gtacacgttc ctgtcagagc attgggtctt gctactagaa     660

ggagagggat cacgtagatg gagaaaaata tcatgcaaat atccaccaca tgttccttta     720

ggacaaggat tgactctcag tggtcgtatg cattacctcg cttgggtgcg tgtgtcggat     780

aaccgtgtgc ttgtgatttt cgatactcat tctgaagaat ttagtatgct ccaagtacct     840

ggagatatct tttggaaata taatggtctt ctagaatacg gtgggaaaat agctatttta     900

aactatacca aagttgatat cgaaggtgtg atggaactat gggttgtgga agatgaagag     960

aagaatcttt ggagcagtaa gatattggtg gtcaatcctt tgcaactgca gatggtcaat    1020

agcattatta gtttgacggt actaggaaca actcgaaacg gcgaagttat cttggtacct    1080

ggtcctgaag acaaaactgt tttcaacatt ttactctatg atttacaaaa gaatcatatt    1140

agaaaaatcg aaatcaaagg aggaccagac cgctatctta acaatatttg ggaagtcgtt    1200

ggaatggatg atgttgagaa cttaatgtat ctttaagttc attggcttgt gtgttaattt    1260

tttttctttt ttaccaattt gtttttctat tattttagtt gttttgttat gctacctaat    1320
```

-continued

```
ttaattgtga agaattcg                                                     1338


<210> SEQ ID NO 70
<211> LENGTH: 411
<212> TYPE: PRT
<213> ORGANISM: Arabidopsis thaliana

<400> SEQUENCE: 70

Met Ala Phe Ser Phe Asp Leu Ala Val Ile Leu Gln Arg Glu Arg Arg
1               5                   10                  15

Arg Thr Lys Arg Arg Arg Arg Asp Leu Cys Lys Ser Arg Gln Pro Ile
            20                  25                  30

Pro Glu Ile Pro Phe Asp Leu Val Ile Glu Ile Leu Thr Arg Leu Pro
        35                  40                  45

Ala Lys Ser Leu Met Arg Phe Lys Ser Val Ser Lys Leu Trp Ser Ser
    50                  55                  60

Leu Ile Cys Ser Arg Asn Phe Thr Asn Arg Leu Leu Lys Leu Ser Ser
65                  70                  75                  80

Pro Pro Arg Leu Phe Met Cys Leu Ser Ser Ser Asp Asn Ser His Leu
                85                  90                  95

Lys Thr Val Leu Leu Ser Leu Ser Ser Pro Pro Asp Ser Asp Ile Thr
            100                 105                 110

Met Ser Ser Ser Val Ile Asp Gln Asp Leu Thr Met Pro Gly Met Lys
        115                 120                 125

Gly Tyr Gln Ile Ser His Val Phe Arg Gly Leu Met Cys Leu Val Lys
    130                 135                 140

Lys Ser Ser Ala Gln Ile Tyr Asn Thr Thr Thr Arg Gln Leu Val Val
145                 150                 155                 160

Leu Pro Asp Ile Glu Glu Ser Thr Ile Leu Ala Glu Glu His Lys Ser
                165                 170                 175

Lys Lys Ile Met Tyr His Ile Gly His Asp Pro Val Tyr Asp Gln Tyr
            180                 185                 190

Lys Val Val Cys Ile Val Ser Arg Ala Ser Asp Glu Val Glu Glu Tyr
        195                 200                 205

Thr Phe Leu Ser Glu His Trp Val Leu Leu Leu Glu Gly Glu Gly Ser
    210                 215                 220

Arg Arg Trp Arg Lys Ile Ser Cys Lys Tyr Pro Pro His Val Pro Leu
225                 230                 235                 240

Gly Gln Gly Leu Thr Leu Ser Gly Arg Met His Tyr Leu Ala Trp Val
                245                 250                 255

Arg Val Ser Asp Asn Arg Val Leu Val Ile Phe Asp Thr His Ser Glu
            260                 265                 270

Glu Phe Ser Met Leu Gln Val Pro Gly Asp Ile Phe Trp Lys Tyr Asn
        275                 280                 285

Gly Leu Leu Glu Tyr Gly Gly Lys Ile Ala Ile Leu Asn Tyr Thr Lys
    290                 295                 300

Val Asp Ile Glu Gly Val Met Glu Leu Trp Val Val Glu Asp Glu Glu
305                 310                 315                 320

Lys Asn Leu Trp Ser Ser Lys Ile Leu Val Val Asn Pro Leu Gln Leu
                325                 330                 335

Gln Met Val Asn Ser Ile Ile Ser Leu Thr Val Leu Gly Thr Thr Arg
            340                 345                 350

Asn Gly Glu Val Ile Leu Val Pro Gly Pro Glu Asp Lys Thr Val Phe
        355                 360                 365
```

-continued

```
Asn Ile Leu Leu Tyr Asp Leu Gln Lys Asn His Ile Arg Lys Ile Glu
    370                 375                 380

Ile Lys Gly Gly Pro Asp Arg Tyr Leu Asn Asn Ile Trp Glu Val Val
385                 390                 395                 400

Gly Met Asp Asp Val Glu Asn Leu Met Tyr Leu
                405                 410


<210> SEQ ID NO 71
<211> LENGTH: 1223
<212> TYPE: DNA
<213> ORGANISM: Arabidopsis thaliana

<400> SEQUENCE: 71

actctttact ctttcttccg tttgctcgaa ccatctagtc taagagaaag aaaaaatact      60

aaagagaaag aagaagagga cttgaatacg gaagcttgag agaatgaaag cgatcgtgat     120

ctcggagcca gatactctcc aaagacttgg cctttataat ccaccacctg gctcaagccc     180

ttaccttggt ctcgaatgtt ctgggaccat tgaatccgtc ggtaaaggcg tctctcgatg     240

gaaagtcgga gaccaggtgt gtgctcttct ttctggagga ggttatgcag agaaagtttc     300

tgttcctgct ggacaaattt tcccaattcc cgctggtatc tctctaaagg atgcagcggc     360

tttccctgaa gtggcatgca ctgtttggtc tactgtcttc atgatgggcc gtctctctgt     420

tggtgaatca ttcttgattc atggaggttc aagtgggatt gggacatttg ctattcagat     480

agctaaacat ctgggagtga gagtatttgt cacagctggg agtgatgaaa agctagctgc     540

gtgcaaagaa ctcggggctg atgtttgtat aaattacaaa accgaggatt ttgttgcaaa     600

ggtaaaagcg gaaaccgatg ggaaaggagt ggatgttatc ttggactgca ttggggcacc     660

gtatttgcag aaaaatctcg acagcttaaa ctttgatgga aggttatgta ttatcggttt     720

aatgggagga gccaatgcag aaataaaact aagtagtctg cttccaaagc gtctcactgt     780

cttaggagct gcattaagac caagaagccc tgaaaacaaa gcagttgttg taagggaagt     840

cgagaagaat gtctggccag cgatagaagc agggaaggta aaaccagtga tttacaagta     900

tttaccattg tcacaagcag cagaaggtca tagccttatg gagagtagca accatattgg     960

taagattctc cttgagactt gattctctgc aaagggagaa atgttcagag acaagagtca    1020

tggtcaataa tcaataaaat ctggtcgatt ctgttcatag atatctcttt acaagagttc    1080

tgtttgttgg cttttatgta tctctgattt ggtcaaaaag acactgtaac tatggaacat    1140

atatagtatc aaataagctg ttgtatacca aacattgatt tcgaagtaga atatgatttt    1200

gtaagaagtt tttatttatt ttg                                            1223


<210> SEQ ID NO 72
<211> LENGTH: 292
<212> TYPE: PRT
<213> ORGANISM: Arabidopsis thaliana

<400> SEQUENCE: 72

Met Lys Ala Ile Val Ile Ser Glu Pro Asp Thr Leu Gln Arg Leu Gly
1               5                   10                  15

Leu Tyr Asn Pro Pro Pro Gly Ser Ser Pro Tyr Leu Gly Leu Glu Cys
            20                  25                  30

Ser Gly Thr Ile Glu Ser Val Gly Lys Gly Val Ser Arg Trp Lys Val
        35                  40                  45

Gly Asp Gln Val Cys Ala Leu Leu Ser Gly Gly Gly Tyr Ala Glu Lys
    50                  55                  60
```

-continued

```
Val Ser Val Pro Ala Gly Gln Ile Phe Pro Ile Pro Ala Gly Ile Ser
65                  70                  75                  80

Leu Lys Asp Ala Ala Ala Phe Pro Glu Val Ala Cys Thr Val Trp Ser
                85                  90                  95

Thr Val Phe Met Met Gly Arg Leu Ser Val Gly Glu Ser Phe Leu Ile
            100                 105                 110

His Gly Gly Ser Ser Gly Ile Gly Thr Phe Ala Ile Gln Ile Ala Lys
        115                 120                 125

His Leu Gly Val Arg Val Phe Val Thr Ala Gly Ser Asp Glu Lys Leu
    130                 135                 140

Ala Ala Cys Lys Glu Leu Gly Ala Asp Val Cys Ile Asn Tyr Lys Thr
145                 150                 155                 160

Glu Asp Phe Val Ala Lys Val Lys Ala Glu Thr Asp Gly Lys Gly Val
                165                 170                 175

Asp Val Ile Leu Asp Cys Ile Gly Ala Pro Tyr Leu Gln Lys Asn Leu
            180                 185                 190

Asp Ser Leu Asn Phe Asp Gly Arg Leu Cys Ile Ile Gly Leu Met Gly
        195                 200                 205

Gly Ala Asn Ala Glu Ile Lys Leu Ser Ser Leu Leu Pro Lys Arg Leu
    210                 215                 220

Thr Val Leu Gly Ala Ala Leu Arg Pro Arg Ser Pro Glu Asn Lys Ala
225                 230                 235                 240

Val Val Val Arg Glu Val Glu Lys Asn Val Trp Pro Ala Ile Glu Ala
                245                 250                 255

Gly Lys Val Lys Pro Val Ile Tyr Lys Tyr Leu Pro Leu Ser Gln Ala
            260                 265                 270

Ala Glu Gly His Ser Leu Met Glu Ser Ser Asn His Ile Gly Lys Ile
        275                 280                 285

Leu Leu Glu Thr
    290
```

<210> SEQ ID NO 73
<211> LENGTH: 1335
<212> TYPE: DNA
<213> ORGANISM: Arabidopsis thaliana

<400> SEQUENCE: 73

```
actctttact ctttcttccg tttgctcgaa ccatctagtc taagagaaag aaaaaatact      60

aaagagaaag aagaagagga cttgaatacg gaagcttgag agaatgaaag cgatcgtgat     120

ctcggagcca ggtaagccgg aggttctgca actccgtgat gtggcagacc cagaagttaa     180

agacgatgag gttctcatca gagttctcgc tactgctttg aatcgtgcag atactctcca     240

aagacttggc ctttataatc caccacctgg ctcaagccct taccttggtc tcgaatgttc     300

tgggaccatt gaatccgtcg gtaaaggcgt ctctcgatgg aaagtcggag accaggtgtg     360

tgctcttctt tctggaggag gttatgcaga gaaagtttct gttcctgctg gacaaatttt     420

cccaattccc gctggtatct ctctaaagga tgcagcggct ttccctgaag tggcatgcac     480

tgtttggtct actgtcttca tgatgggccg tctctctgtt ggtgaatcat tcttgattca     540

tggaggttca agtgggattg ggacatttgc tattcagata gctaaacatc tgggagtgag     600

agtatttgtc acagctggga gtgatgaaaa gctagctgcg tgcaaagaac tcggggctga     660

tgtttgtata aattacaaaa ccgaggattt tgttgcaaag gtaaaagcgg aaaccgatgg     720

gaaaggagtg gatgttatct tggactgcat tggggcaccg tatttgcaga aaaatctcga     780
```

-continued

```
cagcttaaac tttgatggaa ggttatgtat tatcggttta atgggaggag ccaatgcaga    840

aataaaacta agtagtctgc ttccaaagcg tctcactgtc ttaggagctg cattaagacc    900

aagaagccct gaaaacaaag cagttgttgt aagggaagtc gagaagaatg tctggccagc    960

gatagaagca gggaaggtaa aaccagtgat ttacaagtat ttaccattgt cacaagcagc   1020

agaaggtcat agccttatgg agagtagcaa ccatattggt aagattctcc ttgagacttg   1080

attctctgca aagggagaaa tgttcagaga caagagtcat ggtcaataat caataaaatc   1140

tggtcgattc tgttcataga tatctcttta caagagttct gtttgttggc ttttatgtat   1200

ctctgatttg gtcaaaaaga cactgtaact atggaacata tatagtatca aataagctgt   1260

tgtataccaa acattgattt cgaagtagaa tatgattttg taagaagttt ttatttattt   1320

tgggcttaaa aagtg                                                    1335
```

```
<210> SEQ ID NO 74
<211> LENGTH: 325
<212> TYPE: PRT
<213> ORGANISM: Arabidopsis thaliana

<400> SEQUENCE: 74

Met Lys Ala Ile Val Ile Ser Glu Pro Gly Lys Pro Glu Val Leu Gln
1               5                   10                  15

Leu Arg Asp Val Ala Asp Pro Glu Val Lys Asp Asp Glu Val Leu Ile
            20                  25                  30

Arg Val Leu Ala Thr Ala Leu Asn Arg Ala Asp Thr Leu Gln Arg Leu
        35                  40                  45

Gly Leu Tyr Asn Pro Pro Pro Gly Ser Ser Pro Tyr Leu Gly Leu Glu
    50                  55                  60

Cys Ser Gly Thr Ile Glu Ser Val Gly Lys Gly Val Ser Arg Trp Lys
65                  70                  75                  80

Val Gly Asp Gln Val Cys Ala Leu Leu Ser Gly Gly Gly Tyr Ala Glu
                85                  90                  95

Lys Val Ser Val Pro Ala Gly Gln Ile Phe Pro Ile Pro Ala Gly Ile
            100                 105                 110

Ser Leu Lys Asp Ala Ala Ala Phe Pro Glu Val Ala Cys Thr Val Trp
        115                 120                 125

Ser Thr Val Phe Met Met Gly Arg Leu Ser Val Gly Glu Ser Phe Leu
    130                 135                 140

Ile His Gly Gly Ser Ser Gly Ile Gly Thr Phe Ala Ile Gln Ile Ala
145                 150                 155                 160

Lys His Leu Gly Val Arg Val Phe Val Thr Ala Gly Ser Asp Glu Lys
                165                 170                 175

Leu Ala Ala Cys Lys Glu Leu Gly Ala Asp Val Cys Ile Asn Tyr Lys
            180                 185                 190

Thr Glu Asp Phe Val Ala Lys Val Lys Ala Glu Thr Asp Gly Lys Gly
        195                 200                 205

Val Asp Val Ile Leu Asp Cys Ile Gly Ala Pro Tyr Leu Gln Lys Asn
    210                 215                 220

Leu Asp Ser Leu Asn Phe Asp Gly Arg Leu Cys Ile Ile Gly Leu Met
225                 230                 235                 240

Gly Gly Ala Asn Ala Glu Ile Lys Leu Ser Ser Leu Leu Pro Lys Arg
                245                 250                 255

Leu Thr Val Leu Gly Ala Ala Leu Arg Pro Arg Ser Pro Glu Asn Lys
            260                 265                 270
```

-continued

```
Ala Val Val Val Arg Glu Val Glu Lys Asn Val Trp Pro Ala Ile Glu
        275                 280                 285

Ala Gly Lys Val Lys Pro Val Ile Tyr Lys Tyr Leu Pro Leu Ser Gln
    290                 295                 300

Ala Ala Glu Gly His Ser Leu Met Glu Ser Ser Asn His Ile Gly Lys
305                 310                 315                 320

Ile Leu Leu Glu Thr
                325


<210> SEQ ID NO 75
<211> LENGTH: 900
<212> TYPE: DNA
<213> ORGANISM: Arabidopsis thaliana

<400> SEQUENCE: 75

atgagttcgt cgctgcgaca gtggtttgct agagtactcg tgcttacaca gctcatcaat      60

ggagctctgt gttggggaaa agaaggtcac tacacagtct gcaaaatagc cgagagctac     120

tttgaggaag aaactgtagc tgcggtgaag aaacttctac ctaaatcagc tgatggagat     180

ctagcatctg tttgctcatg gcctgatgag attaagcacc attggcaatg gcgatggact     240

agccctttgc actatgttga cacacctgat tacagatgca actacgagta ttgtcgggat     300

tgccatgata ctcataagaa tcaagaccgg tgtgtgacag gagctatttt caattacact     360

atgcaactta tgtccgcttc tgaaaactcg gatactatag tccactacaa cttgacagag     420

gctctcatgt tcttatcaca ttttattgga gatattcacc agcccttgca tgttggtttt     480

ctgggagatg aaggtggaaa cacgataaca gtccgctggt accgtcgcaa aacaaattta     540

caccatgtct gggataacat gataattgag tctgctctta aaacatacta caataaaagt     600

cttccactca tgattgaagc acttcaagcc aatcttacga acgactggtc aaatgatgtt     660

ccattgtggg agtcatgtca acttaaccaa acggcctgtc caaatccgta cgcatctgaa     720

agcataaatc tagcctgcaa gtatgcttat aggaacgcta ccccagggac tactttagga     780

gatgactatt tcctctctcg gttacccatt gtggagaaga gacttgcgca aggtgggata     840

cgcttggcag ccactcttaa ccgtatcttt tcttcaaaac ctaagcatgc tggatcatga     900


<210> SEQ ID NO 76
<211> LENGTH: 299
<212> TYPE: PRT
<213> ORGANISM: Arabidopsis thaliana

<400> SEQUENCE: 76

Met Ser Ser Ser Leu Arg Gln Trp Phe Ala Arg Val Leu Val Leu Thr
1               5                   10                  15

Gln Leu Ile Asn Gly Ala Leu Cys Trp Gly Lys Glu Gly His Tyr Thr
            20                  25                  30

Val Cys Lys Ile Ala Glu Ser Tyr Phe Glu Glu Glu Thr Val Ala Ala
        35                  40                  45

Val Lys Lys Leu Leu Pro Lys Ser Ala Asp Gly Asp Leu Ala Ser Val
    50                  55                  60

Cys Ser Trp Pro Asp Glu Ile Lys His His Trp Gln Trp Arg Trp Thr
65                  70                  75                  80

Ser Pro Leu His Tyr Val Asp Thr Pro Asp Tyr Arg Cys Asn Tyr Glu
                85                  90                  95

Tyr Cys Arg Asp Cys His Asp Thr His Lys Asn Gln Asp Arg Cys Val
            100                 105                 110
```

-continued

```
Thr Gly Ala Ile Phe Asn Tyr Thr Met Gln Leu Met Ser Ala Ser Glu
        115                 120                 125

Asn Ser Asp Thr Ile Val His Tyr Asn Leu Thr Glu Ala Leu Met Phe
    130                 135                 140

Leu Ser His Phe Ile Gly Asp Ile His Gln Pro Leu His Val Gly Phe
145                 150                 155                 160

Leu Gly Asp Glu Gly Gly Asn Thr Ile Thr Val Arg Trp Tyr Arg Arg
                165                 170                 175

Lys Thr Asn Leu His His Val Trp Asp Asn Met Ile Ile Glu Ser Ala
            180                 185                 190

Leu Lys Thr Tyr Tyr Asn Lys Ser Leu Pro Leu Met Ile Glu Ala Leu
        195                 200                 205

Gln Ala Asn Leu Thr Asn Asp Trp Ser Asn Asp Val Pro Leu Trp Glu
    210                 215                 220

Ser Cys Gln Leu Asn Gln Thr Ala Cys Pro Asn Pro Tyr Ala Ser Glu
225                 230                 235                 240

Ser Ile Asn Leu Ala Cys Lys Tyr Ala Tyr Arg Asn Ala Thr Pro Gly
                245                 250                 255

Thr Thr Leu Gly Asp Asp Tyr Phe Leu Ser Arg Leu Pro Ile Val Glu
            260                 265                 270

Lys Arg Leu Ala Gln Gly Gly Ile Arg Leu Ala Ala Thr Leu Asn Arg
        275                 280                 285

Ile Phe Ser Ser Lys Pro Lys His Ala Gly Ser
    290                 295
```

```
<210> SEQ ID NO 77
<211> LENGTH: 1182
<212> TYPE: DNA
<213> ORGANISM: Arabidopsis thaliana

<400> SEQUENCE: 77

aaaaattcaa ggctctttgg cttcttcttt cttctctgca cttgaatcag gttctcattg      60

tttatacact aaaaaaacct tttttgctta ctcggtgttg aaaaactgct tctctgtttt     120

taactttgga aagaaaaaag tagaagcttt tctcagaatg ggttggtcgt tgagaatgtg     180

gattgtgagt atactcgtgc ttacacagct cgttaatgga gctctctgtt ggggagacgc     240

tggtcattac gctgtctgca aaatagctca gagttatttt gaggaagata ctgtagttgc     300

tgtgaagaaa cttctgcctg aatctgcaaa tggtgagcta gcagctgttt gctcatggcc     360

tgatgaaatc aaaaagctcc cgcaatggcg atggactagt gctttgcatt ttgctgatac     420

gcctgattac aaatgcaact atgagtactc tcgggactgt cctaaagact ggtgtgtgac     480

aggggcaatc ttcaattaca ctaaccaact aatgtctact tctgaaaact cacagagtat     540

agtccactat aacttaacag aggctctcat gttcttatca cattatatgg gagatatcca     600

tcagcccttta catgaaggtt ttattggaga tctaggtggt aacaagataa aagttcactg    660

gtacaatcag gaaactaatt tgcaccgtgt gtgggatgat atgataattg agtctgctct     720

agaaacatac tacaattcaa gccttccacg catgattcat gaacttcaag ccaaactcaa     780

gaacggctgg tcaaacgatg taccttcatg ggagtcatgt caacttaacc aaacggcctg     840

cccaaatccg tatgcttctg aaagcattga tcttgcctgc aagtatgctt acaggaacgc     900

caccgcaggg actactttag gagattacta tttcgtctct cggttaccgg tggtagagaa     960

gagacttgca caaggcggaa ttcgcttggc agggactctt aaccgaatat tttctgcaaa    1020

acggaagctt gctagagcat gaaaaaagat ccaggagaat cacttgaaca tccatgaaca    1080
```

ctcttatgta ttaataatgt gtaatggtag tagttaaggt tatggtttgg tattgttcct 1140
gcgttttaac tataataagt atgaaacgaa aactgtacgt ct 1182

<210> SEQ ID NO 78
<211> LENGTH: 294
<212> TYPE: PRT
<213> ORGANISM: Arabidopsis thaliana

<400> SEQUENCE: 78

Met Gly Trp Ser Leu Arg Met Trp Ile Val Ser Ile Leu Val Leu Thr
1 5 10 15

Gln Leu Val Asn Gly Ala Leu Cys Trp Gly Asp Ala Gly His Tyr Ala
20 25 30

Val Cys Lys Ile Ala Gln Ser Tyr Phe Glu Glu Asp Thr Val Val Ala
35 40 45

Val Lys Lys Leu Leu Pro Glu Ser Ala Asn Gly Glu Leu Ala Ala Val
50 55 60

Cys Ser Trp Pro Asp Glu Ile Lys Lys Leu Pro Gln Trp Arg Trp Thr
65 70 75 80

Ser Ala Leu His Phe Ala Asp Thr Pro Asp Tyr Lys Cys Asn Tyr Glu
85 90 95

Tyr Ser Arg Asp Cys Pro Lys Asp Trp Cys Val Thr Gly Ala Ile Phe
100 105 110

Asn Tyr Thr Asn Gln Leu Met Ser Thr Ser Glu Asn Ser Gln Ser Ile
115 120 125

Val His Tyr Asn Leu Thr Glu Ala Leu Met Phe Leu Ser His Tyr Met
130 135 140

Gly Asp Ile His Gln Pro Leu His Glu Gly Phe Ile Gly Asp Leu Gly
145 150 155 160

Gly Asn Lys Ile Lys Val His Trp Tyr Asn Gln Glu Thr Asn Leu His
165 170 175

Arg Val Trp Asp Asp Met Ile Ile Glu Ser Ala Leu Glu Thr Tyr Tyr
180 185 190

Asn Ser Ser Leu Pro Arg Met Ile His Glu Leu Gln Ala Lys Leu Lys
195 200 205

Asn Gly Trp Ser Asn Asp Val Pro Ser Trp Glu Ser Cys Gln Leu Asn
210 215 220

Gln Thr Ala Cys Pro Asn Pro Tyr Ala Ser Glu Ser Ile Asp Leu Ala
225 230 235 240

Cys Lys Tyr Ala Tyr Arg Asn Ala Thr Ala Gly Thr Thr Leu Gly Asp
245 250 255

Tyr Tyr Phe Val Ser Arg Leu Pro Val Val Glu Lys Arg Leu Ala Gln
260 265 270

Gly Gly Ile Arg Leu Ala Gly Thr Leu Asn Arg Ile Phe Ser Ala Lys
275 280 285

Arg Lys Leu Ala Arg Ala
290

<210> SEQ ID NO 79
<211> LENGTH: 1148
<212> TYPE: DNA
<213> ORGANISM: Arabidopsis thaliana

<400> SEQUENCE: 79
aatggataga ttagagaaat agaaaaatca aaagaagctt tggcaaagag ctaaagatca 60

-continued

```
aagcttttct ttgagaatga gattgtggat tgtgagtgta ctcgtgctta cacaccttgt    120

ccatggagct ctctgttggg ggaaggatgg tcactacact gtttgcaaat tagctgaggg    180

attctttgag gatgatacta ttgctgcagt gaagaaactt ctgcctgaat cagttgatgg    240

tggtggacta gcagattttt gctcatggcc tgatgaaatt aaaaaactct cgcaatggca    300

atggactagc actttgcact atgttaacac acctgaatac aggtgcaact acgagtattg    360

ccgggactgc catgacactc ataagcataa ggactggtgt gtgacaggag cgatcttcaa    420

ttacacaaac cagttaatgt ctgcttctga aaactcacag aatatagtcc actacaactt    480

gacagaggct ctcttgttct tgtcacatta tatgggagat gttcatcagc ccttgcatac    540

tggttttctt ggagatctag gtggtaacac aataatagtc aactggtacc ataacaaatc    600

aaatttgcac catgtctggg acaacatgat aattgactct gctctagaaa catactacaa    660

ttcaagcctt ccacacatga ttcaagctct tcaagccaaa ctcaagaacg gctggtcgaa    720

tgatgttccg tcgtggaagt catgtcactt tcaccaaaag gcctgtccaa atctgtatgc    780

ttctgaaagc attgatctcg cctgcaagta tgcttacagg aacgctactc cggggactac    840

tttaggagat gagtatttcc tttctcggtt acccgttgta gagaagagac ttgcacaagg    900

tgggattcgc ttggcagcta ctcttaatcg tatcttttct gcaaaaccga agctcgcagg    960

attatgaatc taagaaaaag atccttgaga acccacgtaa caactccttt taagtgtttt   1020

ttataacact gtgaatggtt gagtcatgac taatgagtga acctccaaaa tcttcatgca   1080

aaaatttgtt attttgggac atggttcaaa cttccaataa caaaccacac taacggataa   1140

cactttgc                                                             1148


<210> SEQ ID NO 80
<211> LENGTH: 296
<212> TYPE: PRT
<213> ORGANISM: Arabidopsis thaliana

<400> SEQUENCE: 80

Met Arg Leu Trp Ile Val Ser Val Leu Val Leu Thr His Leu Val His
1               5                   10                  15

Gly Ala Leu Cys Trp Gly Lys Asp Gly His Tyr Thr Val Cys Lys Leu
            20                  25                  30

Ala Glu Gly Phe Phe Glu Asp Asp Thr Ile Ala Ala Val Lys Lys Leu
        35                  40                  45

Leu Pro Glu Ser Val Asp Gly Gly Gly Leu Ala Asp Phe Cys Ser Trp
    50                  55                  60

Pro Asp Glu Ile Lys Lys Leu Ser Gln Trp Gln Trp Thr Ser Thr Leu
65                  70                  75                  80

His Tyr Val Asn Thr Pro Glu Tyr Arg Cys Asn Tyr Glu Tyr Cys Arg
                85                  90                  95

Asp Cys His Asp Thr His Lys His Lys Asp Trp Cys Val Thr Gly Ala
            100                 105                 110

Ile Phe Asn Tyr Thr Asn Gln Leu Met Ser Ala Ser Glu Asn Ser Gln
        115                 120                 125

Asn Ile Val His Tyr Asn Leu Thr Glu Ala Leu Leu Phe Leu Ser His
    130                 135                 140

Tyr Met Gly Asp Val His Gln Pro Leu His Thr Gly Phe Leu Gly Asp
145                 150                 155                 160

Leu Gly Gly Asn Thr Ile Ile Val Asn Trp Tyr His Asn Lys Ser Asn
                165                 170                 175
```

-continued

```
Leu His His Val Trp Asp Asn Met Ile Ile Asp Ser Ala Leu Glu Thr
            180                 185                 190

Tyr Tyr Asn Ser Ser Leu Pro His Met Ile Gln Ala Leu Gln Ala Lys
        195                 200                 205

Leu Lys Asn Gly Trp Ser Asn Asp Val Pro Ser Trp Lys Ser Cys His
    210                 215                 220

Phe His Gln Lys Ala Cys Pro Asn Leu Tyr Ala Ser Glu Ser Ile Asp
225                 230                 235                 240

Leu Ala Cys Lys Tyr Ala Tyr Arg Asn Ala Thr Pro Gly Thr Thr Leu
                245                 250                 255

Gly Asp Glu Tyr Phe Leu Ser Arg Leu Pro Val Val Glu Lys Arg Leu
            260                 265                 270

Ala Gln Gly Gly Ile Arg Leu Ala Ala Thr Leu Asn Arg Ile Phe Ser
        275                 280                 285

Ala Lys Pro Lys Leu Ala Gly Leu
    290                 295


<210> SEQ ID NO 81
<211> LENGTH: 561
<212> TYPE: DNA
<213> ORGANISM: Arabidopsis thaliana

<400> SEQUENCE: 81

atggaagaga tacaacaaca aacgcagaag gaagaacaaa agcaccgtga agaagaagag      60

gaggaagagg aaggtccgcc tccgggatgg gaatctgcag ttcttcctcc tccaatcgtc     120

accatcaccg ccgccgtaaa ccccaatccc accaccgtag aaattcccga aaaggcccaa     180

atggtatgtg gatcttgcag gcgtttgctt tcttatctaa gaggatccaa acatgttaag     240

tgctcctctt gtcagactgt taatctcgtt cttgaagcta accaggttgg tcaggtgaat     300

tgcaacaatt gcaaactgct actgatgtat ccttatggag ctccagctgt tagatgttcc     360

tcctgcaatt ctgtcacaga tatcagtgaa aacaacaaac gacctccatg gtctgagcag     420

caaggaccac tcaaaagttt aagcagtctc aggagagcag agaattaaac ttgaaccgat     480

ttttgtcaat tttgaaccgg tttgacgact aaaaaccttg taataatgtc gaaggataga     540

tgaaataaaa tcaccattaa t                                               561


<210> SEQ ID NO 82
<211> LENGTH: 155
<212> TYPE: PRT
<213> ORGANISM: Arabidopsis thaliana

<400> SEQUENCE: 82

Met Glu Glu Ile Gln Gln Gln Thr Gln Lys Glu Glu Gln Lys His Arg
1               5                   10                  15

Glu Glu Glu Glu Glu Glu Glu Glu Gly Pro Pro Pro Gly Trp Glu Ser
            20                  25                  30

Ala Val Leu Pro Pro Pro Ile Val Thr Ile Thr Ala Ala Val Asn Pro
        35                  40                  45

Asn Pro Thr Thr Val Glu Ile Pro Glu Lys Ala Gln Met Val Cys Gly
    50                  55                  60

Ser Cys Arg Arg Leu Leu Ser Tyr Leu Arg Gly Ser Lys His Val Lys
65                  70                  75                  80

Cys Ser Ser Cys Gln Thr Val Asn Leu Val Leu Glu Ala Asn Gln Val
                85                  90                  95
```

-continued

```
Gly Gln Val Asn Cys Asn Asn Cys Lys Leu Leu Leu Met Tyr Pro Tyr
            100                 105                 110

Gly Ala Pro Ala Val Arg Cys Ser Ser Cys Asn Ser Val Thr Asp Ile
        115                 120                 125

Ser Glu Asn Asn Lys Arg Pro Pro Trp Ser Glu Gln Gln Gly Pro Leu
    130                 135                 140

Lys Ser Leu Ser Ser Leu Arg Arg Ala Glu Asn
145                 150                 155


<210> SEQ ID NO 83
<211> LENGTH: 1141
<212> TYPE: DNA
<213> ORGANISM: Arabidopsis thaliana

<400> SEQUENCE: 83

aatctctcat tcatcatcct cttttttcaa tctcgtttaa aattaacata atgatgacgc     60

cagtgaagaa aagtatcgcc attagaccgg tgtcgttcta cggaaacggg cttcctcgtc    120

ctcgtttctt cgataatcct aagttcaatg attaccgtgt tgatcctccc ctctctgtgc    180

tagatcctct tctctcatgg gcgagagacg ctcactggtc aatgggtggt ctcaacttca    240

cgcgtctccg tctccaaggc cggatcgaag gaaacgtcaa caagctccgt gcacagcttg    300

agaaatccac ccctgtgaaa ctcgaatctg gaaggaagaa gaagagatct ggttctgagt    360

ctcctccttc tgctccgatt gtggtgaaac gaaggaggta cttagatctg aacgattctg    420

atgatgagga agtcggatct gaagatgaag gtgtggttag aatcaggaga aaactctctg    480

atgattttga tagagtcgct gaagaaagca agactaaact tgttgaagct aacaagaaat    540

cgattaaatc tgagtttgtg gagaagaaga gattgattga gaagaagaag atcgtaaaag    600

ttaacaagac aagttcaacg aggtcatctc caagactggc taagcgtagc tctaattagt    660

tttcatattt agtctcttca ataatttctc ttagggttta gaattgttga gtacttagtt    720

tgtttttttg tatttgtgct tataaatatg gatttatcta tgaactctga ccaatgaact    780

tgaatgcatc aagatatttt tactcactga gttgattctt gtatacaaca aaaatgagaa    840

tcagatttca ctgtagagaa aaaagacagt ttacatgtga ttctctcaat gtctgtgaga    900

acaaagttct ttcaactttt gttccttaag acgtcctgtg actttaccca atctgcaaga    960

ttgttctatc atcaatttgt aaatggaatc ttgttcatgt ggaacaatcc caaagtcatc   1020

gttgaatgtt tccatgcctt ccatgaatag ctgccacact aatgtgcctg cacctgactt   1080

ctttcttttg gctgatttgt aaaccacgtc gaagatgatt ctgtagaact tatctcgctg   1140

c                                                                   1141


<210> SEQ ID NO 84
<211> LENGTH: 202
<212> TYPE: PRT
<213> ORGANISM: Arabidopsis thaliana

<400> SEQUENCE: 84

Met Met Thr Pro Val Lys Lys Ser Ile Ala Ile Arg Pro Val Ser Phe
1               5                   10                  15

Tyr Gly Asn Gly Leu Pro Arg Pro Arg Phe Phe Asp Asn Pro Lys Phe
            20                  25                  30

Asn Asp Tyr Arg Val Asp Pro Pro Leu Ser Val Leu Asp Pro Leu Leu
        35                  40                  45

Ser Trp Ala Arg Asp Ala His Trp Ser Met Gly Gly Leu Asn Phe Thr
    50                  55                  60
```

```
Arg Leu Arg Leu Gln Gly Arg Ile Glu Gly Asn Val Asn Lys Leu Arg
65                  70                  75                  80

Ala Gln Leu Glu Lys Ser Thr Pro Val Lys Leu Glu Ser Gly Arg Lys
                85                  90                  95

Lys Lys Arg Ser Gly Ser Glu Ser Pro Pro Ser Ala Pro Ile Val Val
            100                 105                 110

Lys Arg Arg Arg Tyr Leu Asp Leu Asn Asp Ser Asp Asp Glu Glu Val
        115                 120                 125

Gly Ser Glu Asp Glu Gly Val Val Arg Ile Arg Arg Lys Leu Ser Asp
    130                 135                 140

Asp Phe Asp Arg Val Ala Glu Glu Ser Lys Thr Lys Leu Val Glu Ala
145                 150                 155                 160

Asn Lys Lys Ser Ile Lys Ser Glu Phe Val Glu Lys Lys Arg Leu Ile
                165                 170                 175

Glu Lys Lys Lys Ile Val Lys Val Asn Lys Thr Ser Ser Thr Arg Ser
            180                 185                 190

Ser Pro Arg Leu Ala Lys Arg Ser Ser Asn
        195                 200
```

<210> SEQ ID NO 85
<211> LENGTH: 1651
<212> TYPE: DNA
<213> ORGANISM: Arabidopsis thaliana

<400> SEQUENCE: 85

```
cccttgtttg cttaaagcgt tattgagcga gctatttttt caaatctttg ctaattttct      60

acaaacgatt gatttttccg tctgggtttt ataaaaggtt tgggtttcag agaaattcac     120

ggaacaaggc acagactttt tcttctgggt gggcaccgac taaaaaagga gctctttctc     180

caattctggg tttgaaattt ctgtgtgtgt gtgtgtgaag cagtgaagca ggaggtggca     240

gaagcatggt tcccacaagg aacaggccaa tgctacgaat tctaggtttt tttatatgtg     300

cagctttcat ctatctatca tttcgagatt tgtggttgaa tcacaaaggg aaagcaaagt     360

tagggtttgt gaaaaggaac ggaactcagt ttgtggtgga tgataagcct ctttatgtaa     420

atgggtggaa ctcgtattgg ttcatggacc atgcggttga tgaacatagc agaaaccttg     480

tcggtgaaat gcttgaagct ggagctaaaa tgggtctcac tgtttgtaga acttgggctt     540

tcaatgacgg tggctacaat gctcttcaga tctctcctgg ccgattcgat gagcgagtct     600

ttcaggcttt ggatcatgta attgcagaag cgagaaagca tgatgttaga ttgttgctta     660

gcttagtgaa caacttgcaa gcttatggag ggaagactca gtatgtgaaa tgggcatggc     720

aagaaggtgt tggtcttagt tcttccaatg attccttctt ctttgatcca tctatccgca     780

attacttcaa gaattatctc aaggttctgc tcaccaggaa gaactctgta acgggaatag     840

agtacagaaa cgatcctacg attttcgctt gggagttgat aaacgagcct cgatgcacga     900

ctgatgtctc tggcaaaact ctccaagatt ggatagacga aatgacggga ttcattaagt     960

caatcgatga caagcatctc ctcacagtag gtctggaagg cttctatggt cctaatagcc    1020

cgaaagggct cacagttaat ccagaacagt gggcatccca gctcggaaca gactttgttc    1080

aaaactctaa ctcctcaaac atagattttg catccgttca tatctaccct gatcactggt    1140

ttcataatca gacatttgaa gagaagctaa agtttgtggt gaaatggatg caatctcaca    1200

tagaagatgg attgaaagaa ctaaagaagc cagttctctt cacagagttt ggcctatcaa    1260

accagaacaa ggactacgaa ccatcgcagc gagataagtt ctacagaatc atcttcgacg    1320
```

```
tggtttacaa atcagccaaa agaaagaagt caggtgcagg cacattagtg tggcagctat   1380

tcatggaagg catggaaaca ttcaacgatg actttgggat tgttccacat gaacaagatt   1440

ccatttacaa attgatgata gaacaatctt gcagattggg taaagtcaca ggacgtctta   1500

aggaacaaaa gttgaaagaa ctttgttctc acagacattg agagaatcac atgtaaactg   1560

tctttttct ctacagtgaa atctgattct catttttgtt gtatacaaga atcaactcag   1620

tgagtaaaaa tatcttgatg cattcaagtt c                                  1651


<210> SEQ ID NO 86
<211> LENGTH: 431
<212> TYPE: PRT
<213> ORGANISM: Arabidopsis thaliana

<400> SEQUENCE: 86

Met Val Pro Thr Arg Asn Arg Pro Met Leu Arg Ile Leu Gly Phe Phe
1               5                   10                  15

Ile Cys Ala Ala Phe Ile Tyr Leu Ser Phe Arg Asp Leu Trp Leu Asn
            20                  25                  30

His Lys Gly Lys Ala Lys Leu Gly Phe Val Lys Arg Asn Gly Thr Gln
        35                  40                  45

Phe Val Val Asp Asp Lys Pro Leu Tyr Val Asn Gly Trp Asn Ser Tyr
    50                  55                  60

Trp Phe Met Asp His Ala Val Asp Glu His Ser Arg Asn Leu Val Gly
65                  70                  75                  80

Glu Met Leu Glu Ala Gly Ala Lys Met Gly Leu Thr Val Cys Arg Thr
                85                  90                  95

Trp Ala Phe Asn Asp Gly Gly Tyr Asn Ala Leu Gln Ile Ser Pro Gly
            100                 105                 110

Arg Phe Asp Glu Arg Val Phe Gln Ala Leu Asp His Val Ile Ala Glu
        115                 120                 125

Ala Arg Lys His Asp Val Arg Leu Leu Leu Ser Leu Val Asn Asn Leu
    130                 135                 140

Gln Ala Tyr Gly Gly Lys Thr Gln Tyr Val Lys Trp Ala Trp Gln Glu
145                 150                 155                 160

Gly Val Gly Leu Ser Ser Ser Asn Asp Ser Phe Phe Phe Asp Pro Ser
                165                 170                 175

Ile Arg Asn Tyr Phe Lys Asn Tyr Leu Lys Val Leu Leu Thr Arg Lys
            180                 185                 190

Asn Ser Val Thr Gly Ile Glu Tyr Arg Asn Asp Pro Thr Ile Phe Ala
        195                 200                 205

Trp Glu Leu Ile Asn Glu Pro Arg Cys Thr Thr Asp Val Ser Gly Lys
    210                 215                 220

Thr Leu Gln Asp Trp Ile Asp Glu Met Thr Gly Phe Ile Lys Ser Ile
225                 230                 235                 240

Asp Asp Lys His Leu Leu Thr Val Gly Leu Glu Gly Phe Tyr Gly Pro
                245                 250                 255

Asn Ser Pro Lys Gly Leu Thr Val Asn Pro Glu Gln Trp Ala Ser Gln
            260                 265                 270

Leu Gly Thr Asp Phe Val Gln Asn Ser Asn Ser Ser Asn Ile Asp Phe
        275                 280                 285

Ala Ser Val His Ile Tyr Pro Asp His Trp Phe His Asn Gln Thr Phe
    290                 295                 300

Glu Glu Lys Leu Lys Phe Val Val Lys Trp Met Gln Ser His Ile Glu
```

-continued

```
305                 310                 315                 320

Asp Gly Leu Lys Glu Leu Lys Lys Pro Val Leu Phe Thr Glu Phe Gly
                325                 330                 335

Leu Ser Asn Gln Asn Lys Asp Tyr Glu Pro Ser Gln Arg Asp Lys Phe
            340                 345                 350

Tyr Arg Ile Ile Phe Asp Val Val Tyr Lys Ser Ala Lys Arg Lys Lys
        355                 360                 365

Ser Gly Ala Gly Thr Leu Val Trp Gln Leu Phe Met Glu Gly Met Glu
    370                 375                 380

Thr Phe Asn Asp Asp Phe Gly Ile Val Pro His Glu Gln Asp Ser Ile
385                 390                 395                 400

Tyr Lys Leu Met Ile Glu Gln Ser Cys Arg Leu Gly Lys Val Thr Gly
                405                 410                 415

Arg Leu Lys Glu Gln Lys Leu Lys Glu Leu Cys Ser His Arg His
            420                 425                 430


<210> SEQ ID NO 87
<211> LENGTH: 601
<212> TYPE: DNA
<213> ORGANISM: Arabidopsis thaliana

<400> SEQUENCE: 87

taccataact tcaccaaacc agacacagaa tcataagatc agatctggtg ttctcaaata     60

tggcggataa ggaagaacca gagacgatga cctcgtacaa gttgtttttg agagttataa    120

gcaagagaag aacatgggcc tgtctgtttc ttgtagtcta cgcgatccta ttgtcttctt    180

catggaattc gttgaattca atagttaatt ggtacggaga gaatcatcag acatcatctg    240

gtttgcctgc gatttacgcg tcggtgcttc ttggtgcggt gttcggagtt ttatctatgg    300

cggcggcgct gttcatagcc gtgcctgcga tcgtggtgat ctggatatca gtggtggtga    360

cgatggcgtt cgccggaaaa tctaggaaga gagtggtgat tgaaggaagg aaagtgacga    420

aagagatcgc tggttttgtg tttagggttc ttcttaaaga aggaaacttt gtggctcttc    480

tttgtgctct tcttgcttac ttcgtcttct ttaactctta ctcttcatct tcttgattcg    540

ttttttgaa ttcttgtcat taacgaaaac attcacagct agtatattga aatctttcct    600

c                                                                    601


<210> SEQ ID NO 88
<211> LENGTH: 158
<212> TYPE: PRT
<213> ORGANISM: Arabidopsis thaliana

<400> SEQUENCE: 88

Met Ala Asp Lys Glu Glu Pro Glu Thr Met Thr Ser Tyr Lys Leu Phe
1               5                   10                  15

Leu Arg Val Ile Ser Lys Arg Arg Thr Trp Ala Cys Leu Phe Leu Val
            20                  25                  30

Val Tyr Ala Ile Leu Leu Ser Ser Ser Trp Asn Ser Leu Asn Ser Ile
        35                  40                  45

Val Asn Trp Tyr Gly Glu Asn His Gln Thr Ser Ser Gly Leu Pro Ala
    50                  55                  60

Ile Tyr Ala Ser Val Leu Leu Gly Ala Val Phe Gly Val Leu Ser Met
65                  70                  75                  80

Ala Ala Ala Leu Phe Ile Ala Val Pro Ala Ile Val Val Ile Trp Ile
                85                  90                  95
```

-continued

```
Ser Val Val Val Thr Met Ala Phe Ala Gly Lys Ser Arg Lys Arg Val
            100                 105                 110

Val Ile Glu Gly Arg Lys Val Thr Lys Glu Ile Ala Gly Phe Val Phe
        115                 120                 125

Arg Val Leu Leu Lys Glu Gly Asn Phe Val Ala Leu Leu Cys Ala Leu
    130                 135                 140

Leu Ala Tyr Phe Val Phe Phe Asn Ser Tyr Ser Ser Ser Ser
145                 150                 155


<210> SEQ ID NO 89
<211> LENGTH: 480
<212> TYPE: DNA
<213> ORGANISM: Arabidopsis thaliana

<400> SEQUENCE: 89

atggcggata aggaagaaca agagacgatg acctcgtaca agctgttttt gagagtcata      60

agcaagagga gaacatgggt ctgtctgttt cttgtagtct acgcggtcct tttgtcttct     120

tcaagaaatt cgttgaattc gatagtgaat tggtacggag agaatcatca gacatcatct     180

ggtttgcctg ctatttacgc gtcggttctt cttggtgcgg tgttcggagt tctatctatg     240

gcggcagctc tgttcatcgc tgtgccagcg atcgttgtga tctggatatc ggtagtggtg     300

acaatagcgt tccccgtaaa gtcgaggaag aaagtggtga ttgaaggaag gaaagtgacg     360

aaagaaattg ctggttatgt gtttaaggtt cttcttaaag aaggaaactt tgtggctctt     420

ctttgtgctg ttattgctta ctttgtcttc tttaactctt attactcttc atcttcttga     480


<210> SEQ ID NO 90
<211> LENGTH: 159
<212> TYPE: PRT
<213> ORGANISM: Arabidopsis thaliana

<400> SEQUENCE: 90

Met Ala Asp Lys Glu Glu Gln Glu Thr Met Thr Ser Tyr Lys Leu Phe
1               5                   10                  15

Leu Arg Val Ile Ser Lys Arg Arg Thr Trp Val Cys Leu Phe Leu Val
            20                  25                  30

Val Tyr Ala Val Leu Leu Ser Ser Ser Arg Asn Ser Leu Asn Ser Ile
        35                  40                  45

Val Asn Trp Tyr Gly Glu Asn His Gln Thr Ser Ser Gly Leu Pro Ala
    50                  55                  60

Ile Tyr Ala Ser Val Leu Leu Gly Ala Val Phe Gly Val Leu Ser Met
65                  70                  75                  80

Ala Ala Ala Leu Phe Ile Ala Val Pro Ala Ile Val Val Ile Trp Ile
                85                  90                  95

Ser Val Val Val Thr Ile Ala Phe Pro Val Lys Ser Arg Lys Lys Val
            100                 105                 110

Val Ile Glu Gly Arg Lys Val Thr Lys Glu Ile Ala Gly Tyr Val Phe
        115                 120                 125

Lys Val Leu Leu Lys Glu Gly Asn Phe Val Ala Leu Leu Cys Ala Val
    130                 135                 140

Ile Ala Tyr Phe Val Phe Phe Asn Ser Tyr Tyr Ser Ser Ser Ser
145                 150                 155


<210> SEQ ID NO 91
<211> LENGTH: 1950
<212> TYPE: DNA
<213> ORGANISM: Arabidopsis thaliana
```

<400> SEQUENCE: 91

```
atgttctcta aagtttccat tcttctcttt tccctcgcat ccctactctt gttccgatca     60
accacaggca tcgaattcat ctacaactcc aatttcacca caaccaacac acttctcctc    120
ggcaacgcca ctgttaaatc tccaccgtcg atcctcaccc tcaccaacca aaccactttc    180
tccatcggac gtggcctcta cccttcaaga atcaacgcct cctcctcctc tgcctcgccg    240
ttacctttcg ccacatcatt catcttctcc atggctcctt ttaaacacct ctctcctggc    300
cacggcttcg ccttcgtctt ccttcctttc tccgaaacct ccgccgcaag ctcatctcag    360
catctcggcc tcttcaactt caccaataac ggtgacccca atagccgaat cttcgccgtt    420
gaattcgatg ttttcgctaa ccaagagttc aacgacatca acgacaacca cgtcggcgtc    480
gacgtcaatt ctctcacttc cgttgcatct gaaactgcag gtttctatgg aggcagagac    540
ggccagagat tcacggagct gaagcttaac agtggcgaga attatcaggc gtggatcgag    600
tttaatgggt cagcgatcaa tgtcacgatg gctagagcta gctctagaaa gcccataaga    660
ccactcataa gcattccatt aaatctcact ggagtcttac ttgatgatat gttcgttgga    720
ttcactgcct ccacaggaca actagtgcag agccatagga ttctctcatg gagttttagt    780
aactccaatt tctccattgg tgactctgtt ttgaagtcta aaggcttcat tgctggggtc    840
tctagtggtg ttgtgttgca gagactagaa ggagacgtgg aagattggga aacagagtat    900
tggcctcaca gagtgcaata caaagatgtt ttggaagcaa caaaagggtt ttccgatgag    960
aacatgatcg gatacggagg gaattctaaa gtgtacaggg gagtgttgga aggtaaagaa   1020
gttgcggtta agagaataat gatgagtcct cgagagagcg ttggcgcgac gagtgagttc   1080
ttagctgagg tctcgagctt agggaggttg agacacaaga atatagttgg actaaaaggt   1140
tggtctaaga aaggaggaga gagtctgata ttgatttacg agtatatgga gaatggaagt   1200
gtcgataagc ggatatttga ttgtaacgag atgttgaatt gggaggaaag aatgagagtg   1260
ataagagacc tagcctcagg gatgttgtat ctacacgaag ggtgggagac aaaggtgtta   1320
catagagata taaagtcaag caatgtgttg cttgacaagg atatgaacgc gagggtaggt   1380
gattttgggt tggctaagtt gcagaacact agtaaagaga tggttagcac gacacatgtt   1440
gttggaacag cgggttatat ggcgcctgag ttggttaaga cagggagagc atcagcgcaa   1500
accgatgtgt atagctttgg agtgtttgtg ttggaggtag tgtgtggaag gaggccaata   1560
gaggaaggaa gagaagggat agtggaatgg atatggggac taatggagaa agacaaagtg   1620
gttgatggtt tagacgagag aataaaggcg aatggagtgt tcgtggtcga ggaagtggag   1680
atggctctga gaataggact gttgtgtgtg catcctgatc cgagagtgcg tccgaagatg   1740
agacaagtgg tgcagatatt ggaacaaggg agattagtgg aggatggtgg tgaaagggaa   1800
ataagcttgt tggagagagt gaagagctct tacttgttgg aaactggtga gggaagcaga   1860
caacaacatc ccacgttcca agatgtatgg aattcgtctt cttattctaa ttccttccaa   1920
acttatgatt ctattcttca tggaaggtga                                    1950
```

<210> SEQ ID NO 92
<211> LENGTH: 649
<212> TYPE: PRT
<213> ORGANISM: Arabidopsis thaliana

<400> SEQUENCE: 92

```
Met Phe Ser Lys Val Ser Ile Leu Leu Phe Ser Leu Ala Ser Leu Leu
1               5                   10                  15
```

-continued

```
Leu Phe Arg Ser Thr Thr Gly Ile Glu Phe Ile Tyr Asn Ser Asn Phe
            20                  25                  30

Thr Thr Thr Asn Thr Leu Leu Leu Gly Asn Ala Thr Val Lys Ser Pro
        35                  40                  45

Pro Ser Ile Leu Thr Leu Thr Asn Gln Thr Thr Phe Ser Ile Gly Arg
    50                  55                  60

Gly Leu Tyr Pro Ser Arg Ile Asn Ala Ser Ser Ser Ser Ala Ser Pro
65                  70                  75                  80

Leu Pro Phe Ala Thr Ser Phe Ile Phe Ser Met Ala Pro Phe Lys His
                85                  90                  95

Leu Ser Pro Gly His Gly Phe Ala Phe Val Phe Leu Pro Phe Ser Glu
            100                 105                 110

Thr Ser Ala Ala Ser Ser Ser Gln His Leu Gly Leu Phe Asn Phe Thr
        115                 120                 125

Asn Asn Gly Asp Pro Asn Ser Arg Ile Phe Ala Val Glu Phe Asp Val
    130                 135                 140

Phe Ala Asn Gln Glu Phe Asn Asp Ile Asn Asp Asn His Val Gly Val
145                 150                 155                 160

Asp Val Asn Ser Leu Thr Ser Val Ala Ser Glu Thr Ala Gly Phe Tyr
                165                 170                 175

Gly Gly Arg Asp Gly Gln Arg Phe Thr Glu Leu Lys Leu Asn Ser Gly
            180                 185                 190

Glu Asn Tyr Gln Ala Trp Ile Glu Phe Asn Gly Ser Ala Ile Asn Val
        195                 200                 205

Thr Met Ala Arg Ala Ser Ser Arg Lys Pro Ile Arg Pro Leu Ile Ser
    210                 215                 220

Ile Pro Leu Asn Leu Thr Gly Val Leu Leu Asp Asp Met Phe Val Gly
225                 230                 235                 240

Phe Thr Ala Ser Thr Gly Gln Leu Val Gln Ser His Arg Ile Leu Ser
                245                 250                 255

Trp Ser Phe Ser Asn Ser Asn Phe Ser Ile Gly Asp Ser Val Leu Lys
            260                 265                 270

Ser Lys Gly Phe Ile Ala Gly Val Ser Ser Gly Val Val Leu Gln Arg
        275                 280                 285

Leu Glu Gly Asp Val Glu Asp Trp Glu Thr Glu Tyr Trp Pro His Arg
    290                 295                 300

Val Gln Tyr Lys Asp Val Leu Glu Ala Thr Lys Gly Phe Ser Asp Glu
305                 310                 315                 320

Asn Met Ile Gly Tyr Gly Gly Asn Ser Lys Val Tyr Arg Gly Val Leu
                325                 330                 335

Glu Gly Lys Glu Val Ala Val Lys Arg Ile Met Met Ser Pro Arg Glu
            340                 345                 350

Ser Val Gly Ala Thr Ser Glu Phe Leu Ala Glu Val Ser Ser Leu Gly
        355                 360                 365

Arg Leu Arg His Lys Asn Ile Val Gly Leu Lys Gly Trp Ser Lys Lys
    370                 375                 380

Gly Gly Glu Ser Leu Ile Leu Ile Tyr Glu Tyr Met Glu Asn Gly Ser
385                 390                 395                 400

Val Asp Lys Arg Ile Phe Asp Cys Asn Glu Met Leu Asn Trp Glu Glu
                405                 410                 415

Arg Met Arg Val Ile Arg Asp Leu Ala Ser Gly Met Leu Tyr Leu His
            420                 425                 430
```

-continued

```
Glu Gly Trp Glu Thr Lys Val Leu His Arg Asp Ile Lys Ser Ser Asn
        435                 440                 445

Val Leu Leu Asp Lys Asp Met Asn Ala Arg Val Gly Asp Phe Gly Leu
    450                 455                 460

Ala Lys Leu Gln Asn Thr Ser Lys Glu Met Val Ser Thr Thr His Val
465                 470                 475                 480

Val Gly Thr Ala Gly Tyr Met Ala Pro Glu Leu Val Lys Thr Gly Arg
                485                 490                 495

Ala Ser Ala Gln Thr Asp Val Tyr Ser Phe Gly Val Phe Val Leu Glu
            500                 505                 510

Val Val Cys Gly Arg Arg Pro Ile Glu Glu Gly Arg Glu Gly Ile Val
        515                 520                 525

Glu Trp Ile Trp Gly Leu Met Glu Lys Asp Lys Val Val Asp Gly Leu
    530                 535                 540

Asp Glu Arg Ile Lys Ala Asn Gly Val Phe Val Val Glu Glu Val Glu
545                 550                 555                 560

Met Ala Leu Arg Ile Gly Leu Leu Cys Val His Pro Asp Pro Arg Val
                565                 570                 575

Arg Pro Lys Met Arg Gln Val Val Gln Ile Leu Glu Gln Gly Arg Leu
            580                 585                 590

Val Glu Asp Gly Gly Glu Arg Glu Ile Ser Leu Leu Glu Arg Val Lys
        595                 600                 605

Ser Ser Tyr Leu Leu Glu Thr Gly Glu Gly Ser Arg Gln Gln His Pro
    610                 615                 620

Thr Phe Gln Asp Val Trp Asn Ser Ser Ser Tyr Ser Asn Ser Phe Gln
625                 630                 635                 640

Thr Tyr Asp Ser Ile Leu His Gly Arg
                645
```

```
<210> SEQ ID NO 93
<211> LENGTH: 3779
<212> TYPE: DNA
<213> ORGANISM: Arabidopsis thaliana

<400> SEQUENCE: 93

aaaagacttc aattgtttta tcagcttctc tctctaaata aagctctcaa ttcaattctc     60

tctctttcac ttttttttcc tctgcttgct tcttctgttc atctttttgc ttcgtcaaaa    120

ttttgaccaa agttttgtac ttttttgttg ctgcaatttt tgtgattaga ttggatctgg    180

gcttggagct gaatagcgga tttgtataag gttattatta gtcttctcta tcgttgcggc    240

gttcataagt tggagaaagt ggtaaagact gcttaagtat gtctgtttct atgagagatt    300

tagatccagc tttccaagga gctggacaga aagctggtat tgagatatgg cgtatagaga    360

atttcatccc taccccaatt ccaaaatctt ctattgggaa gtttttcacc ggagattctt    420

acatagtatt gaagacaacg gcgttaaaaa ctggtgcatt gcgccatgat atccattact    480

ggcttggtaa agatacctct caggatgaag ccggtactgc tgcagttaag acagttgaat    540

tagatgctgc tctaggaggt cgtgcagtgc agtatcggga agttcaaggc cacgagactg    600

agaaattctt gtcttatttt aagccatgta tcattcctca agaaggtgga gtagcatcag    660

gattcaagca tgtcgtagct gaagaacata ttacccgctt gttcgtctgc agaggaaaac    720

atgttgtcca tgtcaaagag gttccttttg ctcggagttc attaaaccat gacgatattt    780

acattcttga cacaaagtcc aagattttcc aattcaatgg atccaattct agtatccaag    840

agagagcaaa agcactggaa gtggttcagt acatcaaaga tacttaccat gatgggacat    900
```

-continued

```
gtgaagttgc tacagttgag gatgggaaac ttatggctga tgctgatagt ggagaatttt    960
ggggtttctt tggtgggttt gctccgctac ctaggaaaac agctaatgat gaagacaaaa   1020
cttataattc agatatcacc agattatttt gtgtcgagaa gggacaggca aatcctgttg   1080
aaggcgatac attgaagagg gagatgctgg atacaaacaa gtgttacatt cttgattgtg   1140
gaattgaagt gtttgtttgg atgggaagaa ccacttctct tgatgataga aaaattgcga   1200
gtaaagcagc agaagaaatg atccgttcat ctgaacgacc gaaatcgcaa atgatccgca   1260
taatagaagg gtttgaaaca gtaccattcc gatcaaagtt tgaatcttgg actcaagaaa   1320
ctaatacaac cgtgtcagaa gatggtagag gcagagttgc tgctcttttg caacgacaag   1380
gagtaaatgt cagaggcctg atgaaagctg ctccgcctaa agaagagcct caggttttca   1440
tcgactgcac gggaaatctg caggtttggc gtgtgaatgg tcaggcaaag actctccttc   1500
aagctgctga tcattcaaaa ttctacagtg gagattgcta tgttttccag tattcttatc   1560
ccggagaaga aaaagaagaa gttcttatag gaacgtggtt tggcaaacaa agtgtggagg   1620
aagaaagagg ttctgcagtc tctatggcaa gcaaaatggt tgagtcaatg aaatttgtcc   1680
cagcccaagc tcgcatttat gaaggaaagg aaccaattca attcttcgtg attatgcaaa   1740
gctttatcgt tttcaagggt ggtattagca gtggatacaa gaaatacata gccgagaaag   1800
aagttgatga tgatacatac aatgagaatg gtgttgctct attccgaatt caagggtctg   1860
gtccggaaaa tatgcaagct atacaagttg acccggttgc tgcatcactg aactcctcgt   1920
actattacat actacataat gattcttccg tctttacttg ggctggaaat ttatcaaccg   1980
caactgacca agaactggcg gaaaggcagc tagatctgat taagccaaat caacaatcta   2040
gagcacaaaa ggaaggttca gaatcagaac agttctggga gttattagga ggcaaagctg   2100
aatattcgag ccaaaagctc acaaaggaac ccgagcgtga ccctcacttg ttctcttgta   2160
cattcacaaa agaagttctc aaggtgacag agatatataa ctttacacag gatgacttga   2220
tgaccgaaga tatatttatc atagactgtc actcagaaat ctttgtctgg gttggccaag   2280
aagtagtccc aaagaacaag ttactagctt taactattgg agagaaattc atcgagaaag   2340
attctctcct ggagaagtta tcccctgaag cccctattta tgtgatcatg gaaggcggtg   2400
agccgtcatt cttcacccgg ttcttcactt cttgggattc ctcaaaatcc gctatgcatg   2460
gaaactcatt ccaaagaaaa cttaaaattg tcaaaaatgg tggaactcca gtggcagata   2520
aaccaaaacg aagaactcca gcttcatatg gtggccgtgc cagcgttcct gacaagtcgc   2580
agcagcggtc aagaagcatg tcatttagtc cagacagggt tcgcgtgagg ggcagatctc   2640
cggcgttcaa tgcactcgca gcaacatttg agagccaaaa tgcaagaaac ctgtcaactc   2700
ctcccccagt agttaggaaa ctctacccaa gatctgttac tcctgactcc tcaaagtttg   2760
ctcccgctcc caagtcttca gccatcgctt ctcgaagtgc acttttcgaa aaaatacctc   2820
cacaagaacc ttcaattcca aaaccagtca aagcgagccc gaagacacct gagtctccag   2880
cgccagaatc caattcaaaa gaacaagaag agaaaaagga aaatgacaag gaggagggat   2940
caatgagcag ccggatagaa tctcttacga ttcaagaaga tgctaaagaa ggagtcgaag   3000
acgaggaaga tttaccagct caccccttatg atcgtctcaa gacaacttcc actgatcctg   3060
tctctgacat tgatgtaaca aggagagagg cttacctttc atcagaagag ttcaaggaga   3120
aatttggcat gacgaaagaa gctttctaca agctgcctaa atggaaacag aacaaattca   3180
aaatggctgt tcagcttttc tgagatataa tccttcttct tctccatcaa aagatccgct   3240
```

```
ataaggagaa gatacaaggg acagtgtcag tgcattttaa gctgcttctg ctccccatga   3300

gaagcttaat acatttttca tggcttgttt aaaaaaaaca acccagagca gttttctttt   3360

cttctatttt tctttcttct ccttcaaatc tttctgattt gttttaatga tctgtttgct   3420

tgtttctctc tatttcattc tccatttttt agtttgagta gatttttgtt ttcttcatat   3480

tttgggattg tttcttcttc aggtcacagg ttttgacctt gagtctttga tttatttatt   3540

cttggggtta ttttgatatc aaattgagga aatttggttt caaaagtcaa atttttattt   3600

agtgagattt cataaaaaca aatagactct gtaattttgt tttgcagaag ttgaggattg   3660

agtttttttt tttttttttg tgtacagcaa agtgtacaaa ctaaattgtg cttcctaaac   3720

ttcagatttc tttattttac tacattttct cataaatata gaaataccat ttgttggcc    3779
```

```
<210> SEQ ID NO 94
<211> LENGTH: 974
<212> TYPE: PRT
<213> ORGANISM: Arabidopsis thaliana

<400> SEQUENCE: 94

Met Ser Val Ser Met Arg Asp Leu Asp Pro Ala Phe Gln Gly Ala Gly
1               5                   10                  15

Gln Lys Ala Gly Ile Glu Ile Trp Arg Ile Glu Asn Phe Ile Pro Thr
            20                  25                  30

Pro Ile Pro Lys Ser Ser Ile Gly Lys Phe Phe Thr Gly Asp Ser Tyr
        35                  40                  45

Ile Val Leu Lys Thr Thr Ala Leu Lys Thr Gly Ala Leu Arg His Asp
    50                  55                  60

Ile His Tyr Trp Leu Gly Lys Asp Thr Ser Gln Asp Glu Ala Gly Thr
65                  70                  75                  80

Ala Ala Val Lys Thr Val Glu Leu Asp Ala Ala Leu Gly Gly Arg Ala
                85                  90                  95

Val Gln Tyr Arg Glu Val Gln Gly His Glu Thr Glu Lys Phe Leu Ser
            100                 105                 110

Tyr Phe Lys Pro Cys Ile Ile Pro Gln Glu Gly Gly Val Ala Ser Gly
        115                 120                 125

Phe Lys His Val Val Ala Glu Glu His Ile Thr Arg Leu Phe Val Cys
    130                 135                 140

Arg Gly Lys His Val Val His Val Lys Glu Val Pro Phe Ala Arg Ser
145                 150                 155                 160

Ser Leu Asn His Asp Asp Ile Tyr Ile Leu Asp Thr Lys Ser Lys Ile
                165                 170                 175

Phe Gln Phe Asn Gly Ser Asn Ser Ser Ile Gln Glu Arg Ala Lys Ala
            180                 185                 190

Leu Glu Val Val Gln Tyr Ile Lys Asp Thr Tyr His Asp Gly Thr Cys
        195                 200                 205

Glu Val Ala Thr Val Glu Asp Gly Lys Leu Met Ala Asp Ala Asp Ser
    210                 215                 220

Gly Glu Phe Trp Gly Phe Phe Gly Gly Phe Ala Pro Leu Pro Arg Lys
225                 230                 235                 240

Thr Ala Asn Asp Glu Asp Lys Thr Tyr Asn Ser Asp Ile Thr Arg Leu
                245                 250                 255

Phe Cys Val Glu Lys Gly Gln Ala Asn Pro Val Glu Gly Asp Thr Leu
            260                 265                 270

Lys Arg Glu Met Leu Asp Thr Asn Lys Cys Tyr Ile Leu Asp Cys Gly
        275                 280                 285
```

```
Ile Glu Val Phe Val Trp Met Gly Arg Thr Thr Ser Leu Asp Asp Arg
    290                 295                 300

Lys Ile Ala Ser Lys Ala Ala Glu Glu Met Ile Arg Ser Ser Glu Arg
305                 310                 315                 320

Pro Lys Ser Gln Met Ile Arg Ile Ile Glu Gly Phe Glu Thr Val Pro
                325                 330                 335

Phe Arg Ser Lys Phe Glu Ser Trp Thr Gln Glu Thr Asn Thr Thr Val
            340                 345                 350

Ser Glu Asp Gly Arg Gly Arg Val Ala Ala Leu Leu Gln Arg Gln Gly
        355                 360                 365

Val Asn Val Arg Gly Leu Met Lys Ala Ala Pro Pro Lys Glu Glu Pro
    370                 375                 380

Gln Val Phe Ile Asp Cys Thr Gly Asn Leu Gln Val Trp Arg Val Asn
385                 390                 395                 400

Gly Gln Ala Lys Thr Leu Leu Gln Ala Ala Asp His Ser Lys Phe Tyr
                405                 410                 415

Ser Gly Asp Cys Tyr Val Phe Gln Tyr Ser Tyr Pro Gly Glu Glu Lys
            420                 425                 430

Glu Glu Val Leu Ile Gly Thr Trp Phe Gly Lys Gln Ser Val Glu Glu
        435                 440                 445

Glu Arg Gly Ser Ala Val Ser Met Ala Ser Lys Met Val Glu Ser Met
    450                 455                 460

Lys Phe Val Pro Ala Gln Ala Arg Ile Tyr Glu Gly Lys Glu Pro Ile
465                 470                 475                 480

Gln Phe Phe Val Ile Met Gln Ser Phe Ile Val Phe Lys Gly Gly Ile
                485                 490                 495

Ser Ser Gly Tyr Lys Lys Tyr Ile Ala Glu Lys Glu Val Asp Asp Asp
            500                 505                 510

Thr Tyr Asn Glu Asn Gly Val Ala Leu Phe Arg Ile Gln Gly Ser Gly
        515                 520                 525

Pro Glu Asn Met Gln Ala Ile Gln Val Asp Pro Val Ala Ala Ser Leu
    530                 535                 540

Asn Ser Ser Tyr Tyr Tyr Ile Leu His Asn Asp Ser Ser Val Phe Thr
545                 550                 555                 560

Trp Ala Gly Asn Leu Ser Thr Ala Thr Asp Gln Glu Leu Ala Glu Arg
                565                 570                 575

Gln Leu Asp Leu Ile Lys Pro Asn Gln Gln Ser Arg Ala Gln Lys Glu
            580                 585                 590

Gly Ser Glu Ser Glu Gln Phe Trp Glu Leu Leu Gly Gly Lys Ala Glu
        595                 600                 605

Tyr Ser Ser Gln Lys Leu Thr Lys Glu Pro Glu Arg Asp Pro His Leu
    610                 615                 620

Phe Ser Cys Thr Phe Thr Lys Glu Val Leu Lys Val Thr Glu Ile Tyr
625                 630                 635                 640

Asn Phe Thr Gln Asp Asp Leu Met Thr Glu Asp Ile Phe Ile Ile Asp
                645                 650                 655

Cys His Ser Glu Ile Phe Val Trp Val Gly Gln Glu Val Val Pro Lys
            660                 665                 670

Asn Lys Leu Leu Ala Leu Thr Ile Gly Glu Lys Phe Ile Glu Lys Asp
        675                 680                 685

Ser Leu Leu Glu Lys Leu Ser Pro Glu Ala Pro Ile Tyr Val Ile Met
    690                 695                 700
```

```
Glu Gly Gly Glu Pro Ser Phe Phe Thr Arg Phe Phe Thr Ser Trp Asp
705                 710                 715                 720

Ser Ser Lys Ser Ala Met His Gly Asn Ser Phe Gln Arg Lys Leu Lys
                725                 730                 735

Ile Val Lys Asn Gly Gly Thr Pro Val Ala Asp Lys Pro Lys Arg Arg
            740                 745                 750

Thr Pro Ala Ser Tyr Gly Gly Arg Ala Ser Val Pro Asp Lys Ser Gln
        755                 760                 765

Gln Arg Ser Arg Ser Met Ser Phe Ser Pro Asp Arg Val Arg Val Arg
    770                 775                 780

Gly Arg Ser Pro Ala Phe Asn Ala Leu Ala Ala Thr Phe Glu Ser Gln
785                 790                 795                 800

Asn Ala Arg Asn Leu Ser Thr Pro Pro Pro Val Val Arg Lys Leu Tyr
                805                 810                 815

Pro Arg Ser Val Thr Pro Asp Ser Ser Lys Phe Ala Pro Ala Pro Lys
            820                 825                 830

Ser Ser Ala Ile Ala Ser Arg Ser Ala Leu Phe Glu Lys Ile Pro Pro
        835                 840                 845

Gln Glu Pro Ser Ile Pro Lys Pro Val Lys Ala Ser Pro Lys Thr Pro
    850                 855                 860

Glu Ser Pro Ala Pro Glu Ser Asn Ser Lys Glu Gln Glu Glu Lys Lys
865                 870                 875                 880

Glu Asn Asp Lys Glu Glu Gly Ser Met Ser Ser Arg Ile Glu Ser Leu
                885                 890                 895

Thr Ile Gln Glu Asp Ala Lys Glu Gly Val Glu Asp Glu Glu Asp Leu
            900                 905                 910

Pro Ala His Pro Tyr Asp Arg Leu Lys Thr Thr Ser Thr Asp Pro Val
        915                 920                 925

Ser Asp Ile Asp Val Thr Arg Arg Glu Ala Tyr Leu Ser Ser Glu Glu
    930                 935                 940

Phe Lys Glu Lys Phe Gly Met Thr Lys Glu Ala Phe Tyr Lys Leu Pro
945                 950                 955                 960

Lys Trp Lys Gln Asn Lys Phe Lys Met Ala Val Gln Leu Phe
                965                 970
```

<210> SEQ ID NO 95
<211> LENGTH: 2145
<212> TYPE: DNA
<213> ORGANISM: Arabidopsis thaliana

<400> SEQUENCE: 95

```
aaatgtttta tactctgatt tctagggttt gcttttgatt ctctttcgcg ttccagataa     60

ataaatcctt ttgtggaata atttcgtgat ttcgtttgtg ggttatccga attttgtctg    120

aatttgagtt tttgagaagg aaaggtttgt tttttcgggg gatggtggaa atgaggaaat    180

ctggaggttt aagaccggag tctgaatcgg cggccaggtg ccgagatgag ctaccggtga    240

aattggagat tgctgaagat gatttagaag aagagcatgg tcctctcaac aaacgatcta    300

ggttatggag tcctgggaca agctcatcga caatggcacc agctaagtat aacccgcttg    360

atgagccgag tcctcttgga ttgagtctta agaagagtcc atctttgttg gagttgattc    420

agatgaagat aacgcattgt ggtgatccta aagcagctga aacgttgaaa gctggtgcac    480

ttggctctgg tcttaagaga gaaagtaaaa ctattgctgc tgctgcatca gttggaccga    540

ctttggcgcc aggaagtatt gagaagctga aagcttctaa ctttcctgct tcgcttttga    600
```

-continued

```
agatcgggca gtgggagtat aaatcgaggt atgaaggtga tttggtggca aagtgttact     660

ttgctaaaca caaacttgtt tgggaagtgt tggaacaagg tcttaagagt aaaatcgaga     720

tccagtggtc agatattatg gctttgaagg caaactgtcc tgaagacgga cctggaactt     780

tgactctcgt gcttgctaga cagcccttat ttttccggga aacaaaccca cagcctagaa     840

agcatacctt gtggcaggcg acatcagatt tcactgatgg ccaagccagc atgaacaggc     900

agcattttct gcaatgtgct caagggataa tgaacaaaca ttttgaaaag ctcgttcaat     960

gtgatcatcg tctgttccat ctaagccgac agccggagat agctattgac tctccctact    1020

ttgatgcacg gcaatctatt tttgaggatc caagtgaatc aaaaggccat cctttttggga    1080

atttgaatct tagtacaggt ccttcgatct ctgggactca gaatttagca tctcctgttg    1140

gggctcagtc atcatctgag catatgtatc tgtctcatga agcaccatca cccagctcag    1200

tgatagatgc tcgtgcaaat gaaggaattg gggttctga agcagtcaat tcaagaaaca    1260

gaacagattg tggtcagatc gaagcacctg gaatacacca atctatgtca ctgagtgatt    1320

tccttgcggt tctctgtgat acaaaaaaca caacggattt gaatctggct gacgacgtag    1380

atggactaca ccaatctatg tcagttagtg atttcgttgc atatttatct gattcaagaa    1440

acataactga ttcagatcag ataaaagtac ctggactaca ccaatctatg tcagtgagcg    1500

atttcgttgg acttctctct gattctgctg gtggaagtca tccggaacat atggagaaat    1560

ttgagatcat gaaacagcag ttgctaagtg ataatatcca gttcgaggca ccagatgaga    1620

agtctctcat gccaagggtt aactctttat tcaacctctt gtacaaggat cccaacgtcg    1680

ctgcaaactc acagctcaat accgaaatgt cggttggatt gaagtctgaa cccaagggaa    1740

ttgtttctga caacaacaac aacaacaaca acaacaacag agttcttgat acagcttcta    1800

gcagcaaacc acagggtatg ttaaggaaag actcattcag cgatttgcta ttacacctcc    1860

cccggatcac atccttgcca aagttcttgt ccaacatttc agaagaagat ggtgatgcat    1920

ataatagata atttatagat accgcctttc ttttctggat ttggcaagta taggaacctg    1980

gactagtagc ttttctgttt ttttttcttt gtaaatcaaa attatcactt ggtaactaca    2040

acccccacag ggatttgaag aaacatgttt tgatgattaa tttctgtata ttattcccaa    2100

tataaaccaa agttggcaga ggcaaaagat tccattattt atcct                    2145
```

<210> SEQ ID NO 96
<211> LENGTH: 589
<212> TYPE: PRT
<213> ORGANISM: Arabidopsis thaliana

<400> SEQUENCE: 96

```
Met Val Glu Met Arg Lys Ser Gly Gly Leu Arg Pro Glu Ser Glu Ser
1               5                   10                  15

Ala Ala Arg Cys Arg Asp Glu Leu Pro Val Lys Leu Glu Ile Ala Glu
            20                  25                  30

Asp Asp Leu Glu Glu Glu His Gly Pro Leu Asn Lys Arg Ser Arg Leu
        35                  40                  45

Trp Ser Pro Gly Thr Ser Ser Ser Thr Met Ala Pro Ala Lys Tyr Asn
    50                  55                  60

Pro Leu Asp Glu Pro Ser Pro Leu Gly Leu Ser Leu Lys Lys Ser Pro
65                  70                  75                  80

Ser Leu Leu Glu Leu Ile Gln Met Lys Ile Thr His Cys Gly Asp Pro
                85                  90                  95

Lys Ala Ala Glu Thr Leu Lys Ala Gly Ala Leu Gly Ser Gly Leu Lys
```

-continued

```
            100                 105                 110

Arg Glu Ser Lys Thr Ile Ala Ala Ala Ala Ser Val Gly Pro Thr Leu
        115                 120                 125

Ala Pro Gly Ser Ile Glu Lys Leu Lys Ala Ser Asn Phe Pro Ala Ser
    130                 135                 140

Leu Leu Lys Ile Gly Gln Trp Glu Tyr Lys Ser Arg Tyr Glu Gly Asp
145                 150                 155                 160

Leu Val Ala Lys Cys Tyr Phe Ala Lys His Lys Leu Val Trp Glu Val
                165                 170                 175

Leu Glu Gln Gly Leu Lys Ser Lys Ile Glu Ile Gln Trp Ser Asp Ile
            180                 185                 190

Met Ala Leu Lys Ala Asn Cys Pro Glu Asp Gly Pro Gly Thr Leu Thr
        195                 200                 205

Leu Val Leu Ala Arg Gln Pro Leu Phe Phe Arg Glu Thr Asn Pro Gln
    210                 215                 220

Pro Arg Lys His Thr Leu Trp Gln Ala Thr Ser Asp Phe Thr Asp Gly
225                 230                 235                 240

Gln Ala Ser Met Asn Arg Gln His Phe Leu Gln Cys Ala Gln Gly Ile
                245                 250                 255

Met Asn Lys His Phe Glu Lys Leu Val Gln Cys Asp His Arg Leu Phe
            260                 265                 270

His Leu Ser Arg Gln Pro Glu Ile Ala Ile Asp Ser Pro Tyr Phe Asp
        275                 280                 285

Ala Arg Gln Ser Ile Phe Glu Asp Pro Ser Glu Ser Lys Gly His Pro
    290                 295                 300

Phe Gly Asn Leu Asn Leu Ser Thr Gly Pro Ser Ile Ser Gly Thr Gln
305                 310                 315                 320

Asn Leu Ala Ser Pro Val Gly Ala Gln Ser Ser Ser Glu His Met Tyr
                325                 330                 335

Leu Ser His Glu Ala Pro Ser Pro Ser Ser Val Ile Asp Ala Arg Ala
            340                 345                 350

Asn Glu Gly Ile Gly Gly Ser Glu Ala Val Asn Ser Arg Asn Arg Thr
        355                 360                 365

Asp Cys Gly Gln Ile Glu Ala Pro Gly Ile His Gln Ser Met Ser Leu
    370                 375                 380

Ser Asp Phe Leu Ala Val Leu Cys Asp Thr Lys Asn Thr Thr Asp Leu
385                 390                 395                 400

Asn Leu Ala Asp Asp Val Asp Gly Leu His Gln Ser Met Ser Val Ser
                405                 410                 415

Asp Phe Val Ala Tyr Leu Ser Asp Ser Arg Asn Ile Thr Asp Ser Asp
            420                 425                 430

Gln Ile Lys Val Pro Gly Leu His Gln Ser Met Ser Val Ser Asp Phe
        435                 440                 445

Val Gly Leu Leu Ser Asp Ser Ala Gly Gly Ser His Pro Glu His Met
    450                 455                 460

Glu Lys Phe Glu Ile Met Lys Gln Gln Leu Leu Ser Asp Asn Ile Gln
465                 470                 475                 480

Phe Glu Ala Pro Asp Glu Lys Ser Leu Met Pro Arg Val Asn Ser Leu
                485                 490                 495

Phe Asn Leu Leu Tyr Lys Asp Pro Asn Val Ala Ala Asn Ser Gln Leu
            500                 505                 510

Asn Thr Glu Met Ser Val Gly Leu Lys Ser Glu Pro Lys Gly Ile Val
        515                 520                 525
```

-continued

```
Ser Asp Asn Asn Asn Asn Asn Asn Asn Asn Asn Arg Val Leu Asp Thr
    530                 535                 540

Ala Ser Ser Ser Lys Pro Gln Gly Met Leu Arg Lys Asp Ser Phe Ser
545                 550                 555                 560

Asp Leu Leu Leu His Leu Pro Arg Ile Thr Ser Leu Pro Lys Phe Leu
                565                 570                 575

Ser Asn Ile Ser Glu Glu Asp Gly Asp Ala Tyr Asn Arg
            580                 585
```

<210> SEQ ID NO 97
<211> LENGTH: 3744
<212> TYPE: DNA
<213> ORGANISM: Arabidopsis thaliana

<400> SEQUENCE: 97

```
atgagcggaa gcttcactga gagtttcgcc gatgatggca agcttcttct ttgtgtggct      60

gagaatggcc actcgtttga atttcaatgc agcgagacta cttcagttga atctgtgatg     120

cgtttcgttg aatctgtttc tggtattgcc ttatctgatc agcttcttct ctcgctagac     180

atgaagcttg agccacaaaa gctgctttct gcttttggac ttcctgcaag tgacagggaa     240

gtgtttgttt tcaacaaggc tatgctgcaa agtaactctc atccgccatc accagaagat     300

gtagatttgc aagacgttgc tgatgcttta ccaccggctt cattacatga acatcatccc     360

ttggatgatg catcggatcc agctttaaag gctttacctt tgtatgaaag gcaatttcgt     420

taccatttcc ataaaggccg caccatctac aattgtacgg ttgtgaagca tgagaactgc     480

gaaaggttaa cgagagagca aaaggtacag cagcgggctg ttgaagttgc tactaggaat     540

ctggaacagt attacagggt gatctatcag aactttcttg aatttatgaa gcgttataag     600

catcaacacc gcctccactc tgatttgctg atgaattttg gaagggatat tgagaaattg     660

aggtcagcca agattcaccc ttatcttcaa actgagtcaa ggaaatgctt gttggacttt     720

gtcaaggaag ataacctcaa aaaggctgtg gagaattgtg caagctctca caggcaattt     780

gagaataaga ttgcacagtt ccagcagatg tttgtcgagg tcaagcgcaa ggtagaagag     840

ttgtttgcct gcagggcttc tttatcaatg aagaacttag aagtgactgt taaggatcat     900

gaacgcttca ttgatgagga aaagagcatt atgcagtctc tcagcaaaga tgtcaatacg     960

gttaagaaac ttgtggatga ttgtatgtct agccaagtgt cctcatctct gcgtccccat    1020

gatgctgttt cagccctggg tcctatgtac gaagtgcatg acaagaatca ccttcccaaa    1080

atgcaagctt gctataactc aatttcagaa ttactggatt tctgcaagaa caagaagaat    1140

gagatgaaca actttgtaca cggttacatg caaaagataa catacgtcac atatatcatc    1200

aaagatgcta agttacagtt tcccgttttt agagaggcaa tggttcgcca ggatgactta    1260

tttgcagact tgaagttagt ccgtggtgtt ggcccccgctt atagggcctg tcttgcagag    1320

gtggtgagaa gaaaagcctc tatgaagctt tacatgggca tggctgggca attggcagag    1380

aagcttgcta tgaagaggga aacagaggtc aggaaacgtg aggagtttct taaaacccat    1440

ggcccctttg tacctcgtga cgtgttggct tcaatgggtt tatacgatac tcctactcag    1500

tgtgatgtca atgttgctcc gtatgatact agtttgctca atattgaaat ctcagatgtt    1560

gatcgatatg ctcctgagtt tctagttggg ttacattcga agattgcatc cttaaagagt    1620

tcactgacca tgtctggtga tagctcgctt tccgctgagc ctgaggagat aggtatagac    1680

acttttgaca aagacaattt tgatgatatc ctagcagcct ctgaattaat agagatagct    1740
```

-continued

```
ggaaccagca agatggaagt tgagaatgca aaactaaaag ctgaccttgc ttctgcaatc   1800

tctcggatct gttcattagg cccacaattt gaatatgagg tactggatga aagtgaagta   1860

gaaaatgtgt tgaaaaatgc tgcagataaa acagcagagg cattgcaggc caaagatgag   1920

tatgagaaac atcttctact tatgctcaag gaaaaacaaa tgcactgtga ttcatatgag   1980

aagcgcatcc gtgaactgga acaacgtctc tctgatgagt atctacaggg acagagacat   2040

aataataagg atgtatctgg cttaaacctt atgcatgaaa aagttagtga atacaaagca   2100

gaagcttcaa gtgacgtgga aggcaacaaa actcatgtat ctggttcaga accaatggat   2160

gaggtctctt gtgtttcaaa tcttactagc aagcagccat gtaaagctcg ggaaggtatg   2220

gatgagaata tggtggattc ctctcaggtg ctcagtcaac cgcttgactc atcgatgctg   2280

gaaagccagc aaaacaacga gaaaggtgga aaagatagtg aggctgggga aatgggtgtg   2340

tttctaagta acagttcgac agctgagagc ccacaaaaat ctttggatga taatgtggca   2400

actggcagag gtttagatgc caaagacagt ggtgatatta tcttggaact tagaaatgag   2460

ctgatggaaa agtccaataa actgagtgaa atggagtcca agctaaatgg tgctatggaa   2520

gaggtatcca atttgagcag agagttggaa acgaatcaga agcttctcga agaatcccag   2580

atgaattgtg cgcatttgga gaactgctta catgaagcaa gagaagaagc ccagacccat   2640

ctttgtgctg ctgatcgtag agcttctcag tatactgcac ttcgtgcatc agctgtgaag   2700

atgcgaggtc tctttgaaag attccggagc tctgtctgtg ctggtagtgg gattgctgat   2760

tttgctgact ccttgcgaac tttggctcaa gctttagcca actccgttaa tgaaaatgaa   2820

gatgatggta ctactgagtt ccggaaatgc atccgagtcc tggcagacaa agttagcttc   2880

ctctccaaac accgggagga attattggag aagtgccaaa atcttgaagc cacaagtgaa   2940

cagacaagaa aggatttgga ggaaaagaaa gagctggtga aaacattgta cactaaacac   3000

caacttggga agcaggcaaa taaggaaaag atatcattcg gtcgtcttga agtccatgag   3060

atagcagcat ttgtgctaaa ccaagcaggg cattacgagg caatcaacag gaactgccca   3120

aattactact tgtcctctga atctgaggca ttgttcacag atcatctccc aagccggcct   3180

acatacattg ttggacagat tgtccacata gagcgccaaa tagtgaaact gccatcacaa   3240

ctttcagctt ctgcttctcc tgaggcgggt aagacacatc atctctgctc agaccagggc   3300

tcgagaactc tggcatcaag ttcaatctca acatcaactt cagcaacaac aacatcaaac   3360

ccttatggtc tctcttcagg atgtgaatac ttcatagtga caatagcaat gcttcctgac   3420

actgctattc atcaacaagc ttcctgatcc ttttgcttgt tcctaaggca gcagatagac   3480

gtgatggaag aaaccccctc cccccaaaaa agaacaaaaa atgtaaatac tttgaattca   3540

aataacacaa tctaaaacca gacagcccct ttatatgatt tgtgggtttc atttgtctct   3600

tctttaactt tcttttattt tcatatcttt cttctttatg tacagctgat gatcactgat   3660

cttagtttaa tcttttctcc ttgtattgta catactctgc tataatttga atgctgtaat   3720

aaaaagatta ctaaatatta cgag                                          3744
```

<210> SEQ ID NO 98
<211> LENGTH: 1148
<212> TYPE: PRT
<213> ORGANISM: Arabidopsis thaliana

<400> SEQUENCE: 98

```
Met Ser Gly Ser Phe Thr Glu Ser Phe Ala Asp Asp Gly Lys Leu Leu
1               5                   10                  15
```

-continued

```
Leu Cys Val Ala Glu Asn Gly His Ser Phe Glu Phe Gln Cys Ser Glu
            20                  25                  30

Thr Thr Ser Val Glu Ser Val Met Arg Phe Val Glu Ser Val Ser Gly
        35                  40                  45

Ile Ala Leu Ser Asp Gln Leu Leu Leu Ser Leu Asp Met Lys Leu Glu
    50                  55                  60

Pro Gln Lys Leu Leu Ser Ala Phe Gly Leu Pro Ala Ser Asp Arg Glu
65                  70                  75                  80

Val Phe Val Phe Asn Lys Ala Met Leu Gln Ser Asn Ser His Pro Pro
                85                  90                  95

Ser Pro Glu Asp Val Asp Leu Gln Asp Val Ala Asp Ala Leu Pro Pro
            100                 105                 110

Ala Ser Leu His Glu His His Pro Leu Asp Asp Ala Ser Asp Pro Ala
        115                 120                 125

Leu Lys Ala Leu Pro Leu Tyr Glu Arg Gln Phe Arg Tyr His Phe His
    130                 135                 140

Lys Gly Arg Thr Ile Tyr Asn Cys Thr Val Val Lys His Glu Asn Cys
145                 150                 155                 160

Glu Arg Leu Thr Arg Glu Gln Lys Val Gln Gln Arg Ala Val Glu Val
                165                 170                 175

Ala Thr Arg Asn Leu Glu Gln Tyr Tyr Arg Val Ile Tyr Gln Asn Phe
            180                 185                 190

Leu Glu Phe Met Lys Arg Tyr Lys His Gln His Arg Leu His Ser Asp
        195                 200                 205

Leu Leu Met Asn Phe Gly Arg Asp Ile Glu Lys Leu Arg Ser Ala Lys
    210                 215                 220

Ile His Pro Tyr Leu Gln Thr Glu Ser Arg Lys Cys Leu Leu Asp Phe
225                 230                 235                 240

Val Lys Glu Asp Asn Leu Lys Lys Ala Val Glu Asn Cys Ala Ser Ser
                245                 250                 255

His Arg Gln Phe Glu Asn Lys Ile Ala Gln Phe Gln Gln Met Phe Val
            260                 265                 270

Glu Val Lys Arg Lys Val Glu Glu Leu Phe Ala Cys Arg Ala Ser Leu
        275                 280                 285

Ser Met Lys Asn Leu Glu Val Thr Val Lys Asp His Glu Arg Phe Ile
    290                 295                 300

Asp Glu Glu Lys Ser Ile Met Gln Ser Leu Ser Lys Asp Val Asn Thr
305                 310                 315                 320

Val Lys Lys Leu Val Asp Asp Cys Met Ser Ser Gln Val Ser Ser Ser
                325                 330                 335

Leu Arg Pro His Asp Ala Val Ser Ala Leu Gly Pro Met Tyr Glu Val
            340                 345                 350

His Asp Lys Asn His Leu Pro Lys Met Gln Ala Cys Tyr Asn Ser Ile
        355                 360                 365

Ser Glu Leu Leu Asp Phe Cys Lys Asn Lys Lys Asn Glu Met Asn Asn
    370                 375                 380

Phe Val His Gly Tyr Met Gln Lys Ile Thr Tyr Val Thr Tyr Ile Ile
385                 390                 395                 400

Lys Asp Ala Lys Leu Gln Phe Pro Val Phe Arg Glu Ala Met Val Arg
                405                 410                 415

Gln Asp Asp Leu Phe Ala Asp Leu Lys Leu Val Arg Gly Val Gly Pro
            420                 425                 430

Ala Tyr Arg Ala Cys Leu Ala Glu Val Val Arg Arg Lys Ala Ser Met
```

-continued

```
        435                 440                 445

Lys Leu Tyr Met Gly Met Ala Gly Gln Leu Ala Glu Lys Leu Ala Met
    450                 455                 460

Lys Arg Glu Thr Glu Val Arg Lys Arg Glu Glu Phe Leu Lys Thr His
465                 470                 475                 480

Gly Pro Phe Val Pro Arg Asp Val Leu Ala Ser Met Gly Leu Tyr Asp
                485                 490                 495

Thr Pro Thr Gln Cys Asp Val Asn Val Ala Pro Tyr Asp Thr Ser Leu
            500                 505                 510

Leu Asn Ile Glu Ile Ser Asp Val Asp Arg Tyr Ala Pro Glu Phe Leu
        515                 520                 525

Val Gly Leu His Ser Lys Ile Ala Ser Leu Lys Ser Ser Leu Thr Met
    530                 535                 540

Ser Gly Asp Ser Ser Leu Ser Ala Glu Pro Glu Glu Ile Gly Ile Asp
545                 550                 555                 560

Thr Phe Asp Lys Asp Asn Phe Asp Asp Ile Leu Ala Ala Ser Glu Leu
                565                 570                 575

Ile Glu Ile Ala Gly Thr Ser Lys Met Glu Val Glu Asn Ala Lys Leu
            580                 585                 590

Lys Ala Asp Leu Ala Ser Ala Ile Ser Arg Ile Cys Ser Leu Gly Pro
        595                 600                 605

Gln Phe Glu Tyr Glu Val Leu Asp Glu Ser Glu Val Glu Asn Val Leu
    610                 615                 620

Lys Asn Ala Ala Asp Lys Thr Ala Glu Ala Leu Gln Ala Lys Asp Glu
625                 630                 635                 640

Tyr Glu Lys His Leu Leu Leu Met Leu Lys Glu Lys Gln Met His Cys
                645                 650                 655

Asp Ser Tyr Glu Lys Arg Ile Arg Glu Leu Glu Gln Arg Leu Ser Asp
            660                 665                 670

Glu Tyr Leu Gln Gly Gln Arg His Asn Asn Lys Asp Val Ser Gly Leu
        675                 680                 685

Asn Leu Met His Glu Lys Val Ser Glu Tyr Lys Ala Glu Ala Ser Ser
    690                 695                 700

Asp Val Glu Gly Asn Lys Thr His Val Ser Gly Ser Glu Pro Met Asp
705                 710                 715                 720

Glu Val Ser Cys Val Ser Asn Leu Thr Ser Lys Gln Pro Cys Lys Ala
                725                 730                 735

Arg Glu Gly Met Asp Glu Asn Met Val Asp Ser Ser Gln Val Leu Ser
            740                 745                 750

Gln Pro Leu Asp Ser Ser Met Leu Glu Ser Gln Gln Asn Asn Glu Lys
        755                 760                 765

Gly Gly Lys Asp Ser Glu Ala Gly Glu Met Gly Val Phe Leu Ser Asn
    770                 775                 780

Ser Ser Thr Ala Glu Ser Pro Gln Lys Ser Leu Asp Asp Asn Val Ala
785                 790                 795                 800

Thr Gly Arg Gly Leu Asp Ala Lys Asp Ser Gly Asp Ile Ile Leu Glu
                805                 810                 815

Leu Arg Asn Glu Leu Met Glu Lys Ser Asn Lys Leu Ser Glu Met Glu
            820                 825                 830

Ser Lys Leu Asn Gly Ala Met Glu Glu Val Ser Asn Leu Ser Arg Glu
        835                 840                 845

Leu Glu Thr Asn Gln Lys Leu Leu Glu Glu Ser Gln Met Asn Cys Ala
    850                 855                 860
```

```
His Leu Glu Asn Cys Leu His Glu Ala Arg Glu Glu Ala Gln Thr His
865                 870                 875                 880

Leu Cys Ala Ala Asp Arg Arg Ala Ser Gln Tyr Thr Ala Leu Arg Ala
                885                 890                 895

Ser Ala Val Lys Met Arg Gly Leu Phe Glu Arg Phe Arg Ser Ser Val
            900                 905                 910

Cys Ala Gly Ser Gly Ile Ala Asp Phe Ala Asp Ser Leu Arg Thr Leu
        915                 920                 925

Ala Gln Ala Leu Ala Asn Ser Val Asn Glu Asn Glu Asp Asp Gly Thr
    930                 935                 940

Thr Glu Phe Arg Lys Cys Ile Arg Val Leu Ala Asp Lys Val Ser Phe
945                 950                 955                 960

Leu Ser Lys His Arg Glu Glu Leu Leu Glu Lys Cys Gln Asn Leu Glu
                965                 970                 975

Ala Thr Ser Glu Gln Thr Arg Lys Asp Leu Glu Glu Lys Lys Glu Leu
            980                 985                 990

Val Lys Thr Leu Tyr Thr Lys His  Gln Leu Gly Lys Gln  Ala Asn Lys
        995                 1000                1005

Glu Lys  Ile Ser Phe Gly Arg  Leu Glu Val His Glu  Ile Ala Ala
    1010                1015                1020

Phe Val  Leu Asn Gln Ala Gly  His Tyr Glu Ala Ile  Asn Arg Asn
    1025                1030                1035

Cys Pro  Asn Tyr Tyr Leu Ser  Ser Glu Ser Glu Ala  Leu Phe Thr
    1040                1045                1050

Asp His  Leu Pro Ser Arg Pro  Thr Tyr Ile Val Gly  Gln Ile Val
    1055                1060                1065

His Ile  Glu Arg Gln Ile Val  Lys Leu Pro Ser Gln  Leu Ser Ala
    1070                1075                1080

Ser Ala  Ser Pro Glu Ala Gly  Lys Thr His His Leu  Cys Ser Asp
    1085                1090                1095

Gln Gly  Ser Arg Thr Leu Ala  Ser Ser Ser Ile Ser  Thr Ser Thr
    1100                1105                1110

Ser Ala  Thr Thr Thr Ser Asn  Pro Tyr Gly Leu Ser  Ser Gly Cys
    1115                1120                1125

Glu Tyr  Phe Ile Val Thr Ile  Ala Met Leu Pro Asp  Thr Ala Ile
    1130                1135                1140

His Gln  Gln Ala Ser
    1145
```

<210> SEQ ID NO 99
<211> LENGTH: 808
<212> TYPE: DNA
<213> ORGANISM: Arabidopsis thaliana

<400> SEQUENCE: 99

```
ttggttttcg tcagaagatt tcaaggttta gggtttctgc aattcaacca tggcagagca     60

gacggagaag gcgtttctta agcaaccaaa agttttctta agctcgaaga aatctggtaa    120

gggaaagagg cctggtaaag gaggtaatcg tttctggaag aacattggcc ttggtttcaa    180

aactccaaga gaggctattg aaggaacata cattgaccag aaatgtccct ttactggtac    240

ggtttcaatc aggggtcgca tcttgtctgg aacttgtcac agtgcaaaga tgcagaggac    300

gatcattgtt cgtagggact atcttcattt tgtgaagaag tatcgaagat atgagaaaag    360

acactcaaac attcctgctc atgtttcccc gtgcttccgt gtcaaagaag gagatcgtgt    420
```

-continued

```
taccattggg caatgcaggc cattgtcaaa gacggtgagg ttcaatgtcc tgaaggtcat    480

tccggctgga agctcttcta tcgggaaaaa agcattcact ggaatgtaaa agagattcag    540

atttgttgaa aaggtgcgaa ctagtattct aagagtttag aatttttcta gcagagttat    600

tggattcgtt tcttaagatc tatgatcaaa ggaaaccaga ttttctgttt catttagtga    660

ttcaagtatc aagatatgtc tatggttata gttttactcc aatatatcta gtcatgagtt    720

gctatctact agtcatgatt tcgatgaaaa gtggaattat gcttttgcta tcttgatatt    780

tatctttgtc taatcgatat ttcttgct                                       808


<210> SEQ ID NO 100
<211> LENGTH: 159
<212> TYPE: PRT
<213> ORGANISM: Arabidopsis thaliana

<400> SEQUENCE: 100

Met Ala Glu Gln Thr Glu Lys Ala Phe Leu Lys Gln Pro Lys Val Phe
1               5                   10                  15

Leu Ser Ser Lys Lys Ser Gly Lys Gly Lys Arg Pro Gly Lys Gly Gly
            20                  25                  30

Asn Arg Phe Trp Lys Asn Ile Gly Leu Gly Phe Lys Thr Pro Arg Glu
        35                  40                  45

Ala Ile Glu Gly Thr Tyr Ile Asp Gln Lys Cys Pro Phe Thr Gly Thr
    50                  55                  60

Val Ser Ile Arg Gly Arg Ile Leu Ser Gly Thr Cys His Ser Ala Lys
65                  70                  75                  80

Met Gln Arg Thr Ile Ile Val Arg Arg Asp Tyr Leu His Phe Val Lys
                85                  90                  95

Lys Tyr Arg Arg Tyr Glu Lys Arg His Ser Asn Ile Pro Ala His Val
            100                 105                 110

Ser Pro Cys Phe Arg Val Lys Glu Gly Asp Arg Val Thr Ile Gly Gln
        115                 120                 125

Cys Arg Pro Leu Ser Lys Thr Val Arg Phe Asn Val Leu Lys Val Ile
    130                 135                 140

Pro Ala Gly Ser Ser Ser Ile Gly Lys Lys Ala Phe Thr Gly Met
145                 150                 155
```

GENERATION OF PLANTS WITH ALTERED PROTEIN, FIBER, OR OIL CONTENT

CROSS REFERENCE TO RELATED APPLICATION(S)

This application claims the benefit of U.S. Provisional Application No. 60/866,059, filed Nov. 15, 2006, the entirety of which is incorporated herein by reference.

FIELD OF THE DISCLOSURE

The present disclosure is related to transgenic plants with altered oil, protein, and/or fiber content, as well as methods of making plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243: 1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol.* 103, 467-476; Okuley et al., 1994, *Plant Cell* 6(1): 147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9$^{th}$ *International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods (see, for example, WO 2007/053482 and WO 2005/107437, which are incorporated herein by reference in their entirety).

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. Nos. 5,550,318; 5,538,880, 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, and 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000, *Plant Physiology*, 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 ul 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are obtained from plant parts (e.g. seed) using standard methods.

ImQ Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 1, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 1, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.,* 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.,).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6×single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999*, Nucleic Acids Res.* 27:292). Such sequence variants may be used in the methods disclosed herein.

The disclosed methods may use orthologs of a disclosed *Arabidopsis* IMQ nucleic acid sequence. Representative putative orthologs of each of the disclosed *Arabidopsis* IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.,* 95:5849-5856; Huynen M A et al., 2000*, Genome Research,* 10: 1204-1210).

Programs for multiple sequence alignment, such as CLUSTAL (Thompson J D et al., 1994*, Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989*, Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual*, Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased) protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (Medicago sativa), tobacco (Nicotiana), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.,* 91:694-701), sunflower (Everett et al., 1987, *Bio/Technology,* 5:1201), soybean (Christou et al., 1989, *Proc. Natl. Acad. Sci. USA,* 86:7500-7504; Kline et al., 1987, *Nature,* 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol. Biol.,* 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol. Bio.,* 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 oleosin promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7S$\alpha$ promoter (U.S. Application No. 2003/0093828), the soybean 7S$\alpha$' beta conglycinin promoter, a 7S $\alpha$' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of $\beta$-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10: 1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature,* 334:724-726; van der Krol et al., 1988, *BioTechniques,* 6:958-976); co-suppression (Napoli, et al., 1990, *Plant Cell,* 2:279-289); ribozymes (PCT Publication WO 97/10328); and combinations of sense and antisense (Waterhouse, et al., 1998, *Proc. Natl. Acad. Sci. USA,* 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA,* 85:8805-8809), a partial cDNA sequence including fragments of 5' coding sequence, (Cannon et al., 1990, *Plant Mol. Biol.,* 15:39-47), or 3' non-coding sequences (Ch'ng et al., 1989, *Proc. Natl. Acad. Sci. USA,* 86:10006-10010). Cosuppression techniques may use the entire cDNA sequence (Napoli et al., 1990, *Plant Cell,* 2:279-289; van der Krol et al., 1990, *Plant Cell,* 2:291-299), or a partial cDNA sequence (Smith et al., 1990, *Mol. Gen. Genetics,* 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J. Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.,* 2003 June; 107 (1):181-9; and Lionneton et al., *Genome,* 2002 December; 45(6):1203-15). Thus, in a further aspect of the disclosure, an IMQ nucleic acid is used to identify whether a plant having altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMQ Phenotype and/or an IOQ Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology,* 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979, *J. Agri. Food Chem.,* 27: 1262-1266). Digestible protein content of in a known mass of seed was determined by quantifying the individual amino acids liberated by an acid hydrolysis Steine and Moore (1958, *Anal. Chem.,* 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ53.2 | At4g03480 | W000143264 | 127.95% | 94.43% | 89.75% | |
| IMQ53.3 | At4g03490 | W000143264 | 127.95% | 94.43% | 89.75% | |
| IMQ53.4 | At4g03500 | W000143264 | 127.95% | 94.43% | 89.75% | |
| IMQ53.4 | At4g03500 | W000143264 | 127.95% | 94.43% | 89.75% | |
| IMQ54.1 | At4g05581 | W000111734 | 113.67% | 94.10% | 96.44% | |
| IMQ55.1 | At4g06676 | W000090285 | 110.06% | 90.75% | 94.63% | |
| IMQ56.1 | At4g13660 | W000162122 | 112.35% | 93.32% | 94.53% | |
| IMQ56.2 | At4g13670 | W000162122 | 112.35% | 93.32% | 94.53% | |
| IMQ56.3 | At4g13680 | W000162122 | 112.35% | 93.32% | 94.53% | |
| IMQ56.4 | At4g13690 | W000162122 | 112.35% | 93.32% | 94.53% | |
| IMQ57.1 | At4g14240 | W000169616 | 109.97% | 88.10% | 97.31% | |
| IMQ57.1 | At4g14240 | W000169616 | 109.97% | 88.10% | 97.31% | |
| IMQ57.2 | At4g14250 | W000169616 | 109.97% | 88.10% | 97.31% | |
| IMQ57.3 | At4g14260 | W000169616 | 109.97% | 88.10% | 97.31% | 99.87% |
| IMQ57.4 | At4g14270 | W000169616 | 109.97% | 88.10% | 97.31% | |
| IMQ58.1 | At4g14780 | W000091241 | 112.94% | 86.10% | 90.28% | 100.11% |
| IMQ58.2 | At4g14790 | W000091241 | 112.94% | 86.10% | 90.28% | |
| IMQ59.1 | At4g16890 | W000139253 | 112.83% | 90.85% | 96.84% | |
| IMQ59.2 | At4g16900 | W000139253 | 112.83% | 90.85% | 96.84% | |
| IMQ60.1 | At4g17140 | W000153134 | 118.73% | 90.26% | 92.78% | |
| IMQ60.2 | At4g17150 | W000153134 | 118.73% | 90.26% | 92.78% | |
| IMQ60.3 | At4g17160 | W000153134 | 118.73% | 90.26% | 92.78% | |
| IMQ60.4 | At4g17170 | W000153134 | 118.73% | 90.26% | 92.78% | |
| IMQ61.1 | At4g17710 | W000144188 | 118.65% | 92.13% | 95.33% | 97.68% |
| IMQ61.2 | At4g17720 | W000144188 | 118.65% | 92.13% | 95.33% | |
| IMQ61.3 | At4g17730 | W000144188 | 118.65% | 92.13% | 95.33% | 97.68% |
| IMQ61.4 | At4g17740 | W000144188 | 118.65% | 92.13% | 95.33% | |
| IMQ61.4 | At4g17740 | W000144188 | 118.65% | 92.13% | 95.33% | |
| IMQ61.5 | At4g17750 | W000144188 | 118.65% | 92.13% | 95.33% | |
| IMQ61.6 | At4g17760 | W000144188 | 118.65% | 92.13% | 95.33% | |
| IMQ61.6 | At4g17760 | W000144188 | 118.65% | 92.13% | 95.33% | |
| IMQ62.1 | At4g19900 | W000132512 | 105.96% | 93.33% | 100.59% | |
| IMQ62.2 | At4g19920 | W000132512 | 105.96% | 93.33% | 100.59% | |
| IMQ62.3 | At4g19930 | W000132512 | 105.96% | 93.33% | 100.59% | |
| IMQ62.4 | At4g19940 | W000132512 | 105.96% | 93.33% | 100.59% | |
| IMQ63.1 | At4g21580 | W000049471 | 120.63% | 91.18% | 83.46% | |
| IMQ63.1 | At4g21580 | W000049471 | 120.63% | 91.18% | 83.46% | |
| IMQ63.2 | At4g21585 | W000049471 | 120.63% | 91.18% | 83.46% | |
| IMQ63.3 | At4g21590 | W000049471 | 120.63% | 91.18% | 83.46% | |
| IMQ63.4 | At4g21600 | W000049471 | 120.63% | 91.18% | 83.46% | |
| IMQ63.5 | At4g21610 | W000049471 | 120.63% | 91.18% | 83.46% | |
| IMQ64.1 | At4g28310 | W000086255 | 117.65% | 89.86% | 89.20% | |
| IMQ64.2 | At4g28320 | W000086255 | 117.65% | 89.86% | 89.20% | 99.72% |
| IMQ64.3 | At4g28330 | W000086255 | 117.65% | 89.86% | 89.20% | |
| IMQ64.4 | At4g28340 | W000086255 | 117.65% | 89.86% | 89.20% | |
| IMQ64.5 | At4g28350 | W000086255 | 117.65% | 89.86% | 89.20% | 99.72% |
| IMQ65.1 | At4g30160 | W000181381 | 110.94% | 91.07% | 91.91% | |
| IMQ66.1 | At4g30780 | W000092135 | 105.82% | 89.32% | 100.61% | 101.11% |
| IMQ66.2 | At4g30790 | W000092135 | 105.82% | 89.32% | 100.61% | |
| IMQ66.3 | At4g30800 | W000092135 | 105.82% | 89.32% | 100.61% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ53.2 | At4g03480 | gi\|18412274 | SEQ ID NO: 1 | gi\|15236321 | SEQ ID NO: 2 | protein binding | IPR002110 Ankyrin |
| IMQ53.3 | At4g03490 | gi\|79463133 | SEQ ID NO: 3 | gi\|79463134 | SEQ ID NO: 4 | protein binding | IPR001093 IMP dehydrogenase/GMP reductase; IPR002110 Ankyrin |
| IMQ53.4 | At4g03500 | gi\|30679501 | SEQ ID NO: 5 | gi\|15236325 | SEQ ID NO: 6 | protein binding | IPR002110 Ankyrin |
| IMQ53.4 | At4g03500 | gi\|79463133 | SEQ ID NO: 7 | gi\|79463134 | SEQ ID NO: 8 | protein binding | IPR002110 Ankyrin; IPR001093 IMP dehydrogenase/GMP reductase |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ54.1 | At4g05581 | gi\|22328377 | SEQ ID NO: 9 | gi\|22328378 | SEQ ID NO: 10 | unknown protein | |
| IMQ55.1 | At4g06676 | gi\|30680260 | SEQ ID NO: 11 | gi\|30680261 | SEQ ID NO: 12 | unknown protein | |
| IMQ56.1 | At4g13660 | gi\|30682562 | SEQ ID NO: 13 | gi\|15236330 | SEQ ID NO: 14 | unknown protein | IPR008030 NmrA-like |
| IMQ56.2 | At4g13670 | gi\|30682565 | SEQ ID NO: 15 | gi\|30682566 | SEQ ID NO: 16 | unknown protein | IPR002477 Peptidoglycan-binding domain 1; IPR001305 DnaJ central region |
| IMQ56.3 | At4g13680 | gi\|18414055 | SEQ ID NO: 17 | gi\|15236332 | SEQ ID NO: 18 | unknown protein | IPR005174 Protein of unknown function DUF295 |
| IMQ56.4 | At4g13690 | gi\|18414057 | SEQ ID NO: 19 | gi\|15236333 | SEQ ID NO: 20 | unknown protein | |
| IMQ57.1 | At4g14240 | gi\|79325096 | SEQ ID NO: 21 | gi\|79325097 | SEQ ID NO: 22 | unknown protein | IPR000644 CBS; IPR002550 Protein of unknown function DUF21 |
| IMQ57.1 | At4g14240 | gi\|42566781 | SEQ ID NO: 23 | gi\|42566782 | SEQ ID NO: 24 | unknown protein | IPR000644 CBS; IPR002550 Protein of unknown function DUF21; IPR001093 IMP dehydrogenase/GMP reductase |
| IMQ57.2 | At4g14250 | gi\|18414172 | SEQ ID NO: 25 | gi\|15236456 | SEQ ID NO: 26 | unknown protein | IPR001012 UBX; IPR002171 Ribosomal protein L2; IPR005880 Ribosomal protein L2, bacterial and organelle form |
| IMQ57.3 | At4g14260 | gi\|18414173 | SEQ ID NO: 27 | gi\|18414174 | SEQ ID NO: 28 | unknown protein | IPR005174 Protein of unknown function DUF295 |
| IMQ57.4 | At4g14270 | gi\|30682765 | SEQ ID NO: 29 | gi\|18414176 | SEQ ID NO: 30 | unknown protein | |
| IMQ58.1 | At4g14780 | gi\|30682994 | SEQ ID NO: 31 | gi\|15233574 | SEQ ID NO: 32 | ATP binding/ kinase/protein kinase/protein serine/threonine kinase/protein-tyrosine kinase | IPR000719 Protein kinase; IPR008271 Serine/threonine protein kinase, active site |
| IMQ58.2 | At4g14790 | gi\|30682997 | SEQ ID NO: 33 | gi\|30682998 | SEQ ID NO: 34 | ATSUV3 | IPR001650 Helicase, C-terminal; IPR002048 Calcium-binding EF-hand |
| IMQ59.1 | At4g16890 | gi\|18414772 | SEQ ID NO: 35 | gi\|15235924 | SEQ ID NO: 36 | SNC1 (SUPPRESSOR OF NPR1-1, CONSTITUTIVE 1) | IPR000157 TIR; IPR000767 Disease resistance protein; IPR001611 Leucine-rich repeat; IPR002182 NB-ARC; IPR003593 AAA ATPase; IPR011713 Leucine-rich |
| IMQ59.2 | At4g16900 | gi\|18414775 | SEQ ID NO: 37 | gi\|15235926 | SEQ ID NO: 38 | ATP binding/ transmembrane receptor | IPR000157 TIR; IPR000767 Disease resistance protein; IPR001611 Leucine-rich repeat; IPR002182 NB-ARC; IPR003593 AAA ATPase; IPR011713 Leucine-rich |
| IMQ60.1 | At4g17140 | gi\|18414823 | SEQ ID NO: 39 | gi\|15235978 | SEQ ID NO: 40 | unknown protein | IPR001849 Pleckstrin-like |
| IMQ60.2 | At4g17150 | gi\|79476959 | SEQ ID NO: 41 | gi\|79476960 | SEQ ID NO: 42 | catalytic | IPR000379 Esterase/lipase/thioesterase |
| IMQ60.3 | At4g17160 | gi\|18414828 | SEQ ID NO: 43 | gi\|15235980 | SEQ ID NO: 44 | GTP binding | IPR001806 Ras GTPase; IPR002078 Sigma-54 factor, interaction region; IPR003579 Ras small GTPase, Rab type; IPR005225 Small GTP-binding protein domain |
| IMQ60.4 | At4g17170 | gi\|30683948 | SEQ ID NO: 45 | gi\|15235981 | SEQ ID NO: 46 | AT-RAB2; GTP binding | IPR001806 Ras GTPase; IPR002078 Sigma-54 factor, interaction region; IPR003579 Ras small |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| | | | | | | | GTPase, Rab type; IPR005225 Small GTP-binding protein domain |
| IMQ61.1 | At4g17710 | gi\|30684154 | SEQ ID NO: 47 | gi\|30684155 | SEQ ID NO: 48 | DNA binding/ transcription factor | IPR002913 Lipid-binding START; IPR001356 Homeobox |
| IMQ61.2 | At4g17720 | gi\|42566905 | SEQ ID NO: 49 | gi\|18414951 | SEQ ID NO: 50 | nucleic acid binding | IPR000504 RNA-binding region RNP-1 (RNA recognition motif) |
| IMQ61.3 | At4g17730 | gi\|30684160 | SEQ ID NO: 51 | gi\|18414953 | SEQ ID NO: 52 | SYP23; t-SNARE | IPR000727 Target SNARE coiled-coil region; IPR006011 Syntaxin, N-terminal |
| IMQ61.4 | At4g17740 | gi\|30684168 | SEQ ID NO: 53 | gi\|30684169 | SEQ ID NO: 54 | protein binding/ serine-type peptidase | IPR004447 Peptidase S41A, C-terminal protease; IPR005151 Peptidase S41; IPR001478 PDZ/DHR/GLGF |
| IMQ61.4 | At4g17740 | gi\|30684165 | SEQ ID NO: 55 | gi\|15236628 | SEQ ID NO: 56 | protein binding/ serine-type peptidase | IPR004447 Peptidase S41A, C-terminal protease; IPR005151 Peptidase S41; IPR001478 PDZ/DHR/GLGF |
| IMQ61.5 | At4g17750 | gi\|30684174 | SEQ ID NO: 57 | gi\|15236631 | SEQ ID NO: 58 | HSF1 (*ARABIDOPSIS* HEAT SHOCK FACTOR 1); DNA binding/ transcription factor | IPR000232 Heat shock factor (HSF)-type, DNA-binding; IPR002341 HSF/ETS, DNA-binding |
| IMQ61.6 | At4g17760 | gi\|79325144 | SEQ ID NO: 59 | gi\|79325145 | SEQ ID NO: 60 | unknown protein | |
| IMQ61.6 | At4g17760 | gi\|42566906 | SEQ ID NO: 61 | gi\|30684177 | SEQ ID NO: 62 | damaged DNA binding/ exonuclease | IPR003011 Repair protein Rad1; IPR003021 Repair protein Rad1/Rec1 |
| IMQ62.1 | At4g19900 | gi\|18415401 | SEQ ID NO: 63 | gi\|15235222 | SEQ ID NO: 64 | transferase, transferring glycosyl groups | IPR002885 Pentatricopeptide repeat; IPR007577 Glycosyltransferase sugar-binding region containing DXD motif; IPR007652 Alpha 1,4-glycosyltransferase conserved region |
| IMQ62.2 | At4g19920 | gi\|42566972 | SEQ ID NO: 65 | gi\|42566973 | SEQ ID NO: 66 | transmembrane receptor | IPR000157 TIR |
| IMQ62.3 | At4g19930 | gi\|18415404 | SEQ ID NO: 67 | gi\|15235228 | SEQ ID NO: 68 | unknown protein | IPR006527 F-box protein interaction domain; IPR001810 Cyclin-like F-box |
| IMQ62.4 | At4g19940 | gi\|30684942 | SEQ ID NO: 69 | gi\|15235230 | SEQ ID NO: 70 | unknown protein | IPR006527 F-box protein interaction domain; IPR001810 Cyclin-like F-box |
| IMQ63.1 | At4g21580 | gi\|79325212 | SEQ ID NO: 71 | gi\|79325213 | SEQ ID NO: 72 | oxidoreductase/zinc ion binding | IPR001093 IMP dehydrogenase/GMP reductase; IPR002085 Alcohol dehydrogenase superfamily, zinc-containing; IPR011032 GroES-like |
| IMQ63.1 | At4g21580 | gi\|30685494 | SEQ ID NO: 73 | gi\|15234529 | SEQ ID NO: 74 | oxidoreductase/zinc ion binding | IPR002085 Alcohol dehydrogenase superfamily, zinc-containing; IPR011032 GroES-like |
| IMQ63.2 | At4g21585 | gi\|22328856 | SEQ ID NO: 75 | gi\|22328857 | SEQ ID NO: 76 | endonuclease/ nucleic acid binding | IPR003154 S1/P1 nuclease |
| IMQ63.3 | At4g21590 | gi\|18415726 | SEQ ID NO: 77 | gi\|18415727 | SEQ ID NO: 78 | endonuclease/ nucleic acid binding | IPR003154 S1/P1 nuclease |
| IMQ63.4 | At4g21600 | gi\|18415728 | SEQ ID NO: 79 | gi\|18415729 | SEQ ID NO: 80 | endonuclease/ nucleic acid binding | IPR003154 S1/P1 nuclease; IPR000197 Zinc finger, TAZ-type |
| IMQ63.5 | At4g21610 | gi\|30685506 | SEQ ID NO: 81 | gi\|15234540 | SEQ ID NO: 82 | LOL2 (LSD ONE LIKE 2); transcription factor | IPR005735 Zinc finger, LSD1-type |
| IMQ64.1 | At4g28310 | gi\|30687918 | SEQ ID NO: 83 | gi\|18417168 | SEQ ID NO: 84 | unknown protein | |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ64.2 | At4g28320 | gi\|42567211 | SEQ ID NO: 85 | gi\|15235255 | SEQ ID NO: 86 | hydrolase, hydrolyzing O-glycosyl compounds | IPR001547 Glycoside hydrolase, family 5 |
| IMQ64.3 | At4g28330 | gi\|79487708 | SEQ ID NO: 87 | gi\|79487709 | SEQ ID NO: 88 | unknown protein | |
| IMQ64.4 | At4g28340 | gi\|18417173 | SEQ ID NO: 89 | gi\|15235274 | SEQ ID NO: 90 | unknown protein | |
| IMQ64.5 | At4g28350 | gi\|18417174 | SEQ ID NO: 91 | gi\|15235275 | SEQ ID NO: 92 | ATP binding/ carbohydrate binding/ kinase/protein kinase/protein serine/threonine kinase/protein-tyrosine kinase | IPR000719 Protein kinase; IPR008271 Serine/threonine protein kinase, active site; IPR000985 Legume lectin, alpha; IPR001220 Legume lectin, beta domain |
| IMQ65.1 | At4g30160 | gi\|30688570 | SEQ ID NO: 93 | gi\|15234646 | SEQ ID NO: 94 | VLN4 (*ARABIDOPSIS THALIANA* VILLIN 4); actin binding | IPR003128 Villin headpiece; IPR007122 Gelsolin; IPR007123 Gelsolin region |
| IMQ66.1 | At4g30780 | gi\|42567282 | SEQ ID NO: 95 | gi\|15234853 | SEQ ID NO: 96 | unknown protein | |
| IMQ66.2 | At4g30790 | gi\|30688800 | SEQ ID NO: 97 | gi\|15234869 | SEQ ID NO: 98 | unknown protein | |
| IMQ66.3 | At4g30800 | gi\|30688802 | SEQ ID NO: 99 | gi\|15234873 | SEQ ID NO: 100 | structural constituent of ribosome | IPR000266 Ribosomal protein S17 |

TABLE 3

| | | | | 5. Orthologous Genes: Nucleic Acid/Polypeptide seq. GI# | | |
|---|---|---|---|---|---|---|
| 1. Gene alias | 2. Tair | 3. Nucleic Acid seq. GI# | 4. Polypeptide seq. GI# | Nucleic Acid GI# | Polypeptide GI# | Species |
| IMQ53.2 | At4g03480 | gi\|18412274 | gi\|15236321 | gi\|18412265 | gi\|15236309 | *Arabidopsis thaliana* |
| | | | | gi\|42566786 | gi\|42566787 | *Arabidopsis thaliana* |
| | | | | gi\|30682836 | gi\|18414210 | *Arabidopsis thaliana* |
| IMQ53.3 | At4g03490 | gi\|79463133 | gi\|79463134 | gi\|30679491 | gi\|15236310 | *Arabidopsis thaliana* |
| | | | | gi\|18379122 | gi\|15218888 | *Arabidopsis thaliana* |
| | | | | gi\|18412781 | gi\|18412782 | *Arabidopsis thaliana* |
| | | | | gi\|79324998 | gi\|79324999 | *Arabidopsis thaliana* |
| | | | | gi\|42572834 | gi\|42572835 | *Arabidopsis thaliana* |
| IMQ53.4 | At4g03500 | gi\|30679501 | gi\|15236325 | gi\|42566275 | gi\|42566276 | *Arabidopsis thaliana* |
| | | | | gi\|18379122 | gi\|15218888 | *Arabidopsis thaliana* |
| | | | | gi\|30679491 | gi\|15236310 | *Arabidopsis thaliana* |
| IMQ53.4 | At4g03500 | gi\|79463133 | gi\|79463134 | gi\|30679491 | gi\|15236310 | *Arabidopsis thaliana* |
| | | | | gi\|18379122 | gi\|15218888 | *Arabidopsis thaliana* |
| | | | | gi\|18412781 | gi\|18412782 | *Arabidopsis thaliana* |
| | | | | gi\|79324998 | gi\|79324999 | *Arabidopsis thaliana* |
| | | | | gi\|42572834 | gi\|42572835 | *Arabidopsis thaliana* |
| IMQ54.1 | At4g05581 | gi\|22328377 | gi\|22328378 | gi\|18400229 | gi\|15221231 | *Arabidopsis thaliana* |
| | | | | gi\|18399503 | gi\|15219498 | *Arabidopsis thaliana* |
| | | | | gi\|18401398 | gi\|15219471 | *Arabidopsis thaliana* |
| IMQ55.1 | At4g06676 | gi\|30680260 | gi\|30680261 | gi\|66809904 | gi\|66809905 | *Dictyostelium discoideum* |
| | | | | gi\|71003042 | gi\|71003043 | *Ustilago maydis* 521 |
| | | | | gi\|71411922 | gi\|71411923 | *Trypanosoma cruzi* |
| IMQ56.1 | At4g13660 | gi\|30682562 | gi\|15236330 | gi\|30692639 | gi\|15222571 | *Arabidopsis thaliana* |
| | | | | gi\|1230613 | gi\|1230614 | *Lupinus albus* |
| | | | | gi\|76559885 | gi\|76559886 | *Vitis vinifera* |
| IMQ56.2 | At4g13670 | gi\|30682565 | gi\|30682566 | gi\|50926431 | gi\|50926432 | *Oryza sativa* (*japonica* cultivar-group) |
| | | | | gi\|30581878 | gi\|53688717 | *Nostoc punctiforme* PCC 73102 |
| | | | | gi\|47118302 | gi\|17131838 | *Nostoc* sp. PCC 7120 |
| IMQ56.3 | At4g13680 | gi\|18414055 | gi\|15236332 | gi\|18423728 | gi\|15240489 | *Arabidopsis thaliana* |
| | | | | gi\|18423798 | gi\|18423799 | *Arabidopsis thaliana* |
| | | | | gi\|18423796 | gi\|18423797 | *Arabidopsis thaliana* |
| | | | | gi\|30696471 | gi\|15239672 | *Arabidopsis thaliana* |
| IMQ56.4 | At4g13690 | gi\|18414057 | gi\|15236333 | gi\|37535313 | gi\|37535314 | *Oryza sativa* (*japonica* cultivar-group) |
| IMQ57.1 | At4g14240 | gi\|79325096 | gi\|79325097 | gi\|42566781 | gi\|42566782 | *Arabidopsis thaliana* |
| | | | | gi\|42566779 | gi\|42566780 | *Arabidopsis thaliana* |
| | | | | gi\|34536733 | gi\|46981317 | *Oryza sativa* (*japonica* cultivar-group) |
| IMQ57.1 | At4g14240 | gi\|42566781 | gi\|42566782 | gi\|79325096 | gi\|79325097 | *Arabidopsis thaliana* |
| | | | | gi\|42566779 | gi\|42566780 | *Arabidopsis thaliana* |
| | | | | gi\|34536733 | gi\|46981317 | *Oryza sativa* (*japonica* cultivar-group) |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ57.2 | At4g14250 | gi\|18414172 | gi\|15236456 | gi\|42571472 | gi\|42571473 | *Arabidopsis thaliana* |
| | | | | gi\|30683871 | gi\|18394134 | *Arabidopsis thaliana* |
| | | | | gi\|18406382 | gi\|15218827 | *Arabidopsis thaliana* |
| | | | | gi\|50929542 | gi\|50929543 | *Oryza sativa* (*japonica* cultivar-group) |
| IMQ57.3 | At4g14260 | gi\|18414173 | gi\|18414174 | gi\|30687051 | gi\|30687052 | *Arabidopsis thaliana* |
| | | | | gi\|18422635 | gi\|15237387 | *Arabidopsis thaliana* |
| | | | | gi\|18422636 | gi\|15237388 | *Arabidopsis thaliana* |
| IMQ57.4 | At4g14270 | gi\|30682765 | gi\|18414176 | gi\|8489785 | gi\|8489786 | *Lycopersicon esculentum* |
| | | | | gi\|30688644 | gi\|15227351 | *Arabidopsis thaliana* |
| | | | | gi\|42571168 | gi\|42571169 | *Arabidopsis thaliana* |
| | | | | gi\|30688650 | gi\|30688651 | *Arabidopsis thaliana* |
| | | | | gi\|56481322 | gi\|56481323 | *Pseudotsuga menziesii* var. *menziesii* |
| IMQ58.1 | At4g14780 | gi\|30682994 | gi\|15233574 | gi\|30686769 | gi\|18403507 | *Arabidopsis thaliana* |
| | | | | gi\|50917222 | gi\|50917223 | *Oryza sativa* (*japonica* cultivar-group) |
| | | | | gi\|30678343 | gi\|15232131 | *Arabidopsis thaliana* |
| IMQ58.2 | At4g14790 | gi\|30682997 | gi\|30682998 | gi\|50918648 | gi\|50918649 | *Oryza sativa* (*japonica* cultivar-group) |
| | | | | gi\|18421918 | gi\|15242497 | *Arabidopsis thaliana* |
| | | | | gi\|32479936 | gi\|38344959 | *Oryza sativa* (*japonica* cultivar-group) |
| IMQ59.1 | At4g16890 | gi\|18414772 | gi\|15235924 | gi\|18414777 | gi\|15235928 | *Arabidopsis thaliana* |
| | | | | gi\|30683874 | gi\|30683875 | *Arabidopsis thaliana* |
| | | | | gi\|30683869 | gi\|30683870 | *Arabidopsis thaliana* |
| IMQ59.2 | At4g16900 | gi\|18414775 | gi\|15235926 | gi\|18414777 | gi\|15235928 | *Arabidopsis thaliana* |
| | | | | gi\|18414785 | gi\|15235932 | *Arabidopsis thaliana* |
| | | | | gi\|30683869 | gi\|30683870 | *Arabidopsis thaliana* |
| IMQ60.1 | At4g17140 | gi\|18414823 | gi\|15235978 | gi\|37536929 | gi\|37536930 | *Oryza sativa* (*japonica* cultivar-group) |
| | | | | gi\|50908168 | gi\|50908169 | *Oryza sativa* (*japonica* cultivar-group) |
| | | | | gi\|30694235 | gi\|30694236 | *Arabidopsis thaliana* |
| IMQ60.2 | At4g17150 | gi\|79476959 | gi\|79476960 | gi\|51091942 | gi\|51091948 | *Oryza sativa* (*japonica* cultivar-group) |
| | | | | gi\|18414827 | gi\|15235979 | *Arabidopsis thaliana* |
| | | | | gi\|42566783 | gi\|42566784 | *Arabidopsis thaliana* |
| IMQ60.3 | At4g17160 | gi\|18414828 | gi\|15235980 | gi\|30683948 | gi\|15235981 | *Arabidopsis thaliana* |
| | | | | gi\|1370175 | gi\|1370176 | *Lotus corniculatus* var. *japonicus* |
| | | | | gi\|1208536 | gi\|1208537 | *Glycine max* |
| IMQ60.4 | At4g17170 | gi\|30683948 | gi\|15235981 | gi\|1370175 | gi\|1370176 | *Lotus corniculatus* var. *japonicus* |
| | | | | gi\|1208536 | gi\|1208537 | *Glycine max* |
| | | | | gi\|16755591 | gi\|16755592 | *Nicotiana tabacum* |
| IMQ61.1 | At4g17710 | gi\|30684154 | gi\|30684155 | gi\|42568359 | gi\|42568360 | *Arabidopsis thaliana* |
| | | | | gi\|22475196 | gi\|22475197 | *Gossypium hirsutum* |
| | | | | gi\|33355393 | gi\|33355394 | *Gossypium hirsutum* |
| IMQ61.2 | At4g17720 | gi\|42566905 | gi\|18414951 | gi\|30695062 | gi\|30695063 | *Arabidopsis thaliana* |
| | | | | gi\|58532007 | gi\|58532021 | *Oryza sativa* (*japonica* cultivar-group) |
| | | | | gi\|50928852 | gi\|50928853 | *Oryza sativa* (*japonica* cultivar-group) |
| IMQ61.3 | At4g17730 | gi\|30684160 | gi\|18414953 | gi\|30695059 | gi\|18422725 | *Arabidopsis thaliana* |
| | | | | gi\|76573304 | gi\|76573305 | *Solanum tuberosum* |
| | | | | gi\|22597173 | gi\|22597174 | *Glycine max* |
| IMQ61.4 | At4g17740 | gi\|30684168 | gi\|30684169 | gi\|30684165 | gi\|15236628 | *Arabidopsis thaliana* |
| | | | | gi\|19774138 | gi\|19774139 | *Nicotiana plumbaginifolia* |
| | | | | gi\|999434 | gi\|999435 | *Spinacia oleracea* |
| IMQ61.4 | At4g17740 | gi\|30684165 | gi\|15236628 | gi\|30684168 | gi\|30684169 | *Arabidopsis thaliana* |
| | | | | gi\|19774138 | gi\|19774139 | *Nicotiana plumbaginifolia* |
| | | | | gi\|999434 | gi\|999435 | *Spinacia oleracea* |
| IMQ61.5 | At4g17750 | gi\|30684174 | gi\|15236631 | gi\|19259 | gi\|19260 | *Lycopersicon esculentum* |
| | | | | gi\|19491 | gi\|19492 | *Lycopersicon peruvianum* |
| | | | | gi\|56117814 | gi\|56117815 | *Medicago sativa* |
| IMQ61.6 | At4g17760 | gi\|79325144 | gi\|79325145 | gi\|42566906 | gi\|30684177 | *Arabidopsis thaliana* |
| | | | | gi\|55775015 | gi\|50933529 | *Oryza sativa* (*japonica* cultivar-group) |
| | | | | gi\|55775353 | gi\|55775354 | *Oryza sativa* (*japonica* cultivar-group) |
| | | | | gi\|72095944 | gi\|72095945 | *Strongylocentrotus purpuratus* |
| IMQ61.6 | At4g17760 | gi\|42566906 | gi\|30684177 | gi\|55775015 | gi\|50933529 | *Oryza sativa* (*japonica* cultivar-group) |
| | | | | gi\|55775353 | gi\|55775354 | *Oryza sativa* (*japonica* cultivar-group) |
| | | | | gi\|6755271 | gi\|6755272 | *Mus musculus* |
| IMQ62.1 | At4g19900 | gi\|18415401 | gi\|15235222 | gi\|77548247 | gi\|77551887 | *Oryza sativa* (*japonica* cultivar-group) |
| | | | | gi\|34899807 | gi\|34899808 | *Oryza sativa* (*japonica* cultivar-group) |
| | | | | gi\|18421898 | gi\|15242446 | *Arabidopsis thaliana* |
| IMQ62.2 | At4g19920 | gi\|42566972 | gi\|42566973 | gi\|42572962 | gi\|42572963 | *Arabidopsis thaliana* |
| | | | | gi\|42572960 | gi\|42572961 | *Arabidopsis thaliana* |
| | | | | gi\|30694641 | gi\|30694642 | *Arabidopsis thaliana* |
| IMQ62.3 | At4g19930 | gi\|18415404 | gi\|15235228 | gi\|30684942 | gi\|15235230 | *Arabidopsis thaliana* |
| | | | | gi\|42569823 | gi\|15226784 | *Arabidopsis thaliana* |
| | | | | gi\|18424616 | gi\|15241905 | *Arabidopsis thaliana* |
| IMQ62.4 | At4g19940 | gi\|30684942 | gi\|15235230 | gi\|18415404 | gi\|15235228 | *Arabidopsis thaliana* |
| | | | | gi\|18424596 | gi\|15241861 | *Arabidopsis thaliana* |
| | | | | gi\|42569823 | gi\|15226784 | *Arabidopsis thaliana* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ63.1 | At4g21580 | gi\|79325212 | gi\|79325213 | gi\|30685494 | gi\|15234529 | *Arabidopsis thaliana* |
| | | | | gi\|76160991 | gi\|76160992 | *Solanum tuberosum* |
| | | | | gi\|50915649 | gi\|50915650 | *Oryza sativa* (*japonica* cultivar-group) |
| | | | | gi\|51979437 | gi\|51979438 | *Oryza sativa* (*japonica* cultivar-group) |
| | | | | gi\|51978882 | gi\|51964492 | *Oryza sativa* (*japonica* cultivar-group) |
| | | | | gi\|15144390 | gi\|15451578 | *Oryza sativa* |
| IMQ63.1 | At4g21580 | gi\|30685494 | gi\|15234529 | gi\|76160991 | gi\|76160992 | *Solanum tuberosum* |
| | | | | gi\|50915649 | gi\|50915650 | *Oryza sativa* (*japonica* cultivar-group) |
| | | | | gi\|51979437 | gi\|51979438 | *Oryza sativa* (*japonica* cultivar-group) |
| | | | | gi\|51978882 | gi\|51964492 | *Oryza sativa* (*japonica* cultivar-group) |
| | | | | gi\|15144390 | gi\|15451578 | *Oryza sativa* |
| IMQ63.2 | At4g21585 | gi\|22328856 | gi\|22328857 | gi\|18415728 | gi\|18415729 | *Arabidopsis thaliana* |
| | | | | gi\|18415726 | gi\|18415727 | *Arabidopsis thaliana* |
| | | | | gi\|4099834 | gi\|4099835 | *Zinnia elegans* |
| IMQ63.3 | At4g21590 | gi\|18415726 | gi\|18415727 | gi\|18415728 | gi\|18415729 | *Arabidopsis thaliana* |
| | | | | gi\|22328856 | gi\|22328857 | *Arabidopsis thaliana* |
| | | | | gi\|4099834 | gi\|4099835 | *Zinnia elegans* |
| IMQ63.4 | At4g21600 | gi\|18415728 | gi\|18415729 | gi\|22328856 | gi\|22328857 | *Arabidopsis thaliana* |
| | | | | gi\|18415726 | gi\|18415727 | *Arabidopsis thaliana* |
| | | | | gi\|4099834 | gi\|4099835 | *Zinnia elegans* |
| IMQ63.5 | At4g21610 | gi\|30685506 | gi\|15234540 | gi\|21104672 | gi\|54290847 | *Oryza sativa* (*japonica* cultivar-group) |
| | | | | gi\|34912603 | gi\|34912604 | *Oryza sativa* (*japonica* cultivar-group) |
| | | | | gi\|40809628 | gi\|40809629 | *Oryza sativa* (*japonica* cultivar-group) |
| IMQ64.1 | At4g28310 | gi\|30687918 | gi\|18417168 | gi\|42562704 | gi\|15218192 | *Arabidopsis thaliana* |
| | | | | gi\|55775008 | gi\|34897956 | *Oryza sativa* (*japonica* cultivar-group) |
| | | | | gi\|55775165 | gi\|55775166 | *Oryza sativa* (*japonica* cultivar-group) |
| IMQ64.2 | At4g28320 | gi\|42567211 | gi\|15235255 | gi\|30681095 | gi\|30681096 | *Arabidopsis thaliana* |
| | | | | gi\|34909461 | gi\|34909462 | *Oryza sativa* (*japonica* cultivar-group) |
| | | | | gi\|54291087 | gi\|54291095 | *Oryza sativa* (*japonica* cultivar-group) |
| IMQ64.3 | At4g28330 | gi\|79487708 | gi\|79487709 | gi\|18417173 | gi\|15235274 | *Arabidopsis thaliana* |
| | | | | gi\|30687924 | gi\|15235273 | *Arabidopsis thaliana* |
| | | | | gi\|42566279 | gi\|18412310 | *Arabidopsis thaliana* |
| IMQ64.4 | At4g28340 | gi\|18417173 | gi\|15235274 | gi\|30687924 | gi\|15235273 | *Arabidopsis thaliana* |
| | | | | gi\|42566279 | gi\|18412310 | *Arabidopsis thaliana* |
| | | | | gi\|30678652 | gi\|18379130 | *Arabidopsis thaliana* |
| IMQ64.5 | At4g28350 | gi\|18417174 | gi\|15235275 | gi\|30679932 | gi\|18412759 | *Arabidopsis thaliana* |
| | | | | gi\|37534761 | gi\|37534762 | *Oryza sativa* (*japonica* cultivar-group) |
| | | | | gi\|30687228 | gi\|15224347 | *Arabidopsis thaliana* |
| IMQ65.1 | At4g30160 | gi\|30688570 | gi\|15234646 | gi\|18423963 | gi\|15242097 | *Arabidopsis thaliana* |
| | | | | gi\|52077360 | gi\|52077361 | *Oryza sativa* (*japonica* cultivar-group) |
| | | | | gi\|31339055 | gi\|31339056 | *Lilium longiflorum* |
| IMQ66.1 | At4g30780 | gi\|42567282 | gi\|15234853 | gi\|30682294 | gi\|18400458 | *Arabidopsis thaliana* |
| | | | | gi\|50915543 | gi\|50915544 | *Oryza sativa* (*japonica* cultivar-group) |
| | | | | gi\|20218824 | gi\|20218825 | *Pinus pinaster* |
| IMQ66.2 | At4g30790 | gi\|30688800 | gi\|15234869 | gi\|50252064 | gi\|50252083 | *Oryza sativa* (*japonica* cultivar-group) |
| | | | | gi\|66808868 | gi\|66808869 | *Dictyostelium discoideum* |
| | | | | gi\|39945007 | gi\|39945008 | *Magnaporthe grisea* 70-15 |
| IMQ66.3 | At4g30800 | gi\|30688802 | gi\|15234873 | gi\|30693112 | gi\|15229056 | *Arabidopsis thaliana* |
| | | | | gi\|30689125 | gi\|15237819 | *Arabidopsis thaliana* |
| | | | | gi\|22469 | gi\|22470 | *Zea mays* |

Example 2

Analysis of the *Arabidopsis* IMQ Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318.), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Example 3

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value$\leqq$0.05. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

petri plate, treated with *Agrobacterium* Z707S or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with *Agrobacterium*, these are placed back on the callus induction medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and Timentin are antibiotics used to kill the *Agrobacterium*. The selection agent is used to allow the growth of the transformed cells.

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---|---|---|---|---|---|---|---|---|---|---|
| IMQ55.1 | At4g06676 | Pru::At4g06676 | **0.002** | **0.029** | 0.438 | 0.207 | 95.7% | 104.5% | 99.3% | 98.6% |
| IMQ57.3 | At4g14260 | CsVMV::At4g14260 | 0.383 | 0.342 | 0.936 | 0.181 | 98.5% | 102.6% | 100.0% | 98.6% |
| IMQ57.3 | At4g14260 | Pru::At4g14260 | **0.036** | **0.011** | 0.930 | 0.258 | 102.8% | 97.0% | 100.0% | 100.9% |
| IMQ58.1 | At4g14780 | CsVMV::At4g14780 | 0.166 | 0.088 | 0.099 | 0.208 | 102.7% | 97.2% | 101.3% | 98.8% |
| IMQ58.1 | At4g14780 | Pru::At4g14780 | **0.027** | **0.013** | 0.292 | 0.906 | 103.9% | 94.9% | 100.7% | 100.5% |
| IMQ61.3 | At4g17730 | CsVMV::At4g17730 | **0.008** | 0.140 | **0.047** | 0.507 | 96.08% | 103.13% | 98.70% | 99.48% |
| IMQ61.3 | At4g17730 | Pru::At4g17730 | **0.003** | **0.006** | 0.256 | 0.802 | 104.2% | 95.3% | 100.8% | 99.8% |
| IMQ61.4 | At4g17740 | CsVMV::At4g17740 | **0.022** | **0.032** | **0.005** | **0.048** | 104.4% | 95.7% | 102.1% | 98.5% |
| IMQ61.4 | At4g17740 | Pru::At4g17740 | **0.002** | **0.000** | 0.377 | 0.617 | 105.5% | 93.1% | 100.8% | 100.5% |
| IMQ61.5 | At4g17750 | CsVMV::At4g17750 | **0.003** | **0.017** | 0.731 | 0.087 | 94.1% | 105.2% | 99.7% | 98.1% |
| IMQ61.6 | At4g17760 | Pru::At4g17760 | 0.063 | 0.300 | **0.001** | **0.010** | 102.7% | 98.0% | 102.6% | 96.7% |
| IMQ64.2 | At4g28320 | CsVMV::At4g28320 | **0.003** | **0.003** | 0.098 | 0.764 | 106.3% | 95.3% | 100.9% | 99.7% |
| IMQ64.3 | At4g28330 | CsVMV::At4g28330 | 0.183 | 0.231 | **0.016** | **0.021** | 101.4% | 98.8% | 101.4% | 98.2% |
| IMQ64.4 | At4g28340 | CsVMV::At4g28340 | **0.015** | 0.060 | **0.044** | 0.108 | 103.9% | 97.2% | 101.8% | 98.3% |
| IMQ64.4 | At4g28340 | Pru::At4g28340 | 0.564 | 0.667 | **0.016** | **0.038** | 100.6% | 99.5% | 101.3% | 98.2% |
| IMQ64.5 | At4g28350 | CsVMV::At4g28350 | **0.046** | 0.086 | 0.118 | 0.421 | 104.3% | 96.8% | 101.4% | 99.4% |
| IMQ64.5 | At4g28350 | Pru::At4g28350 | 0.057 | 0.137 | 0.218 | 0.334 | 101.6% | 98.4% | 100.7% | 99.2% |
| IMQ66.1 | At4g30780 | CsVMV::At4g30780 | **0.014** | 0.276 | **0.010** | 0.149 | 104.3% | 98.2% | 102.1% | 98.5% |
| IMQ66.1 | At4g30780 | Pru::At4g30780 | **0.021** | 0.252 | **0.016** | 0.110 | 102.9% | 98.0% | 101.4% | 98.3% |
| IMQ66.3 | At4g30800 | CsVMV::At4g30800 | 0.875 | 0.557 | **0.012** | 0.050 | 100.2% | 100.8% | 101.9% | 98.3% |

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium KIDI (MS medium with 1 mg/l kinetin and 1 mg/l 2,4-D) for 3 days as pre-treatment. The segments are then transferred into a Callus samples from independent events are tested by PCR. All the samples tested are positive for the presence of the transformed gene, whereas the non-transformed controls are negative. Callus samples are confirmed to express the appropriate protein as determined by ELISA.

Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, 1 mg/l selection agent, Carbenicillin and Timentin) shoot regeneration medium. After shoots start to regenerate (approximately 3 weeks), hypocotyl segments along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI. 1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A transgenic plant, comprising a plant transformation vector comprising a nucleotide sequence that encodes an IMQ polypeptide at least 95% identical to the amino acid sequence as set forth in SEQ ID NO: 96, whereby the transgenic plant has an improved meal quality phenotype, relative to control plants.

2. The transgenic plant of claim 1, wherein the IMQ polypeptide comprises the amino acid sequence as set forth in SEQ ID NO: 96.

3. The transgenic plant of claim 1, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

4. The transgenic plant of claim 3, wherein the plant is canola.

5. The transgenic plant of claim 1, wherein an improved meal quality phenotype comprises an increase in available metabolizable energy in meal produced from seeds of the transgenic plant, relative to control plants.

6. The transgenic plant of claim 5, wherein an increase in available metabolizable energy comprises an altered protein content in the seeds of the transgenic plant.

7. The transgenic plant of claim 5, wherein the protein content is increased.

8. A plant part obtained from the plant according to claim 1.

9. The plant part of claim 8, which is a seed.

10. Meal, feed, or food produced from the seed of claim 9.

11. A method of producing meal, comprising growing the transgenic plant of claim 1, and recovering meal from the plant, thereby producing meal.

12. The method of claim 11, wherein the meal is produced from seeds of the plant.

13. A method of producing an improved meal quality phenotype in a plant, said method comprising:

a) introducing into progenitor cells of the plant a plant transformation vector comprising a nucleotide sequence that encodes an IMQ polypeptide comprising the amino acid sequence as set forth in SEQ ID NO: 96, b) growing the transformed progenitor cells to produce transgenic plants, wherein the nucleotide sequence is expressed, c) screening the resultant transgenic plants for an improved meal quality phenotype, wherein at least one of the transgenic plants exhibit an improved meal quality phenotype relative to control plants, and d) selecting at least one of the transgenic plants that exhibit an improved meal quality phenotype;

thereby producing the improved meal quality phenotype in the plant.

14. The method of claim 13, wherein the IMQ polypeptide comprises the amino acid sequence as set forth in SEQ ID NO: 96.

15. A plant obtained by a method of claim 13.

16. The plant of claim 15, which is selected from the group consisting of plants of the *Brassica* species, including canola and rapeseed, soy, corn, sunflower, cotton, cocoa, safflower, oil palm, coconut palm, flax, castor, peanut, wheat, oat, and rice.

17. The plant of claim 16, wherein the plant is canola.

18. The plant of claim 15, wherein the plant is selected from the group consisting of a plant grown from said progenitor cells, a plant that is the direct progeny of a plant grown from said progenitor cells, and a plant that is the indirect progeny of a plant grown from said progenitor cells.

19. A feed, meal, grain, food, or seed comprising a polypeptide encoded by a heterologous nucleic acid sequence at least 95% identical to the nucleic acid sequence as set forth in SEQ ID NO: 95.

20. The feed, meal, grain, food, or seed of claim 19, wherein the polypeptide is encoded by the nucleic acid sequence as set forth in SEQ ID NO: 95.

21. A feed, meal, grain, food, or seed comprising a polypeptide comprising a heterologous amino acid sequence at least 95% identical to the amino acid sequence as set forth in SEQ ID NO: 96.

22. The feed, meal, grain, food, or seed of claim 21, wherein the polypeptide comprises an amino acid sequence as set forth in SEQ ID NO: 96.

* * * * *

UNITED STATES PATENT AND TRADEMARK OFFICE

CERTIFICATE OF CORRECTION

PATENT NO. : 7,855,320 B2
APPLICATION NO. : 11/940279
DATED : December 21, 2010
INVENTOR(S) : Davies et al.

It is certified that error appears in the above-identified patent and that said Letters Patent is hereby corrected as shown below:

On the Title Page: Item (56) References Cited: under OTHER PUBLICATIONS:

Page 1, right column, line 24, "*wrinkledI:*" should read --*wrinkled1:*--.

In the Specification:

Column 13, line 21, "ImQ" should read --IMQ--.

Column 16, line 23, "SEQ ID NO: 1," should read --SEQ ID NO: 11,--.

Column 16, line 44, "SEQ ID NO: 1," should read --SEQ ID NO: 11,--.

Column 39, line 65, "KIDI" should read --K1D1--.

Column 40, line 63, "MSI. 1" should read --MSI.1--.

Signed and Sealed this
Fifth Day of July, 2011

David J. Kappos
*Director of the United States Patent and Trademark Office*